US012068059B2

(12) United States Patent
Khurana et al.

(10) Patent No.: US 12,068,059 B2
(45) Date of Patent: Aug. 20, 2024

(54) METHODS FOR BUILDING GENOMIC NETWORKS AND USES THEREOF

(71) Applicants: Whitehead Institute for Biomedical Research, Cambridge, MA (US); Massachusetts Institute of Technology, Cambridge, MA (US)

(72) Inventors: Vikram Khurana, Cambridge, MA (US); Chee Yeun Chung, Cambridge, MA (US); Susan Lindquist, Brookline, MA (US); Bonnie A. Berger, Newtonville, MA (US); Ernest Fraenkel, Newton, MA (US); Jian Peng, Champaign, IL (US)

(73) Assignees: Whitehead Institute for Biomedical Research, Cambridge, MA (US); Massachusetts Institute of Technology, Cambridge, MA (US)

( * ) Notice: Subject to any disclaimer, the term of this patent is extended or adjusted under 35 U.S.C. 154(b) by 1087 days.

(21) Appl. No.: 16/481,061

(22) PCT Filed: Jan. 25, 2018

(86) PCT No.: PCT/US2018/015331
§ 371 (c)(1),
(2) Date: Jul. 25, 2019

(87) PCT Pub. No.: WO2018/140657
PCT Pub. Date: Aug. 2, 2018

(65) Prior Publication Data
US 2020/0265917 A1 Aug. 20, 2020

Related U.S. Application Data

(60) Provisional application No. 62/450,540, filed on Jan. 25, 2017.

(51) Int. Cl.
| | |
|---|---|
| G01N 33/48 | (2006.01) |
| C12Q 1/02 | (2006.01) |
| G01N 33/50 | (2006.01) |
| G16B 5/00 | (2019.01) |
| G16B 25/00 | (2019.01) |
| G16B 30/10 | (2019.01) |

(52) U.S. Cl.
CPC ............... *G16B 5/00* (2019.02); *C12Q 1/025* (2013.01); *G01N 33/5058* (2013.01); *G16B 25/00* (2019.02); *G16B 30/10* (2019.02); *G01N 2500/10* (2013.01)

(58) Field of Classification Search
None
See application file for complete search history.

(56) References Cited

U.S. PATENT DOCUMENTS

| | | |
|---|---|---|
| 2008/0292603 A1 | 11/2008 | Yoo |
| 2010/0240090 A1 | 9/2010 | Sakurada et al. |
| 2013/0045483 A1 | 2/2013 | Treusch et al. |
| 2016/0041149 A1* | 2/2016 | Lindquist ........... G01N 33/6896 506/10 |
| 2016/0046933 A1 | 2/2016 | Lindquist et al. |

FOREIGN PATENT DOCUMENTS

| | | |
|---|---|---|
| WO | WO 2006/124892 A2 | 11/2006 |
| WO | WO 2018/140657 | 8/2018 |

OTHER PUBLICATIONS

Tuncbag, Nurcan, et al. "Simultaneous reconstruction of multiple signaling pathways via the prize-collecting steiner forest problem." Journal of computational biology 20.2 (2013): 124-136.*
Gupta, Anupam, et al. "An efficient cost-sharing mechanism for the prize-collecting Steiner forest problem." SODA. vol. 7. 2007.*
Colby, David W., et al. "Engineering antibody affinity by yeast surface display." Methods in enzymology. vol. 388. Academic Press, 2004. 348-358.*
Tardiff, et al., "From yeast to patient neurons and back again: Powerful new discovery platforms," Movement Disorders, Aug. 14, 2014, vol. 29, Issue 10, pp. 1231-1240.
Khurana, et al., "Genome-Scale Networks Link Neurodegenerative Disease Genes to α-Synuclein through Specific Molecular Pathways," Cell System, Jan. 25, 2017, vol. 4, Issue 2, pp. 157-170.
Tuncbag, et al. "Simultaneous reconstruction of multiple signaling pathways via the prize-collecting steiner forest problem," Journal of Computational Biology 20.2 (2013): 124-136.
Tardiff, Daniel F., et al. "Yeast reveal a "druggable" Rsp5/Nedd4 network that ameliorates α-synuclein toxicity in neurons." Science 342.6161 (2013): 979-983.
Chung, Chee Yeun, et al. "Identification and rescue of α-synuclein toxicity in Parkinson patient-derived neurons." Science 342.6161 (2013): 983-987.
Huang, Shao-shan Carol, and Ernest Fraenkel. "Integrating proteomic, transcriptional, and interactome data reveals hidden components of signaling and regulatory networks." Science signaling 2.81 (2009): ra40-ra40.
Söding, Johannes, Andreas Biegert, and Andrei N. Lupas. "The HHpred interactive server for protein homology detection and structure prediction." Nucleic acids research 33.suppl_2 (2005): W244-W248.
Szklarczyk, Damian, et al. "STRING v10: protein-protein interaction networks, integrated over the tree of life." Nucleic acids research 43.D1 (2015): D447-D452.

(Continued)

Primary Examiner — Anna Skibinsky
(74) Attorney, Agent, or Firm — Morse, Barnes-Brown & Pendleton, P.C.; Lisa M. Warren, Esq.

(57) ABSTRACT

Disclosed are methods, systems, cells and compositions directed to modeling a physiologic or pathologic process in an animal using a set of yeast genes analogous to a set of animal genes and augmenting the physiologic or pathologic process in the animal with predicted gene interactions based on the interactions between the set of yeast genes. Also disclosed are methods of screening for and using therapeutics for neurodegenerative proteinopathies.

20 Claims, 34 Drawing Sheets

(56) References Cited

OTHER PUBLICATIONS

International Search Report Issued in International Application No. PCT/US2018/015331, dated Jun. 19, 2018.
Cho, et al., "Diffusion Component Analysis: Unraveling Functional Topology in Biological Networks," Res. Comput. Mol. Biol., published online: Mar. 26, 2015.
Keskin, et al., "Predicting Protein-Protein Interactions from the Molecular to the Preoteome Level," Chemical Reviews, 116, 4884-4909, 2016.

* cited by examiner

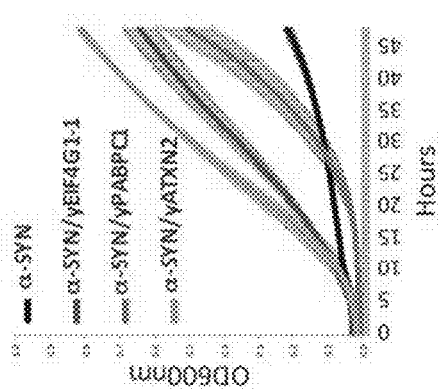
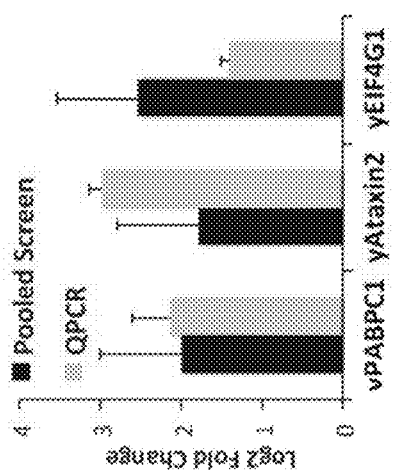
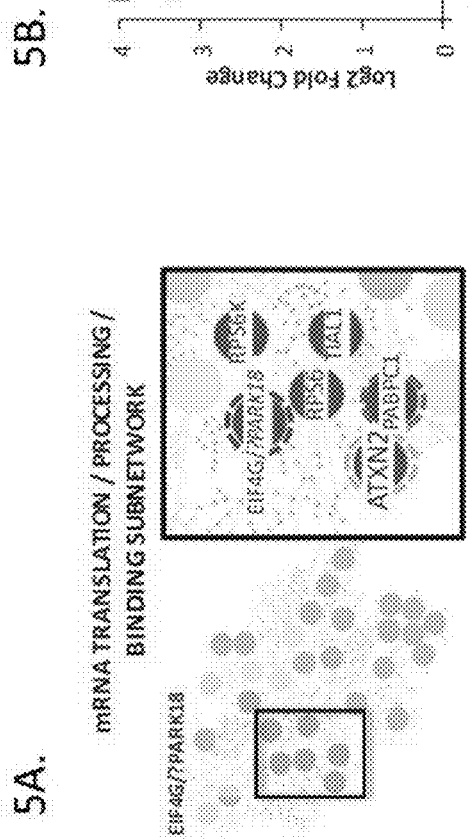
FIGS. 5A-5B

| Precision (%) | | | | | | |
|---|---|---|---|---|---|---|
| %yeast interactions | 0% | 20% | 40% | 60% | 80% | 100% |
| PCSF (our SteinerNet method) | 37 | 43 | 56 | 57 | 61 | 63 |
| DAPPLE | 8 | 8 | 7 | 6 | 6 | 6 |
| PEXA | 9 | 9 | 9 | 9 | 8 | 8 |

| Recall (%) | | | | | | |
|---|---|---|---|---|---|---|
| %yeast interactions | 0% | 20% | 40% | 60% | 80% | 100% |
| PCSF (our SteinerNet method) | 54 | 58 | 67 | 71 | 71 | 74 |
| DAPPLE | 27 | 29 | 38 | 39 | 43 | 47 |
| PEXA | 77 | 77 | 78 | 80 | 82 | 83 |

FIG. 9

11A.
1) Arrayed genome-wide overexpression (long-term, plates, score growth)

2) Arrayed genome-wide deletion (long-term, plates, score growth)

3) Pooled genome-wide overexpression (short-term, liquid, sequence plasmids)

FIG. 21

METHODS FOR BUILDING GENOMIC NETWORKS AND USES THEREOF

RELATED APPLICATIONS

This application is a national stage filing under 35 U.S.C. 371 of International Application No.: PCT/US2018/015331, filed Jan. 25, 2018, which claims the benefit of U.S. Provisional Application No. 62/450,540, filed on Jan. 25, 2017, the entire teachings of which are incorporated herein by reference. International Application No.: PCT/US2018/015331 was published under PCT Article 21(2) in English.

GOVERNMENT SUPPORT

This invention was made with government support under Grant Nos. AG038546, CA184898, GM089903, GM081871, HG006061, HG004233, and HG001715 awarded by the National Institutes of Health. The government has certain rights in the invention.

BACKGROUND OF THE INVENTION

Common neurodegenerative diseases result in the loss of distinct neuronal populations and abnormal accumulation of misfolded proteins. Synucleinopathies—including Parkinson's disease (PD), dementia with Lewy bodies and multiple system atrophy—are associated with abnormal intracellular aggregation of α-synuclein (α-syn). Alzheimer's disease (AD) is associated with amyloid-β (Aβ) and tau accumulation, while amyotrophic lateral sclerosis (ALS) is associated with altered localization and accumulation of TAR DNA-binding protein 43 (TDP-43), and so forth. The richest source of hypotheses regarding the pathogenesis of these diseases has derived from neuropathology of postmortem brain. While providing pivotal insights, these observations are made decades after disease inception.

A revolution in human genetic analysis over the last twenty years has uncovered disease-causing mutations that connect protein-misfolding to the neurodegenerative process. For instance, point mutations and gene multiplication at the α-syn (SNCA) locus lead to rare but early-onset, highly penetrant forms of PD and dementia. Polymorphisms in regulatory regions of the SNCA locus that increase gene expression confer increased risk for late-onset PD (Fuchs et al., 2008; Nalls et al., 2014). These studies enabled the creation of animal and cellular disease models and enriched our understanding of disease mechanisms. But with this knowledge, a new set of challenges has emerged.

First, seemingly disparate genes have been tied to particular clinical phenotypes. For example, parkinsonism is characterized by slowness (bradykinesia), rigidity, tremor and postural instability. The most common form is PD, defined by α-syn pathology and loss of dopaminergic neurons. However, numerous other disease entities—tied to distinct genetic signatures and neuropathology—can lead to parkinsonism, demonstrating that there is not a simple correspondence between genotype, neuropathology and clinical presentation (Martin et al., 2011; Shulman et al., 2010; Verstraeten et al., 2015). Those few genetic loci with parkinsonism as the primary clinical phenotype have been given a numeric "PARK" designation (for example, SNCA/PARK1 locus itself and LRRK2/PARK8), but even mutations in the same gene can produce distinct neuropathology and diverse clinical presentations (Martin et al., 2011; Shulman et al., 2010; Verstraeten et al., 2015). Understanding the inter-relationship between genetic risk factors for parkinsonism, and their relationship to α-syn itself, is vital for patient stratification and targeted therapeutic strategies.

Second, human genetic studies have sometimes produced ambiguous and controversial data. For rare variants, substantial recent genetic divergence of human populations may render traditional methods of cross-validation between different populations unfeasible (Nelson et al., 2012; Tennessen et al., 2012). Inconsistencies in the literature abound—for example, studies implicating UCHL1 as "PARK5" and the translation initiation factor EIF4G1 as "PARK18" have failed to reproduce. For common polymorphisms, the challenge is distinguishing between multiple candidate gene loci in linkage to a SNP. It is becoming clear that biological validation will be required to fully establish which genetic factors are causally related to disease processes, and how (Casals and Bertranpetit, 2012).

One approach to validating candidate gene variants, and understanding their relationship to proteinopathy, is to systematically screen the entire genome to identify every gene that modifies proteotoxicity when over-expressed or deleted. This is achievable in Baker's yeast (Saccharomyces cerevisiae), a unicellular eukaryote of unparalleled genetic tractability. Yeast has proved highly informative for understanding the cytotoxicity induced by misfolded proteins (Khurana and Lindquist, 2010). This is not surprising because human genetic data for neurodegenerative diseases heavily implicate cellular pathways that are among the most highly conserved in eukaryotic evolution, including protein homeostasis and quality control, protein trafficking, RNA metabolism and mitochondrial function (Bras et al., 2015; Guerreiro et al., 2015).

Expressing toxic proteins relevant to neurodegeneration in yeast creates a robust and easily scorable growth/viability defect amenable to genome-wide phenotypic screening in yeast. Toxicities of α-syn, beta-amyloid and TDP-43 have been screened by individually over-expressing one of ~5500 ORFs that comprise the majority of the yeast genome (Khurana and Lindquist, 2010; H.-J. Kim et al., 2013; Treusch et al., 2011; Yeger-Lotem et al., 2009). These screens have guided the discovery of cellular pathologies in neurons and animal models (Cooper et al., 2006; Dhungel et al., 2014; Khurana and Lindquist, 2010; H.-J. Kim et al., 2013), shed important insights on the relationship of genetic modifier data to gene-expression analysis (Yeger-Lotem et al., 2009), and led to the identification of novel human disease genes (Elden et al., 2010). Recently, processes pinpointed by phenotypic screening in a yeast synucleinopathy model led to the discovery of cellular pathologies in induced pluripotent stem cell (iPSc)-derived neurons from patients with PD due to mutations at the α-syn locus (Chung et al., 2013). In that study, integrating high-throughput genetic and small-molecule screens identified genes and small molecules that could correct pathologies from yeast to neurons (Chung et al., 2013; Tardiff et al., 2013; 2014).

SUMMARY OF THE INVENTION

Numerous genes and molecular pathways are implicated in neurodegenerative proteinopathies, but their inter-relationships are poorly understood. We systematically mapped molecular pathways underlying the toxicity of alpha-synuclein (α-syn), a protein central to Parkinson's disease. Genome-wide screens in yeast identified 332 genes that impact α-syn toxicity. To "humanize" this molecular network, we developed a computational method, TransposeNet. This integrates a Steiner prize-collecting approach with homology assignment through sequence, structure and interaction topology. TransposeNet linked α-syn to multiple parkinsonism genes and druggable targets through perturbed protein trafficking/ER quality control and mRNA metabolism/translation. A calcium signaling hub linked these processes to perturbed mitochondrial quality control/function, metal ion transport, transcriptional regulation and signal transduction. Parkinsonism gene interaction profiles spatially opposed in the network (ATP13A2/PARK9, VPS35/PARK17) were highly distinct, and network relationships for specific genes (LRRK2/PARK8, ATXN2 and EIF4G1/PARK18) were confirmed in patient iPS cell-derived neurons. This cross-species platform connected diverse neurodegenerative genes to proteinopathy through specific mechanisms, and may facilitate patient stratification for targeted therapy.

Here, we build genome-scale networks of α-syn and other proteotoxicities by combining a new computational approach with substantially broader yeast genetic screens. To discover meaningful molecular connections in yeast and patient-derived neurons, we develop a TransposeNet algorithm that: 1) maps yeast hits to their human homologs by considering sequence, structure and molecular interactions; 2) builds networks by linking yeast hits and hidden human genes through an optimization framework based on the prize-collecting Steiner forest algorithm (SteinerForest Ensemble); and 3) transposes molecular interactions across species from yeast to human, utilizing the unparalleled density of known molecular interactions in yeast to compensate for the relative sparseness of the human interactome. The networks linked many parkinsonism and neurodegenerative disease risk factors to α-syn toxicity through specific molecular pathways, most notably vesicle trafficking and mRNA metabolism.

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), Current Protocols in Molecular Biology, Current Protocols in Immunology, Current Protocols in Protein Science, and Current Protocols in Cell Biology, all John Wiley & Sons, N.Y., edition as of December 2008; Sambrook, Russell, and Sambrook, Molecular Cloning: A Laboratory Manual, 3rd ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N J, 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange; 10th ed. (2006) or 11th edition (July 2009). Non-limiting information regarding genes and genetic disorders is found in McKusick, V.A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, MD) and National Center for Biotechnology Information, National Library of Medicine (Bethesda, MD), as of May 1, 2010, ncbi.nlm.nih.gov/omim/ and in Online Mendelian Inheritance in Animals (OMIA), a database of genes, inherited disorders and traits in animal species (other than human and mouse), at omia.angis.org.au/contact.shtml. All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

In some aspects, the invention is directed towards a method of modeling a physiologic or pathologic process in a first eukaryote (e.g., fungal, protozoa, insect, plant, vertebrate), comprising (a) providing a set of candidate eukaryotic genes identified in a second eukaryote (e.g., fungal, protozoa, insect, plant, vertebrate) with an analogue of the physiologic or pathologic process in the first eukaryote; (b) providing interactions between eukaryotic genes of the first eukaryote comprising the candidate eukaryotic genes of step (a); (c) providing interactions between genes in the second eukaryote; (d) determining a set of genes in the first eukaryote homologous to the set of candidate eukaryotic genes; and (e) creating a model of the physiologic or pathologic process in the first eukaryote by augmenting interactions between the set of genes in the first eukaryote obtained in step (d) with predicted gene interactions based on the interactions of step (b) from the second eukaryote. In some embodiments, the set of genes in the first and second eukaryotes comprise homologs of each other.

In some embodiments, the physiologic or pathologic process is a neurodegenerative disease. In some embodiments, the physiologic or pathologic process is a neurodegenerative proteinopathy. In some embodiments, the physiologic or pathologic process is a synucleinopathy, Alzheimer's disease, frontotemporal degeneration, a spinocerebellar ataxias, Huntington's disease, or amyotrophic lateral sclerosis. In some embodiments, the synucleinopathy is Parkinson's disease.

In some embodiments, the network topology of both eukaryotes (e.g., human and yeast) as well as the sequence/structural similarity between them are compared to determine homology. In some aspects, sequence and structure similarity scores are converted to a probability distribution, and feature vectors of all pairs of nodes, including the sparse vector representations ones, are jointly computed by minimizing the Kullbeck-Leibler (KL) divergence between the relevance vectors and the parameterized multinomial distributions. "Nodes" refer to genes or proteins.

In some embodiments, inferred homology may be used to augment interactions between genes in a first eukaryote (e.g., human) based on the interactions of genes in a second eukaryote (e.g., yeast). In some embodiments, an inferred interaction may be added to the network of the first eukaryote if an interaction is present in a homologous pair of genes in the second eukaryote. In some embodiments, an inferred interaction is added only at a certain threshold of homology between the pair of genes in the first eukaryote and the pair of genes in the second eukaryote. In some embodiments, the threshold is set so that the density of interactions in the first eukaryote (e.g., human) are similar to the density of interactions in the second eukaryote (e.g., yeast).

In some embodiments, creating a model of the physiologic or pathologic process in a first eukaryote (e.g., human) by augmenting interactions from a second eukaryote comprises using the prize-collecting Steiner forest (PCSF) algorithm (Cho et al., 2015; Tuncbag et al., 2013; 2016.; Voevodski et al., 2009) to connect gene or protein nodes through genetic interactions, physical interactions and annotated pathways from one or more curated databases while minimizing costs to obtain a network. In some embodiments, the objective function parameter for the PCSF algorithm is determined with the Prize-collecting Steiner Tree problem (PCST) and a known message-passing-algorithm. See Bailly-Bechet et al., 2011; Cho et al., 2015.

In some embodiments, the multiple networks are combined using a maximum spanning tree algorithm to find the most robust, representative network. In some embodiments, the statistical significance of the representative network is validated against networks generated from random pairings of genes between the first eukaryote and the second eukaryote.

In some embodiments, the invention is directed to a method of modeling a physiologic or pathologic process in an animal (e.g., human, mouse), comprising: (a) providing a set of candidate yeast genes identified in a yeast analogue of the physiologic or pathologic process in the animal; (b) providing interactions between yeast genes comprising the candidate yeast genes of step (a); (c) providing interactions between genes in the animal; (d) determining a set of genes in the animal homologous to the set of candidate yeast genes; and (e) creating a model of the physiologic or pathologic process in the animal by augmenting interactions between the set of genes in the animal obtained in step (d) with predicted gene interactions based on the interactions of step (b).

In some embodiments, the set of candidate yeast genes of step (a) were obtained by a method comprising: (i) providing a yeast cell modified to have increased or decreased expression or activity of a protein encoded by a yeast gene under conditions being a yeast analogue the physiologic or pathologic process, (ii) determining whether the modification modulates the yeast cell response to the conditions, and (iii) identifying the yeast gene as a candidate yeast gene when the yeast cell response is modulated. In some embodiments, the conditions comprise aberrant expression of one or more genes (e.g., over-expression, reduced expression, eliminated expression). In some embodiments, the one or more genes comprise a non-endogenous gene. In some embodiments, the modulation of yeast cell response of step (ii) comprises a change in at least one phenotype, a change in expression of at least one gene, a change in activity of at least one protein, or a change in cell viability. In some embodiments, the identification of a candidate yeast gene of step (iii) comprises identification of a change in at least one phenotype, a change in expression of at least one gene, a change in activity of at least one protein, or a change in cell viability.

In some embodiments, the model of the physiologic or pathologic process created by the methods herein comprises one or more predicted gene or protein nodes. In some embodiments, the methods disclosed herein further comprise identifying one or more other genes or proteins (e.g., predicted gene or protein) involved in the modeled physiologic or pathologic process. In some embodiments, the predicted gene or protein nodes comprise a druggable target.

Another aspect of the invention is directed to generating a cell comprising (a) obtaining a model of a physiologic or pathologic process generated according to any of the methods disclosed herein; (b) identifying a gene node in the model obtained in step (a); and (c) generating a cell having altered expression of the gene node or altered activity of a gene product of the gene node.

In some aspects, the cell having altered expression of the gene node or altered activity of a gene product of the gene node is obtained by introducing one or more mutations into a cell that alters the expression of the gene or activity of a gene product of the gene. The one or more mutations may comprise one or more of an insertion, deletion, disruption or substitution into the genome of the cell. In some embodiments, the one or more mutations comprise the deletion of the gene. In some embodiments, the one or more mutations comprise insertion of extra copies of the gene or a portion of the gene. In some embodiments, the one or more mutations modify regulatory sequences and increases or decreases expression of a gene product of the gene. In some embodiments, the one or more mutations increase or decrease the activity of a gene product of the gene. In some embodiments, the one or more mutations increase or decrease the cellular degradation rate of a gene product of the gene.

In some aspects, the invention is directed towards a method of screening for a modulator of a physiologic or pathologic process, comprising providing a cell (i.e., altered cell) having altered expression of a gene node or activity of a gene product of the gene node, and using the cell to screen compounds for modulators of a physiologic or pathologic process (e.g., a physiologic or pathologic process modeled by a method disclosed herein). In some embodiments, the cell is obtained by the methods disclosed herein. In some embodiments, the method of screening comprises contacting the altered cell with an agent (e.g., a small molecule, nucleic acid, antibody or polypeptide), and measuring a change in at least one phenotype, a change in expression of at least one gene, a change in activity of at least one protein, or a change in cell viability.

In some aspects, the invention is directed towards methods of screening for a compound to treat a pathologic process in an organism (e.g., human, eukaryote, mammal) comprising (a) modeling a physiologic or pathologic process in the organism by any method disclosed herein, (b) identifying a gene or protein node of the model of step (a), and screening compounds to identify a modulator of the identified gene or protein node.

In some aspects, the invention is directed towards methods of determining one or more targets for therapy in an organism (e.g., eukaryote, human) with a physiologic or pathologic process (e.g., a neurodegenerative condition, disease, disorder) comprising (a) obtaining a model of a physiologic or pathologic process generated according to any of the methods disclosed herein; (b) identifying one or more gene or protein nodes of the model obtained in step (a), and (c) determining whether the organism harbors a mutation, altered expression, or altered activity in any of the gene or protein nodes identified in step (b).

In some aspects, the invention is directed to methods of modeling a physiologic or pathologic process of first eukaryote (e.g., human) in a second eukaryote (e.g., yeast) comprising (a) providing a set of genes identified in the second eukaryote analogue of the physiologic or pathologic process of the first eukaryote; (b) obtaining interactions between the identified genes; and (c) creating a model of the physiologic or pathologic process. In some embodiments, the interactions in step (b) are obtained by using the Prize-Collecting Steiner Forest (PCSF) algorithm to connect gene or protein nodes through genetic interactions, physical interactions and annotated pathways from curated databases while minimizing costs to obtain a network.

In some embodiments, the invention is directed towards a cell comprising an expression construct comprising a promoter operably linked to a nucleic acid encoding a polypeptide comprising a human α-synuclein protein, wherein the cell has been modified to have increased or decreased expression or activity of a protein encoded by a yeast gene listed in any one or more of Table S3:first column, Table S5, Table S6, or Table S7, or has been modified to have increased or decreased expression or activity of a protein encoded by a mammalian homolog of such yeast gene as compared with an unmodified cell of the same type.

Other aspects of the invention are related to a mammalian cell (e.g., human, mouse) that has been modified to have increased or decreased expression or activity of a mammalian protein encoded by a mammalian gene that is a homolog of a yeast gene listed in any of Table S3:first column, Table S5, Table S6, or Table S7 as compared with an unmodified cell of the same type.

Some aspects of the invention are directed towards identifying a compound that inhibits alpha-synuclein-mediated toxicity, the method comprising:
(a) providing a cell as described herein comprising an expression construct comprising a promoter operably linked to a nucleic acid encoding a polypeptide comprising a human α-synuclein protein, wherein the cell has been modified to have increased or decreased expression or activity of a protein encoded by a yeast gene listed in any one or more of Table S3:first column, Table S5, Table S6, or Table S7, or has been modified to have increased or decreased expression or activity of a protein encoded by a mammalian homolog of such yeast gene as compared with an unmodified cell of the same type;
(b) contacting the cell with an agent that modulates expression or activity of a protein encoded by a gene listed in Table S3:first column, Table S5, Table S6, or Table S7 or a mammalian homolog thereof; and
(c) (i) measuring cell viability in the presence of the agent, wherein an increase in cell viability in the presence of the agent as compared to cell viability in the absence of the agent identifies the agent as a compound that inhibits alpha-synuclein-mediated toxicity or (ii) measuring at least one phenotype associated with alpha-synuclein-mediated toxicity in the cell, wherein a decrease in at least one phenotype associated with alpha-synuclein toxicity in the presence of the agent as compared to in the absence of the agent identifies the agent as a compound that inhibits alpha-synuclein-mediated toxicity.

Some aspects of the invention are directed towards a method of identifying a candidate agent for treatment of a synucleinopathy, the method comprising:
(a) providing a cell as described herein comprising an expression construct comprising a promoter operably linked to a nucleic acid encoding a polypeptide comprising a human α-synuclein protein, wherein the cell has been modified to have increased or decreased expression or activity of a protein encoded by a yeast gene listed in any one or more of Table S3:first column, Table S5, Table S6, or Table S7, or has been modified to have increased or decreased expression or activity of a protein encoded by a mammalian homolog of such yeast gene as compared with an unmodified cell of the same type;
(b) contacting the cell with an agent that modulates expression or activity of a protein encoded by a gene listed in Table S3:first column, Table S5, Table S6, or Table S7 or a mammalian homolog thereof; and
(c) (i) measuring cell viability in the presence of the agent, wherein an increase in cell viability in the presence of the agent as compared to cell viability in the absence of the agent identifies the agent as a candidate agent for treatment of a synucleinopathy or (ii) measuring at least one phenotype associated with alpha-synuclein-mediated toxicity in the cell, wherein a decrease in at least one phenotype associated with alpha-synuclein toxicity in the presence of the agent as compared to in the absence of the agent identifies the agent as a candidate agent for treatment of a synucleinopathy.

Some aspects of the invention are directed towards a method of inhibiting alpha-synuclein-mediated toxicity in a human cell or subject comprising modulating the expression or activity of a human protein that is a homolog of a yeast protein encoded by a yeast gene listed in any one or more of Table S3:first column, Table S5, Table S6, or Table S7 in the cell or subject.

In some embodiments, the invention is directed towards a cell comprising an expression construct comprising a promoter operably linked to a nucleic acid encoding a polypeptide comprising a human TDP-43 protein, wherein the cell is has been modified to have increased or decreased expression or activity of a protein encoded by a yeast gene listed in Table S3: second column, or has been modified to have increased or decreased expression or activity of a protein encoded by a mammalian homolog of such yeast gene as compared with an unmodified cell of the same type. In some embodiments, the expression construct comprises a promoter operably linked to a nucleic acid encoding a polypeptide comprising a human TDP-43 protein is integrated into the genome of the cell. In some embodiments, the promoter operably linked to a nucleic acid encoding a polypeptide comprising a human TDP-43 protein is an inducible promoter.

Other aspects of the invention are related to a mammalian cell (e.g., human, mouse) that has been modified to have increased or decreased expression or activity of a mammalian protein encoded by a mammalian gene that is a homolog of a yeast gene listed in Table S3: second column as compared with an unmodified cell of the same type. In some embodiments, the cell comprises an expression construct comprising a promoter operably linked to a nucleic acid encoding a protein encoded by the mammalian gene homolog or harbors a deletion, disruption, or mutation in the mammalian gene homolog.

Some aspects of the invention are directed towards identifying a compound that inhibits TDP-43-mediated toxicity, the method comprising:
(a) providing a cell as described herein comprising an expression construct comprising a promoter operably linked to a nucleic acid encoding a polypeptide comprising a human TDP-43 protein, wherein the cell has been modified to have increased or decreased expression or activity of a protein encoded by a yeast gene listed in Table S3:second column, or has been modified to have increased or decreased expression or activity of a protein encoded by a mammalian homolog of such yeast gene as compared with an unmodified cell of the same type;
(b) contacting the cell with an agent that modulates expression or activity of a protein encoded by a gene listed in Table S3:second column, or a mammalian homolog thereof; and
(c) (i) measuring cell viability in the presence of the agent, wherein an increase in cell viability in the presence of the agent as compared to cell viability in the absence of the agent identifies the agent as a compound that inhibits TDP-43-mediated toxicity or (ii) measuring at least one phenotype associated with TDP-43-mediated toxicity in the cell, wherein a decrease in at least one phenotype associated with TDP-43 toxicity in the presence of the agent as compared to in the absence of the agent identifies the agent as a compound that inhibits TDP-43-mediated toxicity.

Some aspects of the invention are directed towards a method of identifying a candidate agent for treatment of a TDP-43-mediated toxicity, the method comprising:
(a) providing a cell as described herein comprising an expression construct comprising a promoter operably linked to a nucleic acid encoding a polypeptide comprising a human α-synuclein protein, wherein the cell has been modified to have increased or decreased expression or activity of a protein encoded by a yeast gene listed in Table S3:second column, or has been modified to have increased or decreased expression or activity of a protein encoded by a mammalian homolog of such yeast gene as compared with an unmodified cell of the same type;
(b) contacting the cell with an agent that modulates expression or activity of a protein encoded by a gene listed in Table S3:second column, or a mammalian homolog thereof; and
(c) (i) measuring cell viability in the presence of the agent, wherein an increase in cell viability in the presence of the agent as compared to cell viability in the absence of the agent identifies the agent as a candidate agent for treatment of a TDP-43-mediated toxicity or (ii) measuring at least one phenotype associated with TDP-43-mediated toxicity in the cell, wherein a decrease in at least one phenotype associated with TDP-43 toxicity in the presence of the agent as compared to in the absence of the agent identifies the agent as a candidate agent for treatment of a TDP-43-mediated toxicity.

Some aspects of the invention are directed towards a method of inhibiting TDP-43-mediated toxicity in a human cell or subject comprising modulating the expression or activity of a human protein that is homolog of a yeast protein encoded by a yeast gene listed in Table S3: second column in the cell or subject.

In some embodiments, the invention is directed towards a cell comprising an expression construct comprising a promoter operably linked to a nucleic acid encoding a polypeptide comprising a human amyloid beta protein, wherein the cell is has been modified to have increased or decreased expression or activity of a protein encoded by a yeast gene listed in Table S3: third column, or has been modified to have increased or decreased expression or activity of a protein encoded by a mammalian homolog of such yeast gene as compared with an unmodified cell of the same type. In some embodiments, the expression construct comprises a promoter operably linked to a nucleic acid encoding a polypeptide comprising a human amyloid beta protein is integrated into the genome of the cell. In some embodiments, the promoter operably linked to a nucleic acid encoding a polypeptide comprising a human amyloid beta protein is an inducible promoter.

Other aspects of the invention are related to a mammalian cell (e.g., human, mouse) that has been modified to have increased or decreased expression or activity of a mammalian protein encoded by a mammalian gene that is a homolog of a yeast gene listed in Table S3: third column as compared with an unmodified cell of the same type.

Some aspects of the invention are directed towards identifying a compound that inhibits amyloid beta-mediated toxicity, the method comprising:
(a) providing a cell as described herein comprising an expression construct comprising a promoter operably linked to a nucleic acid encoding a polypeptide comprising a human amyloid beta protein, wherein the cell has been modified to have increased or decreased expression or activity of a protein encoded by a yeast gene listed in Table S3:third column, or has been modified to have increased or decreased expression or activity of a protein encoded by a mammalian homolog of such yeast gene as compared with an unmodified cell of the same type;
(b) contacting the cell with an agent that modulates expression or activity of a protein encoded by a gene listed in Table S3:third column, or a mammalian homolog thereof; and
(c) (i) measuring cell viability in the presence of the agent, wherein an increase in cell viability in the presence of the agent as compared to cell viability in the absence of the agent identifies the agent as a compound that inhibits amyloid beta-mediated toxicity or (ii) measuring at least one phenotype associated with amyloid beta-mediated toxicity in the cell, wherein a decrease in at least one phenotype associated with amyloid beta toxicity in the presence of the agent as compared to in the absence of the agent identifies the agent as a compound that inhibits amyloid beta-mediated toxicity.

Some aspects of the invention are directed towards a method of identifying a candidate agent for treatment of a amyloid beta-mediated toxicity, the method comprising:
(a) providing a cell as described herein comprising an expression construct comprising a promoter operably linked to a nucleic acid encoding a polypeptide comprising a human α-synuclein protein, wherein the cell has been modified to have increased or decreased expression or activity of a protein encoded by a yeast gene listed in Table S3:third column, or has been modified to have increased or decreased expression or activity of a protein encoded by a mammalian homolog of such yeast gene as compared with an unmodified cell of the same type;
(b) contacting the cell with an agent that modulates expression or activity of a protein encoded by a gene listed in Table S3:third column, or a mammalian homolog thereof; and
(c) (i) measuring cell viability in the presence of the agent, wherein an increase in cell viability in the presence of the agent as compared to cell viability in the absence of the agent identifies the agent as a candidate agent for treatment of a amyloid beta-mediated toxicity or (ii) measuring at least one phenotype associated with amyloid beta-mediated toxicity in the cell, wherein a decrease in at least one phenotype associated with amyloid beta toxicity in the presence of the agent as compared to in the absence of the agent identifies the agent as a candidate agent for treatment of a amyloid beta-mediated toxicity.

Some aspects of the invention are directed towards a method of inhibiting amyloid beta-mediated toxicity in a human cell or subject comprising modulating the expression or activity of a human protein that is homolog of a yeast protein encoded by a yeast gene listed in Table S3: third column in the cell or subject.

BRIEF DESCRIPTION OF THE DRAWINGS

These and other characteristics of the present invention will be more fully understood by reference to the following detailed description in conjunction with the attached drawings.

FIG. 1A shows the SteinerForest Ensemble methodology vs. conventional approach. 77 genetic modifiers ("hits") from a previous over-expression screen against α-syn toxicity are mapped to the yeast interactome. The conventional approach misses 30 genetic hits and overemphasizes "hub" genes like PMR1. SteinerForest Ensemble includes all 77 hits and predicts additional nodes of biological relevance including the druggable targets Rsp5 and Calcineurin (Cnb1).

FIG. 1B left shows hits from three published over-expression screens for α-syn, Aβ and TDP-43 proteotoxicities in yeast. Venn diagrams indicate the numbers of genetic modifiers recovered. FIG. 1B right shows a comparison of the output SteinerForest Ensemble networks generated from inputting these three sets of screen hits (empirical p-value for 1000 similarly connected random networks is shown for triple-wise comparison).

FIG. 1C shows growth curves demonstrating effects of a compound that activates Rsp5, NAB, on TDP-43 (left) and α-syn (right) toxicity. Yeast expressing either yellow fluorescent protein (YFP), TDP-43(TDP), or α-syn were treated with 20 µM (for TDP-43) or 10 µM (for α-syn) NAB. Growth was monitored over time by optical density (OD) at 600 nm. Results are representative of three experiments.

FIG. 2A shows a "humanized" network that is generated from the 77 α-syn over-expression screen hits by TransposeNet. Each yeast gene (red triangle) is linked to its human homolog(s) (blue circle) by a weight proportional to the homology strength. Edges are weighted based on their experimental level of confidence. Certain nodes are enlarged for emphasis. LRRK2 is linked within network via NSF1 and STUB1. Inset: Density of known molecular interactions in yeast and human (Biogrid, available on the world wide web at wiki.thebiogrid.org/doku.php/statistics). Abbreviations: DCA (diffusion component analysis); PARK (known "parkinsonism" gene). See Supplement for complete network.

FIG. 2B shows the effect on the "humanized" network of withholding yeast edge augmentation.

FIG. 2C shows the accumulation of Nicastrin in the endoplasmic reticulum (ER) in LRRK2$^{G2019S}$ mutant iPSc-derived dopaminergic neurons compared to mutation-corrected control neurons. Endoglycosidase H (Endo H) removes post ER glycosylation and reveals the ER form of Nicastrin, an ER-associated degradation substrate. The post ER-to-ER ratio was calculated using the ratio of the mature form over the deglycosylated ER form. Data are represented as mean±SEM (n=2 for patient 1 and n=3 for patient 2, ***; p<0.0001, two tail t-test).

FIG. 3A-FIG. 3C show a TransposeNet builds genome-scale molecular network for α-syn toxicity from genome-wide deletion and over-expression yeast screens FIG. 3A show a summary of genetic modifiers recovered in screens. 16 genetic modifiers (14 unique) from low-throughput investigations were also incorporated. Yeast homologs of genes linked to PD and other neurodegenerative disorders are listed. "y" preceding the human gene name indicates the "yeast homolog".

FIG. 3B shows a "humanized" network is generated from the 332 α-syn screen hits by TransposeNet. Genes of interest are enlarged, including multiple neurodegeneration-related disease genes (see also FIG. 13 and Table S14). Gene ontology process enrichment within "stems" of the network are shown color-coded (full details in Table S12; gray portions were not enriched). Brown lines indicate extrapolated connections to VCP/Cdc48 through Vms1 (the yeast homolog of Ankzf1) and Hrd1 (the yeast homolog of Syvn1), and from VCP to Parkin/PARK2 and Pink 1/PARK6. A target symbol marks two druggable nodes, Calcineurin (Caraveo et al., 2014) and Nedd4 (a target of NAB (Tardiff et al., 2013)). Inset: Network without transposition of yeast edges. LRRK2 and NFAT not included. Ontologically connected proteins (for example Rab proteins) are dispersed.

FIG. 4A shows the vesicle trafficking subnetwork within the α-syn map (from FIG. 3B) and location of PARK9 (ATP13A2). Green: trafficking proteins; brown: metal ion transporters.

FIG. 4B shows synthetic toxic interactions between trafficking genes and α-syn (spotting assays on agar plates). A-syn transgene is expressed from a galactose-inducible promoter ("on" in galactose, Gal; "off" in glucose, Glc). "y" ahead of the human gene name indicates the yeast homolog. ΔGAL2 strain ("nonspecific enhancer") serves as a (+) control because it grows less well on galactose (regardless of α-syn expression). The (−) control, a deletion (ΔYMR191W), has no deleterious effect in presence of α-syn ("baseline toxicity").

FIG. 4C shows expression of yeast VPS35 (yVps35), human VPS35 (hVps35), and human mutant (D620N) VPS35 in α-syn-expressing Vps35-deleted "IntTox" cells (yeast spotting assay, showing serial 5× dilution from left to right; transgenes are expressed from a galactose-inducible promoter).

FIG. 4D-FIG. 4E show cross-comparison of genetic interactors with similarly toxic HiTox α-syn, α-syn-ΔVPS35/PARK17, α-syn-ΔATP13A2/PARK9 strains. Spotting assay demonstrates relative levels of toxicity among these three strains (FIG. 4D; 5× serial dilution from left to right). In FIG. 4E, data is shown on dot-plots comparing the efficacy of 77 known α-syn modifiers (see FIG. 1) in HiTox α-syn (x-axis) versus ΔPARK17/α-syn (y-axis; D) ΔPARK9/α-syn (y-axis; FIG. 4E). Green: vesicle trafficking genetic modifiers, brown: metal ion transport modifiers. Axis scales represent growth relative to Mig1/Mig3 positive controls (=100, black). Mig1/Mig3 over-expression represses the galactose promoter driving α-syn expression. Each spot assay in this figure was repeated 2-4 times. The dot plot is representative of two experiments performed on separate days with biological replicates. Transformants were plated in quadruplicate for each experiment.

FIG. 5A-FIG. 5E show mRNA translation factors impact α-syn toxicity from yeast to patient-derived neurons.

FIG. 5A shows a mRNA translation subnetwork in α-syn toxicity (from FIG. 3B), including ATXN2, EIF4G1 (PARK18) and PABPC1.

FIG. 5B shows the effects of yPABPC1, yAtaxin2 and yEIF4G1-1 on α-syn toxicity (left: quantitative PCR; right: bioscreen growth assay).

FIG. 5C shows bulk mRNA translation in mutant α-syn$^{A53T}$ iPSc neurons compared to isogenic mutation-corrected control neurons as measured by $^{35}$S-cysteine and $^{35}$S-methionine incorporation over time (phosphorimager scan). Commassie staining shows loading of protein. Two subclones of the mutation-corrected line were compared to α-syn$^{A53T}$ cells (n=4).

FIG. 5D shows TALE-TFs designed to elevate the endogenous levels of ATXN2 or EIF4G1 genes. These bind to the 5' UTR of the target genes, and recruit a transcriptional activator (Sanjana et al., 2012). Q-PCR indicates transcript levels after AAV-mediated TALE-TF delivery into A53T iPS neurons. Sequence of first and second assembled hexamer is SEQ ID NO: 11.

FIG. 5E show the effect of increasing endogenous EIF4G1 or ATXN2 levels on bulk translation in A53T neurons (n=3). Data are represented as mean±SEM. *; p<0.05 **; p<0.01 two tail t-test).

FIG. 7A shows average DCA accuracy across a range of BLAST weights (blue), with only network topology and BLAST terms retained in the extended DCA objective function. Comparison was to the accuracy of BLAST itself (red). FIG. 7B shows the average accuracy of DCA algorithm across a range of HHpred weights with BLAST weight fixed at 10 (blue), compared to the accuracy of HHpred itself (red). FIG. 7C shows the average accuracy of DCA algorithm across a range of Diopt weights with HHpred and BLAST weights fixed at 5 and 10, respectively.

FIG. 9 shows that transposition/injection of yeast interactome "edges" substantially improves precision and recall in simulated yeast genetic screens. To better understand the relevance of genes and predicted pathways recovered by the our PCSF SteinerNet method and the alternative DAPPLE and PEXA methods [see Methods for full details], we designed a well-controlled simulation. To mimic genetic screens of perturbed pathways, we selected individual pathways from the well-known human pathway database KEGG and identified all genes in each pathway. We then identified yeast homologs via stringent Ensemble one-to-one mapping. We treated those human genes with clear yeast homologs as "perturbed" and picked their homologs' genetic interaction neighboring genes as hits from a "virtual yeast genetic screen". Virtual screens like these minimize experimental noise as a confounding factor and enable cleaner evaluation of algorithm performance. Since we know the "true" pathway information, this method can be used to test the sensitivity and specificity of algorithms by quantifying how often "relevant" genes in the original KEGG pathway are recovered as predicted (non-seed) genes. We chose 50 KEGG pathways (Table S15) that had at least 5 human genes with clear yeast homologs and created 50 associated "virtual" screens for testing. We used two performance metrics: precision, i.e. the percentage of predicted hidden genes shown in the original KEGG pathway, and recall, i.e. the percentage of the original KEGG genes shown as hidden nodes in the predicted pathway. We tested how these values changed with different levels of yeast interactome edge transposition (by randomly removing a portion of injected/transposed genetic interactions over 10 trials). This is depicted in the figure. For PCSF, without any yeast edges the average precision and recall values are 37% and 54%. For DAPPLE, the average precision and recall values are 8% and 27% resp. The performance of PCSF and DAPPLE notably improves with yeast edge injection/transposition. The performance becomes reasonable when >40% interactions are injected. The performance of PEXA remains relatively unchanged because it utilizes the human KEGG pathway information in its algorithm, the same pathways used in constructing our simulated screens.

Injecting yeast interactions improves precision and recall of PCSF, and improves recall of DAPPLE. PEXA and DAPPLE generate very large and imprecise networks, regardless of yeast injection. PEXA always has high recall simply because the method uses KEGG pathway input to build networks, and KEGG pathways are used as the basis of these simulated yeast genetic screens.

Figure 10:
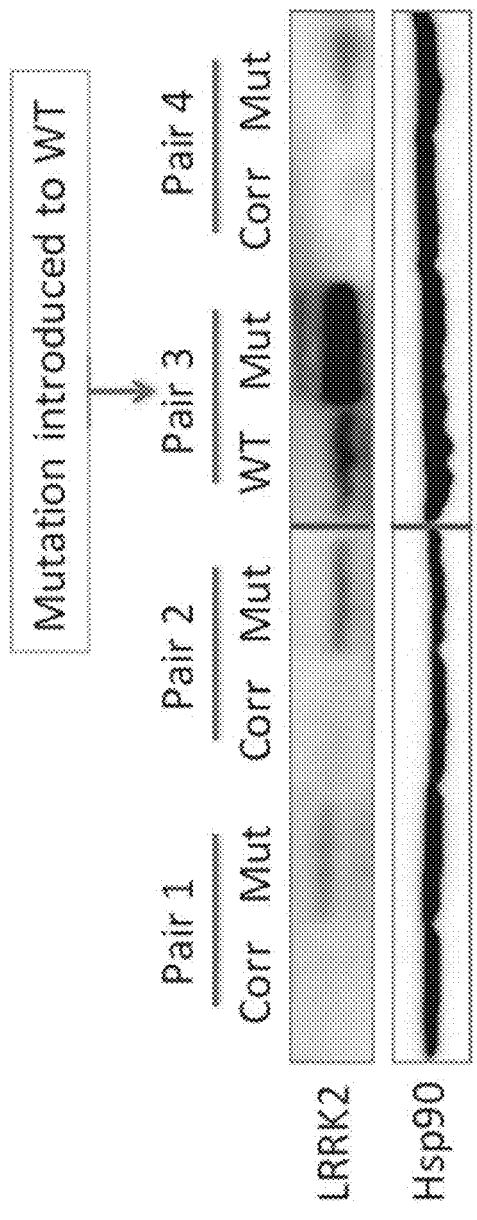

FIG. 10 shows LRRK2 levels compared between LRRK2$^{G2019S}$ dopaminergic neuron-enriched cultures and isogenic controls. Western blot Data is shown for induced pluripotent stem cell-derived lines derived from two patients (Pairs 1, 2 and 4, that include one biological replicate) and a human embryonic stem cell-derived line in which the G2019S mutation was introduced (Pair 3). (Reinhardt et al. 2013).

Figure 11A:
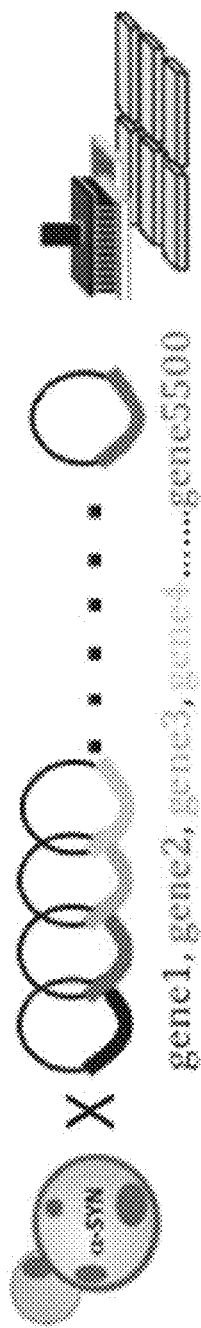
Figure 11A:
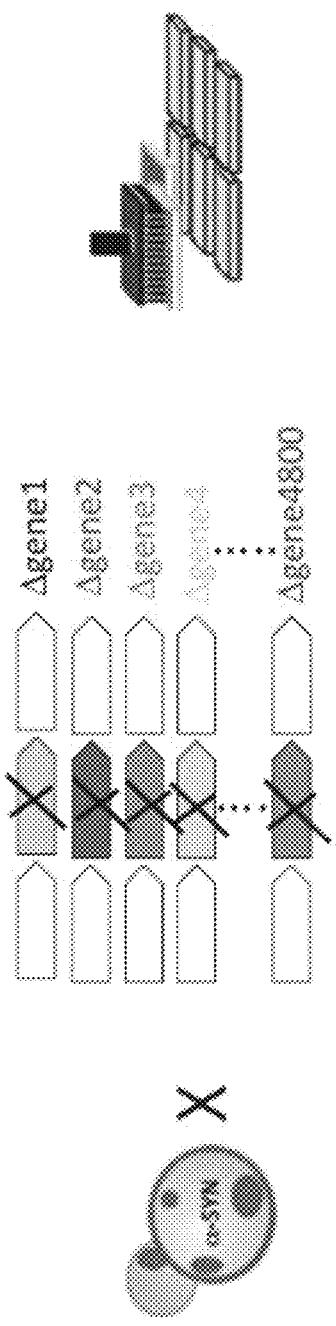
Figure 11A:
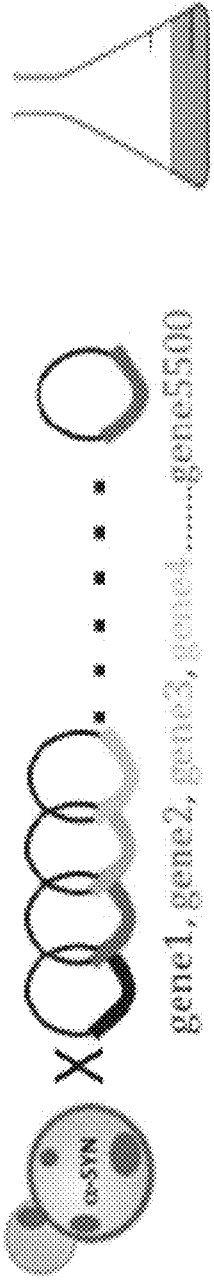
Figures 11B, 11C:
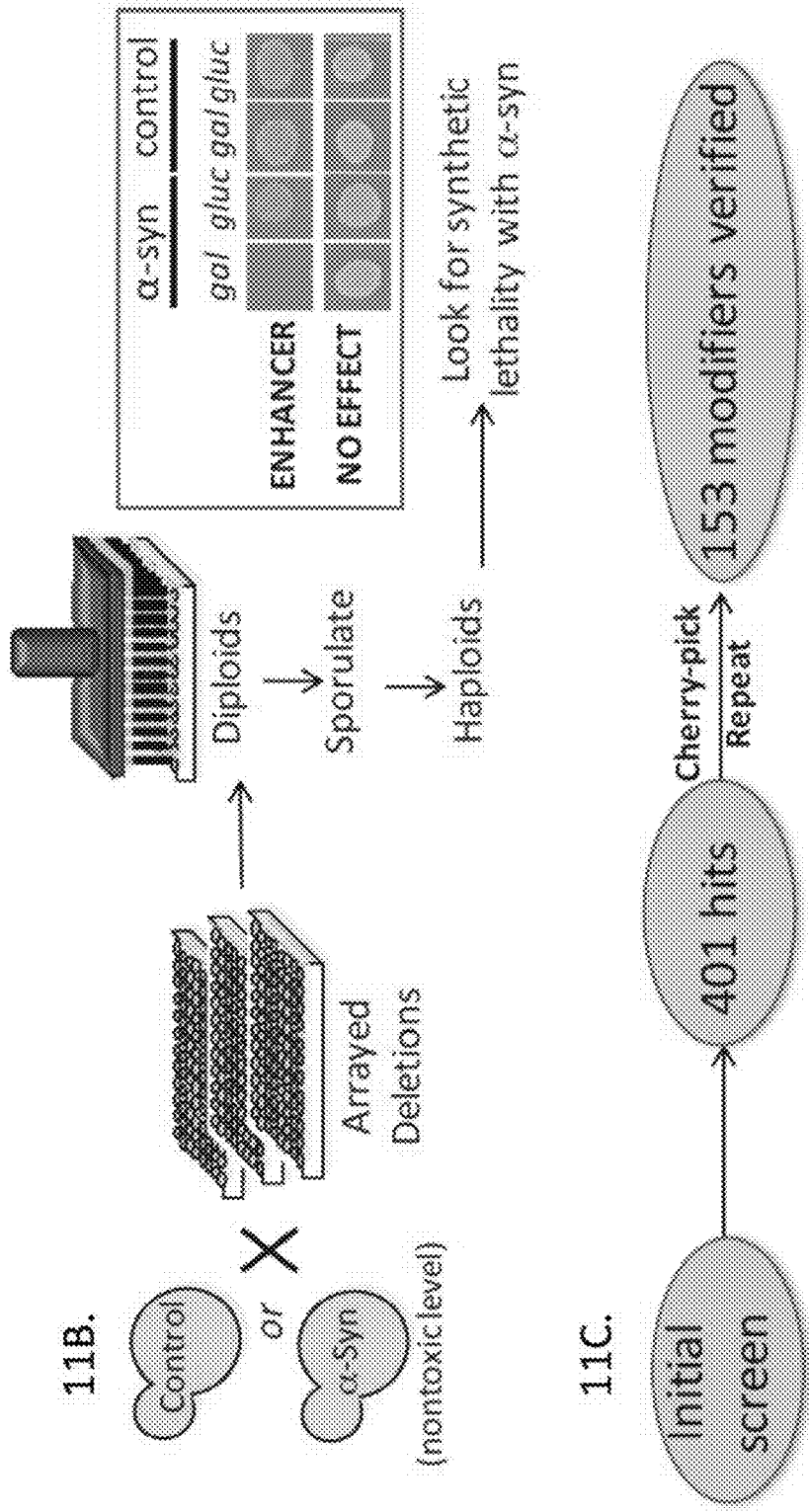

FIG. 11A-FIG. 11C show a schematic of Yeast α-syn deletion screening. FIG. 11A shows that control or α-syn strains were mated with the library of deletion strains. After mating, diploid strains were sporulated and haploid strains were chosen for toxicity assay. In the α-syn-expressing strain, α-syn was expressed at subtoxic levels. FIG. 11B shows initial screening identified over 400 hits that were synthetically lethal in the α-syn, but not the control, strain. FIG. 11C shows that these were cherry-picked and tested in at least two subsequent matings and 153 hits were validated.

Figure 12A:
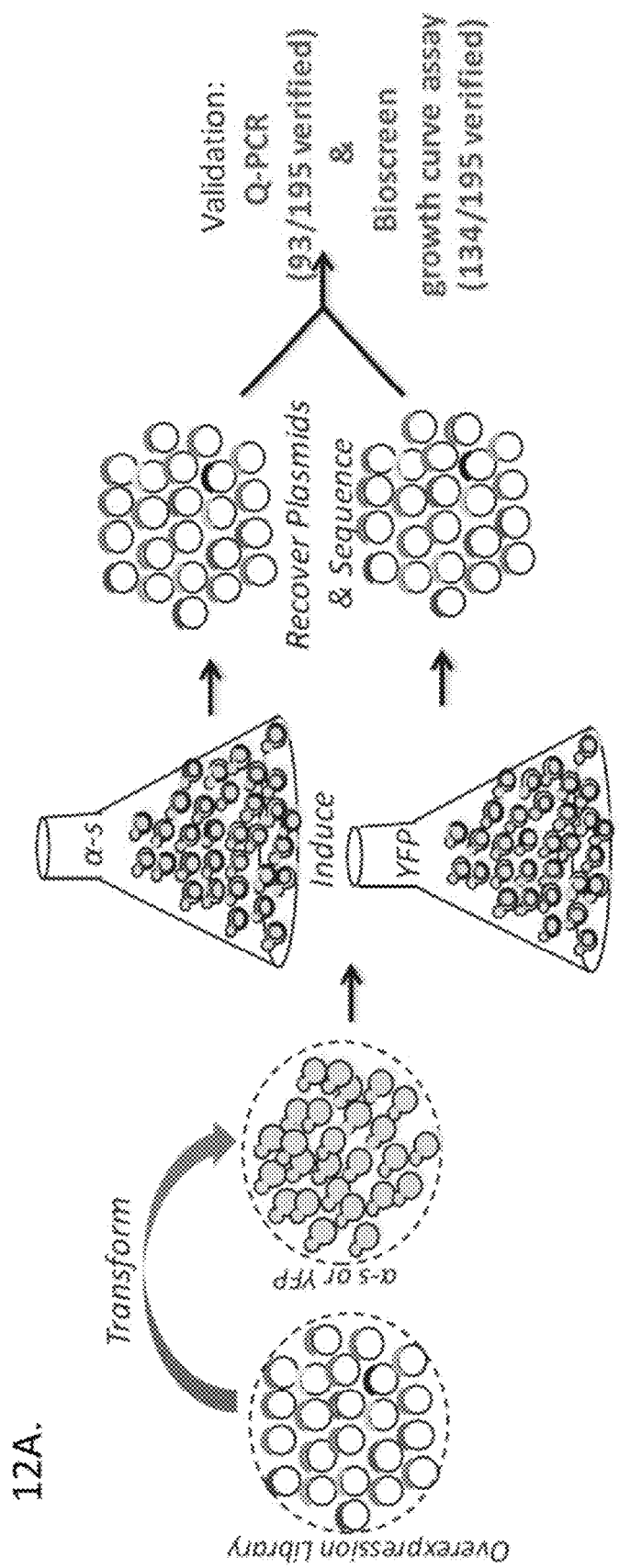
Figure 12B:
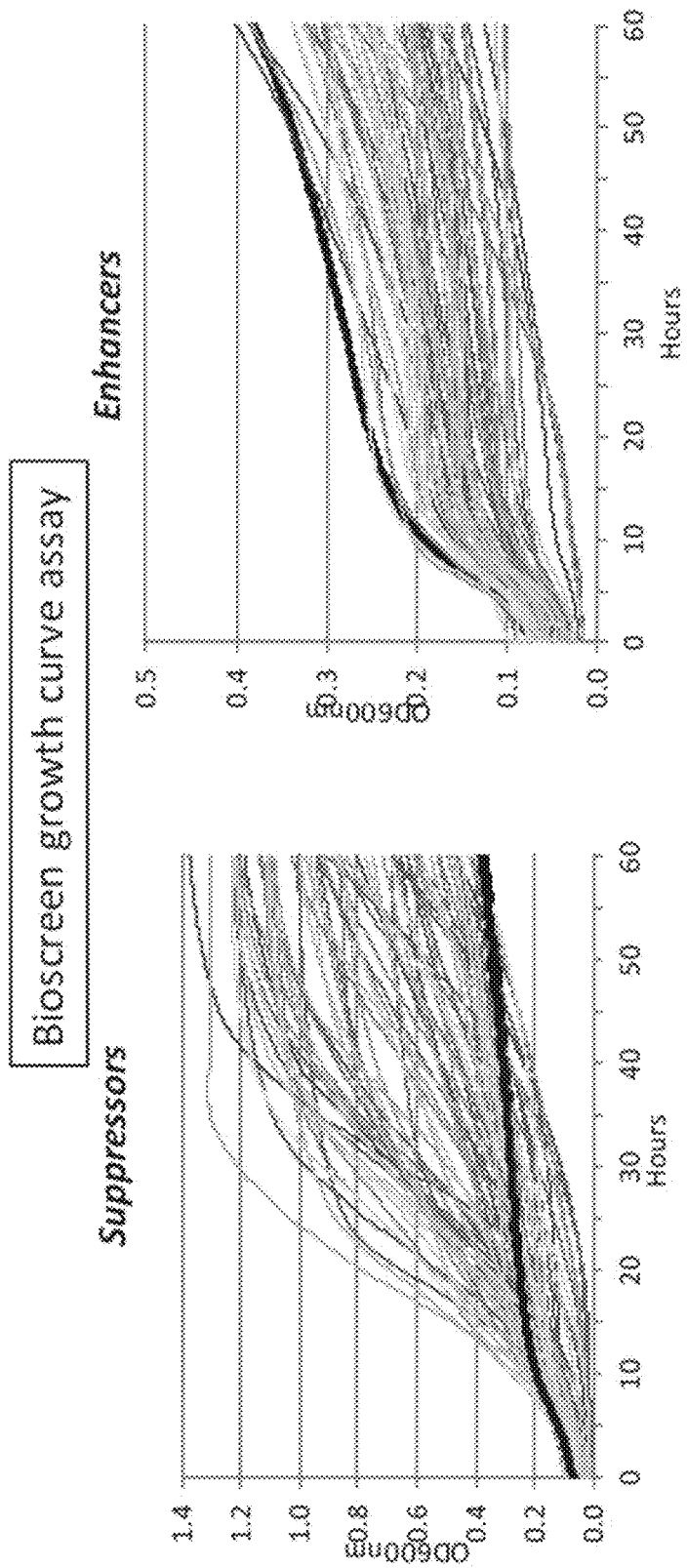

FIG. 12A-FIG. 12B show a schematic for yeast α-syn pooled screening. FIG. 12A shows that the pooled plasmids from the FLEXgene library were transformed en masse into either control YFP or α-syn-expressing yeast strains. After inducing YFP and α-syn, plasmids were recovered and sequenced. Those plasmids with increased reads were putative suppressors (conferring a survival benefit against α-syn toxicity), and those with decreased reads were putative enhancers (depleted under the selective pressure of α-syn toxicity). Those with nonspecific effects on YFP were excluded. Validation of the screen was performed by Q-PCR and Bioscreen growth curve assays. FIG. 12B shows that the dark black line represents the baseline α-syn toxicity. Modifiers that are above this baseline are so-called suppressors of toxicity (ie rescue); modifiers that below this baseline are so-called enhancers of toxicity (ie detrimental). There was excellent concordance between sequencing reads (195 hits), bioscreen (134/195 verified) and QPCR (93/195 verified) assays. All 134 modifiers validated by the bioscreen assay were considered true modifiers.

Figure 13:
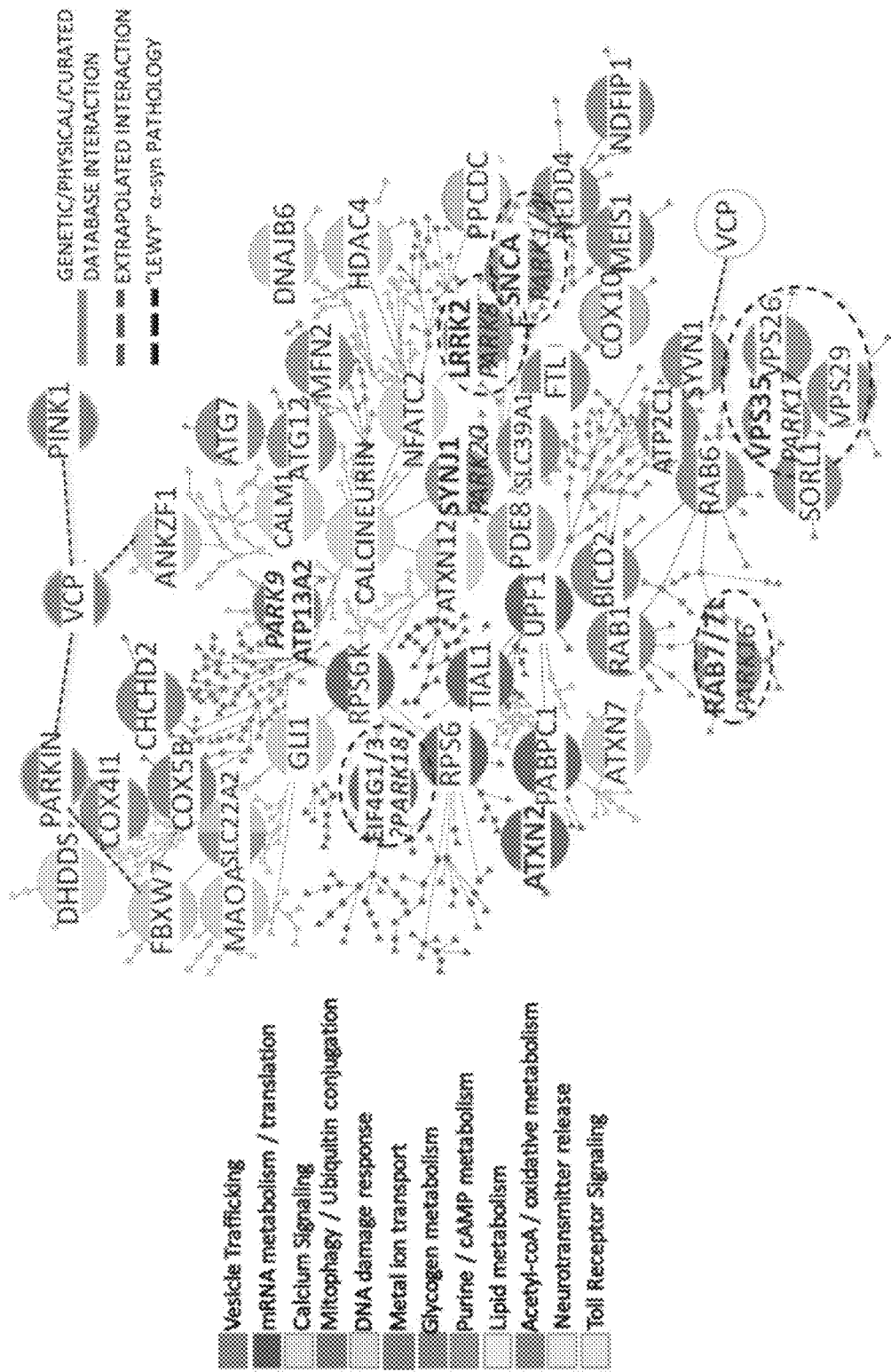

FIG. 13 shows a tractable "humanized" network of α-syn toxicity results when the SteinerNet Ensemble approach is applied to the 332 genetic modifiers of α-syn toxicity. Specific genes of interest are enlarged, including multiple neurodegeneration-related disease genes (see also Table S14).

Figures 14A, 14B:
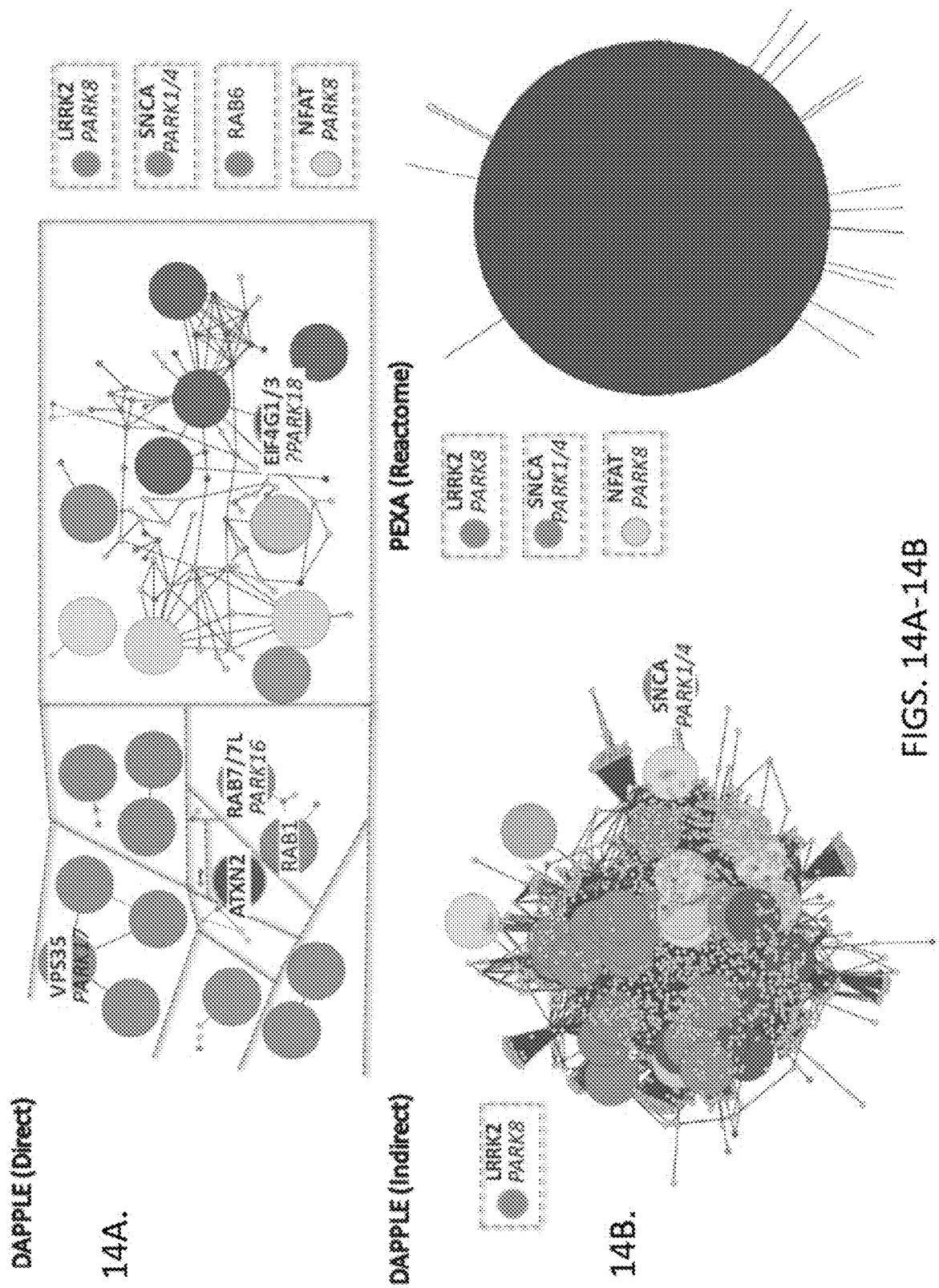

FIG. 14A-FIG. 14B show that DAPPLE and PEXA network tools create either fragmented or hyper-connected networks with our α-syn complete screening dataset, hindering biological interpretation and hypothesis generation.

DAPPLE (Rossin et al. 2011) and PEXA (Tu et al. 2009) are two network building algorithms that we considered alternatives to our PCSF-based method. Both methods take seed genes and identify subnetworks that span the seed genes and reveal possible functional interconnectedness of these genes. The first algorithm, DAPPLE, identifies significant direct and one-hop indirect edges in the human interactome to connect as many seed genes as possible (these are "direct" and "indirect" modes, respectively). The second algorithm, PEXA, utilizes existing pathway annotations, such as KEGG or Reactome, to cover seed genes. Merging and pruning are then applied to link connected components and remove hanging genes. We show in FIG. 9 and the Methods section that PCSF has superior performance to both DAPPLE and PEXA algorithms. Here, we compare these algorithms head to head using our experimental yeast screen data for α-syn toxicity (compare to FIG. 3C). FIG. 14A shows that in direct mode, DAPPLE connects genes with high-confidence interactions, while in the indirect mode DAPPLE uses single hidden genes to connect two seed genes. The sparse network is decomposed into 10 subnetworks. Key interactions are lost, including for LRRK2/synuclein, RAB6 and EIF4G1/ATAXIN-2, as indicated in the figure. FIG. 14B shows that for PEXA [Reactome] and DAPPLE in indirect mode, gigantic and untractable "hairballs" are produced. These clearly hinder generation of sensible biological hypotheses for this dataset. Tellingly, despite their enormity, key interactions, including with LRRK2, are lost with these methods.

Figure 15A:
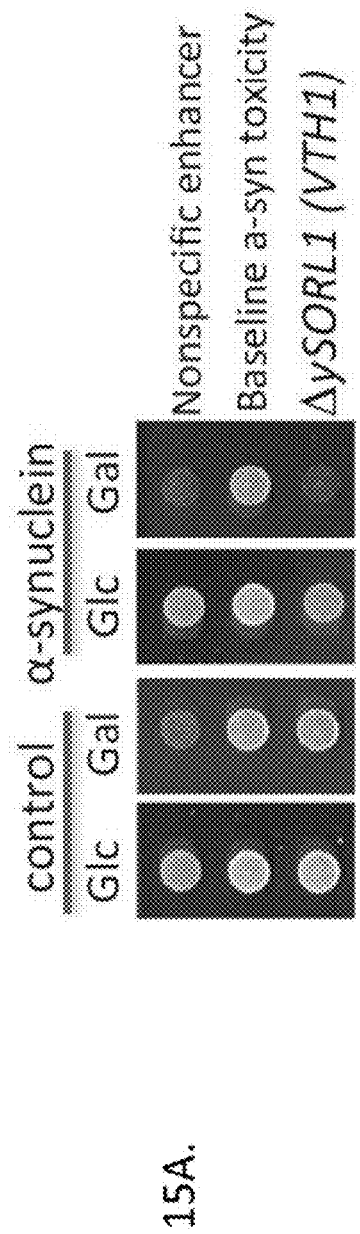
Figure 15B:
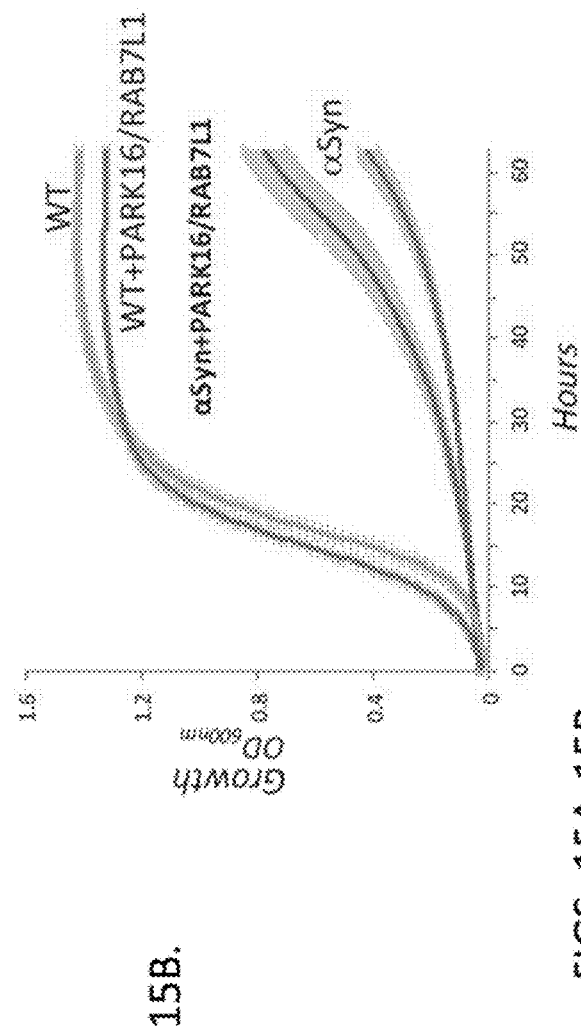

FIG. 15A-FIG. 15B show defects in endocytosis components enhance α-syn toxicity. FIG. 15A shows that deletion of VTH1 (ySORL1) enhances α-syn toxicity. All spot assays were performed 2-4 times (biological replicates). FIG. 15B is a Bioscreen growth curve analysis. Ypt7 (yRAB7L1) overexpression suppresses α-syn toxicity. This was repeated three times (biological replicates).

Figure 16:
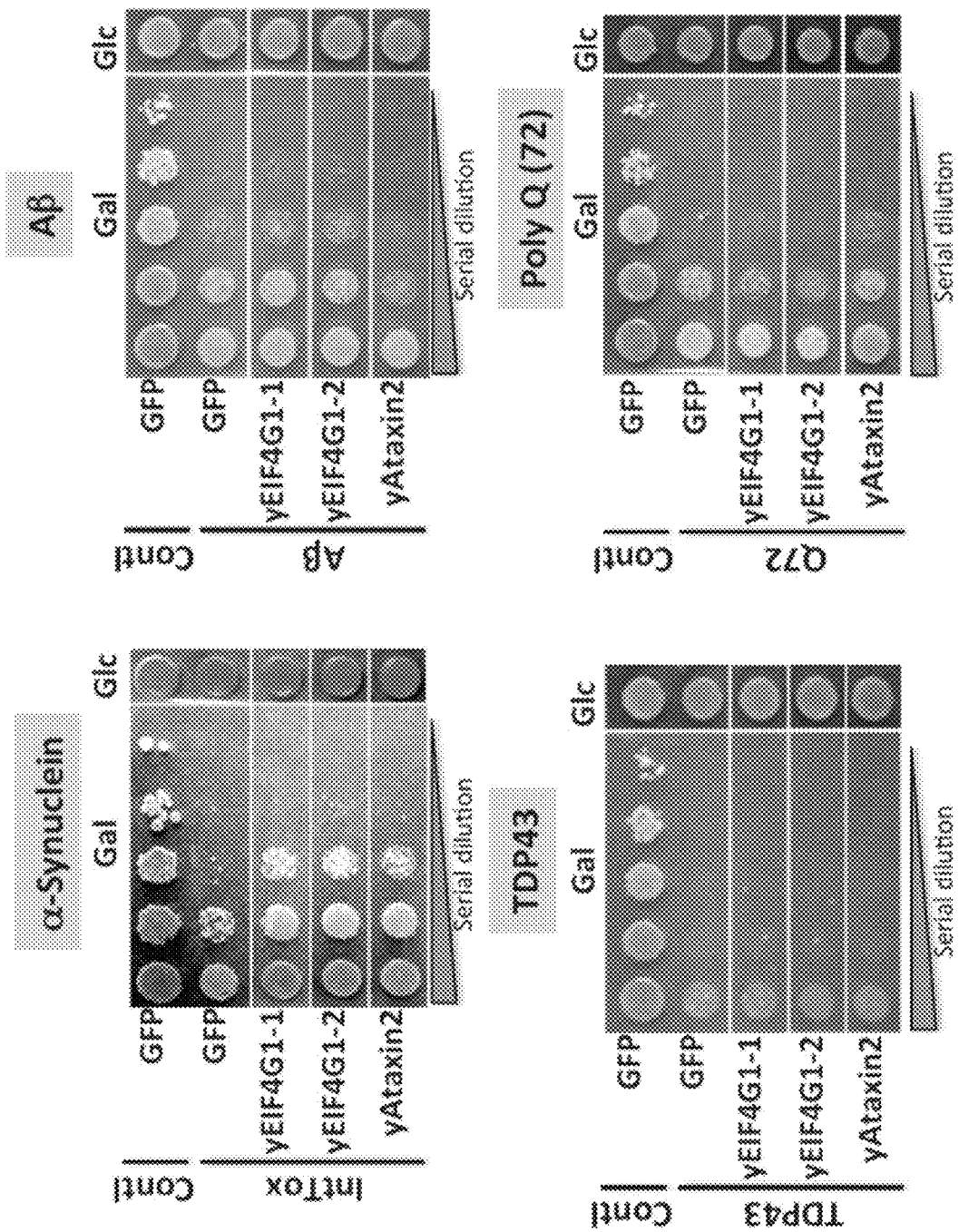

FIG. 16 shows that translation modifiers exhibit distinct genetic interaction pattern with different proteotoxic models. The spot assay demonstrates that yEIF4G1-1 (Tif4631), yEIF4G1-2 (Tif4632) and yAtaxin2 (Pbp1) do not suppress (that is, rescue from) AP, TDP-43 and polyglutamine (Huntingtin Exon 1-72Q) toxicity in yeast, with the exception of a mild growth-suppression effect of Pbp1 on HttEx1-72Q. In fact, yAtaxin2 enhances (that is, exacerbates) AP toxicity. Each spot assay shown in this figure is representative of three experiments (biological replicates).

Figure 17A:
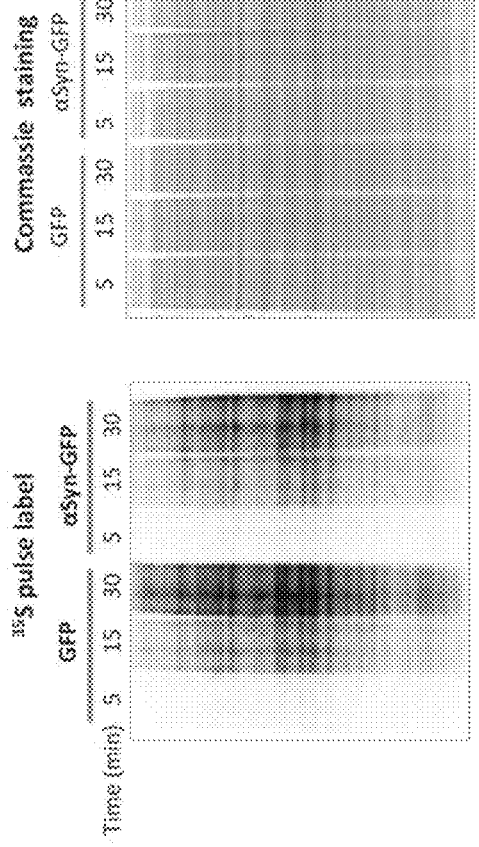
Figure 17B:
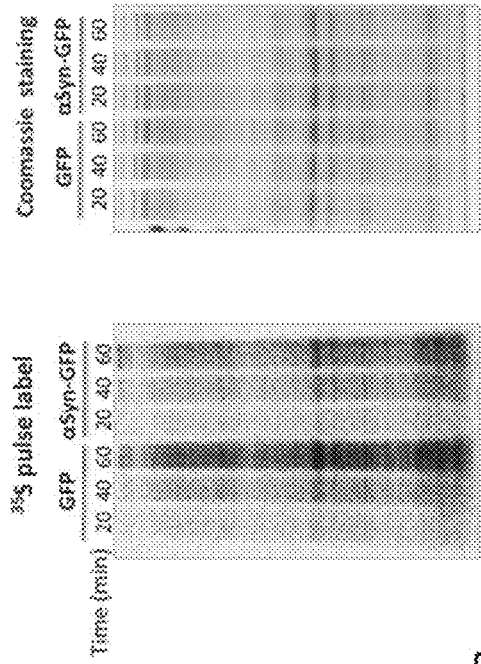
Figure 17C:
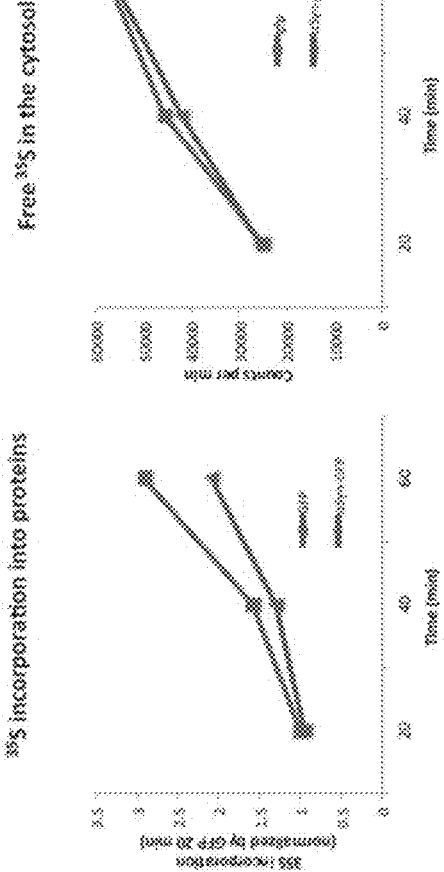
Figure 17D:
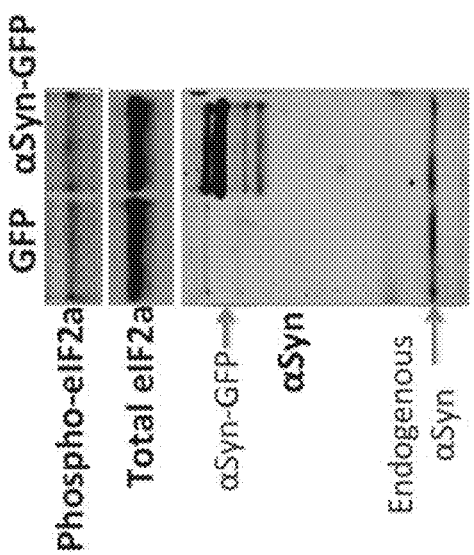

FIG. 17A-FIG. 17D show that a bulk protein translation defect is identified in α-syn-GFP overexpressing cells. FIG. 17A shows HEK cells stably expressing GFP or α-syn-GFP were subject to pulse labeling of $^{35}S$ cysteine and methionine at various durations (5, 15 and 30 min). Cells expressing α-syn-GFP showed a slower incorporation of $^{35}S$ cysteine and methionine. Coomassie staining shows the even loading of the protein samples (n=2 biological replicates). FIG. 17B shows rat primary cortical neurons expressing GFP or α-syn-GFP were pulse-labeled with $^{35}S$ cysteine and methionine for various durations. As with HEK cells, α-syn-GFP overexpression resulted in a reduced rate of $^{35}S$ cysteine and methionine incorporation (n=2 biological replicates). FIG. 17C shows that there was no difference in free cytosolic $^{35}S$ cysteine and methionine between GFP and α-syn-GFP expressing rat primary cortical neurons. Free cytosolic portion of $^{35}S$ cysteine and methionine was obtained by excluding TCA-precipitated intracellular proteins. FIG. 17D shows that phosphorylated eIF2A (p-eIF2A) was measured in rat primary cortical neurons overexpressing either GFP or α-syn GFP. There was no difference in the level of p-eIF2A between the conditions (n=1).

Figures 18A, 18B:
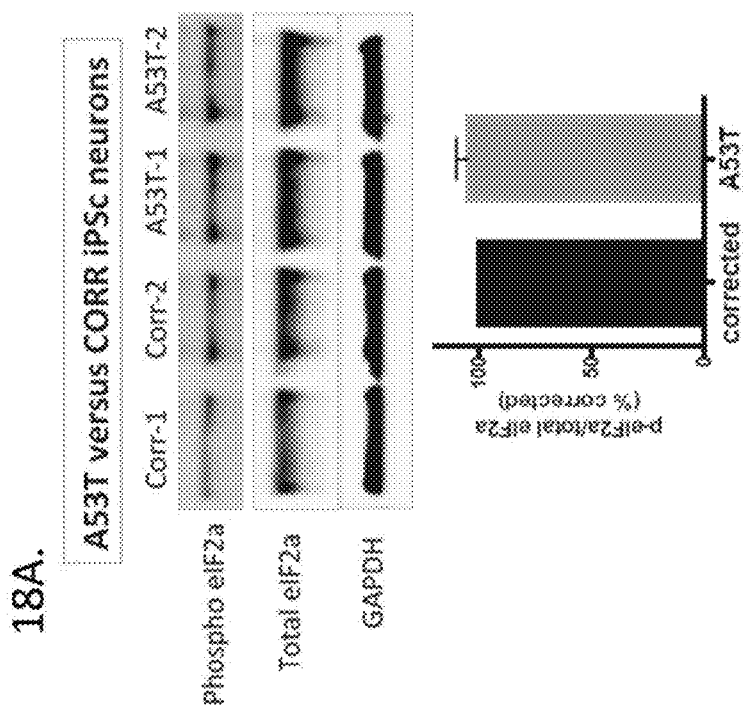

FIG. 18A-FIG. 18B show an absence of canonical unfolded protein response in α-syn$^{A53T}$ mutant neurons.

FIG. 18A shows phosphorylation of EIF2A (pEIF2A) is unchanged in α-syn$^{A53T}$ neurons compared to isogenic mutation-corrected controls at approx. 6 weeks. In this experiment, two subclones of α-syn$^{A53T}$ neurons were compared to 2 subclones of isogenic mutation-corrected controls.

FIG. 18B shows mapping of ribosome protected fragments (RPFs) indicating that the longer IRE1-spliced isoform 2 of the XBP1 transcript is not identified either in α-syn$^{A53T}$ (A53T) or mutation-corrected control (CORR) neurons at 12 weeks. Two clones—A53T-1 and CORR-1—are shown in the figure. RPFs for isoform 2 would have been identified in the region marked by the red box.

FIG. 19A-FIG. 19D show ribosome profiling in PD iPSc-derived neurons reveals perturbed translation of mRNA translation-associated transcripts that specifically relate to α-syn toxicity.

Figure 19A:
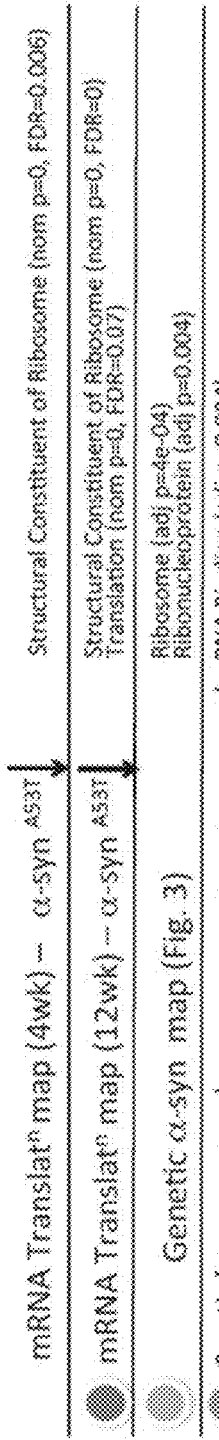

FIG. 19A shows that there is a highly significant decrement in translational efficiency of mRNA transcripts related to ribosomal components and other translation factors in mutant α-syn$^{A53T}$ patient-derived neurons compared to isogenic mutation-corrected controls at 4 weeks and 12 weeks. This specific group of genes is also enriched in the genetic map of α-syn toxicity (FIG. 3) as well as the spatial α-syn map presented in the accompanying manuscript that identifies RNA binding and translation factors in the immediate vicinity of or directly interacting with α-syn in neurons (Chung, Khurana et al. Cell Systems 2016). For ribosomal footprinting, gene set enrichment analysis (GSEA; available on the world-wide web at software.broadinstitute.org/gsea/index.jsp) nominal p-values and false discovery rate (FDR) indicated in the table. Enrichment analysis for genetic map is described in Table S12. Enrichment analysis for spatial map is described in the accompanying manuscript (Chung, Khurana et al. Cell Systems 2016).

Figure 19B:
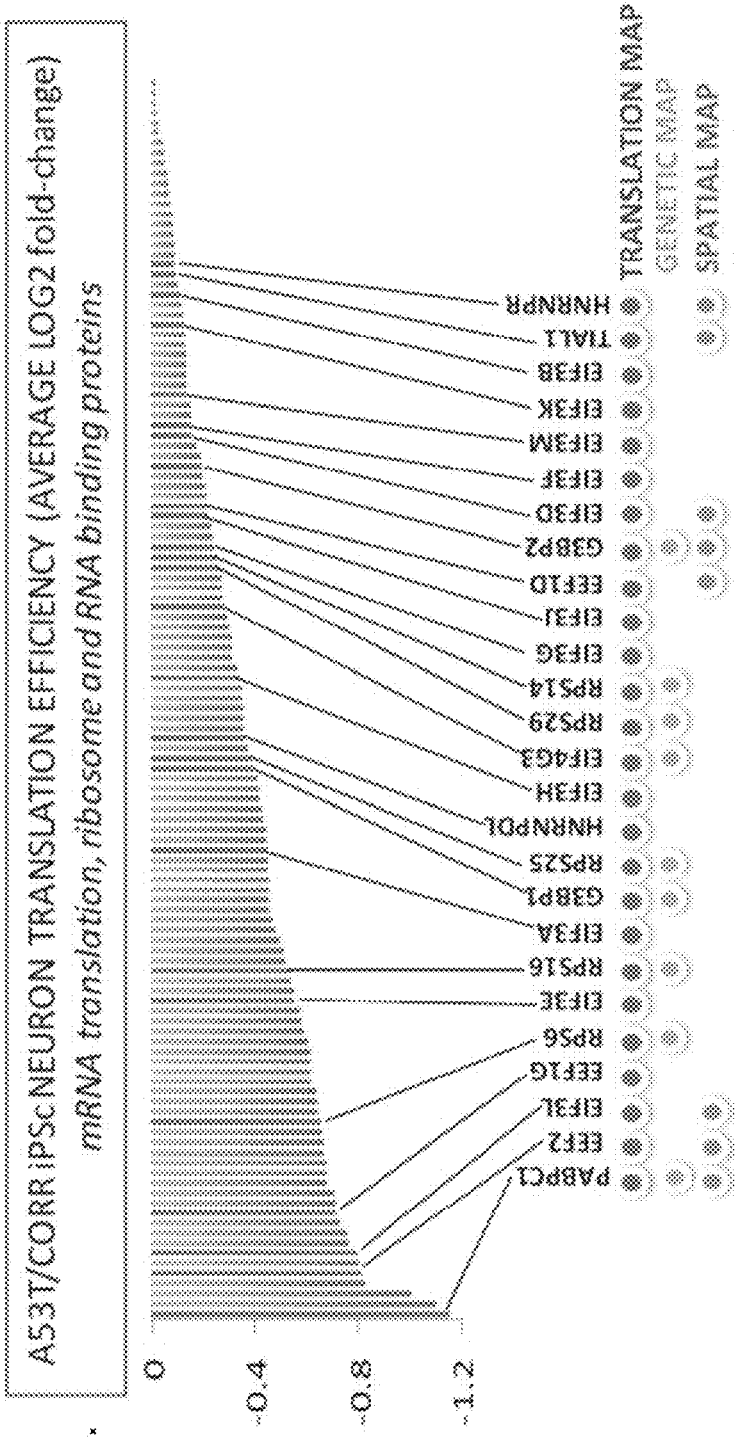
Figure 20:
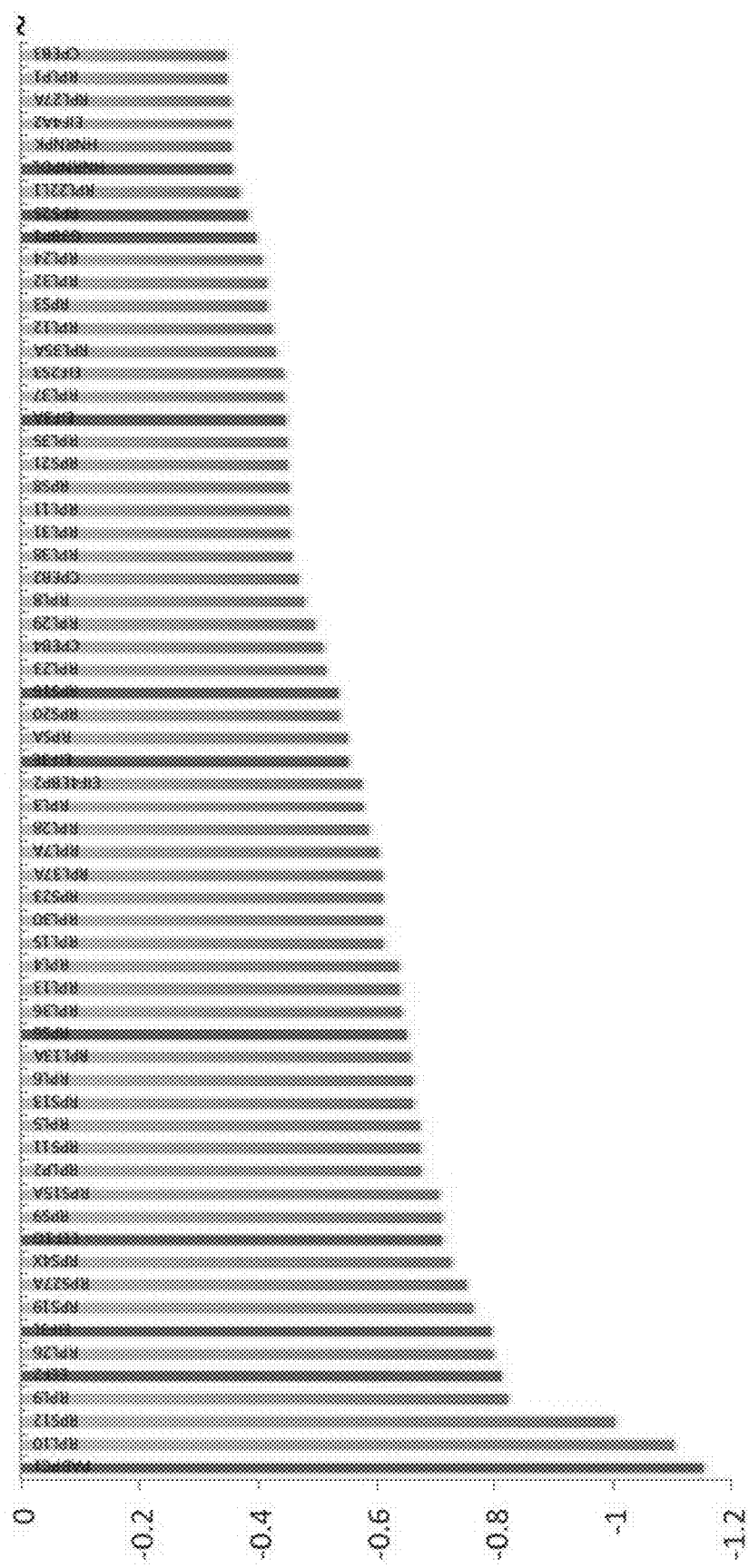
Figure 20:
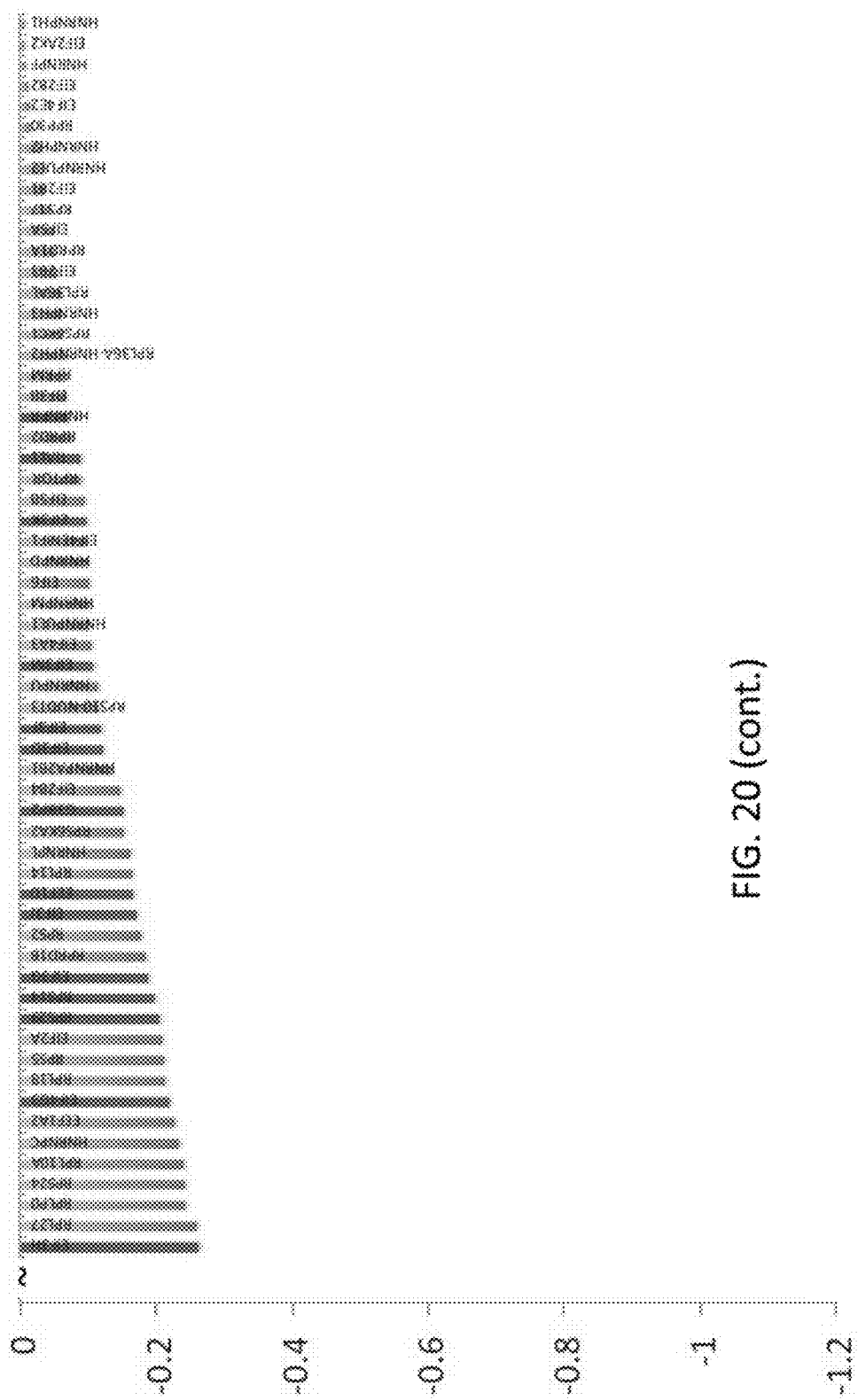

FIG. 19B shows mRNA transcripts related to mRNA translation that contribute to the decrement of the pathway as a whole (see FIG. 19A). The highlighted transcripts overlap with specific genes/proteins/protein complexes identified in the genetic (orange blue dots) and spatial (blue dots) α-syn maps. FIG. 20 shows the fully labeled plot.

Figures 19C, 19D:
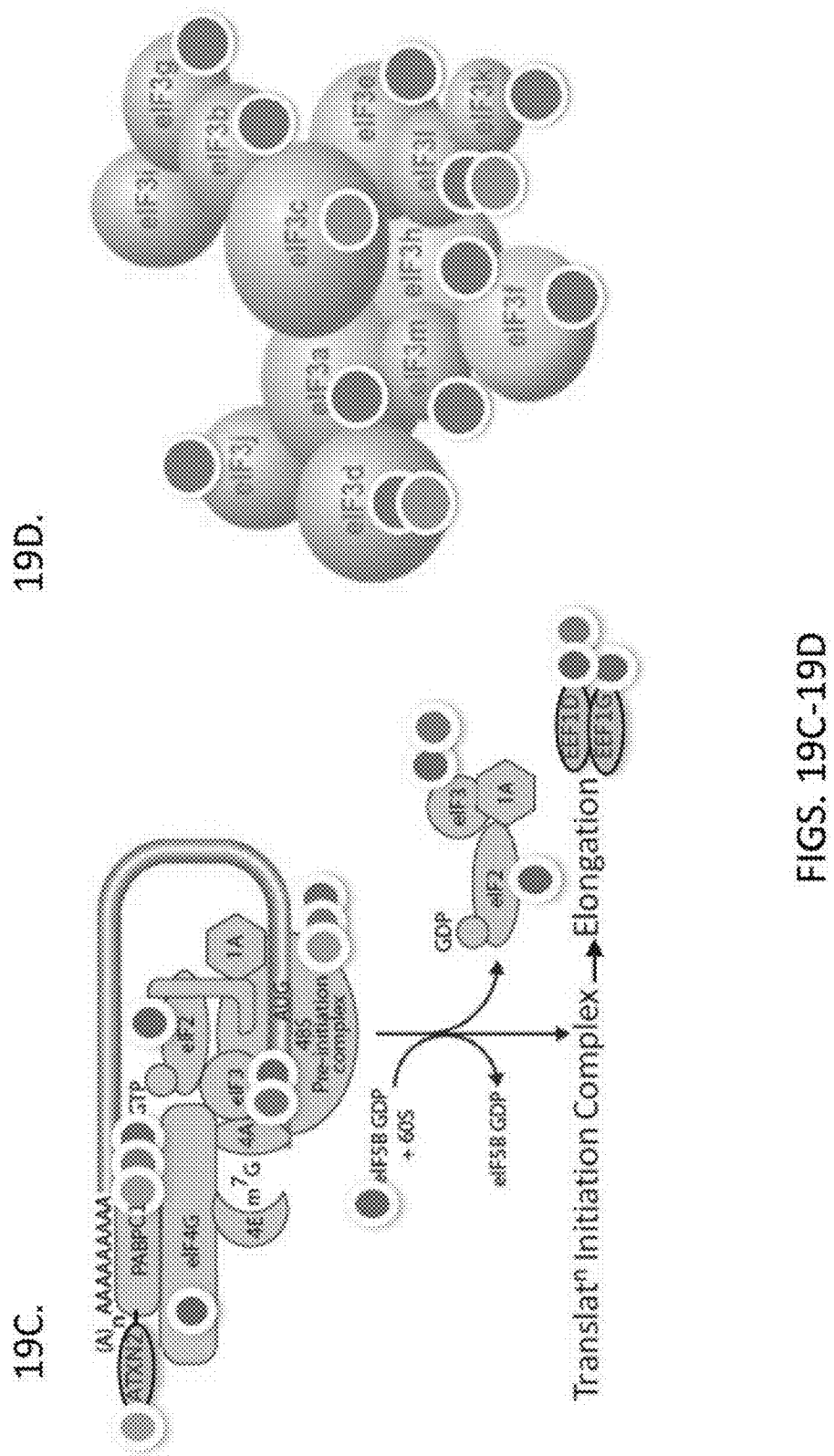

FIG. 19C-FIG. 19D show a schematic of translation initiation and elongation complexes (see FIG. 19A) and the eiF3 scaffold of the translation initiation complex (see FIG. 19B) as examples of pathways/complexes that emerge in orthogonal genetic (orange), spatial (blue) and translational (red) mapping from yeast to neurons.

FIG. 20 shows ribosome profiling in PD α-syn$^{A53T}$ patient-derived neurons (compared to mutation-corrected control neurons) reveals perturbed translation of mRNA translation-associated transcripts that specifically relate to α-syn toxicity. mRNA transcripts related to mRNA translation that contribute to the decrement of the pathway as a whole (see fully labeled plot of FIG. 19B).

Figure 21:
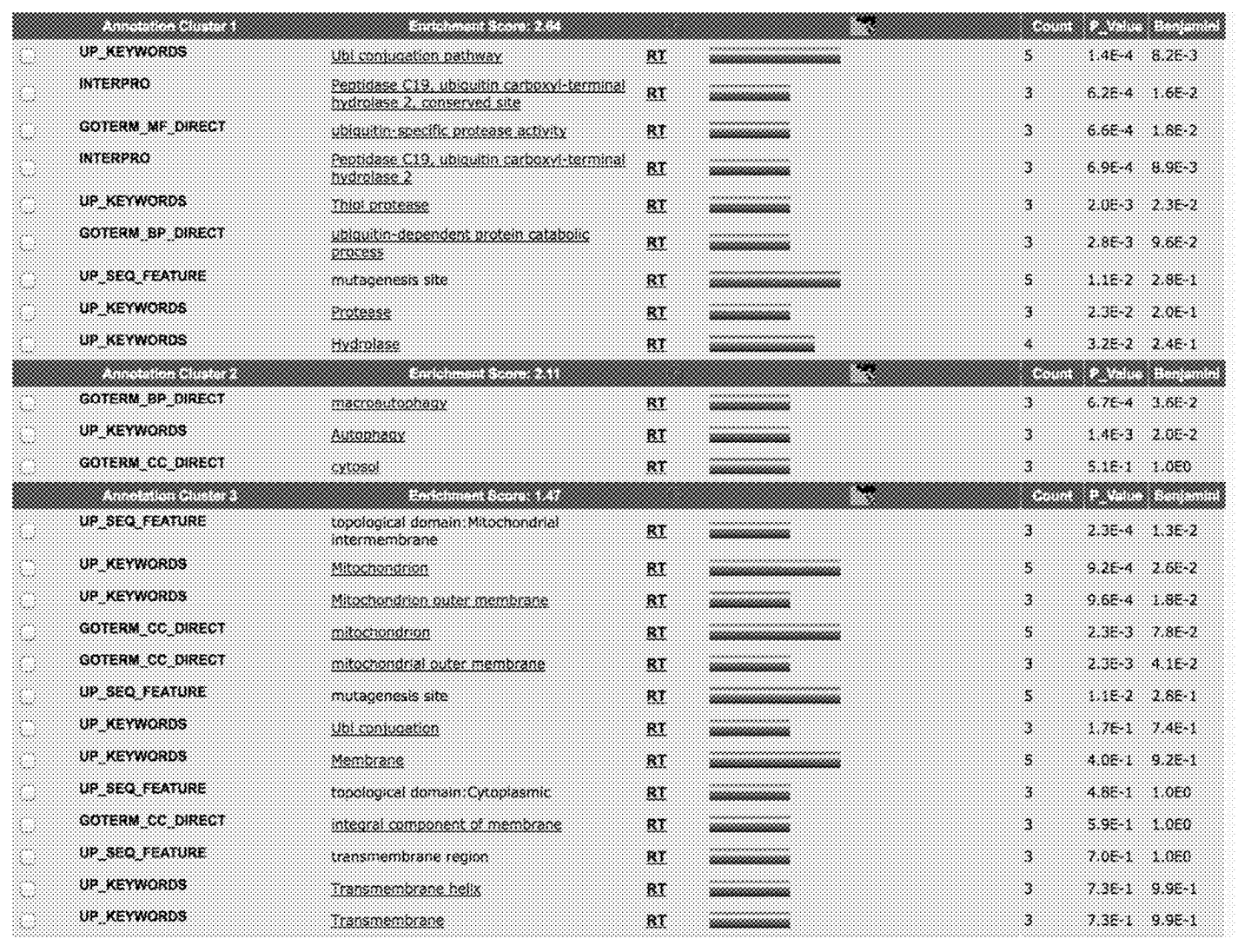

FIG. 21 shows enriched ontologies in humanized alpha-synuclein complete network. Related to Table S12.

DETAILED DESCRIPTION OF THE INVENTION

Augmented Modeling of a Physiologic or Pathologic Process

In some aspects, the invention is directed towards a method of modeling a physiologic or pathologic process in a first eukaryote (e.g., fungal, protozoa, insect, plant, vertebrate), comprising (a) providing a set of candidate eukaryotic genes identified in a second eukaryote (e.g., fungal, protozoa, insect, plant, vertebrate) with an analogue of the physiologic or pathologic process in the first eukaryote; (b) providing interactions between eukaryotic genes of the first eukaryote comprising the candidate eukaryotic genes of step (a); (c) providing interactions between genes in the second eukaryote; (d) determining a set of genes in the first eukaryote homologous to the set of candidate eukaryotic genes; and (e) creating a model of the physiologic or pathologic process in the first eukaryote by augmenting interactions between the set of genes in the first eukaryote obtained in step (d) with predicted gene interactions based on the interactions of step (b) from the second eukaryote. In some embodiments, the first eukaryote is a mammalian cell (e.g., a human cell, a mouse cell, a rat cell, a monkey cell). In some embodiments, the second eukaryote is a yeast cell.

The phrase "physiologic or pathologic process" as used herein refers to any process (e.g., any cellular process involving more than one gene) or pathologic process. The physiologic or pathologic process may be any set of operations or molecular events, with a defined beginning and end, pertinent to the functioning of integrated living units, e.g., cells, tissues, organs, and organisms. Typically it is a series of events accomplished by one or more ordered assemblies of molecular functions. Typically a physiologic or pathologic process encompasses or is carried out via one or more biological pathways. A "biological pathway" may be any series of actions and/or interactions by and among molecules in a cell that leads to a certain product or a change in a cell. In some embodiments, the physiologic or pathologic process is a cellular process. Physiologic or pathologic processes include, for example, processes pertaining to cell signaling, metabolism, genetic information processing (e.g., transcription, translation, RNA transport, RNA degradation; protein folding, sorting, degradation, post-translational modification; DNA replication and repair), environmental information processing (e.g., membrane transport, signal transduction), and cellular processes (e.g., cell cycle, endocytosis, vesicle trafficking), etc. It will be appreciated that the various afore-mentioned cellular processes encompass multiple specific pathways). In some embodiments, the physiologic or pathologic process is a cell cycle, cell division or cell growth process. In some embodiments, the process is associated with a disease or disorder. The disease or disorder is not limited.

In some embodiments, the disorder is cancer. The term "cancer" as used herein is defined as a hyperproliferation of cells whose unique trait—loss of normal controls—results in unregulated growth, lack of differentiation, local tissue invasion, and metastasis. With respect to the inventive methods, the cancer can be any cancer, including any of acute lymphocytic cancer, acute myeloid leukemia, alveolar rhabdomyosarcoma, bladder cancer, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, Hodgkin lymphoma, hypopharynx cancer, kidney cancer, larynx cancer, leukemia, liquid tumors, liver cancer, lung cancer, lymphoma, malignant mesothelioma, mastocytoma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, stomach cancer, testicular cancer, thyroid cancer, ureter cancer, and urinary bladder cancer. As used herein, the term "tumor" refers to an abnormal growth of cells or tissues of the malignant type, unless otherwise specifically indicated and does not include a benign type tissue.

In some embodiments, the disorder is a genetic disorder. In some embodiments, the disorder is a monogenic disorder. In some embodiments, the disorder is a multigenic disorder. In some embodiments, the disorder is a disorder associated with one or more SNPs. Exemplary disorders associated with one or more SNPs include a complex disease described in U.S. Pat. No. 7,627,436, Alzheimer's disease as described in PCT International Application Publication No. WO/2009/112882, inflammatory diseases as described in U.S. Patent Application Publication No. 2011/0039918, polycystic ovary syndrome as described in U.S. Patent Application Publication No. 2012/0309642, cardiovascular disease as described in U.S. Pat. No. 7,732,139, Huntington's disease as described in U.S. Patent Application Publication No. 2012/0136039, thromboembolic disease as described in European Patent Application Publication No. EP2535424, neurovascular diseases as described in PCT International Application Publication No. WO/2012/001613, psychosis as described in U.S. Patent Application Publication No. 2010/0292211, multiple sclerosis as described in U.S. Patent Application Publication No. 2011/0319288, schizophrenia, schizoaffective disorder, and bipolar disorder as described in PCT International Application Publication No. WO/2006/023719A2, bipolar disorder and other ailments as described in U.S. Patent Application Publication No. U.S. 2011/0104674, colorectal cancer as described in PCT International Application Publication No. WO/2006/104370A1, a disorder associated with a SNP adjacent to the AKT1 gene locus as described in U.S. Patent Application Publication No. U.S. 2006/0204969, an eating disorder as described in PCT International Application Publication No. WO/2003/012143A1, autoimmune disease as described in U.S. Patent Application Publication No. U.S. 2007/0269827, fibrostenosing disease in patients with Crohn's disease as described in U.S. Pat. No. 7,790,370, and Parkinson's disease as described in U.S. Pat. No. 8,187,811, each of which is incorporated herein by reference in its entirety.

In some embodiments, the disorder is a chronic infectious disease. A "chronic infectious disease" is a disease caused by an infectious agent wherein the infection has persisted. Such a disease may include hepatitis (A, B, or C), herpes virus (e.g., VZV, HSV-1, HSV-6, HSV-II, CMV, and EBV), and HIV/AIDS. Non-viral examples may include chronic fungal diseases such as Aspergillosis, Candidiasis, Coccidioidomycosis, and diseases associated with *Cryptococcus* and Histoplasmosis. None limiting examples of chronic bacterial infectious agents may be *Chlamydia pneumoniae, Listeria monocytogenes*, and *Mycobacterium tuberculosis*. In some embodiments, the disorder is human immunodeficiency virus (HIV) infection. In some embodiments, the disorder is acquired immunodeficiency syndrome (AIDS).

In some embodiments, the disorder is an autoimmune disorder. The term "autoimmune disease" refers to any disease or disorder in which the subject mounts a destructive immune response against its own tissues. Autoimmune disorders can affect almost every organ system in the subject (e.g., human), including, but not limited to, diseases of the nervous, gastrointestinal, and endocrine systems, as well as skin and other connective tissues, eyes, blood and blood vessels. Examples of autoimmune diseases include, but are not limited to Hashimoto's thyroiditis, Systemic lupus erythematosus, Sjogren's syndrome, Graves' disease, Scleroderma, Rheumatoid arthritis, Multiple sclerosis, Myasthenia gravis and Diabetes.

In some embodiments, the disorder is graft versus host disease (GVHD).

In some embodiments, the physiologic or pathologic process is a neurological disease (e.g., neurodegenerative disease) or disorder. In some embodiments, the neurological disease is Alzheimer's disease, Parkinson's disease, Huntington's disease, or ALS, lysosomal storage diseases, multiple sclerosis, or a spinal cord injury. Neurodegenerative diseases encompass a variety of disorders that involve progressive loss of structure and/or function of neurons in affected regions of the nervous system, often accompanied by neuronal loss. In some neurodegenerative diseases, a human protein aggregates (i.e., proteinopathy) or an RNA aggregates and/or there is a detrimental gain of function mutation in such a protein or RNA or in which there is increased expression of the protein or RNA (e.g., due to the patient having one or more extra copies of the gene). Examples of such proteins and neurodegenerative diseases in which they aggregate and/or are mutated or overexpressed include alpha-synuclein (Parkinson's disease and other disorders characterized by parkinsonism), amyloid beta (Alzheimer's disease), polyglutamine-expanded genes (Huntington's disease, ataxias). A eukaryote (e.g., yeast) analog for such disease can be generated by overexpression of the relevant wild type or mutant human protein in the eukaryote. Such proteins when overexpressed can exert toxic effects. The toxicity can be exploited to identify compounds that alleviate the toxic effects and genes that, when overexpressed or deleted, alleviate the toxic effects. An animal (e.g., human) nervous system cell model for such diseases can be produced by generating induced nervous system cells from patients suffering from the disease or who have a genotype associated with the disease or by engineered inducible overexpression in nervous system cells derived from pluripotent cells or derived by transdifferentiation from non-neuronal cells or derived from neural precursors.

In some neurodegenerative diseases there is a loss of function of a protein (e.g., due to mutation). Eukaryotic analogs for such diseases can be created by inducing loss of function of a homolog of the protein (e.g., with a mutation). An animal (e.g., human) nervous system cell model for such diseases can be produced by generating induced animal nervous system cells from patients suffering from the disease or who have a genotype associated with the disease or by engineering a gene targeted mutation or deletion in the gene or otherwise disabling the gene in nervous system cells derived from pluripotent cells or derived by transdifferentiation from non-neuronal cells or derived from neural precursors.

In some embodiments, the physiologic or pathologic process is a neurodegenerative disease. In some embodiments, the physiologic or pathologic process is a neurodegenerative proteinopathy. In some embodiments, the physiologic or pathologic process is a synucleinopathy, Alzheimer's disease, frontotemporal degeneration, a spinocerebellar ataxias, Huntington's disease, or amyotrophic lateral sclerosis. In some embodiments, the synucleinopathy is Parkinson's disease.

The term "an analogue of the physiologic or pathologic process" is intended to mean a process in a second eukaryote sharing some similarities with a process in a first eukaryote. The similarities may be genotypical or phenotypical. In some embodiments, the analogue may be created by introducing a gene involved in the physiologic or pathologic process in the first eukaryote into the second eukaryote. The expression of the gene or activity of the gene product may be varied to investigate different aspects of the disease. In some embodiments, the analogue may be created by modulating the expression of a gene or activity of a gene product in the second eukaryote that is homologous to a gene involved in the physiologic or pathologic process in the first eukaryote. The involvement of the gene or gene product in the physiologic or pathologic process or analog of the physiologic or pathologic process is not limited. In some embodiments, the gene or gene product is part of a network associated with the physiologic or pathologic process. A network is a set of genes and/or proteins characterized in that each gene or protein interacts with at least one other gene or protein of the set. Interact may be a physical interaction (e.g., binding) or a genetic interaction (e.g., causing a modulation of expression).

As use herein, interactions between eukaryotic (e.g., yeast) genes refers genetic interactions and/or if they encode gene products (protein or RNA) that physically interact. The interactions may be represented as a graph, in which genes that interact are connected by lines (edges). The lines may or may not encode information regarding the nature of the interaction and/or the nature of the interactants. Such information may, for example, be encoded in the form of arrows indicating the way in which one gene affects a gene with which it interacts (e.g., which gene is the effector), or by features of the lines such as colors, width, or pattern. A "node" is a gene or protein that interacts with at least two other genes or proteins in a network. Each gene in a network represents a "node". Genetic interactions encompass any of the various ways in which a first gene or its encoded gene product(s) can affect a second gene or its encoded gene product(s). The effects of a gene are often accomplished by a gene product encoded by the gene, typically a protein, and such effects are exerted on one or more gene products of another gene or genes. Genetic interactions encompass any of the various ways in which the level of expression or activity of a gene product of a first gene can affect the level of expression or activity of a gene product of a second gene or can affect (e.g., suppress or enhance) the phenotypic manifestations of the gene product of the second gene. "Expression or activity of a gene" should be understood as encompassing the expression or activity of a gene product encoded by the gene. Similarly an "effect on the expression or activity of a gene" typically refers to an effect on the expression or activity of gene product of the gene rather than on the gene itself. Examples include, e.g., enhancing or suppressing expression, enhancing or suppressing phenotypic effect, synthetic growth defect, synthetic rescue, synthetic lethality, etc. In some embodiments, the interactions between eukaryotic genes are obtained from publicly available databases (e.g., curated databases). In some embodiments, interactions are obtained from deletion or overexpression screenings (e.g., genome wide screenings). Methods of screening are known in the art. See, for example, US 20110300533. In some embodiments, interactions may be obtained from a combination of publicly available databases and screenings. In some embodiments, interactions may be obtained from only a specific subset of cell types. For instance, in some embodiments, only interactions known in human cells located in neurological tissue (e.g., brain tissue) may be used.

Homology between genes in a first eukaryote (e.g., human) and genes in a second eukaryote (e.g., yeast) may be by any method available in the art. In some embodiments, all pairs of first eukaryote genes (e.g., human) and second eukaryote genes (e.g., yeast) are compared. In some aspects, sequence similarity may be used. Sequence similarity may be obtained by, for example, hamming distance, sequence alignment, BLAST, FASTA, SSEARCH, GGSEARCH, GLSEARCH, FASTM/S/F, NCBI BLAST, WU-BLAST, PSI-BLAST and any combination thereof. Sequence similarity may be obtained with publicly available tools such as BLAST and DIOPT. See Hu et al., 2011. In some embodiments, NCBI protein BLAST with the BLOSUM62 substitution matrix may be used. See Altschul et al., 1990; 1997. In some embodiments, an E-value threshold may be used to determine significance of the similarities. In some embodiments, the E-value threshold=1E-5 is used. In some embodiments, DIOPT (GTEx Consortium, 2013; Hu et al., 2011; Reinhardt et al., 2013; Soding et al., 2005), an integrative ortholog prediction webserver, may be used to predict human orthologs for yeast proteins.

In some embodiments, homology between genes in a first eukaryote (e.g., human) and genes in a second eukaryote (e.g., yeast) may be assessed by assessing evolutionary and/or structural similarity. Evolutionary and/or structural similarity may be determined by any method known in the art. In some embodiments, multiple sequence alignments are created and a remote evolutionary signature is determined. In some embodiments, PSI-BLAST is used to construct a multiple sequence alignment and build a hidden Markov model to encode a remote evolutionary signature. In some embodiments, HHpred (Kriks et al., 2011; Robinson and Oshlack, 2010; Schondorf et al., 2014; Riding et al., 2005; Voevodski et al., 2009) is used with profile hidden Markov models and secondary structure annotations as input, to compare pairs (e.g., all pairs) of first eukaryote genes (e.g., human) and second eukaryote genes (e.g., yeast). In some embodiments, an E-value threshold may be used to determine significance of the similarities. In some embodiments, the E-value threshold=1E-5 is used.

In some embodiments, homology between genes in a first eukaryote (e.g., human) and genes in a second eukaryote (e.g., yeast) may be assessed by molecular interaction similarity (e.g., network topology). A network topology (i.e., Diffusion Component Analysis; DCA) approach attempts to capture functionally-related modules at the protein level, so that each node can be represented with a low-dimensional vector, instead of a single score, that captures homologous proteins in the network, along with conserved patterns of interactions. In some embodiments, a straightforward PageRank-like approach (Cho et al., 2015.; Tuncbag et al., 2016; Voevodski et al., 2009) is used to compute each node's vector. In some embodiments, the dimensionality of the vectors is reduced using sophisticated machine learning techniques. In some embodiments, this approach can reduce noise and be better able to extract topological network information such as functional similarity (Bailly-Bechet et al., 2011; Cho et al., 2015). In some embodiments, network topology is determined by a method called Multi-Network Topology for Functional Analysis of Genes (Mashup) (Cho, H. et al 2016).

In some embodiments, the network topology of both eukaryotes (e.g., human and yeast) as well as the sequence/structural similarity between them are compared to determine homology. In some aspects, sequence and structure similarity scores are converted to a probability distribution, and feature vectors of all pairs of nodes, including the sparse vector representations ones, are jointly computed by minimizing the Kullbeck-Leibler (KL) divergence between the relevance vectors and the parameterized multinomial distributions.

In some embodiments, inferred homology may be used to augment interactions between genes in a first eukaryote (e.g., human) based on the interactions of genes in a second eukaryote (e.g., yeast). In some embodiments, an inferred interaction may be added to the network of the first eukaryote (e.g., human) if an interaction is present in a homologous pair of genes in the second eukaryote (e.g., yeast). In some embodiments, an inferred interaction is added only at a certain threshold of homology between the pair of genes in the first eukaryote and the pair of genes in the second eukaryote. In some embodiments, the threshold is set so that the density of interactions in the first eukaryote (e.g., human) are similar to the density of interactions in the second eukaryote (e.g., yeast).

In some embodiments, creating a model of the physiologic or pathologic process in a first eukaryote (e.g., human) by augmenting interactions from a second eukaryote comprising using the prize-collecting Steiner forest (PCSF) algorithm (Cho et al., 2015; Tuncbag et al., 2013; 2016.; Voevodski et al., 2009) to connect gene or protein nodes through genetic interactions, physical interactions and annotated pathways from one or more curated databases while minimizing costs to obtain a network. In some embodiments, the objective function parameter for the PCSF algorithm is determined with the Prize-collecting Steiner Tree problem (PCST) and a known message-passing-algorithm. See Bailly-Bechet et al., 2011; Cho et al., 2015.

In some embodiments, parameters $\beta$, $\omega$ and $\mu$ of the PCSF algorithm are each varied within set upper and lower bounds to create multiple networks of gene or protein nodes. In some embodiments, the upper and lower bounds are set to contain a sufficient number of predicted proteins (which, in some embodiments, is half of the number of input prize genes) and/or set so the network solution does not introduce hub nodes with more than 1000 neighbors in the input network. In some embodiments, the range of $\beta$ is $\{1,2,4,6,8,10,12\}$; the range of $\omega$ is $\{1,2,3,4,5,6,7,8\}$; and the range of $\mu$ is $\{0.001, 0.003\}$. In some embodiments, the range of $\beta$ is $\{4,6,8,10,12,14,15\}$; the range of $\omega$ is $\{3,4,5,6,7,8,9,10\}$; and the range of $\mu$ is $\{0.003, 0.005\}$. The multiple networks are then combined to obtain a representative network. In some embodiments, the multiple networks are combined using a maximum spanning tree algorithm to find the most robust, representative network. In some embodiments, the statistical significance of the representative network is validated against networks generated from random pairings of genes between the first eukaryote and the second eukaryote.

A publicly available webserver, SteinerNet, which may be used to generate networks using the PCST approach and is accessible on the world wide web at fraenkel.mit.edu/steinernet (Tuncbag, N., et al., Nucl. Acids Res. (2012) 40 (W1): W505-W509). In some embodiments, known disease genes and/or genetic modifiers may be "prized nodes" in a PCST-generated network. Other algorithmic approaches to the problem of constructing a network may be employed, and the invention is not limited in this respect. For example, flow optimization-based methods may be used (Lan, A., et al., Nucleic Acids Res. 2011; 39:W424-W429 and references therein). Other approaches include linear programming, Bayesian networks and maximum-likelihood-based approaches (see references cited in Tuncbag, N., et al.) In some embodiments a network may be visualized using any of a variety of software tools. For example, a network may be visualized using Cytoscape (Available on the world wide web at cytoscape.org/; Cline, M S, et al., Nature Protocols 2, 2366-2382 (2007); Shannon, P., et al., Genome Research 2003 Nov.; 13(11):2498-504).

In some embodiments, the invention is directed to a method of modeling a physiologic or pathologic process in an animal (e.g., human, mammal), comprising: (a) providing a set of candidate yeast genes identified in a yeast analogue of the physiologic or pathologic process in the animal; (b) providing interactions between yeast genes comprising the candidate yeast genes of step (a); (c) providing interactions between genes in the animal; (d) determining a set of genes in the animal homologous to the set of candidate yeast genes; and (e) creating a model of the physiologic or pathologic process in the animal by augmenting interactions between the set of genes in the animal obtained in step (d) with predicted gene interactions based on the interactions of step (b).

In some embodiments, the set of candidate yeast genes of step (a) were obtained by a method comprising: (i) providing a yeast cell modified to have increased or decreased expression or activity of a protein encoded by a yeast gene under conditions being a yeast analogue the physiologic or pathologic process, (ii) determining whether the modification modulates the yeast cell response to the conditions, and (iii) identifying the yeast gene as a candidate yeast gene when the yeast cell response is modulated. In some embodiments, the conditions comprise aberrant expression of one or more genes (e.g., over-expression, reduced expression, eliminated expression). In some embodiments, the one or more genes comprise a non-endogenous gene. In some embodiments, the modulation of yeast cell response of step (ii) comprises a change in at least one phenotype, a change in expression of at least one gene, a change in activity of at least one protein, or a change in cell viability. In some embodiments, the identification of a candidate yeast gene of step (iii) comprises identification of a change in at least one phenotype, a change in expression of at least one gene, a change in activity of at least one protein, or a change in cell viability.

In some embodiments, the candidate eukaryote genes (e.g., yeast genes) are obtained from a genome wide screen. In some embodiments, the genome wide screen comprises a deletion or over-expression screen of the eukaryote genome.

In some embodiments, the Prize-Collecting Steiner Forest (PCSF) algorithm to connect gene or protein nodes through genetic interactions, physical interactions and annotated pathways from one or more curated databases while minimizing costs to obtain a network.

In some embodiments, the PCSF algorithm with varied algorithm parameters is used to generate multiple networks of the first eukaryote, second eukaryote and/or the augments interactions and a representative network from the multiple networks is created with a maximum spanning tree algorithm.

In some embodiments, the model of the physiologic or pathologic process created by the methods herein comprises one or more predicted gene or protein nodes. In some embodiments, the methods disclosed herein further comprise identifying one or more other genes or proteins (e.g., predicted gene or protein) involved in the modeled physiologic or pathologic process. In some embodiments, the predicted gene or protein nodes comprise a druggable target.

A "druggable target" refers to a biological molecule, e.g., a protein or RNA, the level or activity of which is modulatable (capable of being modulated) by a small molecule. In certain embodiments a druggable target is a biological molecule for which at least one small molecule modulator has been identified. In certain embodiments such modulation is detectable in a cell-free assay, e.g., a protein activity assay. In certain embodiments such modulation is detectable in a cell-based assay using a cell that expresses the target. Any suitable assay may be used. One of ordinary skill in the art will be aware of many suitable assays for measuring protein activity and will be able to select an appropriate assay taking into account the known or predicted activit(ies) of the protein. The activity may, for example, be a binding activity, catalytic activity, transporter activity, or any other biological activity. In some embodiments modulation of a target may be detected by at least partial reversal of a phenotype induced by overexpression of the target or by deletion of the gene that encodes the target. In certain embodiments a druggable target is a biological molecule such as a protein or RNA that is known to or is predicted to bind with high affinity to at least one small molecule. In certain embodiments a protein is predicted to be "druggable" if it is a member of a protein family for which other members of the family are known to be modulated by or bind to one or more small molecules. In certain embodiments a protein is predicted to be "druggable" if it has an enzymatic activity that is amenable to the identification of modulators using a cell-free assay. In some embodiments the protein can be produced or purified in active form and has at least one known substrate that can be used to measure its activity.

A "small molecule" as used herein, is an organic molecule that is less than about 2 kilodaltons (kDa) in mass. In some embodiments, the small molecule is less than about 1.5 kDa, or less than about 1 kDa. In some embodiments, the small molecule is less than about 800 daltons (Da), 600 Da, 500 Da, 400 Da, 300 Da, 200 Da, or 100 Da. Often, a small molecule has a mass of at least 50 Da. In some embodiments, a small molecule is non-polymeric. In some embodiments, a small molecule is not an amino acid. In some embodiments, a small molecule is not a nucleotide. In some embodiments, a small molecule is not a saccharide. In some embodiments, a small molecule contains multiple carbon-carbon bonds and can comprise one or more heteroatoms and/or one or more functional groups important for structural interaction with proteins (e.g., hydrogen bonding), e.g., an amine, carbonyl, hydroxyl, or carboxyl group, and in some embodiments at least two functional groups. Small molecules often comprise one or more cyclic carbon or heterocyclic structures and/or aromatic or polyaromatic structures, optionally substituted with one or more of the above functional groups.

In some embodiments, homology between the genes or proteins of a first eukaryote and a second eukaryote comprises comparing at least one of a nucleic acid sequence, polypeptide sequence, protein structure, or molecular interactions between the candidate yeast genes and the animal genes. In some embodiments, homology between the genes or proteins of a first eukaryote and a second eukaryote comprises (i) determining sequence similarity between the animal genes and the candidate yeast genes; (ii) determining evolutionary and structural similarity between the animal genes and the candidate yeast genes; (iii) determining molecular interaction similarity between the animal genes and the candidate yeast genes; and (iv) determining a set of genes in the animal homologous to the set of candidate yeast genes by integrating the similarities in steps (i) through (iii) using diffusion component analysis. In some embodiments, step (i) comprises utilizing NCBI protein BLAST with the BLOSUM62 substitution matrix and/or DIOPT. In some embodiments, step (ii) comprises utilizing PSI-BLAST to construct a multiple sequence alignment and build a profile hidden Markov model to encode a remote evolutionary signal followed by HHpred. In some embodiments, step (iii) comprises utilizing Compact Integration of Multi-Network Topology for Functional Analysis of Genes (Mashup).

In some embodiments, at least one of the eukaryotes is a mammal. In some embodiments, at least one of the eukaryotes is a human, mouse, rat or primate. In some embodiments, at least one of the eukaryotes is a yeast (e.g., baker's yeast). Yeast, e.g., the baker's yeast *Saccharomyces cerevisiae*, has significant advantages as an experimental system. Yeast are straightforward to culture and maintain, have a short generation time, and are highly genetically tractable, meaning that they can be genetically modified, rapidly, predictably, and with high precision using well known and available techniques and reagents, and are amenable to high throughput chemical and genetic screens. Minimal genetic and epigenetic variation within strains contributes to screen reproducibility. Extensive genetic and protein interaction analysis in yeast means that considerable information regarding the yeast interactome, i.e., the set of physical interactions among molecules in a cell and interactions among genes, i.e., genetic interactions, in yeast cells is available. Molecular interactions can occur between molecules belonging to different biochemical families (proteins, nucleic acids, lipids, carbohydrates, etc.) and also within a given family (e.g., protein-protein interactions). While yeast cells lack the complexity of a multicellular organism with a nervous system, the highly conserved genome and eukaryotic cellular machinery that they share with human cells affords the possibility of understanding basic cell-autonomous mechanisms and physical and genetic interactions underlying complex disease processes.

Cells

Another aspect of the invention is directed to generating a cell comprising (a) obtaining a model of a physiologic or pathologic process generated according to any of the methods disclosed herein; (b) identifying a gene node in the model obtained in step (a); and (c) generating a cell having altered expression of the gene node or altered activity of a gene product of the gene node. The cell may be a prokaryotic (e.g., bacterial) or a eukaryotic cell. The eukaryotic cell may be any type disclosed herein. In some embodiments, the cell is a mammalian cell (e.g., human cell, mouse cell). In some embodiments, the cell is a stem cell (e.g., an embryonic stem cell, a mammalian embryonic stem cell, a human embryonic stem cell, a murine embryonic stem cell). In some embodiments, the cell is an embryonic stem cell. In some embodiments, the cell is an induced pluripotent stem cell.

In some embodiments of the methods and compositions disclosed herein, cells include somatic cells, stem cells, mitotic or post-mitotic cells, neurons, fibroblasts, or zygotes. A cell, zygote, embryo, or post-natal mammal can be of vertebrate (e.g., mammalian) origin. In some aspects, the vertebrates are mammals or avians. Particular examples include primate (e.g., human), rodent (e.g., mouse, rat), canine, feline, bovine, equine, caprine, porcine, or avian (e.g., chickens, ducks, geese, turkeys) cells, zygotes, embryos, or post-natal mammals. In some embodiments, the cell, zygote, embryo, or post-natal mammal is isolated (e.g., an isolated cell; an isolated zygote; an isolated embryo). In some embodiments, a mouse cell, mouse zygote, mouse embryo, or mouse post-natal mammal is used. In some embodiments, a rat cell, rat zygote, rat embryo, or rat post-natal mammal is used. In some embodiments, a human cell, human zygote or human embryo is used. The methods described herein can be used in a mammal (e.g., a mouse, a human) in vivo.

Stem cells may include totipotent, pluripotent, multipotent, oligopotent and unipotent stem cells. Specific examples of stem cells include embryonic stem cells, fetal stem cells, adult stem cells, and induced pluripotent stem cells (iPSCs) (e.g., see U.S. Published Application Nos. 2010/0144031, 2011/0076678, 2011/0088107, 2012/0028821 all of which are incorporated herein by reference).

Somatic cells may be primary cells (non-immortalized cells), such as those freshly isolated from an animal, or may be derived from a cell line capable of prolonged proliferation in culture (e.g., for longer than 3 months) or indefinite proliferation (immortalized cells). Adult somatic cells may be obtained from individuals, e.g., human subjects, and cultured according to standard cell culture protocols available to those of ordinary skill in the art. Somatic cells of use in aspects of the invention include mammalian cells, such as, for example, human cells, non-human primate cells, or rodent (e.g., mouse, rat) cells. They may be obtained by well-known methods from various organs, e.g., skin, lung, pancreas, liver, stomach, intestine, heart, breast, reproductive organs, muscle, blood, bladder, kidney, urethra and other urinary organs, etc., generally from any organ or tissue containing live somatic cells. Mammalian somatic cells useful in various embodiments include, for example, fibroblasts, Sertoli cells, granulosa cells, neurons, pancreatic cells, epidermal cells, epithelial cells, endothelial cells, hepatocytes, hair follicle cells, keratinocytes, hematopoietic cells, melanocytes, chondrocytes, lymphocytes (B and T lymphocytes), macrophages, monocytes, mononuclear cells, cardiac muscle cells, skeletal muscle cells, etc.

In some aspects, the cell having altered expression of the gene node or altered activity of a gene product of the gene node is derived from a subject with having altered expression of the gene node or altered activity of a gene product of the gene node. In some embodiments, the cell is an iPSc cell derived from the subject. In some embodiments, the cell is progenitor cell of an iPSC cell derived from the subject.

In some aspects, the cell having altered expression of the gene node or altered activity of a gene product of the gene node is obtained by introducing one or more mutations into a cell that alters the expression of the gene or activity of a gene product of the gene. The one or more mutations may comprise one or more of an insertion, deletion, disruption or substitution into the genome of the cell. In some embodiments, the one or more mutations comprise the deletion of the gene. In some embodiments, the one or more mutations comprise insertion of extra copies of the gene or a portion of the gene. In some embodiments, the one or more mutations modify regulatory sequences and increases or decreases expression of a gene product of the gene. In some embodiments, the one or more mutations increase or decrease the activity of a gene product of the gene. In some embodiments, the one or more mutations increase or decrease the cellular degradation rate of a gene product of the gene.

In some embodiments, the cell having altered expression of the gene node or altered activity of a gene product of the gene node is obtained by altering a regulatory sequence of the cell (e.g., a promoter region for the gene). In some embodiments, the methylation of a regulatory sequence is modified.

In some embodiments, the cell having altered expression of the gene node or altered activity of a gene product of the gene node is obtained by modifying the genome of a cell with a targetable nuclease (e.g., site specific nuclease).

There are currently four main types of targetable nucleases (sometimes also referred to as "site specific nucleases") in use: zinc finger nucleases (ZFNs), transcription activator—like effector nucleases (TALENs), and RNA-guided nucleases (RGNs) such as the Cas proteins of the CRISPR/Cas Type II system, and engineered meganucleases. ZFNs and TALENs comprise the nuclease domain of the restriction enzyme FokI (or an engineered variant thereof) fused to a site-specific DNA binding domain (DBD) that is appropriately designed to target the protein to a selected DNA sequence. In the case of ZFNs, the DNA binding domain comprises a zinc finger DBD. In the case of TALENs, the site-specific DBD is designed based on the DNA recognition code employed by transcription activator-like effectors (TALEs), a family of site-specific DNA binding proteins found in plant-pathogenic bacteria such as *Xanthomonas* species. The Clustered Regularly Interspaced Short Palindromic Repeats (CRISPR) Type II system is a bacterial adaptive immune system that has been modified for use as an RNA-guided endonuclease technology for genome engineering. The bacterial system comprises two endogenous bacterial RNAs called crRNA and tracrRNA and a CRISPR-associated (Cas) nuclease, e.g., Cas9. The tracrRNA has partial complementarity to the crRNA and forms a complex with it. The Cas protein is guided to the target sequence by the crRNA/tracrRNA complex, which forms a RNA/DNA hybrid between the crRNA sequence and the complementary sequence in the target. For use in genome modification, the crRNA and tracrRNA components are often combined into a single chimeric guide RNA (sgRNA or gRNA) in which the targeting specificity of the crRNA and the properties of the tracrRNA are combined into a single transcript that localizes the Cas protein to the target sequence so that the Cas protein can cleave the DNA. The sgRNA often comprises an approximately 20 nucleotide guide sequence complementary or homologous to the desired target sequence followed by about 80 nt of hybrid crRNA/tracrRNA. One of ordinary skill in the art appreciates that the guide RNA need not be perfectly complementary or homologous to the target sequence. For example, in some embodiments it may have one or two mismatches. The genomic sequence which the gRNA hybridizes is typically flanked on one side by a Protospacer Adjacent Motif (PAM) sequence although one of ordinary skill in the art appreciates that certain Cas proteins may have a relaxed requirement for a PAM sequence. The PAM sequence is present in the genomic DNA but not in the sgRNA sequence. The Cas protein will be directed to any DNA sequence with the correct target sequence and PAM sequence. The PAM sequence varies depending on the species of bacteria from which the Cas protein was derived. Specific examples of Cas proteins include Cas1, Cas2, Cas3, Cas4, Cas5, Cas6, Cas7, Cas8, Cas9 and Cas10. In some embodiments, the site specific nuclease comprises a Cas9 protein. For example, Cas9 from *Streptococcus pyogenes* (Sp), *Neisseria meningitides, Staphylococcus aureus, Streptococcus thermophiles,* or *Treponema denticola* may be used. The PAM sequences for these Cas9 proteins are NGG, NNNNGATT, NNAGAA, NAAAAC, respectively. A number of engineered variants of the site-specific nucleases have been developed and may be used in certain embodiments. For example, engineered variants of Cas9 and Fok1 are known in the art. Furthermore, it will be understood that a biologically active fragment or variant can be used. Other variations include the use of hybrid site specific nucleases. For example, in CRISPR RNA-guided FokI nucleases (RFNs) the FokI nuclease domain is fused to the amino-terminal end of a catalytically inactive Cas9 protein (dCas9) protein. RFNs act as dimers and utilize two guide RNAs (Tsai, Q S, et al., *Nat Biotechnol.* 2014; 32(6): 569-576). Site-specific nucleases that produce a single-stranded DNA break are also of use for genome editing. Such nucleases, sometimes termed "nickases" can be generated by introducing a mutation (e.g., an alanine substitution) at key catalytic residues in one of the two nuclease domains of a site specific nuclease that comprises two nuclease domains (such as ZFNs, TALENs, and Cas proteins). Examples of such mutations include D10A, N863A, and H840A in SpCas9 or at homologous positions in other Cas9 proteins. A nick can stimulate HDR at low efficiency in some cell types. Two nickases, targeted to a pair of sequences that are near each other and on opposite strands can create a single-stranded break on each strand ("double nicking"), effectively generating a DSB, which can optionally be repaired by HDR using a donor DNA template (Ran, F. A. et al. Cell 154, 1380-1389 (2013). In some embodiments, the Cas protein is a SpCas9 variant. In some embodiments, the SpCas9 variant is a R661A/Q695A/Q926A triple variant or a N497A/R661A/Q695A/Q926A quadruple variant. See Kleinstiver et al., "High-fidelity CRISPR-Cas9 nucleases with no detectable genome-wide off-target effects," Nature, Vol. 529, pp. 490-495 (and supplementary materials)(2016); incorporated herein by reference in its entirety. In some embodiments, the Cas protein is C2c1, a class 2 type V-B CRISPR-Cas protein. See Yang et al., "PAM-Dependent Target DNA Recognition and Cleavage by C2c1 CRISPR-Cas Endonuclease," Cell, Vol. 167, pp.

1814-1828 (2016); incorporated herein by reference in its entirety. In some embodiments, the Cas protein is one described in US 20160319260 "Engineered CRISPR-Cas9 nucleases with Altered PAM Specificity" incorporated herein by reference.

In some embodiments, the targetable nuclease (e.g., site specific nuclease) has at least 90%, 95% or 99% polypeptide sequence identity to a naturally occurring targetable nuclease.

In some embodiments, the nucleotide sequence of the cell is modified with a site specific nuclease (i.e., a targetable nuclease) and one or more guide sequences. In some embodiments, the site specific nuclease is a Cas protein. A variety of CRISPR associated (Cas) genes or proteins which are known in the art can be used in the methods of the invention and the choice of Cas protein will depend upon the particular situation (e.g., www.ncbi.nlm.nih.gov/gene/?term=cas9). In a particular aspect, the Cas nucleic acid or protein is Cas9. In some embodiments a Cas protein, e.g., a Cas9 protein, may be from any of a variety of prokaryotic species. In some embodiments a particular Cas protein, e.g., a particular Cas9 protein, may be selected to recognize a particular protospacer-adjacent motif (PAM) sequence. In certain embodiments a Cas protein, e.g., a Cas9 protein, may be obtained from a bacteria or archaea or synthesized using known methods. In certain embodiments, a Cas protein may be from a gram positive bacteria or a gram negative bacteria. In certain embodiments, a Cas protein may be from a *Streptococcus*, (e.g., a *S. pyogenes*, a *S. thermophilus*) a *Cryptococcus*, a *Corynebacterium*, a *Haemophilus*, a *Eubacterium*, a *Pasteurella*, a *Prevotella*, a *Veillonella*, or a *Marinobacter*. In some embodiments nucleic acids encoding two or more different Cas proteins, or two or more Cas proteins, may be present, e.g., to allow for recognition and modification of sites comprising the same, similar or different PAM motifs.

In some embodiments, the Cas protein is Cpf1 protein or a functional portion thereof. In some embodiments, the Cas protein is Cpf1 from any bacterial species or functional portion thereof. In certain embodiments, a Cpf1 protein is a *Francisella novicida* U112 protein or a functional portion thereof, a Acidaminococcus sp. BV3L6 protein or a functional portion thereof, or a Lachnospiraceae bacterium ND2006 protein or a function portion thereof. Cpf1 protein is a member of the type V CRISPR systems. Cpf1 protein is a polypeptide comprising about 1300 amino acids. Cpf1 contains a RuvC-like endonuclease domain. See Zetsche B, et al., "Cpf1 is a single RNA-guided endonuclease of a class 2 CRISPR-Cas system," Cell. 2015 Oct. 22; 163(3):759-71. doi: 10.1016/j.cell.2015.09.038. Epub 2015 Sep. 25.) and US20160208243, incorporated herein by reference in their entireties. One of ordinary skill in the art appreciates that Cpf1 does not utilize tracrRNA, and thus requires only a crRNA that contains a single stem-loop, which tolerates sequence changes that retain secondary structure.

In some embodiments a Cas9 nickase may be generated by inactivating one or more of the Cas9 nuclease domains. In some embodiments, an amino acid substitution at residue 10 in the RuvC I domain of Cas9 converts the nuclease into a DNA nickase. For example, the aspartate at amino acid residue 10 can be substituted for alanine (Cong et al, Science, 339:819-823).

In some embodiments, the targetable nuclease may be a catalytically inactive targetable nuclease (e.g., catalytically inactive site specific nuclease). In some embodiments, a catalytically inactive targetable nuclease can be utilized along with an effector domain to modifying the degree of methylation of a regulatory region and therefore increase or decrease expression of a gene product of a gene. Amino acids mutations that create a catalytically inactive Cas9 protein include mutating at residue 10 and/or residue 840. Mutations at both residue 10 and residue 840 can create a catalytically inactive Cas9 protein, sometimes referred herein as dCas9. In some embodiments, dCas9 is a D10A and a H840A Cas9 mutant that is catalytically inactive. As used herein an "effector domain" is a molecule (e.g., protein) that modulates the expression and/or activation of a genomic sequence (e.g., gene). The effector domain may have methylation activity (e.g., DNA methylation activity). In some aspects, the effector domain targets one or both alleles of a gene. The effector domain can be introduced as a nucleic acid sequence and/or as a protein. In some aspects, the effector domain can be a constitutive or an inducible effector domain. In some aspects, a Cas (e.g., dCas) nucleic acid sequence or variant thereof and an effector domain nucleic acid sequence are introduced into the cell as a chimeric sequence. In some aspects, the effector domain is fused to a molecule that associates with (e.g., binds to) Cas protein (e.g., the effector molecule is fused to an antibody or antigen binding fragment thereof that binds to Cas protein). In some aspects, a Cas (e.g., dCas) protein or variant thereof and an effector domain are fused or tethered creating a chimeric protein and are introduced into the cell as the chimeric protein. In some aspects, the Cas (e.g., dCas) protein and effector domain bind as a protein-protein interaction. In some aspects, the Cas (e.g., dCas) protein and effector domain are covalently linked. In some aspects, the effector domain associates non-covalently with the Cas (e.g., dCas) protein. In some aspects, a Cas (e.g., dCas) nucleic acid sequence and an effector domain nucleic acid sequence are introduced as separate sequences and/or proteins. In some aspects, the Cas (e.g., dCas) protein and effector domain are not fused or tethered.

A site specific nuclease or polypeptide (e.g., fusion polypeptide comprising a site-specific nuclease and an effector domain, fusion polypeptide comprising a site-specific nuclease and an effector domain having methylation or de-methylation activity) may be targeted to a unique site in the genome (e.g., a gene identified as a node) of a mammalian cell by appropriate design of the nuclease, guide RNA, or polypeptide. A polypeptide, nuclease and/or guide RNA may be introduced into cells by introducing a nucleic acid that encodes it into the cell. Standard methods such as plasmid DNA transfection, viral vector delivery, transfection with modified or synthetic mRNA (e.g., capped, polyadenylated mRNA), or microinjection can be used. In some embodiments, the modified or synthetic mRNA comprises one or more modifications that stabilize the mRNA or provide other improvements over naturally occurring mRNA (e.g., increased cellular uptake). Examples of modified or synthetic mRNA are described in Warren et al. (Cell Stem Cell 7(5):618-30, 2010, Mandal P K, Rossi D J. Nat Protoc. 2013 8(3):568-82, US Pat. Pub. No. 20120046346 and/or PCT/US2011/032679 (WO/2011/130624). mRNA is also discussed in R.E. Rhoads (Ed.), "Synthetic mRNA: Production, Introduction Into Cells, and Physiological Consequences," Series: Methods in Molecular Biology, Vol. 1428. Additional examples are found in numerous PCT and US applications and issued patents to Moderna Therapeutics, e.g., PCT/US2011/046861; PCT/US2011/054636, PCT/US2011/054617, U.S. Ser. No. 14/390,100 (and additional patents and patent applications mentioned in these.) If DNA encoding the nuclease or guide RNA is introduced, the coding sequences should be operably linked to appropriate regulatory elements for expression, such as a promoter and termination signal. In some embodiments a sequence encoding a guide RNA is operably linked to an RNA polymerase III promoter such as U6 or tRNA promoter. In some embodiments one or more guide RNAs and Cas protein coding sequences are transcribed from the same nucleic acid (e.g., plasmid). In some embodiments multiple guide RNAs are transcribed from the same plasmid or from different plasmids or are otherwise introduced into the cell. The multiple guide RNAs may direct Cas9 to different target sequences in the genome, allowing for multiplexed genome editing. In some embodiments a nuclease protein (e.g., Cas9) may comprise or be modified to comprise a nuclear localization signal (e.g., SV40 NLS). A nuclease protein may be introduced into cells, e.g., using protein transduction. Nuclease proteins, guide RNAs, or both, may be introduced using microinjection. Methods of using site specific nucleases, e.g., to perform genome editing, are described in numerous publications, such as *Methods in Enzymology*, Doudna J A, Sontheimer E J. (eds), The use of CRISPR/Cas9, ZFNs, and TALENs in generating site-specific genome alterations. Methods Enzymol. 2014, Vol. 546 (Elsevier); Carroll, D., Genome Editing with Targetable Nucleases, Annu. Rev. Biochem. 2014. 83:409-39, and references in either of these. See also U.S. Pat. Pub. Nos. 20140068797, 20140186919, 20140170753 and/or PCT/US2014/034387 (WO/2014/172470).

In some embodiments, the one or more guide sequences include sequences that recognize DNA in a site-specific manner. For example, guide sequences can include guide ribonucleic acid (RNA) sequences utilized by a CRISPR system or sequences within a TALEN or zinc finger system that recognize DNA in a site-specific manner. The guide sequences comprise a portion that is complementary to a portion of each of the one or more genomic sequences and comprise a binding site for the catalytically inactive site specific nuclease. In some embodiments, the RNA sequence is referred to as guide RNA (gRNA) or single guide RNA (sgRNA).

In some aspects, a guide sequence can be complementary to one or more (e.g., all) of the genomic sequences that are being modulated or modified. In one aspect, a guide sequence is complementary to a single target genomic sequence. In a particular aspect in which two or more target genomic sequences are to be modulated or modified, multiple (e.g., 2, 3, 4, 5, 6, 7, 8, 9, 10, or more) guide sequences are introduced wherein each guide sequence is complementary to (specific for) one target genomic sequence. In some aspects, two or more, three or more, four or more, five or more, or six or more guide sequences are complementary to (specific for) different parts of the same target sequence. In one aspect, two or more guide sequences bind to different sequences of the same region of DNA. In some aspects, a single guide sequence is complementary to at least two target or more (e.g., all) of the genomic sequences. It will also be apparent to those of skill in the art that the portion of the guide sequence that is complementary to one or more of the genomic sequences and the portion of the guide sequence that binds to the catalytically inactive site specific nuclease can be introduced as a single sequence or as 2 (or more) separate sequences into a cell.

Each guide sequence can vary in length from about 8 base pairs (bp) to about 200 bp. In some embodiments, the RNA sequence can be about 9 to about 190 bp; about 10 to about 150 bp; about 15 to about 120 bp; about 20 to about 100 bp; about 30 to about 90 bp; about 40 to about 80 bp; about 50 to about 70 bp in length.

The portion of each genomic sequence (e.g., a gene identified as a node) to which each guide sequence is complementary can also vary in size. In particular aspects, the portion of each genomic sequence to which the guide sequence is complementary can be about 8, 9, 10, 11, 12, 13, 14, 15, 16, 17, 18, 19, 20, 21, 22, 23, 24, 25, 26, 27, 28, 29, 30, 31, 32, 33, 34,35, 36, 37, 38 39, 40, 41, 42, 43, 44, 45, 46 47, 48, 49, 50, 51, 52, 53,54, 55, 56,57, 58, 59 60, 61, 62, 63, 64, 65, 66, 67, 68, 69, 70, 71, 72, 73, 74, 75, 76, 77, 78, 79, 80 81, 82, 83, 84, 85, 86, 87 88, 89, 90, 81, 92, 93, 94, 95, 96, 97, 98, or 100 nucleotides (contiguous nucleotides) in length. In some embodiments, each guide sequence can be at least about 70%, 75%, 80%, 85%, 90%, 95%, 100%, etc. identical or similar to the portion of each genomic sequence. In some embodiments, each guide sequence is completely or partially identical or similar to each genomic sequence. For example, each guide sequence can differ from perfect complementarity to the portion of the genomic sequence by about 1, 2, 3, 4, 5, 6, 7, 8, 9, 10, 11, 12, 13, 14, 15, 16, 17, 18, 19, 20, etc. nucleotides. In some embodiments, one or more guide sequences are perfectly complementary (100%) across at least about 10 to about 25 (e.g., about 20) nucleotides of the genomic sequence.

In some embodiments, a cell having altered expression of the gene node or altered activity of a gene product of the gene node is obtained by contacting the cell with a nucleic acid that reduces expression of the gene node. The nucleic acid is a polymer of ribose nucleotides or deoxyribose nucleotides having more than three nucleotides in length. The nucleic acid may include naturally-occurring nucleotides; synthetic, modified, or pseudo-nucleotides such as phosphorothiolates; as well as nucleotides having a detectable label such as $P^{32}$, biotin, fluorescent dye or digoxigenin. A nucleic acid that can reduce the expression of the gene node may be completely complementary to a gene node nucleic acid (e.g., mRNA) or a portion thereof. Alternatively, some variability between the sequences may be permitted.

The nucleic acid of the invention can hybridize to a gene node nucleic acid (e.g., mRNA) under intracellular conditions or under stringent hybridization conditions. The nucleic acids of the invention are sufficiently complementary to a gene node nucleic acid (e.g., mRNA) to inhibit expression of the gene node under either or both conditions. Intracellular conditions refer to conditions such as temperature, pH and salt concentrations typically found inside a cell, e.g. a mammalian cell.

Generally, stringent hybridization conditions are selected to be about 5° C. lower than the thermal melting point ($T_m$) for the specific sequence at a defined ionic strength and pH. However, stringent conditions encompass temperatures in the range of about 1° C. to about 20° C. lower than the thermal melting point of the selected sequence, depending upon the desired degree of stringency as otherwise qualified herein. Nucleic acids that comprise, for example, 2, 3, 4, or 5 or more stretches of contiguous nucleotides that are precisely complementary to a transcription factor coding sequence, each separated by a stretch of contiguous nucleotides that are not complementary to adjacent coding sequences, may inhibit the function of a gene node. In general, each stretch of contiguous nucleotides is at least 4, 5, 6, 7, or 8 or more nucleotides in length. Non-complementary intervening sequences may be 1, 2, 3, or 4 nucleotides in length. One skilled in the art can easily use the calculated melting point of an nucleic acid hybridized to a sense nucleic acid to estimate the degree of mismatching that will be tolerated for inhibiting expression of a particular target nucleic acid. Nucleic acids of the invention include, for example, a ribozyme or an antisense nucleic acid molecule.

An antisense nucleic acid molecule may be single or double stranded (e.g. a small interfering RNA (siRNA)), and may function in an enzyme-dependent manner or by steric blocking. Antisense molecules that function in an enzyme-dependent manner include forms dependent on RNase H activity to degrade target mRNA. These include single-stranded DNA, RNA and phosphorothioate molecules, as well as the double-stranded RNAi/siRNA system that involves target mRNA recognition through sense-antisense strand pairing followed by degradation of the target mRNA by the RNA-induced silencing complex. Steric blocking antisense, which are RNase-H independent, interferes with gene expression or other mRNA-dependent cellular processes by binding to a target mRNA and interfering with other processes such as translation. Steric blocking antisense includes 2'-O alkyl (usually in chimeras with RNase-H dependent antisense), peptide nucleic acid (PNA), locked nucleic acid (LNA) and morpholino antisense.

Small interfering RNAs, for example, may be used to specifically reduce the level of mRNA encoding a gene node and/or reduce translation of mRNA encoding a gene node such that the level of a product of the gene node is reduced. siRNAs mediate post-transcriptional gene silencing in a sequence-specific manner. See, for example, Carthew et al., "Origins and Mechanisms of miRNAs and siRNAs," Cell, Volume 136, Issue 4, p642-655, 20 Feb. 2009. Once incorporated into an RNA-induced silencing complex, siRNA mediate cleavage of the homologous endogenous mRNA transcript by guiding the complex to the homologous mRNA transcript, which is then cleaved by the complex. The siRNA may be homologous to any region of a gene node mRNA transcript. The region of homology may be 30 nucleotides or less in length, less than 25 nucleotides, about 21 to 23 nucleotides in length or less, e.g., 19 nucleotides in length. SiRNA is typically double stranded and may have nucleotide 3' overhangs. The 3' overhangs may be up to about 5 or 6 nucleotide '3 overhangs, e.g., two nucleotide 3' overhangs, such as, 3' overhanging UU dinucleotides, for example. In some embodiments, the siRNAs may not include any nucleotide 3' overhangs. Methods for designing siRNAs are known to those skilled in the art. See, for example, Elbashir et al. Nature 411: 494-498 (2001); Harborth et al. Antisense Nucleic Acid Drug Dev. 13: 83-106 (2003). In some embodiments a target site is selected that begins with AA, has 3' UU overhangs for both the sense and antisense siRNA strands and has an approximate 50% G/C content. In some embodiments, a target site is selected that is unique to one or more target mRNAs and not in other mRNAs whose degradation or translational inhibition is not desired. siRNAs may be chemically synthesized, created by in vitro transcription, or expressed from an siRNA expression vector or a PCR expression cassette. See, e.g., the world wide web at ambion.com/techlib/tb/tb.sub.-506html.

When an siRNA is expressed from an expression vector or a PCR expression cassette, the insert encoding the siRNA may be expressed as an RNA transcript that folds into an siRNA hairpin. Thus, the RNA transcript may include a sense siRNA sequence that is linked to its reverse complementary antisense siRNA sequence by a spacer sequence that forms the loop of the hairpin as well as a string of U's at the 3' end. The loop of the hairpin may be any appropriate length, for example, up to 30 nucleotides in length, e.g., 3 to 23 nucleotides in length, and may be of various nucleotide sequences. SiRNAs also may be produced in vivo by cleavage of double-stranded RNA introduced directly or via a transgene or virus. Amplification by an RNA-dependent RNA polymerase may occur in some organisms. The siRNA may be further modified according to any methods known to those having ordinary skill in the art.

An antisense inhibitory nucleic acid may also be used to specifically reduce gene node expression, for example, by inhibiting transcription and/or translation. An antisense inhibitory nucleic acid is complementary to a sense nucleic acid encoding a gene product of a gene node. For example, it may be complementary to the coding strand of a double-stranded cDNA molecule or complementary to an mRNA sequence. It may be complementary to an entire coding strand or to only a portion thereof. It may also be complementary to all or part of the noncoding region of a nucleic acid encoding a gene product of a gene node. The noncoding region includes the 5' and 3' regions that flank the coding region, for example, the 5' and 3' untranslated sequences. An antisense inhibitory nucleic acid is generally at least six nucleotides in length, but may be up to about 8, 12, 15, 20, 25, 30, 35, 40, 45, or 50 nucleotides long. Longer inhibitory nucleic acids may also be used.

An antisense inhibitory nucleic acid may be prepared using methods known in the art, for example, by expression from an expression vector encoding the antisense inhibitory nucleic acid or from an expression cassette. Alternatively, it may be prepared by chemical synthesis using naturally-occurring nucleotides, modified nucleotides or any combinations thereof. In some embodiments, the inhibitory nucleic acids are made from modified nucleotides or non-phosphodiester bonds, for example, that are designed to increase biological stability of the inhibitory nucleic acid or to increase intracellular stability of the duplex formed between the antisense inhibitory nucleic acid and the sense nucleic acid.

Naturally-occurring nucleotides, nucleosides and nucleobases include the ribose or deoxyribose nucleotides adenosine, guanine, cytosine, thymine, and uracil. Examples of modified nucleotides, nucleosides and nucleobases include those comprising 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladeninje, uracil-5oxyacetic acid, butoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl)uracil, (acp3)w, and 2,6-diaminopurine.

Thus nucleic acids of the invention may include modified nucleotides, as well as natural nucleotides such as combinations of ribose and deoxyribose nucleotides, and a nucleic acid of the invention may be of any length discussed above and that is complementary to the nucleic acid sequences of a gene node.

In some embodiments, a nucleic acid modulating expression of a gene node is a small hairpin RNA (shRNA).

shRNA is a sequence of RNA that makes a tight hairpin turn that can be used to silence gene expression by means of RNA interference. The shRNA hairpin structure is cleaved by the cellular machinery into a siRNA, which then binds to and cleaves the target mRNA. shRNA can be introduced into cells via a vector encoding the shRNA, where the shRNA coding region is operably linked to a promoter. The selected promoter permits expression of the shRNA. For example, the promoter can be a U6 promoter, which is useful for continuous expression of the shRNA. The vector can, for example, be passed on to daughter cells, allowing the gene silencing to be inherited. See, McIntyre G, Fanning G, Design and cloning strategies for constructing shRNA expression vectors, BMC BIOTECHNOL. 6:1 (2006); Paddison et al., Short hairpin RNAs (shRNAs) induce sequence-specific silencing in mammalian cells, GENES DEV. 16 (8): 948-58 (2002).

In some embodiments, a nucleic acid modulating expression of a gene node is a ribozyme. A ribozyme is an RNA molecule with catalytic activity and is capable of cleaving a single-stranded nucleic acid such as an mRNA that has a homologous region. See, for example, Cech, Science 236: 1532-1539 (1987); Cech, Ann. Rev. Biochem. 59:543-568 (1990); Cech, Curr. Opin. Struct. Biol. 2: 605-609 (1992); Couture and Stinchcomb, Trends Genet. 12: 510-515 (1996).

Methods of designing and constructing a ribozyme that can cleave an RNA molecule in trans in a highly sequence specific manner have been developed and described in the art. See, for example, Haseloff et al., Nature 334:585-591 (1988). A ribozyme may be targeted to a specific RNA by engineering a discrete "hybridization" region into the ribozyme. The hybridization region contains a sequence complementary to the target RNA that enables the ribozyme to specifically hybridize with the target. See, for example, Gerlach et al., EP 321,201. The target sequence may be a segment of about 5, 6, 7, 8, 9, 10, 12, 15, 20, or 50 contiguous nucleotides. Longer complementary sequences may be used to increase the affinity of the hybridization sequence for the target.

In some embodiments, nucleic acids (e.g., enhanced nucleic acids) (e.g., DNA constructs, synthetic RNAs, e.g., homologous or complementary RNAs described herein, mRNAs described herein, etc.) herein may be introduced into cells of interest via transfection, electroporation, cationic agents, polymers, or lipid-based delivery molecules well known to those of ordinary skill in the art. As used herein, an "enhanced nucleic acid" has an enhanced property (e.g., enhanced stability, enhanced cellular uptake, enhanced binding, enhanced specificity) compared to a naturally occurring counterpart nucleic acid.

In some embodiments, methods of the present disclosure enhance nucleic acid delivery into a cell population, in vivo, ex vivo, or in culture. For example, a cell culture containing a plurality of cells (e.g., eukaryotic cells such as yeast or mammalian cells) is contacted with a composition that contains an enhanced nucleic acid having at least one nucleoside modification and, optionally, a translatable region. In some embodiments, the composition also generally contains a transfection reagent or other compound that increases the efficiency of enhanced nucleic acid uptake into the host cells. The enhanced nucleic acid exhibits enhanced retention in the cell population, relative to a corresponding unmodified nucleic acid. In some embodiments, the retention of the enhanced nucleic acid is greater than the retention of the unmodified nucleic acid. In some embodiments, it is at least about 50%, 75%, 90%, 95%, 100%, 150%, 200%, or more than 200% greater than the retention of the unmodified nucleic acid. Such retention advantage may be achieved by one round of transfection with the enhanced nucleic acid, or may be obtained following repeated rounds of transfection.

The synthetic RNAs (e.g., modified mRNAs, enhanced nucleic acids) of the presently disclosed subject matter may be optionally combined with a reporter gene (e.g., upstream or downstream of the coding region of the mRNA) which, for example, facilitates the determination of modified mRNA delivery to cells. Suitable reporter genes may include, for example, Green Fluorescent Protein mRNA (GFP mRNA), *Renilla* Luciferase mRNA (Luciferase mRNA), Firefly Luciferase mRNA, or any combinations thereof. For example, GFP mRNA may be fused with a mRNA encoding a nuclear localization sequence to facilitate confirmation of mRNA localization in the cells where the RNA transcribed from the at least one regulatory element is taking place.

In some embodiments, RNA can be modified further post-transcription, e.g., by adding a cap or other functional group. In an aspect, a synthetic RNA (enhanced nucleic acid) comprises a 5' and/or a 3'-cap structure. Synthetic RNA can be single stranded (e.g., ssRNA) or double stranded (e.g., dsRNA). The 5' and/or 3'-cap structure can be on only the sense strand, the antisense strand, or both strands. By "cap structure" is meant chemical modifications, which have been incorporated at either terminus of the oligonucleotide (see, for example, Adamic et al., U.S. Pat. No. 5,998,203, incorporated by reference herein). These terminal modifications protect the nucleic acid molecule from exonuclease degradation, and can help in delivery and/or localization within a cell. The cap can be present at the 5'-terminus (5'-cap) or at the 3'-terminal (3'-cap) or can be present on both termini.

Non-limiting examples of the 5'-cap include, but are not limited to, glyceryl, inverted deoxy abasic residue (moiety); 4',5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3-inverted abasic moiety; 3'-2-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety.

Non-limiting examples of the 3'-cap include, but are not limited to, glyceryl, inverted deoxy abasic residue (moiety), 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non-bridging methylphosphonate and 5'-mercapto moieties (for more details see Beaucage and Iyer, 1993, Tetrahedron 49, 1925; incorporated by reference herein).

The synthetic RNA may comprise at least one modified nucleoside, such as pseudouridine, m5U, s2U, m6A, and m5C, N1-methylguanosine, N1-methyladenosine, N7-methylguanosine, 2'-)-methyluridine, and 2'-O-methylcytidine. Polymerases that accept modified nucleosides are known to those of skill in the art. Modified polymerases can be used to generate synthetic, modified RNAs. Thus, for example, a polymerase that tolerates or accepts a particular modified nucleoside as a substrate can be used to generate a synthetic, modified RNA including that modified nucleoside.

In some embodiments, the synthetic RNA provokes a reduced (or absent) innate immune response in vivo or reduced interferon response in vivo by the transfected tissue or cell population. mRNA produced in eukaryotic cells, e.g., mammalian or human cells, is heavily modified, the modifications permitting the cell to detect RNA not produced by that cell. The cell responds by shutting down translation or otherwise initiating an innate immune or interferon response. Thus, to the extent that an exogenously added RNA can be modified to mimic the modifications occurring in the endogenous RNAs produced by a target cell, the exogenous RNA can avoid at least part of the target cell's defense against foreign nucleic acids. Thus, in some embodiments, synthetic RNAs include in vitro transcribed RNAs including modifications as found in eukaryotic/mammalian/human RNA in vivo. Other modifications that mimic such naturally occurring modifications can also be helpful in producing a synthetic RNA molecule that will be tolerated by a cell.

In some embodiments, the synthetic RNA has one or more modifications (e.g., modified 5' and/or 3' UTR sequences, optimized codons) that can enhance mRNA stability and/or translation efficiency in mammalian (e.g., human) cells. See US Pat. Publ. No. 20140206753, incorporated herein by reference in its entirety.

As used herein, the terms "transfect" or "transfection" mean the introduction of a nucleic acid, e.g., a synthetic RNA, e.g., modified mRNA into a cell, or preferably into a target cell. The introduced synthetic RNA (e.g., modified mRNA) may be stably or transiently maintained in the target cell. The term "transfection efficiency" refers to the relative amount of synthetic RNA (e.g., modified mRNA, inhibitory RNA) taken up by the target cell which is subject to transfection. In practice, transfection efficiency may be estimated by the amount of a reporter nucleic acid product expressed by the target cells following transfection. Preferred embodiments include compositions with high transfection efficacies and in particular those compositions that minimize adverse effects which are mediated by transfection of non-target cells. In some embodiments, compositions of the present invention that demonstrate high transfection efficacies improve the likelihood that appropriate dosages of the synthetic RNA (e.g., modified mRNA, inhibitory RNA) will be delivered to the target cell, while minimizing potential systemic adverse effects.

Methods of Screening

In some aspects, the invention is directed towards a method of screening for a modulator of a physiologic or pathologic process, comprising providing a cell (i.e., altered cell) having altered expression of a gene node or activity of a gene product of the gene node, and using the cell to screen compounds for modulators of a physiologic or pathologic process (e.g., a physiologic or pathologic process modeled by a method disclosed herein). In some embodiments, the cell is obtained by the methods disclosed herein. In some embodiments, the method of screening comprises contacting the altered cell with an agent (e.g., a small molecule, nucleic acid, antibody or polypeptide), and measuring a change in at least one phenotype, a change in expression of at least one gene, a change in activity of at least one protein, or a change in cell viability.

In a broad sense, "screening" can include any use of an array in which a test compound or agent having a selected effect (e.g., a potentially therapeutically useful effect) on cell phenotype is sought. Screening often includes assessing the effect of many (e.g., hundreds, thousands, or millions) of distinct test compounds, agents, or test compound/agent combinations on one or more cell phenotypes of interest. In some embodiments, a cell phenotype of interest is a "response" to a compound. A response can be, e.g., an increase or decrease in cell viability or cell proliferation, an alteration in one or more biological functions or processes of the cell, an alteration in expression or activity or subcellular localization or post-translational modification of one or more gene products, etc. A cell that exhibits a particular response of interest when contacted with a compound may be said to "respond" to the compound or to be "sensitive" to the compound. A cell that does not exhibit the response or exhibits a reduced response as compared, for example, with a sensitive cell may be said to be "resistant" to the compound. In many embodiments a cell response of interest in a culture environment (ex vivo) may correspond to or correlate with a response of interest in vivo (i.e., in a human or animal). For example, a reduction in cancer cell viability or proliferation in culture in response to a compound may correlate with reduction in cancer cell viability or proliferation in vivo and may result in therapeutic efficacy in a subject with cancer. Alternatively, a reduction in production of a toxic protein aggregate (e.g., α-syn aggregates) or a reduction in sensitivity to a toxic protein aggregate may correlate with efficacy in a patient with a proteinopathy. In some embodiments a screen is used to identify useful compound combinations or targets that would be useful to modulate (e.g., inhibit) in combination. A "combination therapy" typically refers to administration of two or more compounds sufficiently close together in time to achieve a biological effect (typically a therapeutically beneficial effect on a particular disease or condition) which is greater than or more beneficial or more prolonged than that which would be achieved if any of the compounds were administered at the same dose as a single agent or that would be useful to maintain efficacy (e.g., by inhibiting emergence of drug resistance). In some embodiments two or more compounds are administered at least once within 6 weeks or less of one another. Often, the two or more compounds may be administered within 24 or 48 hours of each other, or within up to 1, 2, 3, or 4 weeks of one another. In some embodiments they may be administered together in a single composition but often they would be administered separately and may be administered using different routes of administration or the same route of administration. Combination therapy may, for example, result in increased efficacy or permit use of lower doses of compounds, which can reduce side effects. Compounds used in a combination therapy may target the same target or pathway or may target different targets or pathways.

In some embodiments a screen may be performed using a cell type that may be of particular relevance with regard to a phenotype of interest, such as cells of a cell type that is affected in a disease for which a drug candidate or target is sought or that may be particularly vulnerable to an undesired side effect of a compound.

In some aspects, the invention is directed towards methods of screening for a compound to treat a pathologic process in an organism (e.g., human, eukaryote, mammal) comprising (a) modeling a physiologic or pathologic process in the organism by any method disclosed herein, (b) identifying a gene or protein node of the model of step (a), and screening compounds to identify a modulator of the identified gene or protein node. The pathological process may be any process disclosed herein. The methods of screening may be by any method disclosed herein or known in the art.

Methods of Determining a Target for Therapy

In some aspects, the invention is directed towards methods of determining one or more targets for therapy in an organism (e.g., eukaryote, human) with a physiologic or pathologic process (e.g., a neurodegenerative condition, disease, disorder) comprising (a) obtaining a model of a physiologic or pathologic process generated according to any of the methods disclosed herein; (b) identifying one or more gene or protein nodes of the model obtained in step (a), and (c) determining whether the organism harbors a mutation, altered expression, or altered activity in any of the gene or protein nodes identified in step (b). Any methods of determining whether the organism harbors a mutation, altered expression, or altered activity in a gene or protein known in the art may be used in the invention. In some embodiments, the method comprises sequencing the genome of the organism or relevant portions of the genome of the organism. In some embodiments, the method comprises assays for detection protein activity or protein concentration in the cell. In some embodiments, the method comprises detecting a degree of protein translation or transcription in the cell.

Methods of Modeling a Physiologic or Pathologic Process (Non-Augmented)

In some aspects, the invention is directed to methods of modeling a physiologic or pathologic process of first eukaryote (e.g., human) in a second eukaryote (e.g., yeast) comprising (a) providing a set of genes identified in the second eukaryote analogue of the physiologic or pathologic process of the first eukaryote; (b) obtaining interactions between the identified genes; and (c) creating a model of the physiologic or pathologic process. In some embodiments, the interactions in step (b) are obtained by using the Prize-Collecting Steiner Forest (PCSF) algorithm to connect gene or protein nodes through genetic interactions, physical interactions and annotated pathways from curated databases while minimizing costs to obtain a network. In some embodiments, methods disclosed herein and known in the art may be used to create the model (e.g., network) of the physiologic or pathologic process.

In some embodiments, the set of second eukaryote genes of step (a) were obtained by a method comprising providing a cell modified to have modulated gene expression or gene product activity, (b) determining whether the modification modulates the cell's response to a condition associated with the physiologic or pathologic process, and (c) identifying the gene as involved in the analogue of the physiologic or pathologic process when the cell response is modulated. In some embodiments, the condition associated with the physiologic or pathologic process comprises aberrant expression (e.g., over-expression, reduced expression, eliminated expression) of one or more genes. In some embodiments, the one or more genes comprise a non-endogenous gene. In some embodiments, the cell response comprises a change in at least one phenotype, a change in expression of at least one gene, a change in activity of at least one protein, or a change in cell viability. In some embodiments, the set of second eukaryote genes is obtained from a genome-wide screen of yeast genes.

In some embodiments, the methods further comprise using the PCSF algorithm with varied algorithm parameters to generate multiple networks and creating a representative network from the multiple networks with a maximum spanning tree algorithm.

Other aspects of the invention are directed to methods of screening for a compound to treat a pathologic process in a eukaryote, comprising modeling the physiologic or pathologic process in the eukaryote by the methods disclosed herein, identifying a gene or protein node of the model, and screening compounds to identify a modulator of the identified gene or protein node.

Cells and Methods: Human α-Synuclein Protein

In some embodiments, the invention is directed towards a cell comprising an expression construct comprising a promoter operably linked to a nucleic acid encoding a polypeptide comprising a human α-synuclein protein, wherein the cell has been modified to have increased or decreased expression or activity of a protein encoded by a yeast gene listed in any one or more of Table S3:first column, Table S5, Table S6, or Table S7, or has been modified to have increased or decreased expression or activity of a protein encoded by a mammalian homolog of such yeast gene as compared with an unmodified cell of the same type. In some embodiments, the expression construct comprises a promoter operably linked to a nucleic acid encoding a polypeptide comprising a human α-synuclein protein is integrated into the genome of the cell. In some embodiments, the promoter operably linked to a nucleic acid encoding a polypeptide comprising a human α-synuclein protein is an inducible promoter.

Mammalian homologs of yeast genes may be determined by any method disclosed herein. In some embodiments, mammalian homologs of yeast genes include homologs shown in Table S9, Table S10 or Table S11.

The promoter is not limited. In some embodiments, the promoter constitutively expresses the nucleic acid. The inducible promoter is not limited. The term "inducible promoter", as used herein, refers to a promoter that, in the absence of an inducer (such as a chemical and/or biological agent), does not direct expression, or directs low levels of expression of an operably linked gene (including cDNA), and, in response to an inducer, its ability to direct expression is enhanced. Exemplary inducible promoters include, for example, promoters that respond to heavy metals (CRC Boca Raton, Fla. (1991), 167-220; Brinster et al. Nature (1982), 296, 39-42), to thermal shocks, to hormones (Lee et al. P.N.A.S. USA (1988), 85, 1204-1208; (1981), 294, 228-232; Klock et al. Nature (1987), 329, 734-736; Israel and Kaufman, Nucleic Acids Res. (1989), 17, 2589-2604), promoters that respond to chemical agents, such as glucose, lactose, galactose or antibiotic (e.g., tetracycline or doxycycline). In some embodiments, the inducible promoter is a galactose inducible promoter.

The modification causing increased or decreased expression or activity of a protein encoded by a yeast gene may be by any method disclosed herein. In some aspects, the modification is a deletion, substitution, addition or disruption introduced in the genome of the cell (e.g., with a targetable nuclease). In some embodiments, the modification reduces the expression of a protein by modifying a regulatory sequence or by inhibiting mRNA translation (e.g., with an interfering nucleic acid). In some embodiments, expression is increased or decreased by changing the methylation of a regulatory sequence.

In some embodiments, the modification is the introduction into the cell an expression construct comprising a promoter operably linked to a nucleic acid encoding a protein encoded by a yeast gene listed in any one or more of Table S3: first column, Table S5, Table S6, or Table S7 or a mammalian homolog thereof. In some embodiments, the expression construct comprising a promoter operably linked to a nucleic acid encoding a protein encoded by a yeast gene listed in any one or more of Table S3:first column, Table S5, Table S6, or Table S7 or a mammalian homolog thereof is integrated in the genome of the cell. Methods and constructs for integrating an expression construct into a genome are known in the art. In some embodiments, a viral vector is used to integrate the expression construct. In some embodiments, homologous recombination is used to integrate the expression construct. In some embodiments, the integrated expression construct comprises or is under the control of an inducible promoter.

The cell may be any cell disclosed herein. In some embodiments, the cell is a yeast cell or a mammalian cell. In some embodiments, the cell is a yeast cell that harbors a deletion, disruption, or mutation in a gene listed in any one or more of Table S3:first column, Table S5, Table S6, or Table S7 or is a mammalian cell that harbors a deletion, disruption, or mutation in a mammalian homolog of such gene.

In some embodiments, the α-synuclein protein is a mutant α-synuclein protein. In some embodiments, the mutant α-synuclein protein shares about 90%, 91%, 92%, 93%, 94%, 95%, 96%, 97%, 98% or 99% sequence identity with a wild-type α-synuclein protein. In some embodiments the mutant α-synuclein protein comprises an A30P, E46K, A53T, H50Q, G51D, A18T, or A29S mutation.

In some embodiments, the yeast gene suppresses α-synuclein-mediated toxicity when overexpressed. In some embodiments, the yeast gene enhances α-synuclein-mediated toxicity when overexpressed. In some embodiments, deletion of the yeast gene enhances α-synuclein-mediated toxicity. In some embodiments, the yeast gene or mammalian homolog thereof is a hidden node (e.g., predicted node) in a α-synuclein toxicity network. In some embodiments, the mammalian homolog is listed in Table S9, Table S10 and/or Table S11.

Other aspects of the invention are related to a mammalian cell (e.g., human, mouse) that has been modified to have increased or decreased expression or activity of a mammalian protein encoded by a mammalian gene that is a homolog of a yeast gene listed in any of Table S3:first column, Table S5, Table S6, or Table S7 as compared with an unmodified cell of the same type. In some embodiments, the mammalian gene homolog is listed in Table S9, Table S10 and/or Table S11. In some embodiments, the cell comprises an expression construct comprising a promoter operably linked to a nucleic acid encoding a protein encoded by the mammalian gene homolog or harbors a deletion, disruption, or mutation in the mammalian gene homolog. The deletion disruption or mutation may be by any method disclosed herein. The promoter may be any suitable promoter known in the art and/or disclosed herein. In some embodiments, the promoter is an inducible promoter.

In some embodiments, the cell is a human cell derived from a subject suffering from a synucleinopathy or harbors a genetic variation associated with a synucleinopathy. In some embodiments, the synucleinopathy is selected from the group of dementia with Lewy bodies, multiple system atrophy with glial cytoplasmic inclusions, Shy-Drager syndrome, striatonigral degeneration, olivopontocerebellar atrophy, neurodegeneration with brain iron accumulation type 1, olfactory dysfunction, and amyotrophic lateral sclerosis. In some embodiments, synucleinopathy is selected from the group of Parkinson's disease (PD), dementia with Lewy bodies and multiple system atrophy.

In some embodiments, the cell (e.g., human cell) has increased expression of alpha-synuclein as compared to a normal mammalian cell of the same type or wherein the cell expresses a mutant α-synuclein protein, optionally wherein the mutant α-synuclein protein comprises A30P, E46K, A53T, H50Q, G51D, A18T, or A29S. In some embodiments, the cell (e.g., human cell) is a neural or glial cell.

Some aspects of the invention are directed towards identifying a compound that inhibits alpha-synuclein-mediated toxicity, the method comprising:

(a) providing a cell as described herein comprising an expression construct comprising a promoter operably linked to a nucleic acid encoding a polypeptide comprising a human α-synuclein protein, wherein the cell has been modified to have increased or decreased expression or activity of a protein encoded by a yeast gene listed in any one or more of Table S3:first column, Table S5, Table S6, or Table S7, or has been modified to have increased or decreased expression or activity of a protein encoded by a mammalian homolog of such yeast gene as compared with an unmodified cell of the same type;

(b) contacting the cell with an agent that modulates expression or activity of a protein encoded by a gene listed in Table S3:first column, Table S5, Table S6, or Table S7 or a mammalian homolog thereof; and (c) (i) measuring cell viability in the presence of the agent, wherein an increase in cell viability in the presence of the agent as compared to cell viability in the absence of the agent identifies the agent as a compound that inhibits alpha-synuclein-mediated toxicity or (ii) measuring at least one phenotype associated with alpha-synuclein-mediated toxicity in the cell, wherein a decrease in at least one phenotype associated with alpha-synuclein toxicity in the presence of the agent as compared to in the absence of the agent identifies the agent as a compound that inhibits alpha-synuclein-mediated toxicity.

Some aspects of the invention are directed towards a method of identifying a candidate agent for treatment of a synucleinopathy, the method comprising:

(a) providing a cell as described herein comprising an expression construct comprising a promoter operably linked to a nucleic acid encoding a polypeptide comprising a human α-synuclein protein, wherein the cell has been modified to have increased or decreased expression or activity of a protein encoded by a yeast gene listed in any one or more of Table S3:first column, Table S5, Table S6, or Table S7, or has been modified to have increased or decreased expression or activity of a protein encoded by a mammalian homolog of such yeast gene as compared with an unmodified cell of the same type;

(b) contacting the cell with an agent that modulates expression or activity of a protein encoded by a gene listed in Table S3:first column, Table S5, Table S6, or Table S7 or a mammalian homolog thereof; and (c) (i) measuring cell viability in the presence of the agent, wherein an increase in cell viability in the presence of the agent as compared to cell viability in the absence of the agent identifies the agent as a candidate agent for treatment of a synucleinopathy or (ii) measuring at least one phenotype associated with alpha-synuclein-mediated toxicity in the cell, wherein a decrease in at least one phenotype associated with alpha-synuclein toxicity in the presence of the agent as compared to in the absence of the agent identifies the agent as a candidate agent for treatment of a synucleinopathy.

In some embodiments of the above methods to identify a compound or candidate agent, the gene is one that suppresses alpha-synuclein toxicity when overexpressed or is one whose deletion enhances alpha-synuclein toxicity, and the agent enhances expression or activity of the protein. In some embodiments of the above methods to identify a compound or candidate agent, the gene is one that enhances alpha-synuclein toxicity when overexpressed or is one whose deletion suppresses alpha-synuclein toxicity when deleted, and the agent inhibits expression or activity of the protein.

Some aspects of the invention are directed to a method of identifying a compound that inhibits alpha-synuclein-mediated toxicity, the method comprising:
(a) providing a cell as described herein comprising an expression construct comprising a promoter operably linked to a nucleic acid encoding a polypeptide comprising a human α-synuclein protein, wherein the cell has been modified to have increased or decreased expression or activity of a protein encoded by a yeast gene listed in any one or more of Table S3:first column, Table S5, Table S6, or Table S7, or has been modified to have increased or decreased expression or activity of a protein encoded by a mammalian homolog of such yeast gene as compared with an unmodified cell of the same type;
(b) contacting the cell with a test agent; and
(c) (i) measuring cell viability in the presence of the agent, wherein an increase in cell viability in the presence of the test agent as compared to cell viability in the absence of the agent identifies the agent as a compound that inhibits alpha-synuclein-mediated toxicity or (ii) measuring at least one phenotype associated with alpha-synuclein-mediated toxicity in the cell, wherein a decrease in at least one phenotype associated with alpha-synuclein toxicity in the presence of the agent as compared to in the absence of the agent identifies the agent as a compound that inhibits alpha-synuclein-mediated toxicity.

Some aspects of the invention are directed to a method of identifying a candidate agent for treatment of a synucleinopathy, the method comprising:
(a) providing a cell as described herein comprising an expression construct comprising a promoter operably linked to a nucleic acid encoding a polypeptide comprising a human α-synuclein protein, wherein the cell has been modified to have increased or decreased expression or activity of a protein encoded by a yeast gene listed in any one or more of Table S3:first column, Table S5, Table S6, or Table S7, or has been modified to have increased or decreased expression or activity of a protein encoded by a mammalian homolog of such yeast gene as compared with an unmodified cell of the same type;
(b) contacting the cell with a test agent; and
(c) (i) measuring cell viability in the presence of the agent, wherein an increase in cell viability in the presence of the test agent as compared to cell viability in the absence of the agent identifies the agent as a candidate agent for treatment of a synucleinopathy or (ii) measuring at least one phenotype associated with alpha-synuclein-mediated toxicity in the cell, wherein a decrease in at least one phenotype associated with alpha-synuclein toxicity in the presence of the agent as compared to in the absence of the agent identifies the agent as a candidate agent for treatment of a synucleinopathy.

Some aspects of the invention are directed to a method of identifying a compound that inhibits alpha synuclein-mediated toxicity, the method comprising: screening to identify an agent that modulates expression or activity of a protein encoded by a gene listed in any one or more of Table S3:first column, Table S5, Table S6, or Table S7 or a mammalian homolog thereof; providing a cell expressing an amount of alpha synuclein that reduces viability of the cell; contacting the cell with the agent; and measuring cell viability in the presence of the agent, wherein an increase in cell viability in the presence of the agent as compared to cell viability in the absence of the agent identifies the agent as a compound that inhibits alpha synuclein-mediated toxicity.

In some embodiments, said screening comprises: providing a cell expressing a protein encoded by a gene listed in any one or more of Table S3:first column, Table S5, Table S6, or Table S7 or a mammalian homolog thereof; contacting the cell with an agent; and measuring the expression of the protein in the presence of the agent, wherein an increase in the expression of the protein in the presence of the agent as compared to the expression of the protein in the absence of the agent identifies the agent as a compound that increases the expression of the protein and wherein a decrease in the expression of the reporter protein in the presence of the agent as compared to the expression of the reporter protein in the absence of the agent identifies that agent as a compound that decreases the expression of the protein.

In some embodiments, said screening comprises: providing a cell comprising a reporter construct comprising (i) a promoter sequence of a gene listed in any one or more of Table S3:first column, Table S5, Table S6, or Table S7 or a mammalian homolog thereof and (ii) a nucleotide sequence encoding a reporter protein; contacting the cell with an agent; and measuring the expression of the reporter protein in the presence of the agent, wherein an increase in the expression of the reporter protein in the presence of the agent as compared to the expression of the protein in the absence of the agent identifies the agent as a compound that increases the expression of the protein and wherein a decrease in the expression of the reporter protein in the presence of the agent as compared to the expression of the reporter protein in the absence of the agent identifies that agent as a compound that decreases the expression of the protein.

In some embodiments, said screening comprises: providing a protein encoded by a gene listed in any one or more of Table S3:first column, Table S5, Table S6, or Table S7 or a mammalian homolog thereof; contacting the protein with an agent; and measuring the activity of the protein in the presence of the agent, wherein an increase in the activity of the protein in the presence of the agent as compared to the activity of the protein in the absence of the agent identifies the agent as a compound that increases the activity of the protein and wherein a decrease in the activity of the protein in the presence of the agent as compared to the activity of the protein in the absence of the agent identifies the agent as a compound that decreases the activity of the protein.

Some aspects of the invention are directed towards a method of inhibiting alpha-synuclein-mediated toxicity in a human cell or subject comprising modulating the expression or activity of a human protein that is a homolog of a yeast protein encoded by a yeast gene listed in any one or more of Table S3:first column, Table S5, Table S6, or Table S7 in the cell or subject.

Some aspects of the invention are directed towards a method of treating a synucleinopathy comprising modulating the expression or activity of a human protein that is a homolog of a yeast protein encoded by a yeast gene listed in any one or more of Table S3:first column, Table S5, Table S6, or Table S7 in a subject in need of treatment for a synucleinopathy.

In some embodiments of the above methods to inhibit alpha-synuclein-mediated toxicity or treat synucleinopathy, modulating the expression or activity of the human protein comprises enhancing the expression or activity of the human protein. The expression or activity of the human protein may be enhanced by any method disclosed herein or known in the art.

In some embodiments of the above methods to inhibit alpha-synuclein-mediated toxicity or treat synucleinopathy, the yeast gene is a suppressor of alpha-synuclein-mediated toxicity when overexpressed or is an enhancer of alpha-synuclein-mediated toxicity when deleted, and wherein modulating the expression or activity of the human protein comprises enhancing the expression or activity of the human protein. The expression or activity of the human protein may be enhanced by any method disclosed herein or known in the art.

In some embodiments of the above methods to inhibit alpha-synuclein-mediated toxicity or treat synucleinopathy, modulating the expression or activity of the human protein comprises inhibiting the expression or activity of the human protein. The expression or activity of the human protein may be inhibited by any method disclosed herein or known in the art.

In some embodiments of the above methods to inhibit alpha-synuclein-mediated toxicity or treat synucleinopathy, the yeast gene is an enhancer of alpha-synuclein-mediated toxicity when overexpressed or is a suppressor of alpha-synuclein-mediated toxicity when deleted, and wherein modulating the expression or activity of the human protein comprises inhibiting the expression or activity of the human protein. The expression or activity of the human protein may be inhibited by any method disclosed herein or known in the art.

In some embodiments of the methods disclosed herein, modulating the expression or activity of the human protein comprising contacting a cell with, or administering to a subject, an agent that modulates the expression or activity of the human protein. In some embodiments expression or activity of the human protein is enhanced, and the agent comprises a nucleic acid that encodes the human protein or a synthetic transcriptional activator that activates transcription of an RNA transcript that encodes the human protein. In some embodiments, expression or activity of the human protein is inhibited, and the agent is a short interfering RNA (siRNA) or antisense nucleic acid, targeted to mRNA encoding the human protein, a synthetic transcriptional repressor that represses transcription of a gene that encodes the human protein, or an aptamer, polypeptide, or small molecule that binds to the human protein.

In embodiments of the above disclosed methods, a human alpha-synuclein may be substituted with a eukaryote or mammalian (e.g., mouse, rat, old world or new world primate, pig, etc.) alpha-synuclein protein or homolog thereof. In some embodiments of the methods disclosed herein a human homolog of a yeast protein is listed in Table S9, Table S10 and/or Table S11.

Cells and Methods: Human TDP-43 Protein

In some embodiments, the invention is directed towards a cell comprising an expression construct comprising a promoter operably linked to a nucleic acid encoding a polypeptide comprising a human TDP-43 protein, wherein the cell is has been modified to have increased or decreased expression or activity of a protein encoded by a yeast gene listed in Table S3: second column, or has been modified to have increased or decreased expression or activity of a protein encoded by a mammalian homolog of such yeast gene as compared with an unmodified cell of the same type. In some embodiments, the expression construct comprises a promoter operably linked to a nucleic acid encoding a polypeptide comprising a human TDP-43 protein is integrated into the genome of the cell. In some embodiments, the promoter operably linked to a nucleic acid encoding a polypeptide comprising a human TDP-43 protein is an inducible promoter.

Mammalian homologs of yeast genes may be determined by any method disclosed herein. In some embodiments, mammalian homologs of yeast genes include homologs shown in Table S11.

The promoter is not limited. In some embodiments, the promoter constitutively expresses the nucleic acid. The inducible promoter is not limited. The term "inducible promoter", as used herein, refers to a promoter that, in the absence of an inducer (such as a chemical and/or biological agent), does not direct expression, or directs low levels of expression of an operably linked gene (including cDNA), and, in response to an inducer, its ability to direct expression is enhanced. Exemplary inducible promoters include, for example, promoters that respond to heavy metals (CRC Boca Raton, Fla. (1991), 167-220; Brinster et al. Nature (1982), 296, 39-42), to thermal shocks, to hormones (Lee et al. P.N.A.S. USA (1988), 85, 1204-1208; (1981), 294, 228-232; Klock et al. Nature (1987), 329, 734-736; Israel and Kaufmnan, Nucleic Acids Res. (1989), 17, 2589-2604), promoters that respond to chemical agents, such as glucose, lactose, galactose or antibiotic (e.g., tetracycline or doxycycline). In some embodiments, the inducible promoter is a galactose inducible promoter.

The modification causing increased or decreased expression or activity of a protein encoded by a yeast gene may be by any method disclosed herein. In some aspects, the modification is a deletion, substitution, addition or disruption introduced in the genome of the cell (e.g., with a targetable nuclease). In some embodiments, the modification reduces the expression of a protein by modifying a regulatory sequence or by inhibiting mRNA translation (e.g., with an interfering nucleic acid). In some embodiments, expression is increased or decreased by changing the methylation of a regulatory sequence.

In some embodiments, the modification is the introduction into the cell an expression construct comprising a promoter operably linked to a nucleic acid encoding a protein encoded by a yeast gene listed in Table S3: second column or a mammalian homolog thereof.

In some embodiments, the expression construct comprising a promoter operably linked to a nucleic acid encoding a protein encoded by a yeast gene listed in Table S3: second column or a mammalian homolog thereof is integrated in the genome of the cell. Methods and constructs for integrating an expression construct into a genome are known in the art. In some embodiments, a viral vector is used to integrate the expression construct. In some embodiments, homologous recombination is used to integrate the expression construct. In some embodiments, the integrated expression construct comprises or is under the control of an inducible promoter.

The cell may be any cell disclosed herein. In some embodiments, the cell is a yeast cell or a mammalian cell. In some embodiments, the cell is a yeast cell that harbors a deletion, disruption, or mutation in a gene listed in Table S3: second column or is a mammalian cell that harbors a deletion, disruption, or mutation in a mammalian homolog (e.g., human) of such gene.

In some embodiments, the TDP-43 protein is a mutant TDP-43 protein. In some embodiments, the mutant TDP-43 shares about 90%, 91%, 92%, 93%, 94%, 95%, 96%, 97%, 98% or 99% sequence identity with a wild-type TDP-43.

In some embodiments, the yeast gene suppresses TDP-43-mediated toxicity when overexpressed. In some embodiments, the yeast gene enhances TDP-43-mediated toxicity when overexpressed. In some embodiments, deletion of the yeast gene enhances TDP-43-mediated toxicity. In some embodiments, the yeast gene or mammalian homolog thereof is a hidden node (e.g., predicted node) in a TDP-43 network.

Other aspects of the invention are related to a mammalian cell (e.g., human, mouse) that has been modified to have increased or decreased expression or activity of a mammalian protein encoded by a mammalian gene that is a homolog of a yeast gene listed in Table S3: second column as compared with an unmodified cell of the same type. In some embodiments, the cell comprises an expression construct comprising a promoter operably linked to a nucleic acid encoding a protein encoded by the mammalian gene homolog or harbors a deletion, disruption, or mutation in the mammalian gene homolog. The deletion disruption or mutation may be by any method disclosed herein. The promoter may be any suitable promoter known in the art and/or disclosed herein. In some embodiments, the promoter is an inducible promoter.

In some embodiments, the cell is a human cell derived from a subject suffering from a TDP-43-associated disease or harbors a genetic variation associated with a TDP-43-associated disease. In some embodiments, the cell has increased expression of TDP-43 as compared to a normal mammalian cell of the same type or wherein the cell expresses a mutant TDP-43 protein. In some embodiments, the cell (e.g., human cell) is a neural or glial cell.

Some aspects of the invention are directed towards identifying a compound that inhibits TDP-43-mediated toxicity, the method comprising:
(a) providing a cell as described herein comprising an expression construct comprising a promoter operably linked to a nucleic acid encoding a polypeptide comprising a human TDP-43 protein, wherein the cell has been modified to have increased or decreased expression or activity of a protein encoded by a yeast gene listed in Table S3:second column, or has been modified to have increased or decreased expression or activity of a protein encoded by a mammalian homolog of such yeast gene as compared with an unmodified cell of the same type;
(b) contacting the cell with an agent that modulates expression or activity of a protein encoded by a gene listed in Table S3:second column, or a mammalian homolog thereof; and
(c) (i) measuring cell viability in the presence of the agent, wherein an increase in cell viability in the presence of the agent as compared to cell viability in the absence of the agent identifies the agent as a compound that inhibits TDP-43-mediated toxicity or (ii) measuring at least one phenotype associated with TDP-43-mediated toxicity in the cell, wherein a decrease in at least one phenotype associated with TDP-43 toxicity in the presence of the agent as compared to in the absence of the agent identifies the agent as a compound that inhibits TDP-43-mediated toxicity.

Some aspects of the invention are directed towards a method of identifying a candidate agent for treatment of a TDP-43-mediated toxicity, the method comprising:
(a) providing a cell as described herein comprising an expression construct comprising a promoter operably linked to a nucleic acid encoding a polypeptide comprising a human α-synuclein protein, wherein the cell has been modified to have increased or decreased expression or activity of a protein encoded by a yeast gene listed in Table S3:second column, or has been modified to have increased or decreased expression or activity of a protein encoded by a mammalian homolog of such yeast gene as compared with an unmodified cell of the same type;
(b) contacting the cell with an agent that modulates expression or activity of a protein encoded by a gene listed in Table S3:second column, or a mammalian homolog thereof; and
(c) (i) measuring cell viability in the presence of the agent, wherein an increase in cell viability in the presence of the agent as compared to cell viability in the absence of the agent identifies the agent as a candidate agent for treatment of a TDP-43-mediated toxicity or (ii) measuring at least one phenotype associated with TDP-43-mediated toxicity in the cell, wherein a decrease in at least one phenotype associated with TDP-43 toxicity in the presence of the agent as compared to in the absence of the agent identifies the agent as a candidate agent for treatment of a TDP-43-mediated toxicity.

In some embodiments of the above methods to identify a compound or candidate agent, the gene is one that that suppresses TDP-43 toxicity when overexpressed or is one whose deletion enhances TDP-43 toxicity, and the agent enhances expression or activity of the protein. In some embodiments of the above methods to identify a compound or candidate agent, the gene is one that that enhances TDP-43 toxicity when overexpressed or is one whose deletion suppresses TDP-43 toxicity when deleted, and the agent inhibits expression or activity of the protein.

Some aspects of the invention are directed to methods of identifying a compound that inhibits TDP-43-mediated toxicity, the methods comprising:
(a) providing a cell as described herein comprising an expression construct comprising a promoter operably linked to a nucleic acid encoding a polypeptide comprising a TDP-43 protein, wherein the cell has been modified to have increased or decreased expression or activity of a protein encoded by a yeast gene listed in Table S3:second column, or has been modified to have increased or decreased expression or activity of a protein encoded by a mammalian homolog of such yeast gene as compared with an unmodified cell of the same type;
(b) contacting the cell with a test agent; and
(c) (i) measuring cell viability in the presence of the agent, wherein an increase in cell viability in the presence of the test agent as compared to cell viability in the absence of the agent identifies the agent as a compound that inhibits TDP-43-mediated toxicity or (ii) measuring at least one phenotype associated with TDP-43-mediated toxicity in the cell, wherein a decrease in at least one phenotype associated with TDP-43 toxicity in the presence of the agent as compared to in the absence of the agent identifies the agent as a compound that inhibits TDP-43-mediated toxicity.

Some aspects of the invention are directed to a method of identifying a candidate agent for treatment of a TDP-43-associated disease, the method comprising:
(a) providing a cell as described herein comprising an expression construct comprising a promoter operably linked to a nucleic acid encoding a polypeptide comprising a human TDP-43 protein, wherein the cell has been modified to have increased or decreased expression or activity of a protein encoded by a yeast gene listed in Table S3:second column, or has been modified to have increased or decreased expression or activity of a protein encoded by a mammalian homolog of such yeast gene as compared with an unmodified cell of the same type;
(b) contacting the cell with a test agent; and
(c) (i) measuring cell viability in the presence of the agent, wherein an increase in cell viability in the presence of the test agent as compared to cell viability in the absence of the agent identifies the agent as a candidate agent for treatment of a TDP-43-associated disease or
(ii) measuring at least one phenotype associated with TDP-43-mediated toxicity in the cell, wherein a decrease in at least one phenotype associated with TDP-43 toxicity in the presence of the agent as compared to in the absence of the agent identifies the agent as a candidate agent for treatment of a TDP-43-associated disease.

Some aspects of the invention are directed to a method of identifying a compound that inhibits TDP-43-mediated toxicity, the method comprising: screening to identify an agent that enhances expression or activity of a protein encoded by a gene listed in Table S3: second column or a mammalian homolog thereof; providing a cell expressing an amount of TDP-43 that reduces viability of the cell; contacting the cell with the agent; and measuring cell viability in the presence of the agent, wherein an increase in cell viability in the presence of the agent as compared to cell viability in the absence of the agent identifies the agent as a compound that inhibits TDP-43-mediated toxicity.

In some embodiments, said screening comprises: providing a cell expressing a protein encoded by a gene listed in Table S3: second column or a mammalian homolog thereof; contacting the cell with an agent; and measuring the expression of the protein in the presence of the agent, wherein an increase in the expression of the protein in the presence of the agent as compared to the expression of the protein in the absence of the agent identifies the agent as a compound that increases the expression of the protein, and wherein a decrease in the expression of the protein in the presence of the agent as compared to the expression of the protein in the absence of the agent identifies that agent as a compound that decreases the expression of the protein.

In some embodiments, said screening comprises: providing a cell comprising a reporter construct comprising (i) a promoter sequence of a gene listed in Table S3: second column or a mammalian homolog thereof and (ii) a nucleotide sequence encoding a reporter protein; contacting the cell with an agent; and measuring the expression of the reporter protein in the presence of the agent, wherein an increase in the expression of the reporter protein in the presence of the agent as compared to the expression of the protein in the absence of the agent identifies the agent as a compound that increases the expression of the protein, and wherein a decrease in the expression of the reporter protein in the presence of the agent as compared to the expression of the reporter protein in the absence of the agent identifies that agent as a compound that decreases the expression of the protein.

In some embodiments, said screening comprises: providing a protein encoded by a gene listed in Table S3: second column or a mammalian homolog thereof; contacting the protein with an agent; and measuring the activity of the protein in the presence of the agent, wherein an increase in the activity of the protein in the presence of the agent as compared to the activity of the protein in the absence of the agent identifies the agent as a compound that increases the activity of the protein, and wherein a decrease in the activity of the protein in the presence of the agent as compared to the activity of the protein in the absence of the agent identifies the agent as a compound that decreases the activity of the protein.

Some aspects of the invention are directed towards a method of inhibiting TDP-43-mediated toxicity in a human cell or subject comprising modulating the expression or activity of a human protein that is homolog of a yeast protein encoded by a yeast gene listed in Table S3: second column in the cell or subject.

Some aspects of the invention are directed towards a method of treating a TDP-43-associated disease comprising modulating the expression or activity of a human protein that is a homolog of a yeast protein encoded by a yeast gene listed in Table S3: second column in a subject in need of treatment for a TDP-43-associated disease.

In some embodiments of the above methods to inhibit TDP-43-mediated toxicity or treat TDP-43 toxicity, modulating the expression or activity of the human protein comprises enhancing the expression or activity of the human protein. The expression or activity of the human protein may be enhanced by any method disclosed herein or known in the art.

In some embodiments of the above methods to inhibit TDP-43-mediated toxicity or treat TDP-43 toxicity, the yeast gene is a suppressor of TDP-43-mediated toxicity when overexpressed or is an enhancer of TDP-43-mediated toxicity when deleted, and wherein modulating the expression or activity of the human protein comprises enhancing the expression or activity of the human protein. The expression or activity of the human protein may be enhanced by any method disclosed herein or known in the art.

In some embodiments of the above methods to inhibit TDP-43-mediated toxicity or treat TDP-43 toxicity, modulating the expression or activity of the human protein comprises inhibiting the expression or activity of the human protein. The expression or activity of the human protein may be inhibited by any method disclosed herein or known in the art.

In some embodiments of the above methods to inhibit TDP-43-mediated toxicity or treat TDP-43 toxicity, the yeast gene is an enhancer of TDP-43-mediated toxicity when overexpressed or is a suppressor of TDP-43-mediated toxicity when deleted, and wherein modulating the expression or activity of the human protein comprises inhibiting the expression or activity of the human protein. The expression or activity of the human protein may be inhibited by any method disclosed herein or known in the art.

In some embodiments of the methods disclosed herein, modulating the expression or activity of the human protein comprising contacting a cell with, or administering to a subject, an agent that modulates the expression or activity of the human protein. In some embodiments expression or activity of the human protein is enhanced, and the agent comprises a nucleic acid that encodes the human protein or a synthetic transcriptional activator that activates transcription of an RNA transcript that encodes the human protein. In some embodiments, expression or activity of the human protein is inhibited, and the agent is a short interfering RNA (siRNA) or antisense nucleic acid, targeted to mRNA encoding the human protein, a synthetic transcriptional repressor that represses transcription of a gene that encodes the human protein, or an aptamer, polypeptide, or small molecule that binds to the human protein.

In embodiments of the above disclosed methods, a human TDP-43 may be substituted with a eukaryote or mammalian (e.g., mouse, rat, old world or new world primate, pig, etc.) TDP-43 protein or homolog thereof. In some embodiments of the methods disclosed herein a human homolog of a yeast protein is listed in Table S11.

Cells and Methods: Human Amyloid Beta Protein

In some embodiments, the invention is directed towards a cell comprising an expression construct comprising a promoter operably linked to a nucleic acid encoding a polypeptide comprising a human amyloid beta protein, wherein the cell is has been modified to have increased or decreased expression or activity of a protein encoded by a yeast gene listed in Table S3: third column, or has been modified to have increased or decreased expression or activity of a protein encoded by a mammalian homolog of such yeast gene as compared with an unmodified cell of the same type. In some embodiments, the expression construct comprises a promoter operably linked to a nucleic acid encoding a polypeptide comprising a human amyloid beta protein is integrated into the genome of the cell. In some embodiments, the promoter operably linked to a nucleic acid encoding a polypeptide comprising a human amyloid beta protein is an inducible promoter.

Mammalian homologs of yeast genes may be determined by any method disclosed herein. In some embodiments, mammalian homologs of yeast genes include homologs shown in Table S11.

The promoter is not limited. In some embodiments, the promoter constitutively expresses the nucleic acid. The inducible promoter is not limited. The term "inducible promoter", as used herein, refers to a promoter that, in the absence of an inducer (such as a chemical and/or biological agent), does not direct expression, or directs low levels of expression of an operably linked gene (including cDNA), and, in response to an inducer, its ability to direct expression is enhanced. Exemplary inducible promoters include, for example, promoters that respond to heavy metals (CRC Boca Raton, Fla. (1991), 167-220; Brinster et al. Nature (1982), 296, 39-42), to thermal shocks, to hormones (Lee et al. P.N.A.S. USA (1988), 85, 1204-1208; (1981), 294, 228-232; Klock et al. Nature (1987), 329, 734-736; Israel and Kaufman, Nucleic Acids Res. (1989), 17, 2589-2604), promoters that respond to chemical agents, such as glucose, lactose, galactose or antibiotic (e.g., tetracycline or doxycycline). In some embodiments, the inducible promoter is a galactose inducible promoter.

The modification causing increased or decreased expression or activity of a protein encoded by a yeast gene may be by any method disclosed herein. In some aspects, the modification is a deletion, substitution, addition or disruption introduced in the genome of the cell (e.g., with a targetable nuclease). In some embodiments, the modification reduces the expression of a protein by modifying a regulatory sequence or by inhibiting mRNA translation (e.g., with an interfering nucleic acid). In some embodiments, expression is increased or decreased by changing the methylation of a regulatory sequence.

In some embodiments, the modification is the introduction into the cell an expression construct comprising a promoter operably linked to a nucleic acid encoding a protein encoded by a yeast gene listed in Table S3: third column or a mammalian homolog thereof.

In some embodiments, the expression construct comprising a promoter operably linked to a nucleic acid encoding a protein encoded by a yeast gene listed in Table S3: third column or a mammalian homolog thereof is integrated in the genome of the cell. Methods and constructs for integrating an expression construct into a genome are known in the art. In some embodiments, a viral vector is used to integrate the expression construct. In some embodiments, homologous recombination is used to integrate the expression construct. In some embodiments, the integrated expression construct comprises or is under the control of an inducible promoter.

The cell may be any cell disclosed herein. In some embodiments, the cell is a yeast cell or a mammalian cell. In some embodiments, the cell is a yeast cell that harbors a deletion, disruption, or mutation in a gene listed in Table S3: third column or is a mammalian cell that harbors a deletion, disruption, or mutation in a mammalian homolog (e.g., human) of such gene.

In some embodiments, the amyloid beta protein is a mutant amyloid beta protein. In some embodiments, the mutant amyloid beta shares about 90%, 91%, 92%, 93%, 94%, 95%, 96%, 97%, 98% or 99% sequence identity with a wild-type amyloid beta.

In some embodiments, the yeast gene suppresses amyloid beta-mediated toxicity when overexpressed. In some embodiments, the yeast gene enhances amyloid beta-mediated toxicity when overexpressed. In some embodiments, deletion of the yeast gene enhances amyloid beta-mediated toxicity. In some embodiments, the yeast gene or mammalian homolog thereof is a hidden node (e.g., predicted node) in a amyloid beta network.

Other aspects of the invention are related to a mammalian cell (e.g., human, mouse) that has been modified to have increased or decreased expression or activity of a mammalian protein encoded by a mammalian gene that is a homolog of a yeast gene listed in Table S3: third column as compared with an unmodified cell of the same type. In some embodiments, the cell comprises an expression construct comprising a promoter operably linked to a nucleic acid encoding a protein encoded by the mammalian gene homolog or harbors a deletion, disruption, or mutation in the mammalian gene homolog. The deletion disruption or mutation may be by any method disclosed herein. The promoter may be any suitable promoter known in the art and/or disclosed herein. In some embodiments, the promoter is an inducible promoter.

In some embodiments, the cell is a human cell derived from a subject suffering from an amyloid beta-associated disease or harbors a genetic variation associated with a amyloid beta-associated disease. In some embodiments, the cell has increased expression of amyloid beta as compared to a normal mammalian cell of the same type or wherein the cell expresses a mutant amyloid beta protein. In some embodiments, the cell (e.g., human cell) is a neural or glial cell.

Some aspects of the invention are directed towards identifying a compound that inhibits amyloid beta-mediated toxicity, the method comprising:
  (a) providing a cell as described herein comprising an expression construct comprising a promoter operably linked to a nucleic acid encoding a polypeptide comprising a human amyloid beta protein, wherein the cell has been modified to have increased or decreased expression or activity of a protein encoded by a yeast gene listed in Table S3:third column, or has been modified to have increased or decreased expression or activity of a protein encoded by a mammalian homolog of such yeast gene as compared with an unmodified cell of the same type;
- (b) contacting the cell with an agent that modulates expression or activity of a protein encoded by a gene listed in Table S3:third column, or a mammalian homolog thereof; and
- (c) (i) measuring cell viability in the presence of the agent, wherein an increase in cell viability in the presence of the agent as compared to cell viability in the absence of the agent identifies the agent as a compound that inhibits amyloid beta-mediated toxicity or (ii) measuring at least one phenotype associated with amyloid beta-mediated toxicity in the cell, wherein a decrease in at least one phenotype associated with amyloid beta toxicity in the presence of the agent as compared to in the absence of the agent identifies the agent as a compound that inhibits amyloid beta-mediated toxicity.

Some aspects of the invention are directed towards a method of identifying a candidate agent for treatment of a amyloid beta-mediated toxicity, the method comprising:
- (a) providing a cell as described herein comprising an expression construct comprising a promoter operably linked to a nucleic acid encoding a polypeptide comprising a human α-synuclein protein, wherein the cell has been modified to have increased or decreased expression or activity of a protein encoded by a yeast gene listed in Table S3:third column, or has been modified to have increased or decreased expression or activity of a protein encoded by a mammalian homolog of such yeast gene as compared with an unmodified cell of the same type;
- (b) contacting the cell with an agent that modulates expression or activity of a protein encoded by a gene listed in Table S3:third column, or a mammalian homolog thereof; and
- (c) (i) measuring cell viability in the presence of the agent, wherein an increase in cell viability in the presence of the agent as compared to cell viability in the absence of the agent identifies the agent as a candidate agent for treatment of a amyloid beta-mediated toxicity or (ii) measuring at least one phenotype associated with amyloid beta-mediated toxicity in the cell, wherein a decrease in at least one phenotype associated with amyloid beta toxicity in the presence of the agent as compared to in the absence of the agent identifies the agent as a candidate agent for treatment of a amyloid beta-mediated toxicity.

In some embodiments of the above methods to identify a compound or candidate agent, the gene is one that that suppresses amyloid beta toxicity when overexpressed or is one whose deletion enhances amyloid beta toxicity, and the agent enhances expression or activity of the protein. In some embodiments of the above methods to identify a compound or candidate agent, the gene is one that that enhances amyloid beta toxicity when overexpressed or is one whose deletion suppresses amyloid beta toxicity when deleted, and the agent inhibits expression or activity of the protein.

Some aspects of the invention are directed to methods of identifying a compound that inhibits amyloid beta-mediated toxicity, the methods comprising:
- (a) providing a cell as described herein comprising an expression construct comprising a promoter operably linked to a nucleic acid encoding a polypeptide comprising a amyloid beta protein, wherein the cell has been modified to have increased or decreased expression or activity of a protein encoded by a yeast gene listed in Table S3:third column, or has been modified to have increased or decreased expression or activity of a protein encoded by a mammalian homolog of such yeast gene as compared with an unmodified cell of the same type;
- (b) contacting the cell with a test agent; and
- (c) (i) measuring cell viability in the presence of the agent, wherein an increase in cell viability in the presence of the test agent as compared to cell viability in the absence of the agent identifies the agent as a compound that inhibits amyloid beta-mediated toxicity or (ii) measuring at least one phenotype associated with amyloid beta-mediated toxicity in the cell, wherein a decrease in at least one phenotype associated with amyloid beta toxicity in the presence of the agent as compared to in the absence of the agent identifies the agent as a compound that inhibits amyloid beta-mediated toxicity.

Some aspects of the invention are directed to a method of identifying a candidate agent for treatment of a amyloid beta-associated disease, the method comprising:
- (a) providing a cell as described herein comprising an expression construct comprising a promoter operably linked to a nucleic acid encoding a polypeptide comprising a human amyloid beta protein, wherein the cell has been modified to have increased or decreased expression or activity of a protein encoded by a yeast gene listed in Table S3:third column, or has been modified to have increased or decreased expression or activity of a protein encoded by a mammalian homolog of such yeast gene as compared with an unmodified cell of the same type;
- (b) contacting the cell with a test agent; and
- (c) (i) measuring cell viability in the presence of the agent, wherein an increase in cell viability in the presence of the test agent as compared to cell viability in the absence of the agent identifies the agent as a candidate agent for treatment of a amyloid beta-associated disease or (ii) measuring at least one phenotype associated with amyloid beta-mediated toxicity in the cell, wherein a decrease in at least one phenotype associated with amyloid beta toxicity in the presence of the agent as compared to in the absence of the agent identifies the agent as a candidate agent for treatment of a amyloid beta-associated disease.

Some aspects of the invention are directed to a method of identifying a compound that inhibits amyloid beta-mediated toxicity, the method comprising: screening to identify an agent that enhances expression or activity of a protein encoded by a gene listed in Table S3: third column or a mammalian homolog thereof; providing a cell expressing an amount of amyloid beta that reduces viability of the cell; contacting the cell with the agent; and measuring cell viability in the presence of the agent, wherein an increase in cell viability in the presence of the agent as compared to cell viability in the absence df the agent identifies the agent as a compound that inhibits amyloid beta-mediated toxicity.

In some embodiments, said screening comprises: providing a cell expressing a protein encoded by a gene listed in Table S3: third column or a mammalian homolog thereof; contacting the cell with an agent; and measuring the expression of the protein in the presence of the agent, wherein an increase in the expression of the protein in the presence of the agent as compared to the expression of the protein in the absence of the agent identifies the agent as a compound that increases the expression of the protein, and wherein a decrease in the expression of the protein in the presence of the agent as compared to the expression of the protein in the absence of the agent identifies that agent as a compound that decreases the expression of the protein.

In some embodiments, said screening comprises: providing a cell comprising a reporter construct comprising (i) a promoter sequence of a gene listed in Table S3: third column or a mammalian homolog thereof and (ii) a nucleotide sequence encoding a reporter protein; contacting the cell with an agent; and measuring the expression of the reporter protein in the presence of the agent, wherein an increase in the expression of the reporter protein in the presence of the agent as compared to the expression of the protein in the absence of the agent identifies the agent as a compound that increases the expression of the protein, and wherein a decrease in the expression of the reporter protein in the presence of the agent as compared to the expression of the reporter protein in the absence of the agent identifies that agent as a compound that decreases the expression of the protein.

In some embodiments, said screening comprises: providing a protein encoded by a gene listed in Table S3: third column or a mammalian homolog thereof; contacting the protein with an agent; and measuring the activity of the protein in the presence of the agent, wherein an increase in the activity of the protein in the presence of the agent as compared to the activity of the protein in the absence of the agent identifies the agent as a compound that increases the activity of the protein, and wherein a decrease in the activity of the protein in the presence of the agent as compared to the activity of the protein in the absence of the agent identifies the agent as a compound that decreases the activity of the protein.

Some aspects of the invention are directed towards a method of inhibiting amyloid beta-mediated toxicity in a human cell or subject comprising modulating the expression or activity of a human protein that is homolog of a yeast protein encoded by a yeast gene listed in Table S3: third column in the cell or subject.

Some aspects of the invention are directed towards a method of treating a amyloid beta-associated disease comprising modulating the expression or activity of a human protein that is a homolog of a yeast protein encoded by a yeast gene listed in Table S3: third column in a subject in need of treatment for a amyloid beta-associated disease.

In some embodiments of the above methods to inhibit amyloid beta-mediated toxicity or treat amyloid beta toxicity, modulating the expression or activity of the human protein comprises enhancing the expression or activity of the human protein. The expression or activity of the human protein may be enhanced by any method disclosed herein or known in the art.

In some embodiments of the above methods to inhibit amyloid beta-mediated toxicity or treat amyloid beta toxicity, the yeast gene is a suppressor of amyloid beta-mediated toxicity when overexpressed or is an enhancer of amyloid beta-mediated toxicity when deleted, and wherein modulating the expression or activity of the human protein comprises enhancing the expression or activity of the human protein. The expression or activity of the human protein may be enhanced by any method disclosed herein or known in the art.

In some embodiments of the above methods to inhibit amyloid beta-mediated toxicity or treat amyloid beta toxicity, modulating the expression or activity of the human protein comprises inhibiting the expression or activity of the human protein. The expression or activity of the human protein may be inhibited by any method disclosed herein or known in the art.

In some embodiments of the above methods to inhibit amyloid beta-mediated toxicity or treat amyloid beta toxicity, the yeast gene is an enhancer of amyloid beta-mediated toxicity when overexpressed or is a suppressor of amyloid beta-mediated toxicity when deleted, and wherein modulating the expression or activity of the human protein comprises inhibiting the expression or activity of the human protein. The expression or activity of the human protein may be inhibited by any method disclosed herein or known in the art.

In some embodiments of the methods disclosed herein, modulating the expression or activity of the human protein comprising contacting a cell with, or administering to a subject, an agent that modulates the expression or activity of the human protein. In some embodiments expression or activity of the human protein is enhanced, and the agent comprises a nucleic acid that encodes the human protein or a synthetic transcriptional activator that activates transcription of an RNA transcript that encodes the human protein. In some embodiments, expression or activity of the human protein is inhibited, and the agent is a short interfering RNA (siRNA) or antisense nucleic acid, targeted to mRNA encoding the human protein, a synthetic transcriptional repressor that represses transcription of a gene that encodes the human protein, or an aptamer, polypeptide, or small molecule that binds to the human protein.

In embodiments of the above disclosed methods, a human amyloid beta may be substituted with a eukaryote or mammalian (e.g., mouse, rat, old world or new world primate, pig, etc.) amyloid beta protein or homolog thereof.

In some embodiments of the methods disclosed herein a human homolog of a yeast protein is listed in Table S11.

Non-Transitory Medium and Systems

In some embodiments, any results of the methods described herein may be stored on a non-transitory computer-readable medium. In some embodiments druggable nodes identified using the methods, and optionally compounds that modulate such druggable nodes, may be stored on a non-transitory computer-readable medium. In some embodiments, networks or models created by the methods described herein or described herein may be stored on a non-transitory computer-readable medium.

Some aspects of the invention are directed towards a system configured to facilitate the methods described herein, the system comprising: a computer system comprising one or more processors programmed to execute one or more computer-executable instructions which, when executed, causes the computer system to perform at least one of the steps of the methods described herein. In some embodiments, system is configured to facilitate determining homology between genes in a first eukaryote (e.g., human) and a second eukaryote (e.g., yeast), the system comprising: a computer system comprising one or more processors programmed to execute one or more computer-executable instructions which, when executed, cause the computer system to determine a set of genes in the first eukaryote homologous to a set of genes in a second eukaryote and/or create a model of the physiologic or pathologic process in a eukaryote by augmenting interactions between the set of genes with interactions from homologous set of genes from a second eukaryote. In some embodiments, the system further comprises a screen for displaying a model generated by any of the methods disclosed herein.

Specific examples of the inventions disclosed herein are set forth below in the Examples.

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more nucleic acids, polypeptides, cells, species or types of organism, disorders, subjects, or combinations thereof, can be excluded.

Where the claims or description relate to a composition of matter, e.g., a nucleic acid, polypeptide, cell, or non-human transgenic animal, it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., it is to be understood that methods of making compositions useful for performing the method, and products produced according to the method, are aspects of the invention, unless otherwise indicated or unless it would be evident to one of ordinary skill in the art that a contradiction or inconsistency would arise.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated".

EXAMPLES

Figure 1A:
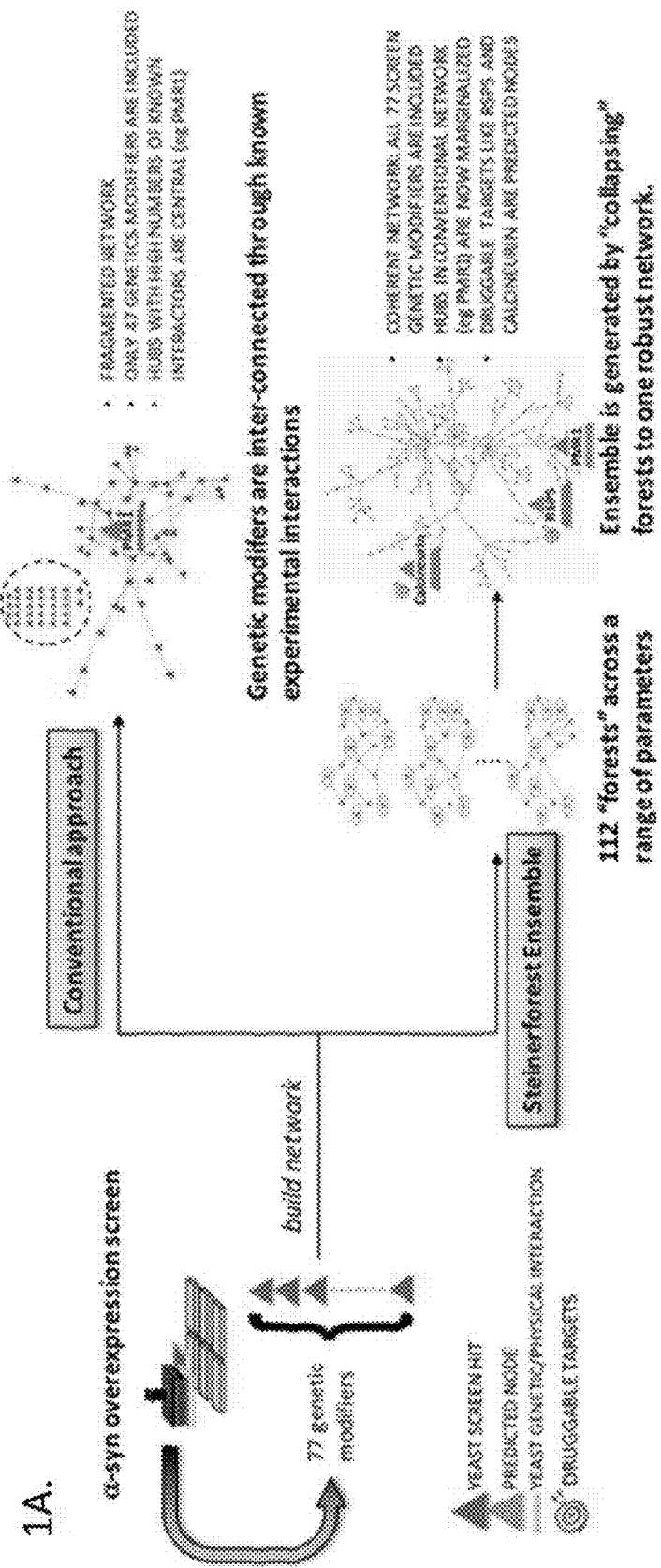
FIG. 1A-FIG. 1C show SteinerForest Ensemble builds proteotoxicity networks for yeast and uncovers druggable targets.

SteinerForest Ensemble Networks Uncover Biological Connections Between α-Syn Screen Hits One conventional approach to creating a network from a gene list is to connect them via known genetic or physical protein-protein interactions. To illustrate, we considered 77 genes that modify α-syn toxicity in our previous overexpression screen (Table S1 and Table S2). Even with the rich yeast interactome, 30 hits were not incorporated into the network (FIG. 1A, upper panel). Moreover, some genes ("hubs") occupied a central position in the network, not because of their importance to proteotoxicity, but because they were connected to more genes. For example, PMR1 is a hub that has 955 annotated interactions in BioGRID compared to the median of 70 interactions across the 77 modifiers (FIG. 1A, upper right; Table S2).

TABLE S1: INDEX OF NETWORKS GENERATED IN THIS STUDY, Related to FIGS. 1, 2 and 3.

TABLE S2: YEAST MODIFIERS RECOVERED IN PREVIOUS OVEREXPRESSION SCREENS, Related to FIGS. 1 and 2.

To build more inclusive networks, we adapted the "Prize-collecting Steiner Forest (PCSF) algorithm", which connects gene or protein "nodes" through molecular interactions, or "edges" (S.-S. C. Huang and Fraenkel, 2009; Tuncbag et al., 2013; 2016) (FIG. 1A, lower). Edges can include genetic or physical interactions, or annotated pathways from curated databases (Szklarczyk et al., 2014) and are refined by minimizing "cost." Costs increase 1) when a "prized" node (an original hit from a genetic screen) is excluded; 2) when an "edge" connecting two nodes derives from a low-confidence interaction; or 3) when edges connect to hubs. To ensure that our PCSFs were not dependent on specific parameterization, we generated an ensemble of 112 individual forests with different algorithm parameters, and created an averaged, or "collapsed", representative network through a maximum spanning-tree algorithm ("Steinernet Ensemble'"; FIG. 1A, lower right).

To encompass the largest number of prized nodes while avoiding unlikely interactions, the PCSF method introduces "predicted nodes", which are proteins or genes not part of the original prized hit list, (FIG. 1A, green triangles). Predicted nodes will occur between two nodes within the network. However, as the final network is a superposition of many different networks, these may be at the periphery in the final Ensemble output. Predicted nodes can add biological value because any high-throughput screen will miss many true biological connections.

When we applied SteinerForest Ensemble to our previous α-syn over-expression screen data, the fragmented networks became more coherently connected. All 77 modifier-genes were now incorporated in the network, (FIG. 1A, lower left; Table S1; Table S3). By penalizing the exclusion of genetic modifiers and the inclusion of hubs, the PCSF algorithm favored the biological context at the expense of hubs. To establish specificity of the network output, we generated ensembles of forests from 1000 sets of 77 genes randomly chosen from the yeast genome with identical connectivity (degree distribution) to the α-syn modifier list. An empiric p-value for each node (based probability of occurring in a network by chance) was significant (p=0.025, SD=0.021).

TABLE S3: NETWORK OUTPUT (MODIFIERS+PREDICTED NODES) FOR 3 PROTEOTOXICITY SCREENS, Related to FIG. 1.

Importantly, predicted nodes (FIG. 1A, green triangles) included genetic modifiers of α-syn toxicity not hit in the original screen but uncovered through other studies, including Sec14 (Phospholipase D) (Outeiro and Lindquist, 2003), and Pbp1 (yeast homolog of Ataxin-2 see below and FIG. 3). This network also identified two druggable targets: Cnb1 (Calcineurin subunit B) and Rsp5 (FIG. 1A, lower right). Cnb1 is targeted by FK506, a drug that ameliorates α-syn toxicity (Caraveo et al., 2014). Rsp5 is the target of a specific N-arylbenzimidazole (NAB) that protects against α-syn toxicity (Tardiff et al., 2013). The SteinerForest Ensemble methodology thus connects genetic screen hits through biologically relevant pathways, including druggable targets.

Figure 1B:
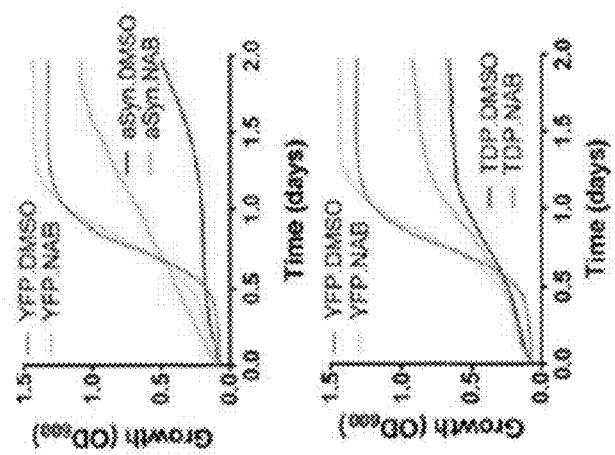
Figure 1C:
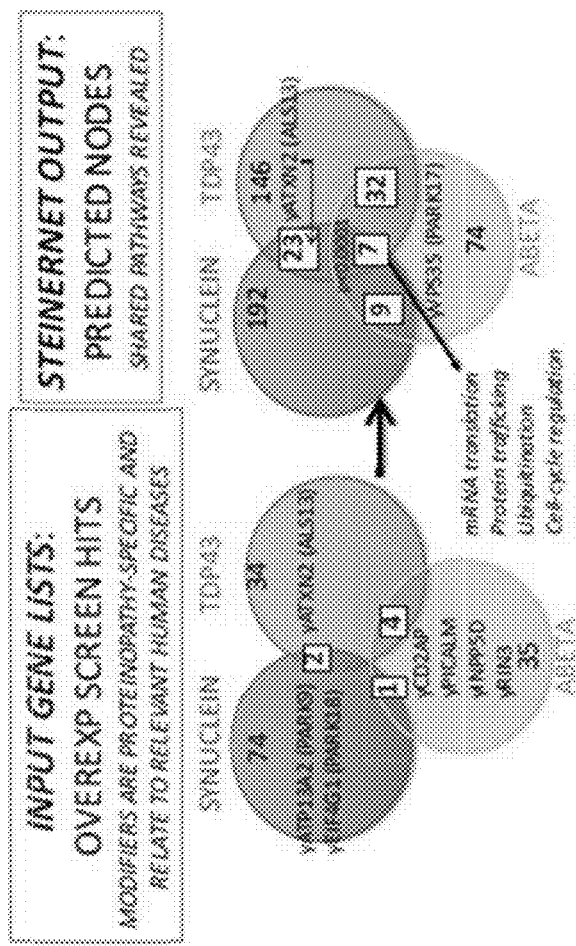

Cross-Comparison of α-Syn, TDP-43 and Aβ Proteinopathies Reveals Distinct and Shared Mechanisms To cross-compare different proteinopathies, we examined previous Aβ and TDP-43 over-expression screens (FIG. 1B;

"yeast over-expression networks" in Table S1) and found virtually no overlap (FIG. 1B, left; Table S2). There was, however, reassuring overlap between the yeast genetic modifiers and disease genes associated with the human disorders including: putative parkinsonism genes recovered in the α-syn screen [ATP13A2 (PARK9) and EIF4G1 (PARK18)]; AD risk factors in the Aβ screen [PICALM, CD2AP, INPP5D and RIN3]; an ALS genetic risk factor in the TDP-43 screen (Elden et al., 2010).

SteinerForest Ensembles from these screen hits revealed more biological overlap between these proteinopathies including protein trafficking, mRNA translation, ubiquitination and cell-cycle genes (Table S3 and Table S4; FIG. 1B right). There was also a cross-over between genetic risk factors for distinct human diseases: the ATXN2 homolog was a predicted node in the α-syn network (confirmed as a modifier of α-syn toxicity; FIGS. 3 and 4); the homolog of the parkinsonism gene VPS35 (PARK17) was a predicted node in the yeast Aβ network. VPS35 encodes a key component of the retromer complex, and defective retromer function has been identified in AD brain and animal models (Small et al., 2005). These overlaps were unrelated to increasing the number of genes. Empirical p-values for 1000 similarly connected random networks were statistically significant, whether considered pairwise (p<=0.002) or triple-wise (p<=0.001).

TABLE S4: COMPARING PROTEOTOXICITIES: OVEREXPRESSION SCREEN HIT INPUTS VERSUS STEINER NETWORK OUTPUTS, Related to FIG. 1.

Figure 6:
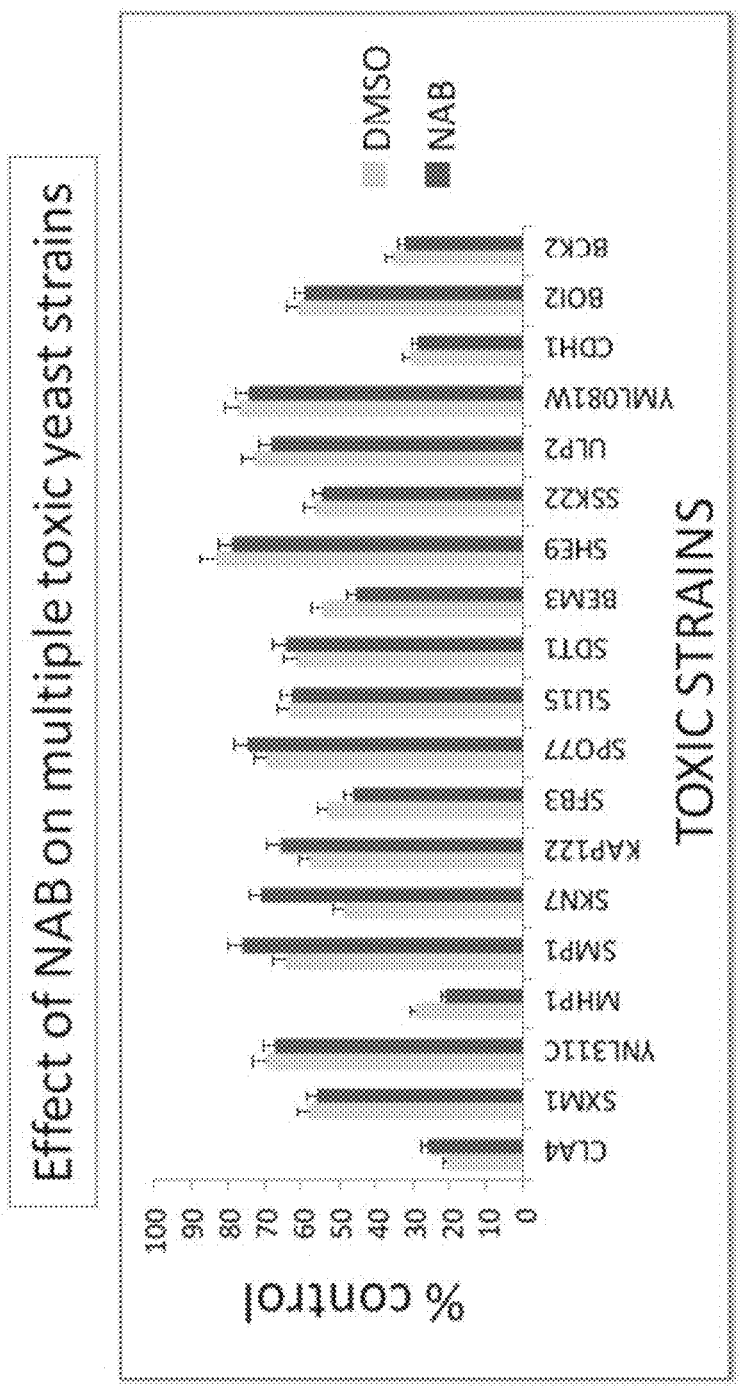
FIG. 6 shows that NAB (N-aryl benzimidazole) does not appreciably rescue growth of 20 distinct toxic yeast strains. A panel of twenty "toxic tester" yeast strains was generated by individually over-expressing the genes, indicated on the x-axis. NAB did not substantially rescue toxicity in any of these strains. The experiment was performed three times (biological replicates) with an error of ±5%.

One trafficking gene predicted to be a common node between all three proteinopathies was Rsp5, a ubiquitin ligase activated by NAB. Indeed, NAB was originally recovered in a small-molecule screen against TDP-43 proteinopathy in yeast. We utilized a sensitive bioscreen assay to test NAB on growth defects induced by these proteinopathies. Indeed, NAB rescued all three proteinopathies as predicted by the network. It was most effective for α-syn (FIG. 1C) and only rescued against Aβ toxicity synergistically in combination with other compounds known to protect from Aβ toxicity (data not shown). NAB failed to provide significant rescue for any 20 unrelated toxic yeast strains (FIG. 6).

TransposeNet Generates "Humanized" Network

It would be desirable to identify connections between our yeast molecular networks to human genes, including human disease genes that have no straightforward homologs in yeast. We therefore developed TransposeNet, a suite of computational methods to "humanize" yeast molecular networks (FIG. 2A).

Figure 2A:
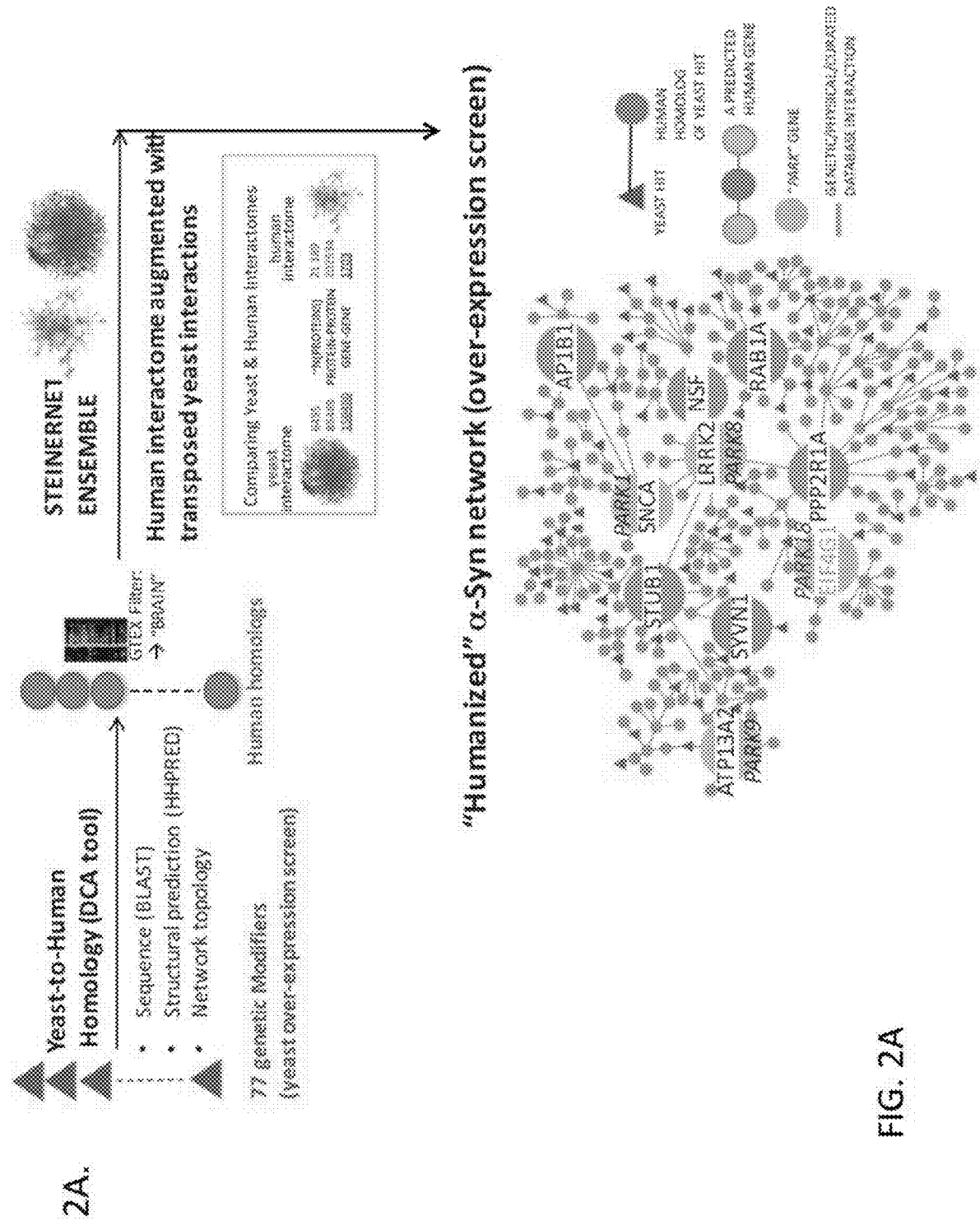
FIG. 2A-FIG. 2C show a "humanized" TransposeNet network that incorporates LRRK2 into the α-syn proteotoxicity network.

The first step in Transposenet is assignment of yeast-to-human homology by considering sequence similarity (BLAST and DIOPT (Hu et al., 2011) scores), yeast-to-human structure alignments (using the HHpred tool) (Söding et al., 2005), and incorporating network topology (FIG. 2A, upper left). Network topology assesses neighborhoods of genetic and physical molecular interactions around a given protein, positing "guilt-by-association" logic that the topological place within a network relates to biological function (Cho et al., 2016). Thus sharing similar neighbors should be a factor in determining whether two proteins are homologs. The relative weight of each homology method was carefully tuned (STAR Methods and FIG. 7 for full details) providing a more comprehensive and unified protein homology score (Berger et al., 2013; Singh et al., 2008; Söding et al., 2005). The underlying framework that relates genes according to these different features is known as diffusion component analysis (DCA). DCA has also been used as the core algorithm in Mashup, a tool for integrating multiple heterogeneous interactomes. More information can be found in the Method Details section of the STAR Methods and in Cho et al., (2016).

Our method assigned 4923 yeast proteins to human homologs and conversely predicted yeast homologs for 15,200 human proteins, a substantial improvement over BLAST (4023 yeast to human and 7248 human to yeast) or BLAST with HHpred (4312 yeast to human and 9577 human to yeast). Additionally, our method improved predictions as determined by gene ontology (GO) accuracy and Jaccard similarity scores (STAR Methods; FIG. 8) and did not introduce false-positives for high confidence yeast-human proteins pairs (EnsemblCompara; STAR Methods).

This high conservation of core eukaryotic biology from yeast to man, and pivotal complementation studies in yeast have determined the functions of many genes in other species, including human (Osborn and Miller, 2007) (Kachroo et al., 2015). On this basis, we used our homology tool to augment the human interactome with interactions inferred from the much better-curated yeast interactome. This was the key advance that enabled TransposeNet. Importantly, this cross-species "edge" transposition did not increase the rate of false-positive hits. Rather, it substantially improved network performance. In fact, for our screen hits the PCSF-based SteinerForest Ensemble out-performed two alternative network building methodologies, DAPPLE (Rossin et al., 2011) and PEXA (Tu et al., 2009) (STAR Methods and FIG. 9).

In our "humanized networks" (indexed in Table S1; FIG. 2A, right) each yeast gene (red triangle) is connected to one or more human homologs (circles) based on our homology tool-generated score. SteinerForest Ensemble then interconnects each resulting human gene/protein, through edges generated from the human interactome augmented with the "humanized" yeast molecular interactome. If a particular human homolog of a yeast genetic modifier had been implicated as a parkinsonism gene, a small inclusion weight is given. However, no special preference was given to any human disease genes other close homologs of our yeast hits.

Humanized Network from Over-Expression Screen Connects α-Syn to Other Human Disease Genes We tested the humanized network approach on the 77 modifiers from the α-syn over-expression screen ("α-syn over-expression humanized network"; Table S1, Table S9 and Table S11; FIG. 2A, right). Several predicted human nodes in the resultant humanize network had no obvious homologs in the yeast proteome, the most striking example being α-syn itself. α-syn was connected to ER quality control and protein trafficking modifiers through a predicted node Ap1b1 (FIG. 2A, right), a component of the clathrin adapter complex that localizes in the immediate vicinity of α-syn in neurons (accompanying manuscript; Chung et al. Cell Systems 2016). The emergence of α-syn in the humanized network strongly indicates that a functional, highly interconnected relationship between our original yeast genetic hits and α-syn is conserved from yeast to man.

TABLE S9: HUMANIZED ALPHA-SYNUCLEIN OVEREXPRESSION INTERACTION NETWORK, YEAST-HUMAN PAIRING (INPUT AND STEINERFOREST ENSEMBLE OUTPUT), Related to FIG. 2.

TABLE S11: Predicted Nodes Inferred in Humanized Networks, Related to FIGS. 2 and 3.

LRRK2 and α-Syn are Connected Through ER Stress and Vesicle Trafficking

Figure 2B:
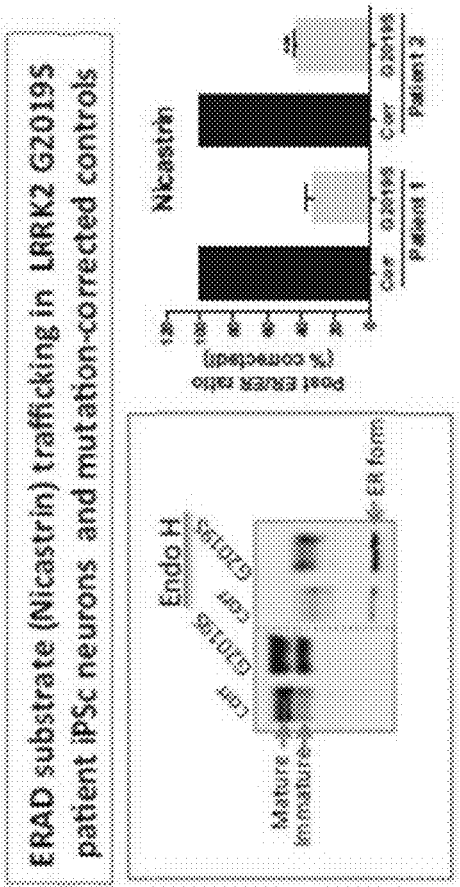
Figure 2C:
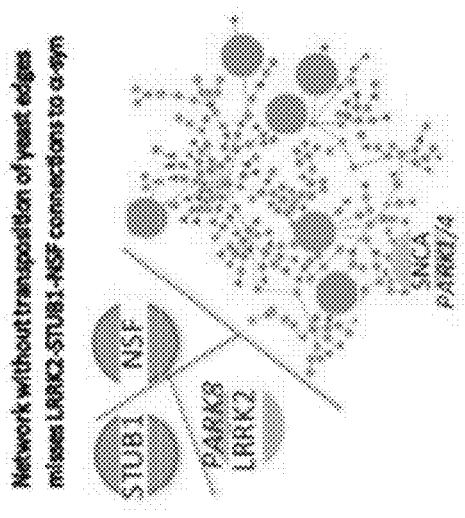

The kinase/GTPase LRRK2, another PD gene-encoded protein without an obvious yeast homolog, was centrally incorporated into the humanized network (FIG. 2A, right). We tested the robustness and specificity of this finding by computationally generating ensembles of humanized Steiner forests from 1000 lists of genes that were randomly selected (matching the size of our original α-syn genetic modifier list. LRRK2 and α-syn (SNCA) occurred together in 72% of humanized networks generated through PCSF from our input list (individually, SNCA appeared in 86% and LRRK2 in 76% of networks). Neither was incorporated in any of the humanized networks generated from Aβ or TDP-43 screen hits ("TDP-43"- and "Aβ"-"over-expression humanized networks" in Table S1). LRRK2 and α-syn appeared together in 0/1000 networks of the randomly generated ensembles. Without transposition of yeast interaction information into our networks, α-syn was peripherally placed and its connection to Ap1b1 (see above) was lost and LRRK2 was entirely absent (FIG. 2B). Thus, the inclusion of LRRK2 and α-syn is robust, specific, and dependent upon augmentation of human networks with yeast interaction data.

LRRK2 was related to the humanized α-syn network through proteins involved in ER-to-Golgi trafficking (Nsf1, Rab1a) and ER quality control (Stub1/Chip/Scar6, Sgk1, Syvn1), pathways previously implicated in LRRK2-(Cho et al., 2014; G. Liu et al., 2012) and α-syn- (Chung et al., 2013; Cooper et al., 2006) induced toxicity. Our data suggested they might be a key point of convergence. We previously showed that the A53T mutation and triplication of wild-type α-syn leads to pathologic accumulation of specific trafficked proteins in the ER of patient-derived neurons, including Nicastrin (Chung et al., 2013). Using previously generated LRRK2 mutant iPSc-derived neurons, we recapitulated this phenotype (FIG. 10). As early as 4 weeks after initiating differentiation, Nicastrin accumulated in the ER of LRRK2$^{G2019S}$ cells compared to isogenic mutation-corrected controls (FIG. 2D) phenocopying the previously described pathology in neurons derived from patients with α-syn mutations. Thus, the humanized α-syn network correctly predicted a convergence of cellular pathologies in distinct forms of parkinsonism. A Nicastrin trafficking defect has also been demonstrated in LRRK2 knockout mouse fibroblasts (Cho et al., 2014), raising the possibility that the G2019S mutation may lead to deficiency of a LRRK2-related function in protein trafficking.

Genome-Wide Pooled Overexpression and Deletion Screens Against α-Syn Toxicity

For a more comprehensive view, we executed two additional genome-wide screens against α-syn toxicity (FIG. 11A number 1): 1) a genome-wide deletion screen identified nonessential genes that, when deleted, lead to an extreme sensitivity to low levels of α-syn that would otherwise not be toxic (FIG. 11A number 2; FIG. 11; Table S5); 2) a pooled screen in which the galactose-inducible over-expression library was transformed en masse into our α-syn HiTox strain (FIG. 11A number 3; Supp FIG. 7; Table S6). 3) For pooled screens, we sequence plasmid DNA to identify genes specifically over- or under-represented under selective conditions comparing plasmid DNA sequences from a similarly transformed YFP control strain to identify α-syn-specific modifiers. These are putative suppressors and enhancers of toxicity, respectively. Pooled screens are far more rapid, and theoretically more sensitive, than individually transforming each library plasmid into the α-syn strain and measuring growth.

These screens encompassed tests of approximately 10,000 potential genetic interactions (~5500 over-expression, ~4500 deletion). After extensive validation of the hits (FIG. 11C and FIG. 12B), we recovered 318 genetic modifiers.

Figure 3A:
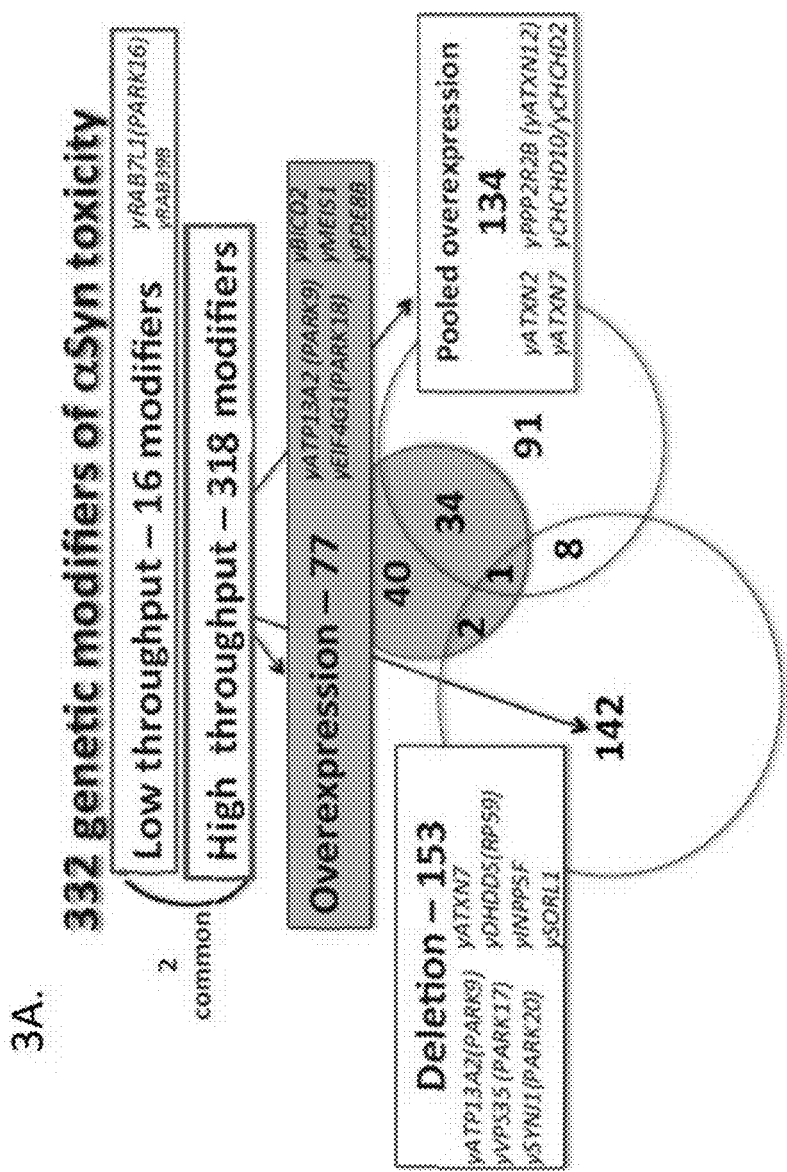
Figure 3B:
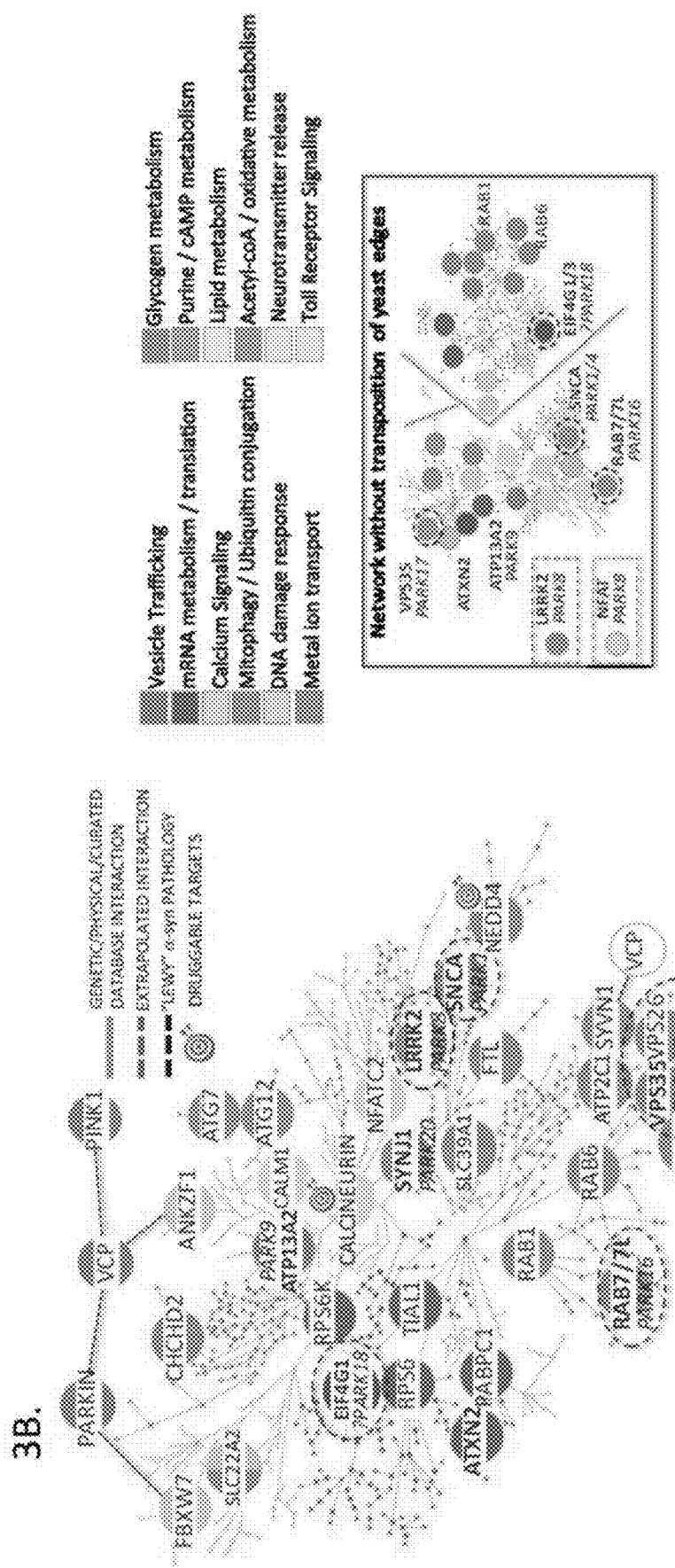

Very little overlap existed between the specific genes recovered in the deletion versus the over-expression screens (FIG. 3B). However, we found considerable overlap in the biological pathways represented (see network analysis below). 16 modifiers have emerged in independent work from our laboratory (Caraveo et al., 2014; Chung et al., 2013) or were identified herein (Table S7). Fourteen of these were distinct from our screen hits, leading to a total of 332 genetic modifiers of α-syn toxicity (FIG. 3B).

TABLE S5: ALPHA-SYNUCLEIN GENOME-WIDE DELETION SCREEN MODIFIERS (all enhancers with synthetic lethal interactions with α-syn), Related to FIG. 3.

TABLE S6: ALPHA-SYNUCLEIN POOLED OVEREXPRESSION SCREEN MODIFIERS, Related to FIG. 3.

TABLE S7: Additional low-throughput "Candidate-based" Modifiers of ALPHA-SYNUCLEIN toxicity (hypothesis-based studies), Related to FIG. 3.

Homologs of PARK and Other Neurodegeneration Genes Modify α-Syn Toxicity in Yeast Modifiers of α-syn toxicity included homologs of many known genetic risk factors for parkinsonism and other neurodegenerative disease phenotypes (FIG. 3A and Table S14). These included genes involved in vesicle trafficking (yRAB7L1, yRAB39B, ySORL1, ySYNJ1/PARK20, yVPS35/PARK17), mRNA translation (yATXN2, yEIF4G1/PARK18), mitochondrial quality control/function (yCHCHD2/10), metal ion transport (yATP13A2), transcriptional regulation (yAMTN7), metabolism (yDHDDS) and signaling (yPDE8B, yPPP2R2B/ATXN12), among others. Many of these genes, including those at so-called PARK loci, have been implicated in neuronal pathologies quite distinct from the α-syn pathology that defines PD. Their recovery in our screens suggested that mechanisms of neurotoxicity related to diverse neurodegenerative disease genes may be shared.

Of the 19 PARK loci, 9 have clear yeast homologs (Table S8). Four of these emerged in our screens: yATP13A2 (PARK9) [YPK9 in yeast], yVPS35(PARK17) [VPS35], yEIF4G1(PARK18) [TIF4631, TIF4632] and ySYNJ1 (PARK20) [INP53]. A fifth putative PARK gene, yRAB7L1 (PARK16) [YPT7], emerged as a genetic modifier when tested as a candidate (see below). The probability of recovering homologs of these genes by chance is p=0.00013 (hypergeometric test. None of these yPARK genes were modifiers in the Aβ or TDP-43 over-expression screens (Table S2). These findings underscore the biological specificity of the α-syn screen hits in yeast.

TABLE S14. SUMMARY OF NEURODEGENERATION GENES CONNECTED BY OUR NETWORK TO α-SYN TOXICITY, Related to FIG. 3. Unless otherwise provided, recent reviews in parkinsonism genetics provide references. "N/A" is used when there is no clear yeast homolog of the human gene (these genes appeared as "predicted nodes" in our humanized networks). Genes highlighted in red are strongly associated with classic PD/PDD, and either known or strongly presumed to have α-syn (Lewy) pathology. Most of these genes relate to diseases quite distinct from PD. While some genes (including EIF4G1 and UCHL1) are considered highly controversial PD genes, they are nevertheless recovered in our α-syn toxicity network. Abbreviations: AD: Autosomal dominant; ALS: Amyotrophic lateral sclerosis. AR: Autosomal recessive; CBD: Corticobasal degeneration; DA: Dopaminergic DLB: Dementia with Lewy bodies; Enh: Enhancer of toxicity; GWAS: Genome-wide association studies; NBIA: Neurodegeneration with Brain Iron Accumulation. OE: over-expression screen. PD: Parkinson's disease; PDD: Parkinson's disease dementia; polyQ: polygutamine expansion due to CAG repeat expansion within gene; PSP: progressive supranuclear palsy; Supp: Suppressor of toxicity. Note that "PD" refers to parkinsonism in association with α-syn (Lewy body) pathology. "Parkinsonism" refers to the clinical phenotype with different (or unknown) pathology.

TABLE S8: 'PARK" LOCI AND GENES, Related to FIG. 3.

TransposeNet Generates a Genome-Scale "Map" of α-Syn Toxicity

We applied TransposeNet to homologs of the 332 α-syn toxicity modifiers to generate a humanized network, or "map" ("Complete α-syn humanized network" in Table S1, Table S10 and Table S11; FIG. 3B; FIG. 13). Multiple genes implicated in neurodegeneration emerged in this α-syn network by direct homology to yeast hits or as predicted network nodes (FIG. 3B; FIG. 13; Table S14).

We superimposed gene ontologies onto "branches" in our map (FIG. 3B) and various vesicle-mediated transport processes dominated. Genetic risk factors associated with typical PD (SNCA itself, LRRK2, RAB7L1, VPS35) were concentrated in the subnetwork enriched in vesicle trafficking genes (FIG. 3B). In contrast, the majority of neurodegeneration genes associated with non-Lewy neuropathology, atypical parkinsonism or non-parkinsonian neurodegenerative phenotypes (Table S14) were distant from the vesicle trafficking network. A full analysis of the biological processes enriched in the network "branches" is provided in Table S12. Notably, this humanized network elucidates the molecular context in which the previously identified druggable targets NEDD4 (Tardiff et al., 2013) and calcineurin and NFAT (Caraveo et al., 2014) impact α-syn toxicity (FIG. 3B).

Furthermore, both α-syn itself and LRRK2 are predicted as nodes, just as in the over-expression network (FIG. 2A). In the ensemble of Steiner forests generated from our list of 332 modifiers, α-syn appeared in 100% and LRRK2 in 70%. In 1000 random sets of 332 genes, even when we forced the incorporation of fiveyPARK genes recovered in our genetic experiments (yPARK9, yPARK16, yPARK17, yPARK18, yPARK20). α-syn and LRRK2 appeared together in only 0.6% of humanized networks. Thus, yeast modifiers of α-syn toxicity generated a specific humanized network in which the PD-associated proteins α-syn and LRRK2 emerged as critical network nodes.

TransposeNet generated a coherent network: 295 out of 332 of yeast modifier genes in a single tree network (Table S10) with biologically intuitive "stems" comprising genes of similar ontology (FIG. 3B). Networks generated from these 332 modifiers without transposition of yeast interactome data (FIG. 3B, inset;) produced three fragmented networks comprising 136, 2 and 122 yeast genes, respectively (FIG. 3B, inset). Genes that should be related biologically through involvement in common cellular processes were not (FIG. 3B). Moreover, LRRK2 and NFAT were not incorporated. Testable hypotheses, such as the relationship of EIF4G1 and ATXN2 (FIG. 5 and FIG. 6, below), did not emerge because these proteins landed in different networks. DAPPLE (Rossin et al., 2011) and PEXA (Tu et al., 2009) also produced highly fragmented or dense "hairball" networks useless for hypothesis generation (FIG. 14) and, strikingly, did not include critical nodes like LRRK2 (FIG. 15). Thus, transposition of yeast networks to augment the human interactome created a coherent, biologically meaningful α-syn network.

TABLE S10: Humanized ALPHA-SYNUCLEIN Complete network (OVEREXPRESSION, POOLED OVEREX- PRESSION, DELETION SCREENS), yeast-human pairing (input and STEINERFOREST ENSEMBLE output), Related to FIG. 3.

TABLE S12. ENRICHED ONTOLOGIES IN HUMANIZED ALPHA-SYNUCLEIN COMPLETE NETWORK, Related to FIG. 3.

Figures 4A, 4B:
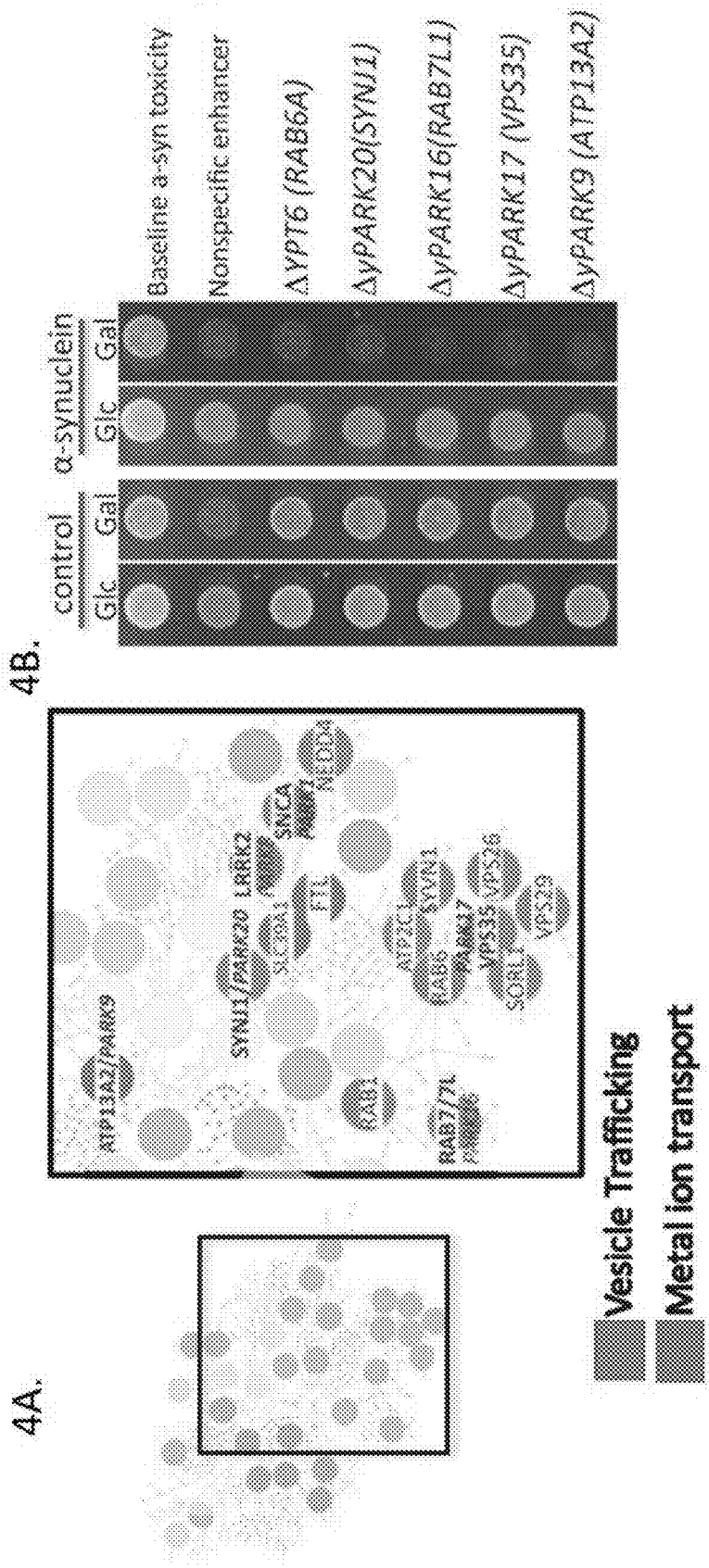
FIG. 4A-FIG. 4E show that genetic dissection of parkinsonism susceptibility genes reveals distinct biology.
Figures 4C, 4D:
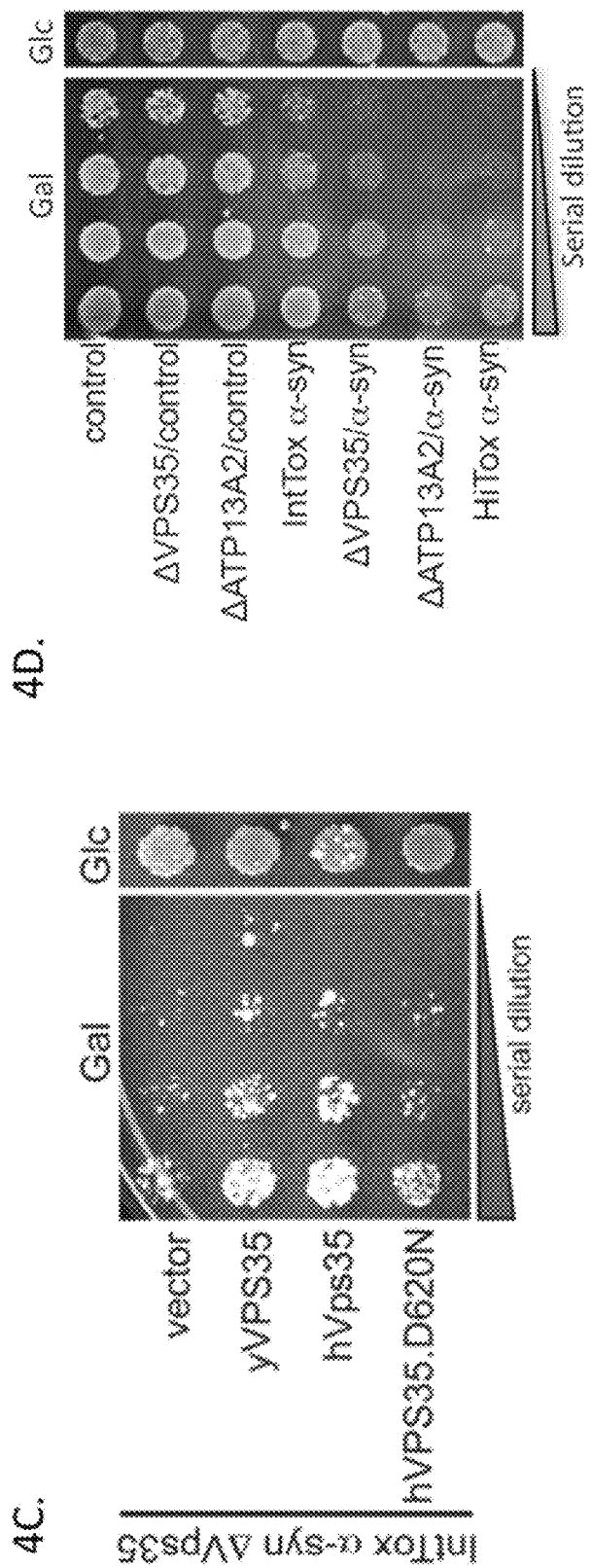

An endocytic and retrograde trafficking subnetwork in the α-syn toxicity map Incorporates yeast homologs of RAB7L1 (PARK16) and VPS35 (PARK17). In the α-syn map, homologs of some parkinsonism genes coalesced in a sub-network around YPT6, the yeast homolog of RAB6A (Soper et al., 2011)(FIG. 4A). Included were YPT7, VTHJ and VPS35, which encode proteins involved in endosomal trafficking. YPT7 is a close homolog of RAB7L1, a leading candidate for the PARK16 locus(Macleod et al., 2013; Nalls et al., 2014), and also of the Mendelian parkinsonism risk factor RAB39B(Wilson et al., 2014). VTH1 is a close yeast homolog of SORL1, an established AD risk modifier(Rogaeva et al., 2007) that encodes a protein involved in intracellular sorting (Nykjaer and Willnow, 2012). VPS35 is homologous to the Mendelian risk factor for classic PD, VPS35 (PARK17)(Zimprich et al., 2011). VPS35, with VPS26 and VPS29, comprise the retromer complex that transports cargo from endosomal to golgi compartments. In an upcoming study (Chung et al. Cell Systems 2016), we show that deletion of the VSP26 and VPS29 core retromer components strongly enhances α-syn toxicity. A fourth gene involved in golgi-to-endosome and endocytic trafficking, INP53, is homologous to the Mendelian parkinsonism gene SYNJ1(PARK20)(Olgiati et al., 2014). Deletion of any one of these genes was not toxic in a wild type strain. However, deletion of any one of these genes in a strain expressing low (nontoxic) levels of α-syn produced a strong and synergistic growth defect (Table S5, FIG. 4B and FIG. 15A). Importantly, ectopic expression of yeast or human VPS35 rescued the toxicity induced by deleting VPS35, but expression of a disease-causing mutation (VPS35-D620N) did not (FIG. 4C). Finally, yRAB7L1 enhanced α-syn toxicity when deleted, but rescued from this toxicity when over-expressed (FIG. 15B).

The α-syn map predicts diverging genetic interaction profiles in ΔPARK9 (ATP13A2) and APARK17 (VPS35)-sensitized yeast models To test functional consequences of being located in distinct subnetworks of our α-syn map, we compared VPS35 (PARK17) and ATP13A2 (PARK9). ATP13A2 is a type 5 P-ATPase implicated in cation transport and metal ion homeostasis (Kong et al., 2014; Park et al., 2014; Ramonet et al., 2012; Tsunemi and Krainc, 2014). Mutations in ATP13A2 lead to juvenile-onset parkinsonism or Kufor-Rakeb syndrome, which is distinct from PD (Schneider et al., 2010).yATP13A2 suppressed α-syn toxicity in our overexpression screen (FIG. 1C) and deletion of yATPJ3A2 strongly enhanced α-syn toxicity (FIG. 4B). In our humanized network, ATP13A2 was spatially distant from VPS35 lying well outside the vesicle trafficking subnetwork (FIG. 3C and FIG. 4A). We asked whether this spatial separation reflected differences in underlying biology.

We generated three strains with similar toxicities (FIG. 4D). In one strain toxicity resulted from overexpression of α-syn (HiTox). In two other strains, mild toxicity induced by intermediate levels of α-syn expression was enhanced by deletion of yeast ATP13A2 (hereafter, ΔATP13A2/α-syn) or VPS35 (hereafter, ΔVPS35/α-syn). These three yeast strains thus modeled cellular pathologies related to three forms of familial Parkinsonism: two with typical α-syn pathology (PD related to α-syn multiplication and VPS35 (PARK17)- associated parkinsonism) and one with strikingly different pathology, PARK9 (ATP13A2).

While ΔATP13A2 sensitizes cells to metal ion stress (Kong et al., 2014), ΔVPS35 strains exhibit retrograde trafficking defects (Seaman et al., 1997) suggesting that ΔATP13A2 and ΔVPS35 strains were differentially sensitized to α-syn toxicity. We asked whether our 77 α-syn over-expression screen hits affected the toxicity of our ΔVPS35/α-syn and ΔATP13A2/α-syn models.

Figure 4E:
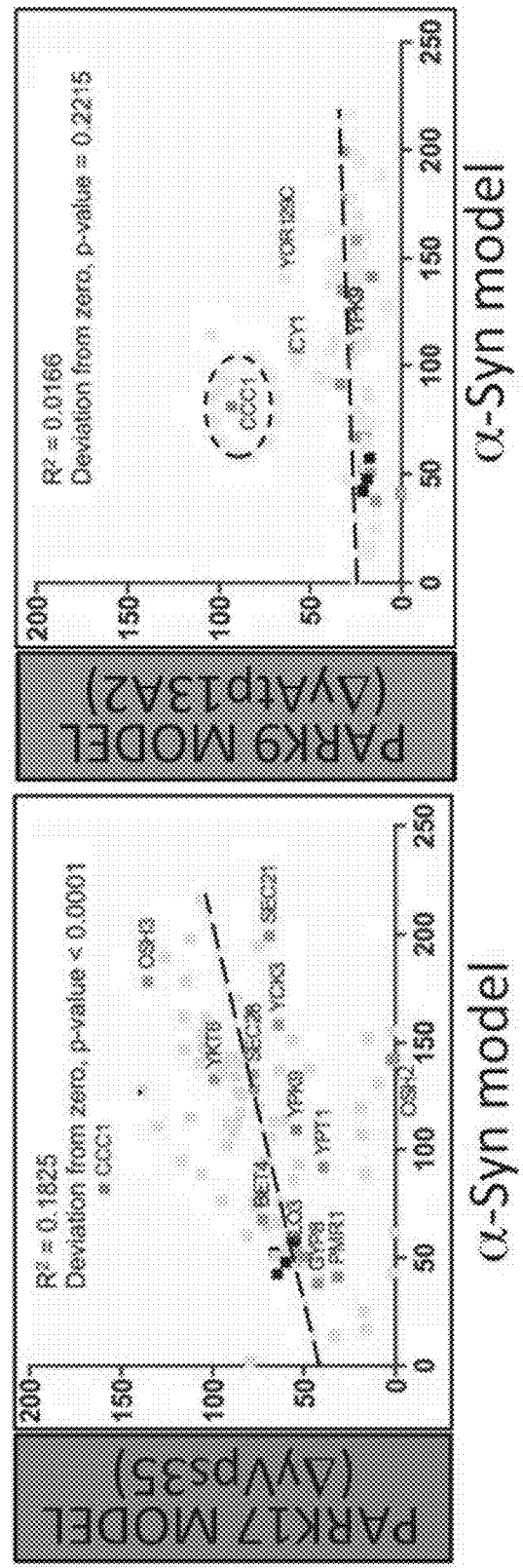

We expressed these α-syn toxicity modifiers in each of the yeast models and monitored growth. For the α-syn HiTox and ΔVPS35/α-syn models, 69/77 genes overlapped (FIG. 4E, left), correlating well with the similar pathology associated with these genetic forms of parkinsonism. Notably, the overlapping modifiers were enriched in vesicle trafficking genes (Table S13). In contrast, there were only 3/77 modifiers in common between α-syn HiTox and ΔATP13A2/α-syn (FIG. 4E, right). These were involved in iron and manganese homeostasis (CCC1) and actin cytoskeleton rearrangements (ICY1, AFI1), respectively. Notably, metal ion homeostasis is strongly implicated in Kufor-Rakeb syndrome (Schneider et al., 2010) and its mammalian models (Park et al., 2014). Thus, neurodegenerative diseases that are genetically, clinically and neuropathologically distinct may nonetheless share some key molecular pathologies.

TABLE S13. OVERLAP BETWEEN ALPHA-SYN (HITOX) AND ALPHA-SYN/ΔVPS35 STRAIN MODIFIER, AND GENE ENRICHMENT, Related to FIG. 4.

mRNA translation subnetwork links α-syn to PABPC1, EIF4G1 and ATXN2

In our over-expression screen against α-syn toxicity, TIF4632 (hereafter, yEIF4G1-2) emerged as a suppressor. TIF4632 is a yeast homolog of the of translational initiation factor EIF4G1. The genome-wide deletion and pooled overexpression screens identified additional genetic modifiers related to mRNA translation, including initiation factors and multiple ribosomal subunits (FIG. 3B and FIG. 5A; Table S5 and Table S6). These included PABPC1 (cytoplasmic poly (A)-binding protein-encoding), the homolog PAB1; the ATXN2 homolog PBP1; and the second EIF4G family homolog in yeast, TIF4631 (hereafter, yEIF4G1-1). These hits were confirmed by quantitative PCR (FIG. 5B, left), and overexpression of these genes suppressed α-syn toxicity in bioscreen (FIG. 5B, right) and/or spot (FIG. 16) growth assays. Genetic experiments in different proteinopathy models revealed that the effects of these modifiers on α-syn toxicity were specific (FIG. 16). Thus, perturbation of mRNA translation was not simply a generic proteotoxic response.

Protein Translation is Perturbed in PD Patient-Derived Neurons

Figures 5C, 5D:
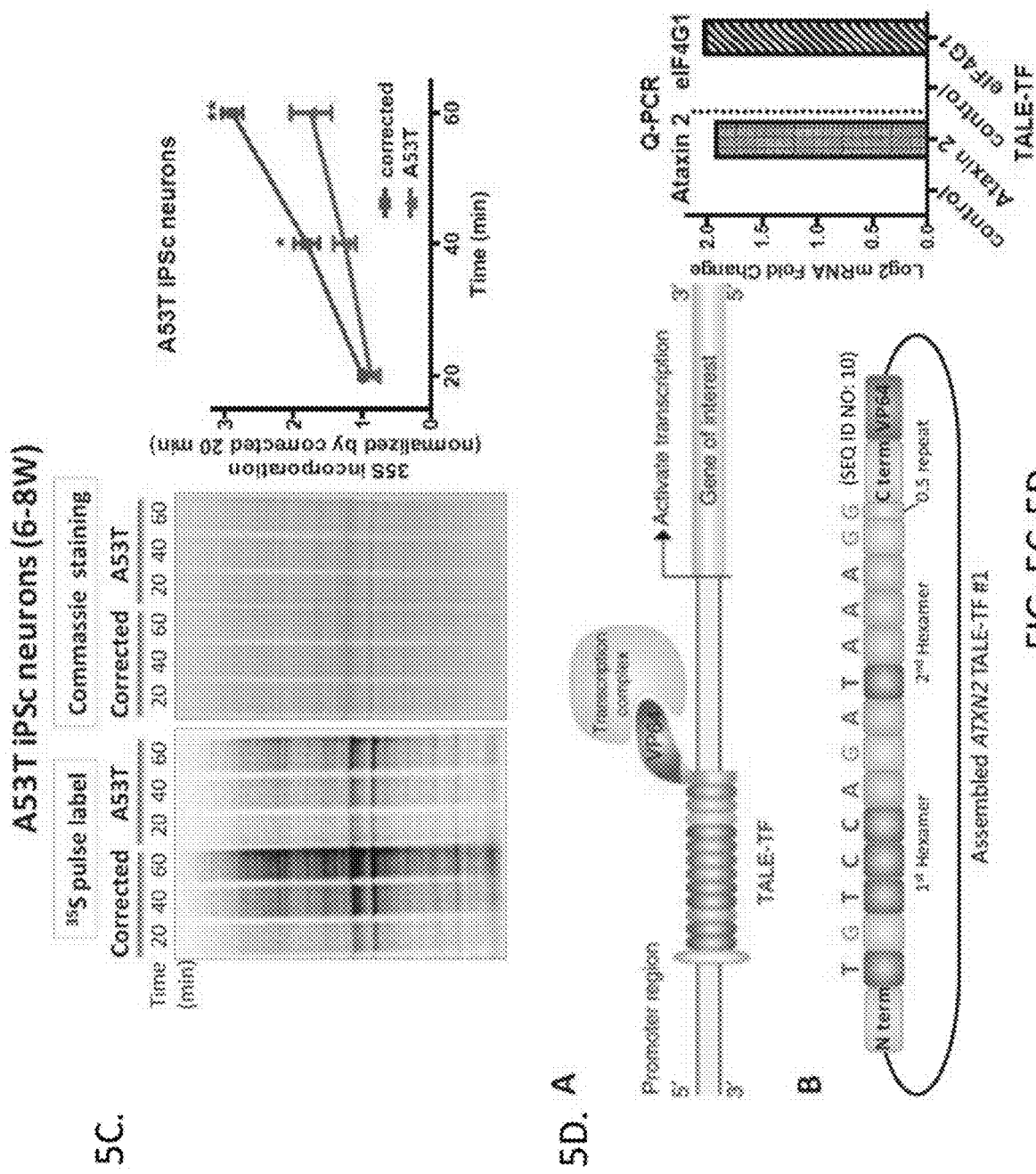

Because we recovered numerous genetic modifiers in the mRNA translation and mRNA processing pathways (FIG. 3 and FIG. 5), we asked whether protein translation was perturbed in cellular synucleinopathy models, including PD patient-derived neurons. Bulk changes in protein production were initially assessed by determining the rate at which $S^{35}$-radiolabeled methionine and cysteine is incorporated into protein over time after a brief "pulse labeling". Overexpression of α-syn in HEK (human embryonic kidney) cells and primary rat cortical neurons reduced the accumulation of $S^{35}$-Met/Cys without changing amino acid uptake (FIG. 17). Similarly, in 6-8 week-old iPSc neurons harboring the α-syn$^{A53T}$ mutation, $S^{35}$-Met/Cys incorporation into protein was reduced compared to isogenic mutation-corrected controls (FIG. 5C). Thus, our α-syn screens and network analysis identified a strong effect of α-syn toxicity on bulk mRNA translation in cellular models of synucleinopathy. This effect was not attributable to a canonical ER stress response, because phosphorylation of EIF2A (FIG. 17D; FIG. 18A) or XBP1 splicing (FIG. 18B) was not altered in these neurons.

Conserved Genetic Interactions of ATXN2 and EIF4G1 from Yeast to Patient Neurons We next tested whether human homologs of two translation factors that suppressed α-syn toxicity when over-expressed—ATXN2 and EIF4G1—could similarly reverse the protein translation defect in neurons. We generated TALE-TF constructs to transcriptionally upregulate neuronal isoforms of EIF4G1 and ATXN2 (Sanjana et al., 2012) (FIG. 5D, left). These constructs were then delivered with an adeno-associated viral vector to differentiated α-syn$^{A53T}$ iPSc-derived neuronal cultures.

Figure 5E:
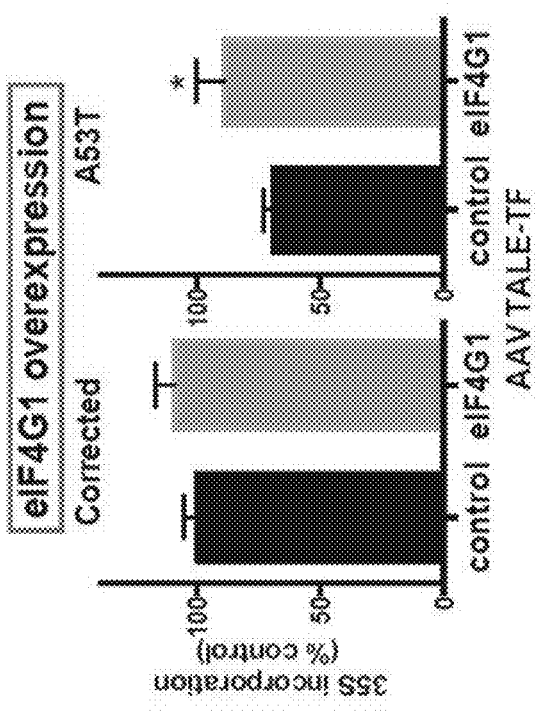
Figure 5E:
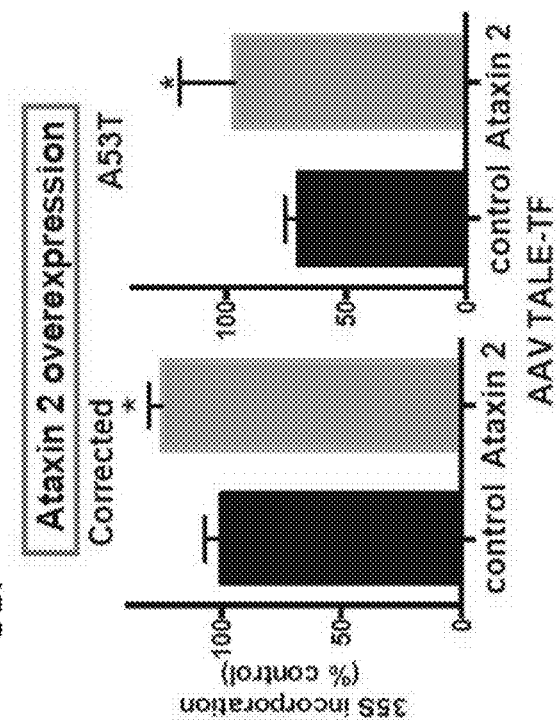

Ten days after transduction, endogenous EIF4G1 and ATXN2 mRNA levels increased by approximately 4-fold, as measured by quantitative PCR (FIG. 5D, right). This increased expression substantially reversed the defect in bulk protein translation we had observed in α-syn$^{A53T}$ neurons (FIG. 5E). Over-expression of EIF4G1 increased translation in A53T neurons but not in mutation-corrected controls. ATXN2 over-expression equally increased bulk translation in mutant and control cells (FIG. 5F).

Thus, our cross-species molecular network predicted a biological interaction between α-syn and mRNA translation factors in PD patient-derived neurons. These data strengthen the argument that perturbed mRNA translation is an important aspect of α-syn toxicity. Interestingly, we identified a strong signature of decreased translation of mRNA translation-related transcripts in ribosomal footprinting experiments of α-syn$^{A53T}$ iPSc-derived cortical neurons at 4 and 12 weeks of differentiation compared to isogenic mutation-corrected control neurons (FIGS. 19A and 14B, FIG. 20). Indeed, mRNA-related translation factors, ribonucleoproteins and ribosomal proteins were not only enriched in our genetic and translational maps of α-syn toxicity, but also among proteins in the immediate vicinity of α-syn in neurons (pending publication, Chung et al, *Cell Systems* 2016, FIG. 4; "spatial α-syn map", FIG. 20A). Moreover, a number of mRNA translation proteins directly complexed with α-syn. This convergence of genetic, translational and spatial maps suggests the connection between α-syn toxicity and mRNA metabolism is deeply rooted in α-syn biology.

Discussion

We describe a coherent, systems-level analysis of how α-syn misfolding and mistrafficking perturbs cell biology. Genome-wide screens identified modifiers of the toxic consequences of α-syn expression in Baker's yeast *S. cerevisiae*. Our key computational contribution, TransposeNet, coupled richly annotated molecular interactions in yeast with a Steiner prize-collecting algorithm and a sophisticated cross-species homology tool to visualize the screen hits as a "humanized" molecular network. TransposeNet revealed that α-syn pathology is deeply connected to human genetic risk factors for parkinsonism, and parsed out the molecular pathways through which these connections occur. We envisage TransposeNet as a valuable resource for the community, easily generalizable to the modeling of any physiologic or pathologic process in genetically tractable organisms A pressing challenge in neurodegeneration is to determine whether genes associated with highly distinct pathologies, but that nevertheless converge on similar clinical phenotypes, are related at a molecular level or not. Our network tied α-syn not only to genes that cause classical PD (Ogaki et al., 2015), but also genes that cause parkinsonism with different pathologies, and genes associated with other neurodegenerative phenotypes altogether (Table S14). The relationships were highly specific to α-syn. Moreover, genes tied to classical PD or α-syn pathology (like RAB7L1, VPS35 and LRRK2) were concentrated in a vesicle trafficking-associated subnetwork, while genes tied to "atypical" parkinsonism (like ATP13A2 and ATXN2) were in separate subnetworks. For a few examples, our network revealed convergent and divergent molecular pathologies related to the spatial location on the map. Thus, LRRK2 and α-syn pathologies were connected at the level of perturbed protein trafficking, confirmed in patient-derived neurons. In another example, VPS35 and ATP13A2 exhibited highly distinct genetic modifier profiles in yeast. Other network and model-organism studies provide important support for our results, including connections between α-syn and LRRK2(Cho et al., 2014; G. Liu et al., 2012), RAB7L1 and LRRK2 (Macleod et al., 2013) (Beilina et al., 2014) and between VPS35 and α-syn (Dhungel et al., 2014).

For some genes connected to α-syn toxicity by our network, including EIF4G1(PARK18) and CHCHD2, human genetic data is limited or controversial (Funayama et al., 2015; Z. Liu et al., 2015; Ogaki et al., 2015) (Chartier-Harlin et al., 2011; Nuytemans et al., 2013). Another gene, RAB7L1, is one of two candidates in linkage with a parkinsonism-associated common gene variant (PARK16). Our analysis affirms a connection between such genes and α-syn proteinopathy and provides the biological context in which to place these interactions. For example, we make no claim that the translation factor EIF4G1 should be designated a "PD gene." However, EIF4G1 and α-syn toxicity are connected in the context of an important and previously unrecognized direct effect of α-syn on mRNA biology and protein translation. This was confirmed by multiple hits in our genetic analysis (FIG. 3) and in our mRNA translational profiling of neurons (FIG. 19). Interestingly, an emerging connection is emerging between mRNA translation and other parkinsonism-related genes (Gehrke et al., 2015) (Martin et al., 2014). Moreover, a connection to mRNA translation and metabolism was also confirmed in our spatial mapping of α-syn in neurons (Chung et al., Cell Systems 2016, accompanying manuscript). This map revealed that α-syn is in the immediate vicinity and complexed to proteins involved in mRNA translation and protein trafficking, suggesting that these perturbations may be upstream or proximal events in α-syn toxicity.

Finally, by identifying connections between druggable targets and gene networks, our approach provides a glimpse of how treatments might in the future be targeted to specific genetic lesions. We envisage that the inflexibility of a single clinical or pathologic diagnosis will yield to a more nuanced molecular diagnosis. In this scenario, genetic lesions will be matched to compound targets, and confirmed in "personalized" cellular models in which combinatorial genetic lesions are introduced to reflect specific genetic risk and biology. Emerging genome-editing technologies will enable such models to be developed in patient-derived cells, and genome-wide screening to be carried out as well (Hasson et al., 2013; Khurana et al., 2015; Shalem et al., 2014; Wang et al., 2014). These will unquestionably be welcome advances, but impressive developments will continue in simple model organisms. Variomic libraries in yeast, for example, now enable mutagenesis at single-amino acid resolution across the entire yeast proteome (Z. Huang et al., 2013), unlocking enormous potential for target identification in phenotypic screens. We envision multi-faceted, cross-species approaches will continue to evince critical insights into many complex diseases, and perhaps fulfill therapeutic promises in the post-genomics era.

TABLE S1

INDEX OE NETWORKS GENERATED IN THIS STUDY

| Network Name | Input Nodes (number) | Node "Prize" (=100) | Source Edges | Edge Weights |
|---|---|---|---|---|
| α-SYNUCLEIN OE yeast | Yeast OE α-syn screen modifiers (77) | Yeast OE α-syn screen modifiers | STRING yeast experimental (genetic/physica)/database | $qij = 1 - (1 - q\hat{}exp)*(1 - q\hat{}data)$ |
| TDP-43 OE yeast | yeast OE TDP-43 screen modifiers (40) | Yeast OE TDP-43 screen modifiers | STRING yeast experimental (genetic/physica)/database | $qij = 1 - (1 - q\hat{}exp)*(1 - q\hat{}data)$ |
| Aβ-OE yeast | Yeast OE Aβ screen modifiers (40) | Yeast OE Aβ screen modifiers | STRING yeast (genetic/physica)/database | $qij = 1 - (1 - q\hat{}exp)*(1 - q\hat{}data)$ |
| α-SYNUCLEIN OE humanized | Yeast OE α- syn screen modifiers (77) | Yeast OE α-syn screen modifiers | STRING human genetic/physical/database | $qij = 1 - (1 - q\hat{}exp)*(1 - q\hat{}data)$ |
| | | | CCSB human physical/ curated (Rolland Cell 2014) | 0.6 |
| | | | Humanized yeast interactions (STRING) | $qij = 1 - (1 - q\hat{}exp)*(1 - q\hat{}data)$ |
| | | | Yeast-to-human unpublished Y2H (Zhong submitted) | 0.6 |
| TDP-43 OE humanized | Yeast OD TDP-43 screen modifiers (40) | Yeast OE TDP-43 screen modifiers | STRING human genetic/physical/database | $qij = 1 - (1 - q\hat{}exp)*(1 - q\hat{}data)$ |
| | | | CCSB human physical/ curated (Rolland Cell 2014) | 0.6 |
| | | | Humanized yeast interactions (STRING) | $qij = 1 - (1 - q\hat{}exp)*(1 - q\hat{}data)$ |
| | | | Yeast-to-human unpublished Y2H (Zhong submitted) | 0.6 |
| Aβ-OE humanized | Yeast OE Aβ screen modifiers (40) | Yeast OE Aβ screen modifiers | STRING human genetic/physical/database | $qij = 1 - (1 - q\hat{}exp)*(1 - q\hat{}data)$ |
| | | | CCSB human physical/ curated (Rolland Cell 2014) | 0.6 |
| | | | Humanized yeast interactions (STRING) | $qij = 1 - (1 - q\hat{}exp)*(1 - q\hat{}data)$ |
| | | | Yeast-to-human unpublished Y2H (Zhong submitted) | 0.6 |
| α-SYNUCLEIN full humanized | 331 unique hits in total, dervived from: | Yeast OE α-syn screen modifiers | STRING human genetic/physical/database | $qij = 1 - (1 - q\hat{}exp)*(1 - q\hat{}data)$ |
| | Yeast OE α-syn screen modifiers (77) | Yeast pooled OE α-syn screen modifiers | CCSB human physical/ curated (Rolland Cell 2014) | 0.6 |
| | Yeast pooled OE α-syn screen modifiers (135) | Yeast OE α-syn screen modifiers | Humanized yeast interactions (STRING) | $qij = 1 - (1 - q\hat{}exp)*(1 - q\hat{}data)$ |
| | Yeast OE α-syn screen modifiers (152) | Yeast low-throughput candidates | Yeast-to-human unpublished Y2H (Zhong submitted) | 0.6 |
| | Yeast low-throughput candidates (14) | Human homologs of yeast hits that are known neurodegeneration genes | Yeast hit-to-human homolog edge weight Yeast hit-to-human neurodegen gene edge weight | Integrated score pij (see methods) pij + 0.5 |

OE—overexpression
"FULL"—refers to the network dervived from the complete list of α-syn genetic modifiers-3 genome-wide screens and candidate-based modifiers

DATA S2

YEAST MODIFIERS RECOVERED IN PREVIOUS OVEREXPRESSION SCREENS

| α-SYNUCLEIN OE screen hits | Number of physical/genetic interactions (Biogrid) [interactors; interactions] | Modification (Suppressor or Enhancer of Toxicity) | TDP-43 OE screen hits | Modification (Supp/Enh) | Aβ-OE OE screen hits | Modification (Supp/Enh) |
|---|---|---|---|---|---|---|
| AFI1 | 7(13) | S | ADY3 | S | ADE12 | S |
| AVT4 | 0(0) | S | BFR1 | S | BOP3 | E |
| BET4 | 13(16) | E | CDC6 | E | CRM1 | S |
| BRE5 | 899(1422) | S | CYC8 | S | FCY21 | S |
| CAB3(PPCDC) | 30(66) | S | DIP5 | E | FMP48 | S |
| CAX4 | 44(51) | E | FMP48 | S | GRR1 | S |

DATA S2-continued

YEAST MODOFIERS RECOVERED IN PREVIOUS OVEREXPRESSION SCREENS

| α-SYNUCLEIN OE screen hits | Number of physical/genetic interactions (Biogrid) [interactors; interactions] | Modification (Suppressor or Enhancer of Toxicity) | TDP-43 OE screen hits | Modification (Supp/Enh) | Aβ-OE OE screen hits | Modification (Supp/Enh) |
|---|---|---|---|---|---|---|
| CCC1 | 41(58) | S | HRP1 | E | INP52 (yINPP5D) | S |
| CDC4 (FBXW7, ?PARKIN PARK2-related) | 131(270) | S | HSP104 | S | IVY1 | E |
| CDC5 | 178(360) | S | ICS2 | S | KAR9 | E |
| CUP9 | 70(88) | S | KEL1 | E | MBP1 | S |
| DIP5 | 59(62) | S | KIN3 | E | MID2 | E |
| EPS1 | 25(40) | E | MEC1 | E | MUM2 | S |
| ERV29 | 114(147) | S | MSA1 | E | MVP1 | E |
| FZF1 | 26(30) | S | MSN5 | E | NAB3 | S |
| GIP2 | 35(41) | S | MTH1 | E | OPY1 | S |
| GLO3 | 256(423) | E | NNK1 | S | PBS2 | E |
| GOS1 | 188(333) | E | PBP1 (yATXN2) | E | PET111 | E |
| GYP8 | 65(77) | E | PBP2 | E | PKC1 | E |
| HAP4 | 117(133) | S | PCL6 | E | PMT2 | E |
| HRD1 (SYVN1, VCP-related) | 127(286) | S | PGM1 | S | POG1 | E |
| ICY1 | 8(8) | S | PIB2 | E | PPR1 | S |
| ICY2 | 24(24) | S | RDR1 | S | PSK1 | E |
| IDS2 | 16(17) | E | RGA2 | E | ROM1 | E |
| IME2 | 156(175) | S | RIM15 | S | RTG3 | S |
| ISN1 | 16(17) | S | ROM2 | E | RTS1 | S |
| IZH3 | 41(57) | E | SAK1 | E | SKT5 | E |
| JSN1 | 64(74) | S | SFG1 | E | SLA1(yCD2AP) | S |
| LST8 | 199(244) | S | SLF1 | E | SLF1 | S |
| MATALPHA1 | 4(4) | E | SLG1 | E | SLS1 | E |
| MGA2 | 226(388) | S | SOL1 | E | SPO7 | E |
| MKS1 | 145(173) | E | SRO9 | E | SPT21 | S |
| MUM2 | 185(204) | S | TIS11 | S | SRO9 | S |
| NTH1 | 60(101) | S | TSC11 | E | SVL3 | E |
| NVJ1 | 27(32) | S | UBP7 | E | TEC1 | E |
| OSH2 | 50(66) | S | VHS1 | E | VPS9 (yRIN3) | S |
| OSH3 | 62(67) | S | VTS1 | S | WHI5 | S |
| PDE2 (PDE8B) | 236(322) | S | XRN1 | E | XRN1 | E |
| PFS1 | 46(65) | S | XRS2 | S | YAP1802 (yPICALM) | S |
| PHO80 | 288(478) | S | YCK2 | E | YBL086C | S |
| PMR1 | 536(955) | E | YHR131C | E | YPL014W | S |
| PPZ1 | 192(277) | E | | | | |
| PPZ2 | 51(82) | E | | | | |
| PTC4 | 86(98) | S | | | | |
| PTP2 | 47(86) | S | | | | |
| QDR3 | 14(14) | S | | | | |
| RCK1 | 184(218) | S | | | | |
| RKM3 | 28(31) | S | | | | |
| SEC21 | 112(169) | S | | | | |
| SEC28 | 348(619) | S | | | | |
| SEC31 | 69(116) | E | | | | |
| SFT1 | 34(50) | S | | | | |
| SIT4 | 178(295) | E | | | | |
| SLY41 | 44(57) | E | | | | |
| STB3 | 37(42) | S | | | | |
| SUT2 | 53(64) | E | | | | |
| TIF4632 (EIF4G1 PARK18) | 68(126) | S | | | | |
| TPO4 | 46(56) | E | | | | |
| TPS3 | 52(73) | S | | | | |
| TRS120 | 21(58) | E | | | | |
| UBP11 | 24(24) | E | | | | |
| UBP3 | 875(1235) | S | | | | |
| UBP7 | 55(70) | E | | | | |
| UGP1 | 69(79) | S | | | | |
| UIP5 | 14(18) | S | | | | |
| VHR1 | 13(13) | S | | | | |
| YCK3 | 104(115) | S | | | | |
| YDL121C | 19(22) | S | | | | |
| YDR374C | 16(17) | S | | | | |
| YIP3 | 90(128) | E | | | | |
| YKL063C | 26(37) | S | | | | |

DATA S2-continued

YEAST MODIFIERS RECOVERED IN PREVIOUS OVEREXPRESSION SCREENS

| α-SYNUCLEIN OE screen hits | Number of physical/genetic interactions (Biogrid) [interactors; interactions] | Modification (Suppressor or Enhancer of Toxicity) | TDP-43 OE screen hits | Modification (Supp/Enh) | Aβ-OE OE screen hits | Modification (Supp/Enh) |
|---|---|---|---|---|---|---|
| YKT6 | 83(188) | S | | | | |
| YML081W | 24(25) | S | | | | |
| YML083C | 18(18) | S | | | | |
| YMR111C | 44(46) | S | | | | |
| YNR014W | 12(14) | S | | | | |
| YPK9 (ATP13A2 PARK9) | 76(90) | S | | | | |
| YPT1 | 148(245) | S | | | | |

TABLE S3

NETWORK OUTPUT (MODIFIERS + PREDICTED NODES) FOR 3 PROTEOTOXICITY SCREENS

| NETWORK OUTPUT α-SYNUCLEIN OE yeast | NETWORK OUTPUT: TDP-43 OE yeast | NETWORK OUTPUT: Aβ OE yeast |
|---|---|---|
| ADE4 | ACE2 | ACE2 |
| AFI1 | ACK1 | ADE12 |
| ALY2 | ADE16 | ADE16 |
| APC4 | ADY3 | APC2 |
| ARO2 | AKR1 | AVO1 |
| AVT4 | ALY2 | BCK2 |
| BCY1 | APC1 | BMH2 |
| BET2 | ARP2 | BSP1 |
| BET4 | ASE1 | CCW12 |
| BET5 | AVO1 | CDC33 |
| BFR1 | BBC1 | CDC34 |
| BMH2 | BCK2 | CDC4 |
| BRE5 | BCY1 | CEG1 |
| CAB3 | BEM3 | CHC1 |
| CAX4 | BFR1 | CKS1 |
| CCC1 | BUL1 | CLB6 |
| CCT6 | BZZ1 | CLN1 |
| CDC28 | CBC2 | CLN2 |
| CDC4 | CCR4 | CRM1 |
| CDC48 | CDC14 | CRN1 |
| CDC5 | CDC27 | CSR2 |
| CDH1 | CDC28 | CYC8 |
| CHA4 | CDC33 | DHH1 |
| CLB2 | CDC4 | EDE1 |
| CLF1 | CDC40 | EXO70 |
| CLN2 | CDC42 | EXO84 |
| CMD1 | CDC6 | FCY21 |
| CNB1 | CDH1 | FMP48 |
| CNM67 | CEG1 | GIP2 |
| CPR1 | CHA4 | GLC7 |
| CRP1 | CHC1 | GRR1 |
| CUP9 | CKA2 | GTS1 |
| CYC8 | CKB2 | HIS4 |
| CYR1 | CLB1 | IMD4 |
| DBF2 | CLB2 | INP52 |
| DIP5 | CLB5 | IVY1 |
| DMA2 | CLN2 | KAR1 |
| DPM1 | CNM67 | KAR9 |
| DSL1 | CSR2 | LAS17 |
| EMC5 | CYC8 | LSB5 |
| EPS1 | DAD2 | MBP1 |
| ERV29 | DAD3 | MID2 |
| FBP26 | DAM1 | MPT5 |
| FMP41 | DFR1 | MTF2 |
| FPK1 | DHH1 | MUM2 |
| FPR4 | DIF1 | MVP1 |
| FUS1 | DIP5 | NAB3 |
| FZF1 | DNA2 | NAB6 |
| GAL10 | EDC3 | NMD3 |
| GCS1 | EIS1 | NRD1 |
| GDI1 | EXO1 | OPY1 |
| GIP2 | FAR1 | PAB1 |
| GLO3 | FMP48 | PAN1 |
| GOS1 | GAL10 | PBS2 |
| GPA2 | GAL7 | PET111 |
| GRR1 | GCR1 | PIL1 |
| GSC2 | GEM1 | PKC1 |
| GSY2 | GIP1 | PMT2 |
| GUK1 | GIP2 | POG1 |
| GYP8 | GLC7 | PPH21 |
| HAP4 | GLC8 | PPR1 |
| HEK2 | GPR1 | PRP24 |
| HOG1 | GRR1 | PRP40 |
| HPT1 | GSP1 | PSK1 |
| HRD1 | GTR1 | PSK2 |
| HRD3 | GTR2 | RAS2 |
| HSE1 | GTS1 | REG1 |
| HTB2 | HIS4 | RGA1 |
| ICY1 | HPR1 | RHO1 |
| ICY2 | HRP1 | RNA1 |
| IDH1 | HSE1 | ROM1 |
| IDP1 | HSF1 | RPL37b |
| IDS2 | HSM3 | RPO21 |
| IMD3 | HSP104 | RSP5 |
| IME2 | HSP42 | RTG3 |
| ISN1 | HXK2 | RTR1 |
| IVY1 | HXT5 | RTS1 |
| IZH3 | ICS2 | RVS167 |
| JSN1 | IGO2 | SEC3 |
| KES1 | IMD4 | SEC6 |
| KIC1 | IPL1 | SEN1 |
| KIN2 | IRA2 | SET1 |
| KIN4 | KAP104 | SHE2 |
| KOG1 | KAR1 | SIR3 |
| LST8 | KEL1 | SKI3 |
| MAD2 | KIN3 | SKI5 |
| MATALPHA1 | LAS17 | SLA1 |
| MDS3 | LIF1 | SLA2 |
| MEP2 | LSP1 | SLF1 |
| MGA2 | MEC1 | SLG1 |
| MIA40 | MEH1 | SLS1 |
| MKS1 | MEP1 | SMI1 |
| MLC1 | MEP2 | SMM1 |
| MLH1 | MEX67 | SNA3 |
| MMF1 | MIF2 | SPB4 |
| MMS4 | MIG1 | SPC110 |

TABLE S3-continued

NETWORK OUTPUT (MODIFIERS + PREDICTED NODES) FOR 3 PROTEOTOXICITY SCREENS

| NETWORK OUTPUT α-SYNUCLEIN OE yeast | NETWORK OUTPUT: TDP-43 OE yeast | NETWORK OUTPUT: Aβ OE yeast |
|---|---|---|
| MOT2 | MLH3 | SPC29 |
| MPS2 | MPC54 | SPC72 |
| MPS3 | MPS2 | SPO14 |
| MPT5 | MSA1 | SPO7 |
| MRS6 | MSH6 | SPT21 |
| MUDI | MSN2 | SRO9 |
| MUM2 | MSN5 | SST2 |
| MYO1 | MSS1 | STE2 |
| NAM8 | MTH1 | STE4 |
| NDT80 | MYO3 | STU2 |
| NPL4 | NNK1 | SVL3 |
| NTH1 | NSA1 | SWI4 |
| NVJ1 | NUP100 | SYP1 |
| OSH2 | NUP85 | TEC1 |
| OSH3 | PAB1 | TID3 |
| PAA1 | PAP1 | TIF4632 |
| PBP1 (ATXN2) | PBP1 | UBP2 |
| PDE2 | PBP2 | VPS35 (PARK17) |
| PDS1 | PCL6 | VPS9 |
| PEP4 | PDB1 | WHI5 |
| PFS1 | PEF1 | XRN1 |
| PHO80 | PGM1 | YAP1802 |
| PIN4 | PIB2 | YBL086C |
| PMR1 | PKC1 | YP014W |
| PNC1 | PMS1 | ZDS2 |
| PNP1 | PRE8 | |
| POL1 | PRP40 | |
| POP2 | PRS2 | |
| PPH22 | PSK2 | |
| PPH3 | PUF6 | |
| PPZ1 | RAT1 | |
| PPZ2 | RDR1 | |
| PSA1 | REG1 | |
| PTC2 | RGA1 | |
| PTC4 | RGA2 | |
| PTP2 | RGD2 | |
| QDR3 | RGT1 | |
| RAD9 | RGT2 | |
| RAS2 | RIM15 | |
| RCK1 | RNA15 | |
| REC8 | RNR2 | |
| REG1 | RNR4 | |
| RKM3 | ROM2 | |
| RNQ1 | RPB10 | |
| RRI2 | RPC31 | |
| RSP5 | RPN1 | |
| SCH9 | RRM3 | |
| SDS23 | RSP5 | |
| SEC14 | SAK1 | |
| SEC21 | SEF1 | |
| SEC23 | SFG1 | |
| SEC28 | SFL1 | |
| SEC31 | SIP1 | |
| SER33 | SIP4 | |
| SFL1 | SKI3 | |
| SFP1 | SKI5 | |
| SFT1 | SLF1 | |
| SIS2 | SLG1 | |
| SIT4 | SLM1 | |
| SLN1 | SLM4 | |
| SLT2 | SNA4 | |
| SLY41 | SNF1 | |
| SMD1 | SNF3 | |
| SNC1 | SOL1 | |
| SNF4 | SOL2 | |
| SOV1 | SPA2 | |
| SPC42 | SPC110 | |
| SPC72 | SPC42 | |
| SPO13 | SPO21 | |
| SPO14 | SPT16 | |
| SPO21 | SRM1 | |
| SPT23 | SRO9 | |
| SSA1 | SSB1 | |
| SSD1 | SSP1 | |
| STB3 | SSZ1 | |
| STE11 | STE20 | |
| STI1 | STH1 | |
| STM1 | STI1 | |
| SUT2 | SUT1 | |
| SWH1 | SWE1 | |
| SWI5 | SWI4 | |
| TAO3 | SWI5 | |
| TAP42 | SYF1 | |
| TDA11 | TID3 | |
| TEC1 | TIS11 | |
| TEM1 | TOF2 | |
| TIF1 | TOR2 | |
| TIF2 | TPK2 | |
| TIF4632 | TSC11 | |
| TIM10 | TSR1 | |
| TIM18 | UBP7 | |
| TIM9 | URE2 | |
| TIP41 | VHS1 | |
| TOM6 | VTS1 | |
| TOR2 | WHI5 | |
| TOS4 | WTM1 | |
| TPK3 | XRN1 | |
| TPO4 | XRS2 | |
| TPS1 | YAK1 | |
| TPS2 | YBR137W | |
| TPS3 | YCK2 | |
| TRP2 | YDJ1 | |
| TRS120 | YGR054W | |
| TRS33 | YHR131C | |
| TSL1 | YKU70 | |
| TUB2 | YKU80 | |
| UBP11 | YPK2 | |
| UBP3 | YPK3 | |
| UBP7 | YRA2 | |
| UGP1 | YSCB4 | |
| UIP5 | ZUO1 | |
| VAC8 | | |
| VHR1 | | |
| VHS3 | | |
| YAK1 | | |
| YCK3 | | |
| YDL121C | | |
| VDR186C | | |
| YDR374C | | |
| YGR054W | | |
| YIF1 | | |
| YIP1 | | |
| YIP3 | | |
| YKL063C | | |
| YKT6 | | |
| YKT6 | | |
| YML081W | | |
| YNR014W | | |
| YPK1 | | |
| YPK9 | | |
| YPT1 | | |
| YPT11 | | |

TABLE S4

COMPARING PROTEOTIXICITIES, OVEREXPRESSION SCREEN HIT INPUTS versus STEINER NETWORK OUTPUTS

| Screen | ORF | Standard Name | Description |
|---|---|---|---|
| OVERLAPPING SCREEN INPUT: α-syn, TDP-43 and Aβ OE yeast screen hits | | | |
| α-syn/TDP-43 | YIL156W | UBP7 | Ubiquitin-specific protease that cleaves ubiquitin-protein fusions; UBP7 has a paralog, UBP11, that arose from the whole genome duplication |
| | YPL265W | DIP5 | Dicarboxylic amino acid permease; mediates high-affinity and high-capacity transport of L-glutamate and L-aspartate; also a transporter for Gln, Asn, Ser, Ala, and Gly; relocalizes from plasma membrane to vacuole upon DNA replication stress |
| α-syn/Aβ | YBR057C | MUM2 | Protein essential for meotic DNA replication and sporulation; cytoplasmic protein; subunit of the MIS complex which controls mRNA methylation during during the induction of sporulation; also interacts with Orc2p, which is a component of the origin recognition complex |
| TDP-43/Aβ | YCL037C | SRO9 | Cytoplasmic RNA-binding protein; shuttles between nucleus and cytoplasm and is exported from the nucleus in an mRNA export-dependent manner; associates with translating ribosomes; involved in heme regulation of Hap1p as a component of the HMC complex, also involved in the organzation of actin filaments; contains a La motif; SRO9 has paralog, SLF1, that arose from the whole genome duplication |
| | YDR515W | SLF1 | RNA binding protein that associates with polysomes; may be involved in regulating mRNA translation; involved in the copper-dependent mineralization of cooper sulfide complexes, on cell surface in cells cultured in copper salts; SLF1 has a paralog: SRO9, that arose from the whole genome duplication; protein abundance increases in response to DNA replication stress |
| | YGL173C | XRN1 | Evolutionarily-conserved 5'-3' exonuclease; component of cytoplasmic processing (P) bodies involved in mRNA decay; also enters the nucleus and positively regulates transcription initiation and elongation; plays a role in microtubule-rnediated processes, filamentous groveth, ribosomal RNA maturation, and telomere maintenance; activated by the scavenger decapping enzyme Dcs1p |
| | YGR052W | FMP48 | Putative protein of unknown function; the authentic, non-tagged protein is detected in highly purified mitochondria in high-throughput studies; induced by treatment with 8-methoxypsoralen and UVA irradiation |

TABLE S4-continued

COMPARING PROTEOTIXICITIES, OVEREXPRESSION SCREEN HIT INPUTS versus STEINER NETWORK OUTPUTS

| Screen | ORF | Standard Name | Description |
|---|---|---|---|
| OVERLAPPING NETWORK OUTPUT: α-syn, TDP-43 and Aβ OE yeast networks | | | |
| YFL009W | YFL009W | CDC4 | F-box protein required for both the G1/S: and G2/M phase transitions; modular substrate specificity factor which associates with core SCF (Cdc53p, Skp1p and Hrt1p/Rbx1p) to form the SCFCdc4 complex; SCFCdc4 acts as a ubiquitin-protein ligase directing ubiquitination of cyclin-dependent kinase (CDK) phosphorylated substrates, such as: Sic1p, Far1p, Cdc6p, Clb6p, and Cln3p |
| YPL256C | YPL256C | CLN2 | G1 cyclin involved in regulation of the cell cycle; activates Cdc28p kinase to promote the G1 to S phase transition; late G1 specific expression depends on transcription factor complexes, MBF (Swi6p-Mbp1p) and SBF (Swi6p-Swi4p); CLN2 has a paralog, CLN1, that arose from the whole genome duplication |
| YBR112C | YBR112C | CYC8 | General transcriptional co-repressor; acts together with Tup1p; also acts as part of a transcriptional co-activator complex that recruits the SWI/SNF and SAGA complexes to promoters; can form the prion [OCT+] |
| YER054C | YER054C | GIP2 | Putative regulatory subunit of protein phosphatase Glc7p; involved in glycogen metabolism; contains a conserved motif (GVNK motif) that is also found in Gac1p, Pig1p, and Pig2p; GIP2 has a paralogs PIG2, that arose from the whole genome duplication |
| YJR090C | YJR090C | GRR1 | F-box protein component of an SCF ubiquitin-ligase complex; modular substrate specificity factor which associates with core SCF (Cdc53p, Skp1p and Hr1p/Rbx1p) to form the SCH(Grr1) complex; SCF(Grr1) acts as a ubiquitin-protein ligase directing ubiquitination of substrates such as: Gic2p, Mks1p, Mth1p, Cln1p, Cln2p and Cln3p; involved in carbon catabolite repression, glucose-dependent divalent cation transport, glucose transport, morphogenesis, and sulfite detoxification |
| YDR028C | YDR038 | REG1 | Regulatory subunit of type 1 protein phosphatase Glc7p; involved in negative regulation of glucose-repressible genes; involved in regulation of the nucleocytoplasmic shuttling of Hxk2p; REG1 has a paralog, REG2, that arose from the whole genome duplication |
| YER125W | YEF125W | RSP5 | E3 ubiquitin ligase of NEDD4 family; regulates many cellular processes including MVB sorting, heat shock response, transcription, endocytosis, ribiosome stability; mutant tolerates aneuploidy; autoubiquitinates; ubiquitinates Sec23p and Sna3p; |

TABLE S4-continued

COMPARING PROTEOTIXICITIES, OVEREXPRESSION SCREEN HIT INPUTS versus STEINER NETWORK OUTPUTS

| Screen | ORF | Standard Name | Description |
|---|---|---|---|
| | | | deubiquitinated by Ubp2p; activity regulated by SUMO ligase Siz1p, in turn regulates Siz1p SUMO ligase activity; required for efficient Golgi-to-ER trafficking in COPI mutants; human homolog implicated in Liddle syndrome |
| OVERLAPPING NETWORK OUTPUT: α-syn and TDP-43 OE yeast networks | | | |
| YJL084C | YJL084C | ALY2 | Alpha arrestin; controls nutrient-mediated intracellular sorting of permease Gap1p; interacts with AP-1 subunit Apl4p; phosphorylated by Nnr1p and also by cyclin-CDK complex Pcl7p-Pho85p; promotes endocytosis of plasma membrane proteins; ALY2 has a paralog, ALY1, that arose from the whole genome duplication |
| YIL033C | YIL033C | BCY1 | Regulatory subunit of the cyclic AMP-dependent protein kinase (PKA); PKA is a component of a signaling pathway that controls a variety of cellular processes, including metabolism, cell cycle, stress response, stationary phase, and sporulation |
| YOR198C | YOR198C | BFR1 | Component of mRNP complexes associated with polyribosomes; involved in localization of mRNAs to P bodies; implicated in secretion and nuclear segregation; multicopy suppressor of BFA (Brefeidin A) sensitivity |
| YBR160W | YBR160W | CDC28 | Cyclin-dependent kinase (CDK) catalytc subunit; master regulator of mitotic and meiotic cell cycles; alternately associates with G1 (CLNs), S and Gs/M (CLBs) phase cyclins, which provide substrate specificity, regulates cell cycle and basal transcription, chromosome duplication and segregation, lipid biosynthesiss membrane trafficking, polarized growth, and morphogenesis; abundance increases in DNA replication stress; transcript induction in osmostress involves antisense RNA |
| YFL009W | YFL009W | CDC4 | F-box protein required for both the G1/S and G2/M phase transitions; modular substrate specificity factor which associates with core SCF (Cdc53p, Skp1p and Hrt1p/Rbx1p) to form the SCFCdc4 complex; SCFCdc4 acts as a ubiquitin-protein ligase directing ubiquitination of cyclin-dependent kinase (CDK) phosphorylated substrates, such as Sic1p, Far1p, Cdc6p, Clb6p, and Cln3p |
| YGL003C | YGL003C | CDH1 | Activator of anaphase-promoting complex/cyclosome (APC/C); cell-cycle regulated; directs ubiquitination of cyclins resulting in mitotic exit; targets the APC/C to specific substrates including Cdc20p, Ase1p, Cin8p and Fin1p |
| YLR098C | YLR098C | CHA4 | DNA binding transcriptional activator; mediates serine/threonine activation of the catabolic L-serine (L-threonine) |

TABLE S4-continued

COMPARING PROTEOTIXICITIES, OVEREXPRESSION SCREEN HIT INPUTS versus STEINER NETWORK OUTPUTS

| Screen | ORF | Standard Name | Description |
|---|---|---|---|
| | | | deaminase (CHA1); Zinc-finger protein with Zn[2]-Cys[6] fungal-type binuclear cluster domain |
| YPR119W | YPR119W | CLB2 | B-type cyclin involved in cell cycle progression; activates Cdc28p to promote the transition from G2 to M phase; accumulates during Gs and M, then targeted via a destruction box motif for ubiquitin-mediated degradation by the proteasome; CLB2 has a paralog, CLB1, that arose from the whole genome duplication |
| YPL256C | YPL256C | CLN2 | G1 cyclin involved in regulation of the cell cycle; activates Cdc28p kinase to promote the G1 to S phase transition; late G1 specific expression depends on transcription factor complexes, MBF (Swi6p-Swi4p); and SBF (Swi6p-Swi4p); CLN2 has a paralog, CLN1, that arose from the whole genome duplication |
| YNL22SC | YNL225C | CNM167 | Component of the spindle pole body outer plaque; required for spindle orientation and mitotic nuclear migration; CNM67 has a paralog, ADY3, that arose from the whole genome duplication |
| YBR112C | YBR112C | CYC8 | General transcriptional co-repressor; acts together with Tup1p; also acts as part of a transcriptional co-activator complex that recruits the SWI/SNF and SAGA complexes to promoters; can form the prion [OCT+] |
| YPL265W | YPL265W | DIPS | Dicarboxylic amino acid permaase; mediates high-affinity and high-capacity transport of L-glutamate and L-aspartate; also a transporter for Gln, Asn, Ser, Ala, and Gly; relocalizes from plasma membrane to vacuole upon DNA replication stress |
| YBR019C | YBR019C | GAL10 | UDP-glucose-4-epimerase; catalyzes the interconversion of UDP-galactose and UDP-D-glucose in galactose metabolism; also catalyzes the conversion of alpha-D glucose or alpha-D-galactose to their beta-anomers |
| YER054C | YER054C | GIP2 | Putative regulatory subunit of protein phosphatase Glc7p; involved in glycogen metabolism; contains a conserved motif (GVNK motif) that is also found in Gac1p, Pig1p, and Pig2p; GIP2 has a paralog, PIG2, that arose from the whole genome duplication |
| YJR090C | YJR090C | GRR1 | F-box protein component of an SCF ubiquitin-ligase complex; modular substrate specificity factor which associates with core SCF (Cdc53p, Skp1p and Hrt1p/Rbx1p) to form the SCF(Grr1) complex; SCF(Grr1) acts as a uhiquitin-protein ligase directing ubiquitination of substrates such as; Gic2p, Mks1p; Mth1p, Cln1p, Cln2p and Cln3p; involved in carbon catabolite repression, glucose-dependent |

TABLE S4-continued

COMPARING PROTEOTIXICITIES, OVEREXPRESSION SCREEN HIT INPUTS versus STEINER NETWORK OUTPUTS

| Screen | ORF | Standard Name | Description |
|---|---|---|---|
| YHL002W | YHL002W | HSE1 | divalent cation transport, glucose transport, morphogenesis, and sulfite detoxification<br>Subunit of the endosomal Vps27p-Hse1p complex; complex is required for sorting of ubiquitinated membrane proteins into intralumenal vesicles prior to vacuolar degradation, as well as for recycling of Golgi proteins and formation of lumenal membranes |
| YNL142W | YNL142W | MEP2 | Ammonium permease involved in regulation of pseudohyphal growth; belongs to a ubiquitous family of cytoplasmic membrane proteins that transport only ammonium (NH4+); expression is under the nitrogen catabolite repression regulation |
| YGL075C | YGL075C | MPS2 | Essential membrane protein localized at nuclear envelope and SPBs; required for insertion of the newly duplicated spindle pole body into the nuclear envelope; potentially phosphorylated by Cdc28p; MPS2 has a paralog, CSM4 that arose from the whole genome duplication |
| YGR178C | YGR178C | PBP1 | Component of glucose deprivation induced stress granules; involved in P-body-dependent granule assembly; similar to human ataxin-2; interacts with Pab1p to regulate RNA polyadenylation; interacts with Mkt1p to regulate HO translation; protein increases in abundance and relative distribution to the nucleus increases upon DNA replication stress |
| YDR028C | YDR028C | REG1 | Regulatory subunit of type 1 protein phosphatase Glc7p; involved in negative regulation of glucose-repressible genes; involved in regulation of the nucleocytoplasmic shuttling of Hxk2p; REG1 has a paralog, REG2, that arose from the whole genome duplication |
| YER125W | YER125W | RSP5 | E3 ubiquitin ligase of NEDD4 family; regulates many cellular processes including MVB sorting, heat shock response, transcription endocytosis, ribosome stability; mutant tolerates aneuploidy; autoubiquitinates; ubiquitinates Set23p and Sna3p; deubiquitinated by Ubp2p; activity regulated by SUMO ligase Siz1p, in turn regulates Siz1p SUMO ligase activity; required for efficient Golgi-to-ER trafficking in COPI mutants; human homolog implicated in Liddle syndrome |
| YOR140W | YOR140W | SFL1 | Transcriptional repressor and activator; involved in repression of flocculation-related genes, and activation of stress responsive genes; negatively regulated by cAMP-dependent protein kinase A subunit Tpk2p; premature stop codon (C1430T, Q477-stop) in SK1 background is linked to the |

TABLE S4-continued

COMPARING PROTEOTIXICITIES, OVEREXPRESSION SCREEN HIT INPUTS versus STEINER NETWORK OUTPUTS

| Screen | ORF | Standard Name | Description |
|---|---|---|---|
| | | | aggressively invasive phenotype of SK1 relative to BY4741 (S288C) |
| YKL042W | YKL042W | SPC42 | Central plaque component of Spindle pole body (SPB); involved in SPB duplication, may facilitate attachment of the SPB to the nuclear membrane |
| YOL091W | YOL091W | SPO21 | Component of the meiotic outer plaque of the spindle pole body; involved in modifying the meiotic outer plaque that is required prior to prospore membrane formation; SPO21 has a paralog, YSW1, that arose from the whole genome duplication |
| YOR027W | YOR027W | STI1 | Hsp90 cochaperone; interacts with the Ssa group of the cytosolic Hsp70 chaperones and activates Ssa1p ATPase activity; interacts with Hsp90 chaperones and inhibits their ATPase activity; homolog of mammalian Hop |
| YDR146C | YDR146C | SWI5 | Transcription factor that recruits Mediator and Swi/Snf complexes; activates transcription of genes expressed at the M/G1 Phase boundary and in G1 phase; required for expression of the HO gene controlling mating type switching; localization to nucleus occurs during G1 and appears to be regulated by phosphorylation by Cdc28p kinase; SWI5 has a paralog, ACE2, that arose from the whole genome duplication |
| YKL203C | YKL203C | TOR2 | PIK-related protein kinase an rapamycin target; subunit of TORC1, a complex that regulates growth in response to nutrients and TORC2, a complex that regulates cell-cycle dependent polarization of the actin cytoskeleton; involved in meiosis; TOR2 has a paralog, TOR1, that arose from the whole genome duplication |
| YIL156W | YIL156W | UBP7 | Ubiquitin-specific protease that cleaves ubiquitin-protein fusions; UBP7 has a paralog, UBP11, that arose from the whole genome duplication |
| YJL141C | YJL141C | YAK1 | Serine-threonine protein kinase; component of a glucose-sensing system that inhibits growth in response to glucose availability upon nutrient deprivation Yak1p phosphorylates Pop2p to regulate mRNA deadenylation, the co-repressor Crf1p to inhibit transcription of ribosomal gene and the stress-responsive transcription factors Hsf1p nd Msn2p; nuclear localization negatively regulated by the Ras/PKA signaling pathway in the presence of glucose |
| YGR054W | YGR054W | YGR054W | Eukaryotic initiation factor (eIF) 2A; associates specifically with both 40S subunits and 80 S ribosomes, and interacts genetically with both eIF5b and eIF4E; homologous to mammalian eIF2A |

TABLE S4-continued

COMPARING PROTEOTIXICITIES, OVEREXPRESSION SCREEN HIT INPUTS versus STEINER NETWORK OUTPUTS

| Screen | ORF | Standard Name | Description |
|---|---|---|---|
| OVERLAPPING NETWORK OUTPUT: α-syn and Aβ OE yeast networks | | | |
| YDR099W | YDR099W | BMH2 | 14-3-3 protein, minor isoform; controls proteome at post-transcriptional level, binds proteins and DNA, involved in regulation of many processes including exocytosis, vesicle transport, Ras/MAPK signaling, and rapamycin-sensitive signaling; protein increases in abundance and relative distribution to the nucleus increases upon DNA replication stress; BMH2 has a paralog, BMH1 that arose from the whole genome duplication |
| YFL009W | YFL009W | CDC4 | F-box protein required for both the G1/S and G2/M phase transitions; modular substrate specificity factor which associates with core SCF (Cdc53p, Skp1p and Hrt1p/Rbx1p) to form the SCFCdc4 complex; SCFCdc4 acts as a ubiquitin-protein ligase directing ubiquitination of cyclin-dependent kinase (CDK) phosphorylated substrates, such as Sic1p, Far1p, Cdc6p, Clb6p, and Cln3p |
| YPL256C | YPL256C | CLN2 | G1 cyclin involved in regulation of the cell cycle; activates Cdc28p kinase to promote the G1 to S phase transition; late G1 specific expression depends on transcription factor complexes, MBF (Swi6p-Mbp1p) and SBF (Swi6p-Swi4p); CLN2 has a paralog, CLN1, that arose from the whole genome duplication |
| YBR112C | YBR112C | CYC8 | General transcriptional co-repressor; acts together with Tup1p; also acts as part of a transcriptional co-activator complex that recruits the SWI/SNF and SAGA complexes to promoters; can form the prion [OCT+] |
| YER054C | YER054C | GIP2 | Putative regulatory subunit of protein phosphatase Glc7p; involved in glycogen metabolism; contains a conserved motif (GVNK motif) that is also found in Gac1p, Pig1p, and Pig2p; GIP2 has a paralog, PIG2, that arose from the whole genome duplication |
| YJR090C | YJR090C | GRR1 | F-box protein component of an SCF ubiquitin-ligase complex; modular substrate specificity factor which associates with core SCF (Cdc53p, Skp1p and Hrt1p/Rbx1p) to form the SCF(Grr1) complex; SCF(Grr1) acts as a ubiquitin-protein ligase directing ubiquitination of substrates such as: Gic2p, Mks1p, Mth1p, Cln1p, Cln2p and Cln3p; involved in carbon catabolite repression, glucose-dependent divalent cation transport, glucose transport, morphogenesis., and sulfite detoxification |
| YDR229W | YDR229W | IVY1 | Phospholipid-binding protein that interacts with both Ypt7p and |

TABLE S4-continued

COMPARING PROTEOTIXICITIES, OVEREXPRESSION SCREEN HIT INPUTS versus STEINER NETWORK OUTPUTS

| Screen | ORF | Standard Name | Description |
|---|---|---|---|
| | | | Vps33p; may partially counteract the action of Vps33p and vice versa, localizes to the rim of the vacuole as cells approach stationary phase |
| YGL178W | YGL178W | MPT5 | mRNA-binding protein of the PUF family; binds to the 3' UTR of specific mRNAs, including those involved in mating type switching, cell wall integrity, chronological lifespan, chromatin modification, and spindle pole body architecture; recruits the CCR4-NOT deadenylase complex to mRNAs along with Dhh1p and Dcp1p to promote deadenylation, decapping, and decay; also interacts with the Caf20p translational initiation repressor, affecting its mRNA target specificity |
| YBR057C | YBR057C | MUM2 | Protein essential for meiotic DNA replication and sporulation; cytoplasmic protein; subunit of the MIS complex which controls mRNA methylation during during the induction of sporulation; also interacts with Orc2p, which is a component of the origin recognition complex |
| YNL098C | YNL098C | RAS2 | GTP-binding protein; regulates nitrogen starvation response, sporulation, and filamentous growth; farnesylation and palmitoylation required for activity and localization to plasma membrane; homolog of mammalian Ras proto-oncogenes; RAS2 has a paralog, RAS1, that arose from the whole genome duplication |
| YDR028C | YDR028C | REG1 | Regulatory subunit of type 1 protein phosphatase Glc7p; involved in negative regulation of glucose-repressible genes; involved in regulation of the nucleocytoplasmic shuttling of Hxk2p; REG1 has a paralog, REG2, that arose from the whole genome duplication |
| YER125W | YER125W | RSP5 | E3 ubiquitin ligase of NEDD4 family; regulates many cellular processes including MVB sorting, heat shock response, transcription, endocytosis, ribosome stability; mutant tolerates aneuploidy; autoubiquitinates; ubiquitinates Sec23p and Sna3p; deubiquitinated by Ubp2p; activity regulated by SUMO ligase Siz1p, in turn regulates Siz1p SUMO ligase activity; required for efficient Golgi-to-ER trafficking in COPI mutants; human homolog implicated in Liddle syndrome |
| YAL074C | YAL047C | SPC72 | Component of the cytoplasmic Tub4p (gamma-tubulin) complex; binds spindle pole bodies and links them to microtubules, is regulated by Cdc5 kinase; has roles in astral microtubule formation and stabilization |
| YKR031C | YKR031C | SPO14 | Phospholipase D; catalyzes the hydrolysis of phosphatidylcholine, producing choline and |

TABLE S4-continued

COMPARING PROTEOTIXICITIES, OVEREXPRESSION SCREEN HIT INPUTS versus STEINER NETWORK OUTPUTS

| Screen | ORF | Standard Name | Description |
|---|---|---|---|
| | | | phosphatidic acid; involved in Sec14p-independent secretion; required for meiosis and spore formation; differently regulated in secretion and meiosis; participates in transcription initiation and/or early elongation of specific genes; interacts with "foot domain" of RNA polymerase II; deletion results in abnormal CTD Ser5 phosphorylation of RNA polymerase II at specific promoter regions |
| YBR083W | YBR083W | TEC1 | Transcription factor targeting filamentation genes and Ty1 expression; Ste12p activation of most filamentation gene promoters depends on Tec1p and Tec1p transcriptional activity is dependent on its association with Ste12p; binds to TCS elements upstream of filamentation genes, which are regulated by Tec1p/Ste12p/Dig1p complex; competes with Dig2p for binding to Ste12p/Dig1p; positive regulator of chronoiogicel life span; TEA/ATTS DNA-binding domain family member |
| YGL049C | YGL049C | TIF4632 | Translation initiation factor eIF4G; subunit of the mRNA cap-binding protein complex (eIF4F) that also contans eIF4E (Cdc33p); associates with the poly(A)-binding protein Pab1p, aso interacts with eIF4A (Tif1p); TIF4632 has a paralog, TIF4631, that arose from the whole genome duplication |
| OVERLAPPING NETWORK OUTPUT: TDP-43 and Aβ OE yeast networks | | | |
| YLR131C | YLR131C | ACE2 | Transcription factor required for septum destruction after cytokinesis; phosphorylation by Cbk1p blocks nuclear exit during M/G1 transition, causing localization to daughter cell nuclei, and also increases Ace2p activity; phosphorylation by Cdc28p and Pho85p prevents nuclear inport during cell cycle phases other than cytokinesis; part of RAM network that regulates cellular polarity and morphogenesis; ACE2 has a paralog, SWI5, that arose from the whole genome duplication |
| YLR028C | YLR028C | ADE16 | Enzyme of 'de novo' purine bicsynthesis; contains both 5-aminoimidazole-4-carboxamide ribonuceotide transformylase and inosine monophosphate cydohydroase activities; ADE16 has a paralog, ADE17, that arose from the whole genome duplication; ade16 ade17 mutants require adenine and histidine |
| YLR127C | YLR127C | APC2 | Subunit of the Anaphase-Promoting Complex/Cyclosome (APC/C); which is a ubiquitin-protein ligase required for degradation of anaphase inhibitors, including mitotic cyclins, during the metaphase/anaphase transition; component of the |

TABLE S4-continued

COMPARING PROTEOTIXICITIES, OVEREXPRESSION SCREEN HIT INPUTS versus STEINER NETWORK OUTPUTS

| Screen | ORF | Standard Name | Description |
|---|---|---|---|
| | | | catalytic core of the APC/C; has similarity to cullin Cdc53p |
| YOL078W | YOL078W | AVO1 | Component of a membrane-bound compex containing the Tor2p kinase-contains Tor2p kinase and other proteins may have a role in regulation of cell growth |
| YEF167W | YER167W | BCK2 | Serine/threonine-rich protein involved in PKC1 signaling pathway; protein kinase C (PKC1) signaling pathway controls cell integrity; overproduction suppresses pkc1 mutations |
| YOL139C | YOL139C | CDC33 | mRNA cap binding protein and translation initiaton factor eIF4E; the eIf4E-complex is responsible for mediating cap-deperdent mRNA translation via interactions with translation initiation factor eIf4G (Tif4631p or Tif4632p); protein abundance increases response to DNA replication stress; mutants are defective for adhesion and pseudohyphal growth |
| YFL009W | YFL009W | CDC4 | F-box protein required for both the G1/S and G2/M phase transitions; modular substrate specificity factor which associates with core SCF (Cdc53p, Skp1p and Hrt1p/Rbx1p) to form the SCFCdc4 complex; SCFCdc4 acts as a ubiquitin-protein ligase directing ubiquitination of cyclin-dependent kinase (CDK) phosphorylated substrates, such as: Sic1p, Far1p, Cdc6p, Clb6p, and Cln3p |
| YGL130W | YGL130W | CEG1 | Guanylytransferase involved in mRNA 5' capping; subunit of the mRNA capping enzyme, which is a heterotetramer composed of two molecules of Ceg1p and a homodimer of Cet1p, the mRNA 5?-triphosphatase subunit; nuclear import of Ceg1p requires interaction with Cet1p; mammalian capping enzyme is a single bifunctional polypeptide |
| YGL206C | YGL206C | CHC1 | Clathrin heavy chain; subunit of the major coat protein involved in intracellular protein transport and endocytosis, the clathrin triskelion is a trimeric molecule composed of three heavy chains that radiate from a vertex and three light chains which bind noncovalently near the vertex of the triskelion; the light chain (CLC1) is thought to regulate function |
| YPL256C | YPL256C | CLN2 | G1 cyclin involved in regulation of the cell cycle; activates Cdc28p kinase to promote the G1 to S phase transition; late G1 specific expression depends on transcription factor complexes, MBF (Swi6p-Mbp1p) and SBF (Swi6p-Swi4p); CLN2 has a paralog, CLN1, that arose from the whole genome duplication |
| YPR030W | YPR030W | CSR2 | Nuclear ubiquitin protein ligase binding protein; may regulate utilization of nonfermentable carbon sources and endocytosis of plasma membrane proteins; overproduction suppresses chs5 |

TABLE S4-continued

COMPARING PROTEOTIXICITIES, OVEREXPRESSION SCREEN HIT INPUTS versus STEINER NETWORK OUTPUTS

| Screen | ORF | Standard Name | Description |
|---|---|---|---|
| | | | spa2 lethality at high temp; ubiquitinated by Rsp5p, deubiquitinated by Ubp2p; CSR2 has a paralog, ECM21, that arose from the whole genome duplication |
| YBR112C | YBR112C | CYC8 | General transcriptional co-repressor; acts together with Tup1p; also acts as part of a transcriptional co-activator complex that recruits the SWI/SNF and SAGA complexes to promoters; can form the prion [OCT+] |
| YDL160C | YDl160C | DHH1 | Cytoplasmic DExD/H-box helicase, stimulates mRNA decapping; coordinates distinct steps in mRNA function and decay, interacts with both the decapping and deadenylase complexes, role in translational repression, mRNA decay, and processing body dynamics; may have a role in mRNA export; C-terminus of Dhh1p interacts with Ngr1p and promotes POR1, but not EDC1 mRNA decay; forms cytopasmic foci upon DNA replication stress |
| YFR052W | YGR052W | FMP48 | Putative protein of unknown function; the authentic, non-tagged protein is detected in highly purified mitochondria in high-throughput studies; induced by treatment with 8-methoxypsoralen and UVA irradiation |
| YER054C | YER054C | GIP2 | Putative regulatory subunit of protein phosphatase Glc7p; involved in glycogen metabolism; contains a conserved motif (GVNK motif) that is also found in Gac1p, Pig1p, and Pig2p; GIP2 has a paralog, PIG2, that arose from the whole genome duplication |
| YER133W | YER133W | GLC7 | Type 1 serine/threonine protein phosphatase catalytic subunit; cleavage and polyadenylation factor (CPF) component; involved in various processes including glycogen metabolism, sporulations mitosis; accumulates at mating projections by interaction with Afr1p; interacts with many regulatory subunits; involved in regulation of the nucleocytoplasmic shuttling of Hxk2p; import into nucleus is inhibited during spindle assembly checkpoint arrest |
| YJR090C | YJR090C | GRR1 | F-box protein component of an SCF ubiquitin-ligase complex; modular substrate specificity factor which associates with core SCF (Cdc53p, Skp1p and Hrt1p/Rbx1p) to form the SCF(Grr1) complex; SCF(Grr1) acts as a ubiquitin-protein ligase directing ubiquitination of substrates such as: Gic2p, Mks1p, Mth1p, Cln1p, Cln2p and Cln3p; involved in carbon catabolite repression, glucose-dependent divalent cation transport, glucose transport, morphogenesis, and sulfite detoxification |

TABLE S4-continued

COMPARING PROTEOTIXICITIES, OVEREXPRESSION SCREEN HIT INPUTS versus STEINER NETWORK OUTPUTS

| Screen | ORF | Standard Name | Description |
| --- | --- | --- | --- |
| YGL181W | YGL181W | GTS1 | Protein involved in Arf3p regulation and in transcription regulation; localizes to the nucleus and to endocytic patches; contains an N-terminal Zn-finger and ArfGAP homology domain, a C-terminal glutamine-rich region, and a UBA (ubiquitin associated) domain: gts1 mutations affect budding, cell size, heat tolerance, sporulation, life span, ultradian rhythms, endocytcsis; expression oscillates in a pattern similar to metabolic oscillations |
| YCL030C | YCL030C | HIS4 | Multifunctional enzyme containing phosphoribosyl-ATP pyrophosphatase; phosphoribosyl-AMP cyclohydrolase, and histidinol dehydrogenase activities; catalyzes the second, third, ninth and tenth steps in histidine biosynthesis |
| YML056C | YML056C | IMD4 | Inosine monophosphate dehydrogenase; catalyzes the rate-limiting step in the de novo synthesis of GTP; member of a four gene family in S. cerevisiae, constitutively expressed; IMD4 has a paralog, IMD3, that arose from the whole genome duplication |
| YNL188W | YNL188W | KAR1 | Protein involved in karyogamy and spindle pole body duplication; involved in karyogamy during mating; involved in spinde pole body duplication during rnitosis; localizes to the half-bridge of the spindle pole body; interacts with Spc72p during karyogamy; also interacts with Cdc31p; essential gene |
| YOR181W | YOR181W | LAS17 | Actin asembly factor; C-terminal WCA domain activates Arp2/3 complex-mediated nucleation of branched actin filaments and a polyproline domain which can nucleate actin filaments independent of Arp2/3; mutants are defective in actin cytoskeleton dependent processes such as: endocytosis, bud site selection and cytokinesis; localizes with the Arp2/3 convex to actin cortical patches; homolog of the Wiskott-Aldrich Syndrome protein (WASP), implicated in severe immunodeficiency |
| YER165W | YER165W | PAB1 | Poly(A) binding protein; part of the 3'-end RNA-processing complex, mediates interactions between the 5' cap structure and the 3' mRNA poly(A) tail involved in control of poly(A) tail length, interacts with translation factor eIF-4G; stimulates, but is not required for the deadenylation activity of the Pan2p-Pan3p poly(A)-ribonuclease complex |
| YBL105C | YBL105C | PKC1 | Protein serine/threonine kinase; essential for cell wall remodeling during growth; localized to sites of polarized growth and the mother-daughter bud neck; homolog of the alpha, beta, and gamma isoforms of mammalian protein kinase C (PKC) |

TABLE S4-continued

COMPARING PROTEOTIXICITIES, OVEREXPRESSION SCREEN HIT INPUTS versus STEINER NETWORK OUTPUTS

| Screen | ORF | Standard Name | Description |
| --- | --- | --- | --- |
| YKL012W | YKL012W | PRP40 | U1 snRNP protein involved in splicing; interacts with the branchpoint-binding protein during the formation of the second commitment complex |
| YOL045W | YOL045W | PSK2 | PAS-domain containing serine/threonirie protein kinase; regulates sugar flux and translation in response to an unknown metabolite by phosphorylating Ugp1p and Gsy2p (sugar flux) and Caf20p, Tif11p and Sro9p (translation); PSK2 has a paralogs PSK1, that arose from the whole genome duplication |
| YDR028C | YDR028C | REG1 | Regulatory subunit of type 1 protein phosphatase Glc7p; involved in negative regulation of glucose-repressible genes; involved in regulation of the nucleocytoplasmic shuttling of Hxk2p; REG1 has a paralog, REG2, that arose from the whole genome duplication |
| YOR127W | YOR127W | RGA1 | GTPase-activatng protein for polarity-establishment protein Cdc42p; implicated in control of septin organization, pheromone response, and haploid invasive growth; relocalizes from bud neck to cytoplasm upon DNA replication stress RGA1 has a paraolg, RGA2, that arose from the hole genome duplication |
| YER125W | YER125W | RSP5 | E3 ubiquitin ligase NEDD4 family; regulates many cellular processes including MVB sorting, heat shock response transcription, endocytosis, ribosome stability; mutant tolerates aneuploidy; autoubiquitinates; ubiquitinates Sec23p and Sna3p; deubiquitinated by Ubp2p; activity regulated by SUMO ligase Siz1p, in turn regulates Siz1p SUMO ligase activity; required for efficient Golgi-to-ER trafficking in COPI mutants; human homolog implicated in Liddle syndrome |
| YPR189W | YPR189W | SKI3 | Ski compex component and TPR protein; mediates 3'-5' RNA degradation by the cytoplasmic exosome; null mutants have superkiller phenotype of increased viral dsRNAs and are synthetic lethal with mutations in 5'-3', mRNA decay; mutatons in the human ortholog, TTC37, causes Syndromic diarrhea/Trichohepatoenteric (SD/THE) syndrome |
| YBL061C | YB061C | SKT5 | Activator of Chs3p (chitin synthase III) during vegetative growth; recruits Chs3p to the bud neck via interaction with Bni4p; SKT5 has a paralog, SHC1, that arose from the whole genome duplication |
| YDR515W | YDR515W | SLF1 | RNA binding protein that associates with polysomes; may be involved in regulating mRNA translation; involved in the copper-dependent mineralization of copper sulfide complexes on cell surface in cells cultured in copper salts; SLF1 has a paralog SRO9, |

TABLE S4-continued

COMPARING PROTEOTIXICITIES, OVEREXPRESSION SCREEN HIT INPUTS versus STEINER NETWORK OUTPUTS

| Screen | ORF | Standard Name | Description |
|---|---|---|---|
| | | | that arose from the whole genome duplication; protein abundance increases in response to DNA replication stress |
| YOR008C | YOR008C | SLG1 | Sensor-transducer of the stress-activated PKC1-MPK1 kinase pathway; involved in maintenance of cell wall integrity; required for mitophag involved in organization of the actin cytoskeleton; secretory pathway Wsc1p is required for the arrest of secretion response |
| YDR356W | YDR356W | SPC110 | Inner plaque spindle pole body (SPB) component; ortholog of human kendrin; involved in connecting nuclear microtubules to SPB; interacts with Tub4p-complex and calmodulin; phosphorylated by Mps1p in cell cycle-dependent manner |
| YCL037C | YCL037C | SRO9 | Cytoplasmic RNA- binding protein; shuttles between nucleus and cytoplasm and is exported from the nucleus in an mRNA export-dependent manner; associates with translating ribosomes; involved in heme regulation of Hap1p as a component of the HMC complex, also involved in the organization of actin filaments; contains a La motif; SRO9 has paralog, SLF1, that arose from the whole genome duplication |
| YER111C | YER111C | SWI4 | DNA binding component of the SBF complex (Swi4p-Swi6p); a transcriptional activator that in concert with MBF (Mhp1-Swi6p) regulates late G1-specific transcription of targets including cyclins and genes required for DNA synthesis and repair; Slt2p-independent regulator of cold growth; acetylation at two sites, K1016 and K1066, regulates interaction with Swi6p |
| YIL144W | YIL144W | TID3 | Component of the kinetochore-associated Ndc80 complex; conserved coiled-coil protein involved in chromosome segragation, spindle checkpoint activity, and kinetochore assembly and clustering; evolutionarily conserved; other members include Ndc80p, Nuf2p, Scp24p, and Spc25p; modified by sumoylation |
| YOR083W | YOR083W | WHI5 | Repressor of G1 transcription; binds to SCB binding factor (SBF) at SCB target promoters in early G1; phosphorylation of Whi5p by the CDK, Cln3p/Cdc28p relieves repression and promoter binding by Whi5; periodically expressed in G1; WHI5 has a paralo,. SRL3, that arose from the whole genome duplication |
| YGL173C | YGL173C | XRN1 | Evolutionarily-conserved 5'-3' exonuclease; component cytopasmic processing (P), bodies involved in mRNA decay; also enters the nucleus and positively regulates transcription initiation and elongation; plays a role in microtubule-mediated processes, filamentous growth, ribosomal |

TABLE S4-continued

COMPARING PROTEOTIXICITIES, OVEREXPRESSION SCREEN HIT INPUTS versus STEINER NETWORK OUTPUTS

| Screen | ORF | Standard Name | Description |
|---|---|---|---|
| | | | RNA maturation, and telomere maintenance; activated by the scavenger decapping enzyme Dcs1p |

TABLE 55

α-syn GENOME-WIDE DELETION SCREEN MODIFIERS (all emhancers)

Deletion α-syn yeast screen

| Gene | Modification all enhancers of toxicity when deleted |
|---|---|
| ACE2 | E |
| ALP1 | E |
| APJ1 | E |
| APL5 | E |
| APM4 | E |
| APQ12 | E |
| APS2 | E |
| ARO10 | E |
| ASN1 | E |
| ATE1 | E |
| ATG23 | E |
| ATG7 | E |
| AVT7 | E |
| AYR1 | E |
| BPH1 | E |
| BRE4 | E |
| BSC5 | E |
| BSD2 | E |
| CCZ1 | E |
| CDA2 | E |
| CLD1 | E |
| CMP2 | E |
| COA4 | E |
| COG5 | E |
| COG6 | E |
| COG7 | E |
| COX10 | E |
| CRN1 | E |
| CRT10 | E |
| CSG2 | E |
| CS12 | E |
| CT16 | E |
| DAK2 | E |
| DCV1 | E |
| DET1 | E |
| DLD1 | E |
| EDC1 | E |
| EEB1 | E |
| ELM1 | E |
| EMC2 | E |
| EM15 | E |
| ENV10 | E |
| ERG2 | E |
| ERP1 | E |
| ERP6 | E |
| ERV14 | E |
| FAT1 | E |
| FMP23 | E |
| FMS1 | E |
| FUS2 | E |
| FYV1 | E |
| GET1 | E |
| GSF2 | E |
| GSY2 | E |
| HAM1 | E |
| HDA1 | E |
| HEF3 | E |
| HFA1 | E |
| HMT1 | E |
| KMX1 | E |
| HNT2 | E |
| HPC2 | E |
| HSC82 | E |
| HYR1 | E |
| IMP2 | E |
| INM1 | E |
| INO4 | E |
| INP53 | E |
| KSS1 | E |
| LAT1 | E |
| MCT1 | E |
| MNT4 | E |
| MSC6 | E |
| MSN2 | E |
| NAM7 | E |
| NMD2 | E |
| NOP6 | E |
| NRP1 | E |
| PBP4 | E |
| PET8 | E |
| PFS1 | E |
| PHO23 | E |
| PHO90 | E |
| PKR1 | E |
| PMR1 | E |
| PMT6 | E |
| POX1 | E |
| PPH21 | E |
| PRM8 | E |
| RAD27 | E |
| RGD1 | E |
| RPE1 | E |
| RPL17B | E |
| RPN10 | E |
| RPN4 | E |
| RPS14A | E |
| RPS16B | E |
| RPS18B | E |
| RPS25A | E |
| RPS28B | E |
| RPS30A | E |
| RPS6B | E |
| RRD1 | E |
| RTS1 | E |
| RUD3 | E |
| SAF1 | E |
| SAP30 | E |
| SGF11 | E |
| SGF73 | E |
| SMI1 | E |
| SMY1 | E |
| SNF5 | E |
| SNF6 | E |
| SRN2 | E |

TABLE 55-continued

α-syn GENOME-WIDE DELETION SCREEN MODIFIERS (all emhancers)

Deletion α-syn yeast screen

| Gene | Modification all enhancers of toxicity when deleted |
|---|---|
| SRT1 | E |
| SUR1 | E |
| SWS1 | E |
| TDA1 | E |
| TIP1 | E |
| TMA17 | E |
| TPK2 | E |
| TRM82 | E |
| TRP3 | E |
| TSA1 | E |
| TSL1 | E |
| TUL1 | E |
| UBA4 | E |
| UBP15 | E |
| UBP16 | E |
| URA8 | E |
| VMS1 | E |
| VPS35 | E |
| VTH1 | E |
| YBR062C | E |
| YBR224W | E |
| YDL062W | E |
| YDL162C | E |
| YGR017W | E |
| YGR151C | E |
| YJL120W | E |
| YKL075C | E |
| YLR001C | E |
| YLR149C | E |
| YMR173W-A | E |
| YMR187C | E |
| YOL024W | E |
| YOR296W | E |
| YPK9 | E |
| YPT6 | E |
| ZRT2 | E |

TABLE S6

α-syn POOLED OVEREXPRESSION SCREEN MODIFIERS
Pooed overexpression α-syn pooled yeast screen

| Gene | Modification (Enhancer or Suppressor of toxicity when over-expressed) |
|---|---|
| ADE16 | E |
| AIM34 | E |
| ALG6 | E |
| AVT4 | S |
| BCK2 | S |
| BDF1 | E |
| BRE5 | S |
| BRL1 | S |
| BUD9 | E |
| CAX4 | E |
| CCC1 | S |
| CDA2 | E |
| CDC4 (FBXW7) | S |
| CDC5 | S |
| CDC55 (ATXN12) | E |
| CMC2 | S |
| CNE1 | E |
| COG5 | E |
| COG7 | S |
| COX9 | E |
| CTH1 | S |
| DAK2 | E |
| DAT1 | S |
| DIP5 | S |
| DMA1 | S |
| DOA4 | E |
| DOS2 | E |
| ECL1 | S |
| EPS1 | E |
| FAA2 | E |
| FMP48 | S |
| FUN14 | S |
| FUN19 | E |
| FUS3 | S |
| FZF1 | S |
| GIP2 | S |
| GIS3 | S |
| GMH1 | S |
| GOS1 | S |
| GYP8 | E |
| ICY1 | S |
| ICY2 | S |
| IMH1 | E |
| IWR1 | S |
| LEU3 | S |
| LSM3 | S |
| MBR1 | E |
| MET8 | E |
| MIC17 | E |
| MKS1 | E |
| MRN1 | S |
| MRPL11 | E |
| MUM2 | S |
| NGR1 | S |
| OSH3 | S |
| OSH6 | E |
| PAB1 (yPABPC1) | S |
| PAN2 | S |
| PBP1 (yATXN2) | S |
| PDE2 (PDE8B) | S |
| PFK2 | E |
| PHD1 | S |
| PMR1 | E |
| POR1 | E |
| PSP1 | S |
| PSR1 | S |
| PTP2 | S |
| RCY1 | E |
| REB1 | S |
| RKM1 | S |
| RLM1 | S |
| ROG3 | E |
| ROM2 | S |
| RPA43 | E |
| RPS14A | S |
| RPS26B | E |
| RPS29B | E |
| RSM25 | E |
| RTS1 | S |
| RTT109 | S |
| SAN1 | S |
| SAT4 | E |
| SDT1 | E |
| SEC21 | S |
| SEC28 | S |
| SEC31 | E |
| SGE1 | E |
| SGF73 (yATXN7) | S |
| SIA1 | E |
| SLK19 | E |
| SLY41 | E |
| SQS1 | S |
| SRL2 | E |
| SRT1 | S |

TABLE S6-continued

α-syn POOLED OVEREXPRESSION SCREEN MODIFIERS
Pooed overexpression α-syn pooled yeast screen

| Gene | Modification (Enhancer or Suppressor of toxicity when over-expressed) |
|---|---|
| SSN8 | E |
| STB3 | S |
| STN1 | E |
| STP1 | E |
| STP3 | S |
| STP4 | S |
| SUB1 | S |
| SUL1 | E |
| SUT2 | E |
| SVP26 | E |
| SYC1 | E |
| TDA11 | E |
| TIF4631 (yEIF4G1-1) | S |
| TIS11 | S |
| TOD6 | S |
| TOS3 | E |
| TPS2 | E |
| TPS3 | S |
| TRM44 | S |
| TRS120 | E |
| TUS1 | E |
| UBP3 | S |
| URE2 | S |
| UTR1 | E |
| VHR1 | S |
| YBL059W | E |
| YCK3 | S |
| YCP4 | E |
| YHR177W | S |
| YIG1 | S |
| YKT6 | S |
| YLR162W | S |
| YML083C | S |
| YMR114C | E |
| YMR31 | E |
| YNR014W | S |
| YOR338W | E |
| YPK2 | E |
| YPT1 | S |
| YTH1 | S |

TABLE S7

Additional low throughput "Candidate-based" Modifiers of α-syn toxicity (hypothesis-based studies)

| ORF | Standard Name | Description |
|---|---|---|
| YBR109C | CMD1 | Calmodulin; Ca++ binding protein that regulates Ca++ independent processes (mitosis, bud growth, actin organization, endocytosis, etc.) and Ca++ dependent processes (stress-activated pathways), targets include Nuf1p, Myo2p and calcineurin |
| YLR433C | CNA1 | Calcineurin A; one isoform {the other is Cmp2p) of the catalytic subunit of calcineurin, a Ca++/calmodulin-regulated protein phosphatase which regulates Crz1p (a stress-response transcription factor), the other calcineurin subunit is CNB1; regulates the function of Aly1p alpha-arrestin; CNA1 has a paralog, CMP2, that arose from the whole genome duplication |
| YKL190W | CNB1 | Calcineurin B; regulatory subunit of calcineurin, a Ca++/calmodulin-regulated type 2B protein phosphatase which regulates Crz1p (stress-response transcription factor); other calcineurin subunit encoded by CNA1 and/or CMP1; regulates function of Aly1p alpha-arrestin; myristoylation by Nmt1p reduces calcineurin activity in response to submaximal Ca signals, is needed to prevent constitutive phosphatase activity; protein abundance increases in response to DNA replication stress |
| YGL187C | COX4 | Subunit IV of cytochrome c oxidase; the terminal member of the mitochondrial inner membrane electron transport chain; precursor N-terminal 25 residues are cleaved during mitochondrial import; phosphorylated; spermidine enhances translation |
| YNL052W | COX5A | Subunit Va of cytochrome c oxidase; cytochrome c oxidase is the terminal member of the mitochondrial inner membrane electron transport chain; Cox5Ap is predominantly expressed during aerobic growth while its isoform Vb (Cox5Bp) is expressed during anaerobic growth; COX5A has a paralog, COX5B, that arose from the whole genome duplication |
| YIL111W | COX5B | Subunit Vb of cytochrome c oxidase; cytochrome c oxidase is the terminal member of the mitochondrial inner membrane electron transport chain; Cox5Bp is predominantly expressed during anaerobic growth while its isoform Va (Cox5Ap) is expressed during aerobic growth; COX5B has a paralog, COX5A, that arose from the whole genome duplication |
| YNL027W | CRZ1 | Transcription factor, activates transcription of stress response genes; nuclear localization is positively regulated by calcineurin-mediated dephosphorylation; rapidly localizes to |

TABLE S7-continued

Additional low throughput "Candidate-based" Modifiers of α-syn toxicity (hypothesis-based studies)

| ORF | Standard Name | Description |
|---|---|---|
| YOR324C | FRT1 | the nucleus under blue light stress; can be activated in stochastic pulses of nuclear localization in response to calcium Tail-anchored ER membrane protein of unknown function; substrate of the phosphatase calcineurin; interacts with homolog Frt2p; promotes cell growth in stress conditions, possibly via a role in posttranslational translocation; FRT1 has a paralog, FRT2, that arose from the whole genome duplication |
| YJL053W | PEP8 | Vacuolar protein component of the retromer; forms part of the multimeric membrane-associated retromer complex involved in vacuolar protein sorting along with Vps35p, Vps29p, Vps17p, and Vps5p; essential for endosome-to-Golgi retrograde protein transport; interacts with Ypt7p; protein abundance increases in response to DNA replication stress |
| YKL159C | RCN1 | Protein involved in calcineurin regulation during calcium signaling; has similarity to *H. sapiens* DSCR1 which is found in the Down Syndrome candidate region |
| YOR220W | RCN2 | Protein of unknown function; green fluorescent protein (GFP)-fusion protein localizes to the cytoplasm; phosphorylated in response to alpha factor; protein abundance increases in response to DNA replication stress |
| YER125W | RSP5 | E3 ubiquitin ligase of NEDD4 family; regulates many cellular processes including MVB sorting, heat shock response, transcription, endocytosis, ribosome stability; mutant tolerates aneuploidy; autoubiquitinates; ubiquitinates Sec23p and Sna3p; deubiquitinated by Ubp2p; activity regulated by SUMO ligase Siz1p, in turn regulates Siz1p SUMO ligase activity; required for efficient Golgi-to-ER trafficking in COPI mutants; human homolog implicated in Liddle syndrome |
| YJL053W | VPS26 (PEP8) | Vacuolar protein component of the retromer; forms part of the multimeric membrane-associated retromer complex involved in vacuolar protein sorting along with Vps35p, Vps29p, Vps17p, and Vps5p; essential for endosome-to-Golgi retrograde protein transport; interacts with Ypt7p; protein abundance increases in response to DNA replication stress |
| YHR012W | VPS29 | Subunit of the membrane-associated retromer complex; endosomal protein; essential for endosome-to-Golgi retrograde transport; forms a subcomplex with Vps35p and Vps26p that selects cargo proteins for endosome to Golgi retrieval |
| YJL154C | VPS35 | Endosomal subunit of membrane-associated retromer complex; required for retrograde transport; receptor that recognizes retrieval signals on cargo proteins, forms subcomplex with Vps26p and Vps29p that selects cargo proteins for retrieval; interacts with Ypt7p |
| YML001W | YPT7 | Rab family GTPase; GTP-binding protein of the rab family; required for homotypic fusion event in vacuole inheritance, for endosome-endosome fusion; interacts with the cargo selection/retromer complex for retrograde sorting; similar to mammalian Rab7 |

TABLE S8

PARK LOCI AND GENES
(Adapted in part from Klein C, Westenberger A. Genetics of Parkinson's Disease. Cold Spring Harbor Perspectives in Medicine 2012;2(1):a008888. doi:10.1101/cshperspect.a008888)

| Symbol | Disorder | Inheritance (Autosomal Dominant versus Autosomal Recessive) | Gene | Mode of identification | Yeast homolog? | Appearance in yeast screen (or as hidden node in humanized OE or Full α-syn networks) |
|---|---|---|---|---|---|---|
| PARK1/4 | Early PD, DLB | AD | SNCA (α-syn in this study) | Linkage analysis, GWAS | No clear homolog | [Hidden Node: OE, Full] |
| PARK2 | Juvenile parkinsonism; some with α-syn pathology | AR | PARKIN | Linkage analysis | No clear homolog | [related to Cdc4 (yFBXW7) and to VCP, |

TABLE S8-continued

PARK LOCI AND GENES
(Adapted in part from Klein C, Westenberger A. Genetics of Parkinson's Disease.
Cold Spring Harbor Perspectives in Medicine 2012;2(1):a008888. doi:10.1101/cshperspect.a008888)

| Symbol | Disorder | Inheritance (Autosomal Dominant versus Autosomal Recessive) | Gene | Mode of identification | Yeast homolog? | Appearance in yeast screen (or as hidden node in humanized OE or Full α-syn networks) |
|---|---|---|---|---|---|---|
| | | | | | | an extrapolated node in the Full network] |
| PARK3 | Classical PD | AD | Unknown | Linkage analysis | N/A | N/A |
| PARK5 | Classical PD | AD | UCHL1 (controversial) | Functional candidate gene approach | YUH1 | [Hidden Node: OE] |
| PARK6 | Juvenile parkinsonism | AR | PINK1 | Linkage analysis | No clear homolog | N/A |
| PARK7 | Juvenile parkinsonism | AR | PARK (DJ-1) | Linkage analysis | HSP31 | No |
| PARK8 | Most classical PD (occasionally Tau or mixed pathology) | AD | LRRK2 | Linkage analysis, GWAS | No clear homolog | [Hidden Node: OE, Full] |
| PARK1/4 | Early PD, DLB | AD | SNCA (α-syn in this study) | Linkage analysis, GWAS | No clear homolog | [Hidden Node: OE, Full] |
| PARK9 | Kufor-Rakeb syndrome; juvenile parkinsonism with dementia; brain iron accumulation | AR | ATP13A2 | Linkage analysis | YPK9 | OE screen, Deletion screen |
| PARK10 | Classical PD | Risk factor | Unknown | Linkage analysis | N/A | N/A |
| PARK11 | Late-onset PD | AD | GIGYF2 | Linkage analysis | SYH1 | No |
| PARK12 | Classical PD | Risk factor | Unknown | Linkage analysis | N/A | N/A |
| PARK13 | Classical PD | AD or risk factor | HTRA2 (controversial) | Candidate gene approach | NMA111 | No clear homolog |
| PARK14 | Early-onset dystonia-parkinsonism; brain iron accumulation | AR | PLA2G6 | Linkage analysis (homozygosity mapping) | No clear homolog | N/A |
| PARKI5 | Atypical early-onset parkinsonian-pallido-pyramidal syndrome | AR | FBX07 | Linkage analysis | No clear homolog | N/A |
| PARK16 | Classical PD | Risk factor | RA87L1 - NUCKS1 (linkage to both) | GWAS | YPT7 | Low throughput OE and deletion |
| PARK17 | Classical PD | AD | VPS35 | Exome sequencing | VPS35 | Deletion screen |
| PARK18 | Classical PD | AD | EIF4G1 (controversial) | Linkage analysis | TIF4631, TIF4632 | OE screen, pooled OE screen |
| PARK1/4 | Early PD, DLB | AD | SNCA (α-syn in this study) | Linkage analysis, GWAS | No clear homolog | [Hidden Node: OE, Full] |
| PARK19 | Atypical early-onset parkinsonism, retardation, seizures | AR | DNAJC6 | Exome sequencing, Linkage analysis | SWA2 | No |

TABLE S8-continued

PARK LOCI AND GENES
(Adapted in part from Klein C, Westenberger A. Genetics of Parkinson's Disease.
Cold Spring Harbor Perspectives in Medicine 2012;2(1):a008888. doi:10.1101/cshperspect.a008888)

| Symbol | Disorder | Inheritance (Autosomal Dominant versus Autosomal Recessive) | Gene | Mode of identification | Yeast homolog? | Appearance in yeast screen (or as hidden node in humanized OE or Full α-syn networks) |
|---|---|---|---|---|---|---|
| PARK20 | Atypical early-onset parkinsonism, retardation, seizures, dystonia | AR | SYNJ1 | Exome sequencing, Linkage analysis | INP51, INP52, | Deletion screen |

TABLE S9

Humanized Overexpression α-synuclein network yeast-human pairing (input and output)

Humanized Overexpression Synuclein Network INPUT

| Yeast Gene (ORF) | Standard Name | Selected Human Homolog | Homology weight (DCA analysis) |
|---|---|---|---|
| YDR169C | STB3 | AKNAD1 | 0.755162 |
| YER122C | GLO3 | ARFGAP2 | 0.306472 |
| YOR291W | YPK9 | ATP13A3 | 0.388248 |
| YGL167C | PMR1 | ATP2C1 | 0.415736 |
| YOR129C | AFI1 | AVL9 | 0.697488 |
| YKL006C-A | SFT1 | BET1 | 0.210969 |
| YGL254W | FZF1 | C8orf85 | 1.52442 |
| YGL158W | RCK1 | CAMK1G | 1.4952 |
| YIR033W | MGA2 | CAMTA1 | 1.50077 |
| YHR195W | NVJ1 | CCDC66 | 1.29817 |
| YOL001W | PHO80 | CCNYL2 | 1.99969 |
| YMR261C | TPS3 | CEP350 | 0.456942 |
| YIL076W | SEC28 | COPE | 0.740073 |
| YNL287W | SEC21 | COPG | 1.50865 |
| YER123W | YCK3 | CSNK1G3 | 0.301902 |
| YGR036C | CAX4 | DOLPP1 | 1.10328 |
| YMR111C | YMR111C | EHBP1 | 1.10777 |
| YGL049C | TIF4632 | EIF4G3 | 1.6349 |
| YFL009W | CDC4 | FBXW7 | 0.800785 |
| YNR051C | BRE5 | G3BP1 | 1.01847 |
| YIL056W | VHR1 | GAB4 | 0.182946 |
| YHL031C | GOS1 | GOSR1 | 0.868238 |
| YJL146W | IDS2 | GYG2 | 0.445428 |
| YJL106W | IME2 | ICK | 1.9999 |
| YHR073W | OSH3 | IRS2 | 1.99987 |
| YKR044W | UIP5 | LMAN2L | 1.99975 |
| YNL006W | LST8 | MLST8 | 0.495471 |
| YDL019C | OSH2 | OSBPL1A | 0.631514 |
| YLR023C | IZH3 | PAQR3 | 0.615166 |
| YOR360C | PDE2 | PDE9A | 1.4853 |
| YPL177C | CUP9 | PKNOX1 | 1.99991 |
| YMR001C | CDC5 | PLK3 | 0.999936 |
| YOR155C | ISN1 | PMM2 | 0.616682 |
| YKL063C | YKL063C | POTEB | 1.76306 |
| YKL088W | CAB3 | PPCDC | 0.362952 |
| YBR125C | PTC4 | PPM1G | 0.665247 |
| YER054C | GIP2 | PPP1R3C | 0.735681 |
| YML016C | PPZ1 | PPP2CB | 0.874471 |
| YDR436W | PPZ2 | PPP4C | 1.26342 |
| YDL047W | SIT4 | PPP6C | 0.266599 |
| YOR208W | PTP2 | PTPRJ | 1.33916 |
| YFL038C | YPT1 | RAB1A | 0.985717 |
| YNL044W | YIP3 | RABAC1 | 1.9996 |
| YJL031C | BET4 | RABGGTA | 1.02793 |
| YDL195W | SEC31 | SEC31A | 0.365859 |
| YBR030W | RKM3 | SETD6 | 0.665248 |
| YBR043C | QDR3 | SLC22A15 | 0.484984 |
| YOR307C | SLY41 | SLC35E1 | 0.12187 |
| YNL101W | AVT4 | SLC36A1 | 1.34482 |

TABLE S9-continued

Humanized Overexpression α-synuclein network yeast-human pairing (input and output)

| | | | |
|---|---|---|---|
| YPL265W | DIP5 | SLC7A2 | 0.597354 |
| YOR273C | TPO4 | SPNS3 | 0.495604 |
| YNL076W | MKS1 | STOX2 | 1.06964 |
| YGR284C | ERV29 | SURF4 | 1.99991 |
| YOL013C | HRD1 | SYVN1 | 1.32616 |
| YFL027C | GYP8 | TBC1D20 | 0.78967 |
| YIL005W | EPS1 | TMX4 | 1.99965 |
| YJR091C | JSN1 | TOR1A | 0.929739 |
| YDR407C | TRS120 | TRAPPC9 | 0.702355 |
| YDR001C | NTH1 | TREH | 1.75303 |
| YKL109W | HAP4 | TSKS | 0.999977 |
| YKL035W | UGP1 | UGP2 | 0.507537 |
| YER151C | UBP3 | USP10 | 0.468537 |
| YIL156W | UBP7 | USP24 | 0.20444 |
| YKR098C | UBP11 | USP45 | 1.27086 |
| YBR057C | MUM2 | WTAP | 0.872191 |
| YKL196C | YKT6 | YKT6 | 1.15414 |
| YDR374C | YDR374C | YTHDF2 | 0.932147 |
| YML081W | TDA9 | ZNFS18B | 0.49445 |

Humanized Overexpression Synuclein Network OUTPUT
(does not include predicted nodes)

| Yeast Gene (ORF) | Standard Name | Selected Human Homolog in Network Output |
|---|---|---|
| YOR360C | PDE2 | ADCY3 |
| YDR169C | STB3 | AKNAD1 |
| YIR033W | MGA2 | ANKDD1A |
| YIR033W | MGA2 | ANKRD1 |
| YER122C | GLO3 | ARFGAP2 |
| YER122C | GLO3 | ARFGAP3 |
| YOR291W | YPK9 | ATP13A2 |
| YOR291W | YPK9 | ATP13A3 |
| YGL167C | PMR1 | ATP2A3 |
| YGL167C | PMR1 | ATP2C1 |
| YOR129C | AFI1 | AVL9 |
| YOR360C | PDE2 | B4GALT2 |
| YKL006C-A | SFT1 | BET1 |
| YMR111C | YMR111C | BICD2 |
| YFL009W | CDC4 | BTRC |
| YGL254W | FZF1 | CA7 |
| YGL158W | RCK1 | CAMK1G |
| YGL158W | RCK1 | CAMK4 |
| YGL158W | RCK1 | CAMKV |
| YIR033W | MGA2 | CAMTA1 |
| YOR360C | PDE2 | CANT1 |
| YFL038C | YPT1 | CCDC64B |
| YHR195W | NVJ1 | CCDC66 |
| YOL001W | PHO80 | CCNY |
| YOL001W | PHO80 | CCNYL2 |
| YMR261C | TPS3 | CEP350 |
| YIL076W | SEC28 | COPE |
| YNL287W | SEC21 | COPG |
| YER123W | YCK3 | CSNK1A1 |
| YER123W | YCK3 | CSNK1D |
| YBR057C | MUM2 | CTTNBP2NL |
| YGR036C | CAX4 | DOLPP1 |
| YML081W | TDA9 | EGR1 |
| YML081W | TDA9 | EGR4 |
| YMR111C | YMR111C | EHBP1 |
| YGL049C | TIF4632 | EIF4G1 |
| YGL049C | TIF4632 | EIF4G3 |
| YOR360C | PDE2 | EXTL3 |
| YGL254W | FZF1 | FAM162A |
| YFL009W | CDC4 | FBXW7 |
| YNR051C | BRE5 | G3BP1 |
| YNR051C | BRE5 | G3BP2 |
| YIL056W | VHR1 | GAB4 |
| YGL254W | FZF1 | GLISE |
| YHL031C | GOS1 | GOSR1 |
| YJL146W | IDS2 | GYG1 |
| YJ146W | IDS2 | GYG2 |
| YJL106W | IME2 | HIPK4 |
| YJR091C | JSN1 | HNRNPL |
| YGL254W | FZF1 | KLF15 |
| YKRD44W | UIP5 | LMAN2 |
| YPL177C | CUP9 | MEIS1 |

TABLE S9-continued

Humanized Overexpression α-synuclein network yeast-human pairing (input and output)

| | | |
|---|---|---|
| YPL177C | CUP9 | MEIS2 |
| YPL177C | CUP9 | MEIS3 |
| YNLOO6W | LST8 | MLST8 |
| YGL254W | FZF1 | MTF1 |
| YDL019C | OSH2 | OSBPL1A |
| YHR073W | OSH3 | OSBPL1A |
| YHR073W | OSH3 | OSBPL2 |
| YHR073W | OSH3 | OSBPL3 |
| YLR023C | IZH3 | PAQR3 |
| YOR360C | PDE2 | PDE8B |
| YOR360C | PDE2 | PDE9A |
| YILOO5W | EPS1 | PDIA5 |
| YPL177C | CUP9 | PKNOX1 |
| YMR001C | CDC5 | PLK2 |
| YMR001C | CDC5 | PLK3 |
| YOR155C | ISN1 | PMM1 |
| YOR155C | ISN1 | PMM2 |
| YKL063C | YKL063C | POTEC |
| YKL088W | CAB3 | PPCDC |
| YBR125C | PTC4 | PPM1G |
| YBR125C | PTC4 | PPM1K |
| YER054C | GIP2 | PPP1R3B |
| YER054C | GIP2 | PPP1R3C |
| YER054C | GIP2 | PPP1R3D |
| YDL047W | SIT4 | PPP6C |
| YDR436W | PPZ2 | PPP6C |
| YML016C | PPZ1 | PPP6C |
| YOR208W | PTP2 | PTPN13 |
| YOR208W | PTP2 | PTPRC |
| YOR208W | PTP2 | PTPRF |
| YOR208W | PTP2 | PTPRJ |
| YFL038C | YPT1 | RAB1A |
| YFL038C | YPT1 | RABBA |
| YNL044W | YIP3 | RABAC1 |
| YJL031C | BET4 | RABGGTA |
| YDL195W | SEC31 | SEC31A |
| YDL195W | SEC31 | SEC31B |
| YBR030W | RKM3 | SETD6 |
| YOR273C | TPO4 | SLC22A15 |
| YOR307C | SLY41 | SLC35E1 |
| YNL101W | AVT4 | SLC36A1 |
| YNL101W | AVT4 | SLC36A2 |
| YPL265W | DIP5 | SLC7A2 |
| YPL265W | DIP5 | SLC7A3 |
| YBR043C | QDR3 | SPNS3 |
| YOR273C | TPO4 | SPNS3 |
| YNL076W | MKS1 | STOX2 |
| YGR284C | ERV29 | SURF4 |
| YO273C | TPO4 | SVOP |
| YOL013C | HRD1 | SYVN1 |
| YFL027C | GYP8 | TBC1D20 |
| YHR195W | NVJ1 | TCEAL5 |
| YIL005W | EPS1 | TMX3 |
| YJR091C | JSN1 | TOR1A |
| YDR407C | TRS120 | TRAPPC9 |
| YDR001C | NTH1 | TREH |
| YKL109W | HAP4 | TSKS |
| YIL005W | EPS1 | TXNDC5 |
| YKL035W | UGP1 | UGP2 |
| YER151C | UBP3 | USP10 |
| YIL156W | UBP7 | USP2 |
| YKR098C | UBP11 | USP2 |
| YKR098C | UBP11 | USP21 |
| YIL156W | UBP7 | USP35 |
| YKR098C | UBP11 | USP45 |
| YBR057C | MUM2 | WTAP |
| YKL196C | YKT6 | YKT6 |
| YDR374C | YDR374C | YTHDF1 |
| YDR374C | YDR374C | YTHDF2 |
| YDR374C | YDR374C | YTHDF3 |
| YML0811W | TDA9 | ZNFS16 |
| YKL109W | HAP4 | ZNF654 |

TABLE S10

| Humanized Complete (OE, pooled, deletion screens) Synuclein Network INPUT Yeast Gene (ORF) | Standard Name | Selected Human Homolog | Homology weight (DCA analysis) | Humanized Complete (OE, pooled, deletion screens) Synuclein Network OUTPUT (does not include predicted nodes) Yeast Gene (ORF) | Standard Name | Selected Human Homolog in Network Output |
|---|---|---|---|---|---|---|
| YAL008W | FUN14 | FUNDC2 | 1.52022 | YAL008W | FUN14 | FUNDC2 |
| YAL034C | FUN19 | TADA2A | 0.522498 | YAL034C | FUN19 | TADA2A |
| YAL058W | CNE1 | CANX | 1.4357 | YAL058W | CNE1 | CANX |
| YAR002C-A | ERP1 | TMED4 | 0.594116 | YAR002C-A | ERP1 | TMED9 |
| YBL016W | FUS3 | MAPK7 | 0.315846 | YBL016W | FUS3 | MAPK1 |
| YBL054W | TOD6 | MYB | 0.500324 | YBL054W | TOD6 | MYBL2 |
| YBL059C-A | CMC2 | C16orf61 | 1.99994 | YBL059C-A | CMC2 | C16orf61 |
| YBL059W | YBL059W | AQP12B | 1.47757 | YBL059W | YBL059W | DOCK11 |
| YBR030W | RKM3 | SETD6 | 0.755162 | YBR030W | RKM3 | SETD6 |
| YBR034C | HMT1 | PRMT1 | 1.25102 | YBR034C | HMT1 | PRMT1 |
| YBR036C | CSG2 | SLC35F5 | 0.553813 | YBR036C | CSG2 | SLC35F5 |
| YBR041W | FAT1 | SLC27A4 | 0.916194 | YBR041W | FAT1 | SLC27A1 |
| YBR043C | QDR3 | SLC22A15 | 0.306472 | YBR043C | QDR3 | SPNS3 |
| YBR049C | REB1 | DMTF1 | 0.62136 | YBR049C | REB1 | DMTF1 |
| YBR057C | MUM2 | WTAP | 0.388248 | YBR057C | MUM2 | WTAP |
| YBR062C | YBR062C | PJA1 | 0.817883 | YBR062C | YBR062C | RNF115 |
| YBR067C | TIP1 | TREML2 | 1.99992 | YBR067C | TIP1 | TREML2 |
| YBR109C | CMD1 | C2orf61 | 0.999926 | YBR109C | CMD1 | CALM1 |
| YBR125C | PTC4 | PPM1G | 0.415736 | YBR125C | PTC4 | PPM1G |
| YBR181C | RPS6b | RPS6 | 1.24848 | YBR181C | RPS6b | RPS6 |
| YBR212W | NGR1 | C6orf52 | 0.500414 | YBR212W | NGR1 | TIAL1 |
| YBR215W | HPC2 | KDM3A | 1.06194 | YBR215W | HPC2 | GPRIN3 |
| YBR260C | RGD1 | HMHA1 | 0.666101 | YBR260C | RGD1 | ARHGAP23 |
| YBR280C | SAF1 | WBSCR16 | 0.426424 | YBR280C | SAF1 | WBSCR16 |
| YBR289W | SNF5 | SMARCB1 | 1.50657 | YBR289W | SNF5 | SMARCB1 |
| YBR290W | BSD2 | NDFIP1 | 1.99988 | YBR290W | BSD2 | NDFIP1 |
| YBR294W | SUL1 | SLC26A11 | 0.853045 | YBR294W | SUL1 | SLC26A5 |
| YCR004C | YCP4 | NQO2 | 0.812874 | YCR004C | YCP4 | NQO1 |
| YCR008W | SAT4 | TLK1 | 0.226346 | YCR008W | SAT4 | HUNK |
| YCR031C | RPS14a | RPS14 | 1.26846 | YCR031C | RPS14a | RPS14 |
| YCR032W | BPH1 | WDFY3 | 1.50239 | YCR032W | BPH1 | LRBA |
| YDL019C | OSH2 | OSBPL1A | 0.697488 | YDL019C | OSH2 | OSBPL1A |
| YDL020C | RPN4 | KLF1 | 0.482899 | YDL047W | SIT4 | PPP6C |
| YDL047W | SIT4 | PPP6C | 0.210969 | YDL048C | STP4 | EGR3 |
| YDL048C | STP4 | ATN1 | 0.911372 | YDL053C | PBP4 | ZC3H4 |
| YDL053C | PBP4 | ZC3H4 | 1.46903 | YDL061C | RPS29b | RPS29 |
| YDL061C | RPS29b | RPS29 | 1.49583 | YDL083C | RPS16b | RPS16 |
| YDL083C | RPS16b | RPS16 | 1.24967 | YDL115C | IWR1 | SNX5 |
| YDL115C | IWR1 | SLC7A6OS | 1.00001 | YDL122W | UBP1 | USP30 |
| YDL122W | UBP1 | PRPH2 | 0.999972 | YDL134C | PPH21 | PPP1CB |
| YDL134C | PPH21 | PPP1CC | 0.494472 | YDL167C | NRP1 | RBM10 |
| YDL167C | NRP1 | TEX13A | 1.08936 | YDL174C | DLD1 | LDHD |
| YDL174C | DLD1 | LDHD | 1.33038 | YDL195W | SEC31 | SEC31A |
| YDL195W | SEC31 | SEC31A | 1.52442 | YDL202W | MRPL11 | MRPL10 |
| YDL202W | MRPL11 | MRPL10 | 1.99986 | YDL213C | NOP6 | CCDC104 |
| YDL213C | NOP6 | HEATR4 | 0.607131 | YDR001C | NTH1 | TREH |
| YDR001C | NTH1 | TREH | 1.4952 | YDR049W | VMS1 | ANKZF1 |
| YDR049W | VMS1 | ANKZF1 | 1.99986 | YDR051C | DET1 | CENPK |
| YDR051C | DET1 | CENPK | 0.475583 | YDR068W | DOS2 | BSDC1 |
| YDR068W | DOS2 | B5DC1 | 1.99987 | YDR069C | DOA4 | USP21 |
| YDR069C | DOA4 | USP8 | 1.20479 | YDR074W | TPS2 | PMM1 |
| YDR074W | TPS2 | ALG11 | 0.287398 | YDR082W | STN1 | OBFC1 |
| YDR082W | STN1 | OBFC1 | 0.999977 | YDR143C | SAN1 | RNF115 |
| YDR143C | SAN1 | FAM189A2 | 0.606907 | YDR151C | CTH1 | ZFP36 |
| YDR151C | CTH1 | ZFP36L1 | 0.862559 | YDR165W | TRM82 | WDR4 |
| YDR165W | TRM82 | WDR4 | 1.05292 | YDR169C | STB3 | AKNAD1 |
| YDR169C | STB3 | AKNAD1 | 1.50077 | YDR257C | RKM4 | SETD3 |
| YDR305C | HNT2 | FHIT | 1.99968 | YDR257C | RKM4 | SETD6 |
| YDR374C | YDR374C | YTHDF2 | 1.29817 | YDR305C | HNT2 | FHIT |
| YDR380W | ARO10 | TLR5 | 0.600105 | YDR374C | YDR374C | YTHDF1 |
| YDR407C | TRS120 | TRAPPC9 | 1.99987 | YDR380W | ARO10 | TLR5 |
| YDR436W | PPZ2 | PPP4C | 0.456942 | YDR407C | TRS120 | TRAPPC9 |
| YDR463W | STP1 | GLI1 | 0.121309 | YDR436W | PPZ2 | PPP6C |

TABLE S10-continued

Humanized Complete a-synuclein network yeast-|

| Humanized Complete (OE, pooled, deletion screens) Synuclein Network INPUT Yeast Gene (ORF) | Standard Name | Selected Human Homolog | Homology weight (DCA analysis) | Humanized Complete (OE, pooled, deletion screens) Synuclein Network OUTPUT (does not include predicted nodes) Yeast Gene (ORF) | Standard Name | Selected Human Homolog in Network Output |
|---|---|---|---|---|---|---|
| YDR492W | IZH1 | PAQR3 | 0.682542 | YDR463W | STP1 | IKZF4 |
| YDR492W | IZH1 | PAQR3 | 0.682542 | YDR492W | IZH1 | ADIPOR2 |
| YER015W | FAA2 | ACSL1 | 0.638065 | YDR492W | IZH1 | PAQR3 |
| YER054C | GIP2 | PPP1R3C | 0.740073 | YER015W | FAA2 | ACSL1 |
| YER122C | GLO3 | ARFGAP2 | 1.50865 | YER054C | GIP2 | PPP1R3B |
| YER123W | YCK3 | CSNK1G3 | 0.301902 | YER122C | GLO3 | ARFGAP2 |
| YER125W | RSP5 | SMURF1 | 1.12275 | YER123W | YCK3 | CSNK1A1 |
| YER131W | RPS26b | RPS26 | 1.49988 | YER125W | RSP5 | NEDD4 |
| YER151C | UBP3 | USP10 | 1.10328 | YER131W | RPS26b | RPS26 |
| YER16SW | PAB1 | PABPC1 | 1.29816 | YER151C | UBP3 | USP10 |
| YER167W | BCK2 | HLA-E | 1.47102 | YER165W | PAB1 | PABPC1 |
| YFL009W | CDC4 | FBXW7 | 1.10777 | YER167W | BCK2 | KIAA1383 |
| YFL027C | GYP8 | TBC1D20 | 1.6349 | YFL009W | CDC4 | FBXW7 |
| YFL038C | YPT1 | RAB1A | 0.800785 | YFL027C | GYP8 | TBC1D20 |
| YFL053W | DAK2 | DAK | 1.52053 | YFL038C | YPT1 | RAB1A |
| YFR022W | ROG3 | RAPGEF3 | 0.482166 | YFL053W | DAK2 | DAK |
| YFR049W | YMR31 | MRPS36 | 1.99989 | YFR022W | ROG3 | RAPGEF3 |
| YGL002W | ERP6 | TMED4 | 0.624138 | YFR049W | YMR31 | MRPS36 |
| YGL005C | COG7 | NUP62 | 0.497706 | YGL002W | ERP6 | TMED9 |
| YGL017W | ATE1 | ATE1 | 1.9999 | YGL005C | COG7 | MXD4 |
| YGL020C | GET1 | WRB | 1.9999 | YGL017W | ATE1 | ATE1 |
| YGL049C | TIF4632 | EIF4G3 | 1.01847 | YGL020C | GET1 | WRB |
| YGL053W | PRM8 | SLC7A2 | 0.99999 | YGL049C | TIF4632 | EIF4G1 |
| YGL054C | ERV14 | CNIH4 | 1.15466 | YGL053W | PRM8 | SLC7A2 |
| YGL066W | SGF73 | ATXN7L2 | 1.41953 | YGL054C | ERV14 | CNIH4 |
| YGL094C | PAN2 | PAN2 | 1.9998 | YGL066W | SGF73 | ATXN7 |
| YGL158W | RCK1 | CAMK1G | 0.182946 | YGL094C | PAN2 | PAN2 |
| YGL167C | PMR1 | ATP2C1 | 0.868238 | YGL158W | RCK1 | CAMK4 |
| YGL179C | TOS3 | CAMKK1 | 0.509578 | YGL167C | PMR1 | ATP2C1 |
| YGL179C | TOS3 | CAMKK1 | 0.509578 | YGL179C | TOS3 | CAMKK1 |
| YGL187C | COX4 | COX5B | 1.99983 | YGL179C | TOS3 | STK36 |
| YGL190C | CDC55 | PPP2R2A | 1.3033 | YGL187C | COX4 | COX5B |
| YGL205W | POX1 | ACOX1 | 1.66337 | YGL190C | CDC55 | PPP2R2A |
| YGL209W | MIG2 | GLI3 | 0.326357 | YGL205W | POX1 | ACOX3 |
| YGL209W | MIG2 | GLI3 | 0.326357 | YGL222C | EDC1 | AFF2 |
| YGL222C | EDC1 | AFF2 | 1.15887 | YGL224C | SDT1 | NANP |
| YGL224C | SDT1 | HDHD3 | 0.675352 | YGL254C | FZF1 | KLF11 |
| Y6L254W | FZF1 | C8orf85 | 0.445428 | YGR017W | YGR017W | PNPO |
| YGR017W | YGR017W | PNPO | 0.99998 | YGR027C | RPS25a | RPS25 |
| YGR027C | RPS25a | RPS25 | 1.505 | YGR036C | CAX4 | DOLPP1 |
| YGR036C | CAX4 | DOLPP1 | 1.9999 | YGR040W | KSS1 | MAPK1 |
| YGR040W | KSS1 | MAPK1 | 0.327122 | YGR041W | BUD9 | PRRT2 |
| YGR041W | BUD9 | PRRT2 | 1.2594 | YGR052W | FMP48 | STK36 |
| YGR052W | FMP48 | LMTK3 | 0.999963 | YGR110W | CLD1 | ABHD4 |
| YGR110W | CLD1 | ABHD4 | 0.803946 | YGR146C | ECL1 | FAM83D |
| YGR146C | ECL1 | KIAA0913 | 1.01134 | YGR162W | TIF4631 | EIF4G1 |
| YGR162W | TIF4631 | EIF4G3 | 1.02409 | YGR178C | PBP1 | ATXN2 |
| YGR178C | PBP1 | ATXN2 | 1.50305 | YGR199W | PMT6 | POMT1 |
| YGR199W | PMT6 | POMT1 | 0.818242 | YGR229C | SMI1 | DCLRE1C |
| YGR229C | SMI1 | FBXO3 | 0.772076 | YGR284C | ERV29 | SURF4 |
| YGR284C | ERV29 | SURF4 | 1.99987 | YHL025W | SNF6 | NUCB1 |
| YHL025W | SNF6 | NUCB1 | 1.00014: | YHL031C | GOS1 | GOSR1 |
| YHL031C | GOS1 | GOSR1 | 1.999751 | YHL039W | EFM1 | SETD3 |
| YHR012W | VPS29 | VPS29 | 1.99991 | YHL039W | EFM1 | SETD4 |
| YHR036W | BRL1 | ZNF639 | 1.00008 | YHR012W | VPS29 | VPS29 |
| YHR046C | INM1 | IMPA1 | 0.801869 | YHR036W | BRL1 | ZNF639 |
| YHR073W | OSH3 | IRS2 | 0.495471 | YHR046C | INM1 | IMPA2 |
| YHR077C | NMD2 | UPF2 | 1.99989 | YHR073W | OSH3 | OSBPL1A |
| YHR111W | UBA4 | MOCS3 | 1.9999 | YHR077C | NMD2 | UPF2 |
| YHR115C | DMA1 | CHFR | 0.666039 | YHR111W | UBA4 | MOCS3 |
| YHR171W | ATG7 | ATG7 | 1.99982 | YHR115C | DMA1 | RNF8 |
| YHR181W | SVP26 | TEX261 | 1.99992 | YHR171W | ATG7 | ATG7 |
| YHR195W | NVJ1 | CCDC66 | 0.631514 | YHR181W | SVP26 | TEX261 |

TABLE S10-continued

Humanized Complete a-synuclein network yeast-1

| Humanized Complete (OE, pooled, deletion screens) Synuclein Network INPUT Yeast Gene (ORF) | Standard Name | Selected Human Homolog | Homology weight (DCA analysis) | Humanized Complete (OE, pooled, deletion screens) Synuclein Network OUTPUT (does not include predicted nodes) Yeast Gene (ORF) | Standard Name | Selected Human Homolog in Network Output |
|---|---|---|---|---|---|---|
| YHR200W | RPN10 | PSMD4 | 1.99996 | YHR195W | NVJ1 | CCDC66 |
| YIL005W | EPS1 | TMX4 | 0.615166 | YHR200W | RPN10 | PSMD4 |
| YIL056W | VHR1 | GAB4 | 1.4853 | YIL005W | EPS1 | TXNDC5 |
| YIL076W | SEC28 | COPE | 1.99991 | YIL056W | VHR1 | GAB4 |
| YIL088C | AVT7 | SLC32A1 | 0.352523 | YIL076W | SEC28 | COPE |
| YIL093C | RSM25 | MRPS23 | 1.99986 | YIL088C | AVT7 | SLC32A1 |
| YIL111W | COX5b | COX4I2 | 1.01218 | YIL093C | RSM2S | MRPS23 |
| YIL124W | AYR1 | HSD11B2 | 0.668722 | YIL111W | COX5b | COX4I1 |
| YIL153W | RRD1 | PPP2R4 | 1.5068 | YIL124W | AYR1 | BDH1 |
| YIL156W | UBP7 | USP24 | 0.999936 | YIL153W | RRD1 | PPP2R4 |
| YIL173W | VTH1 | SORL1 | 0.488728 | YIL156W | UBP7 | USP16 |
| YIR033W | MGA2 | CAMTA1 | 0.616682 | YIL173W | VTH1 | SORL1 |
| YIR037W | HYR1 | GPX7 | 0.677978 | YIR033W | MGA2 | ANKRD1 |
| YJL031C | BET4 | RABGGTA | 1.76306 | YIR037W | HYR1 | GPX7 |
| YJL053W | PEP8 | VPS268 | 1.50553 | YJL031C | BET4 | RABGGTA |
| YJL106W | IME2 | ICK | 0.362952 | YJL053W | PEP8 | VPS26B |
| YJL121C | RPE1 | RPE | 1.9999 | YJL106W | IME2 | HIPK4 |
| YJL146W | IDS2 | GYG2 | 0.665247 | YJL121C | RPE1 | RPE |
| YJL154C | VPS35 | VPS35 | 1.99988 | YJL146W | IDS2 | GYG1 |
| YJL177W | RPL17b | RPL17 | 1.49352 | YJL154C | VPS35 | VPS35 |
| YJL198W | PHO90 | SLC13A5 | 0.925738 | YJL177W | RPL17b | RPL17 |
| YJL204C | RCY1 | EXOC5 | 1.00012 | YJL198W | PHO90 | SLC13A3 |
| YJR049C | UTR1 | NADK | 1.41547 | YJL204C | RCY1 | EXOC5 |
| YJR058C | APS2 | AP2S1 | 0.698774 | YJR049C | UTR1 | NADK |
| YJR069C | HAM1 | ITPA | 1.99988 | YJR058C | APS2 | AP2S1 |
| YJR088C | EMC2 | TTC35 | 1.24073 | YJR069C | HAM1 | ITPA |
| YJR091C | JSN1 | TOR1A | 0.735681 | YJR088C | EMC2 | TTC35 |
| YJR103W | URA8 | CTPS2 | 1.14199 | YJR091C | JSN1 | TOR1A |
| YKL006C-A | SFT1 | BET1 | 0.874471 | YJR103W | URA8 | CTPS2 |
| YKL034W | TUL1 | RAPSN | 0.482772 | YKL006C-A | SFT1 | BET1 |
| YKL035W | UGP1 | UGP2 | 1.26342 | YKL034W | TUL1 | RNF11 |
| YKL043W | PHD1 | RUNX3 | 1.45564 | YKL035W | UGP1 | UGP2 |
| YKL048C | ELM1 | MOS | 0.44013 | YKL043W | PHD1 | RUNX3 |
| YKL063C | YKL063C | POTEB | 0.266599 | YKL048C | ELM1 | CAMKK1 |
| YKL079W | SMY1 | KIF58 | 0.191053 | YKL063C | YKL063C | POTEC |
| YKL088W | CAB3 | PPCDC | 1.33916 | YKL079W | SMY1 | KIF13A |
| YKL109W | HAP4 | TSKS | 0.985717 | YKL088W | CAB3 | PPCDC |
| YKL113C | RAD27 | FEN1 | 1.34416 | YKL109W | HAP4 | TSKS |
| YKL159C | RCN1 | RCAN3 | 1.34827 | YKL113C | RAD27 | FEN1 |
| YKL190W | CNB1 | PPP3R1 | 0.987017 | YKL159C | RCN1 | RCAN2 |
| YKL196C | YKT6 | YKT6 | 1.9996 | YKL190W | CNB1 | PPP3R1 |
| YKL211C | TRP3 | GMPS | 0.99999 | YKL196C | YKT6 | YKT6 |
| YKR003W | OSH6 | OSBPL8 | 0.552946 | YKL211C | TRP3 | GMPS |
| YKR030W | GMH1 | UNC50 | 1.99978 | YKR003W | OSH6 | OSBPL8 |
| YKR044W | UIP5 | LMAN2L | 1.02793 | YKR030W | GMH1 | UNC50 |
| YKR098C | UBP11 | USP45 | 0.365859 | YKR044W | UIP5 | LMAN2 |
| YLL010C | PSR1 | CTDSPL | 0.650813 | YKR098C | UBP11 | USP21 |
| YLR001C | YLR001C | POSTN | 1.53215 | YLL010C | PSR1 | CTD5PL |
| YLR023C | IZH3 | PAQR3 | 0.665248 | YLR001C | YLR001C | TGFBI |
| YLR028C | ADE16 | ATIC | 1.49929 | YLR023C | IZH3 | PAQR3 |
| YLR065C | ENV10 | TMEM208 | 1.9999 | YLR028C | ADE16 | ATIC |
| YLR094C | GIS3 | SSX5 | 1.99989 | YLR065C | ENV10 | TMEM208 |
| YLR099C | ICT1 | ABHD5 | 0.904463 | YLR094C | GIS3 | SSX5 |
| YLR099C | ICT1 | ABHD5 | 0.904463 | YLR099C | ICT1 | ABHD4 |
| YLR119W | SRN2 | VPS37B | 1.16887 | YLR099C | ICT1 | ABHD5 |
| YLR130C | ZRT2 | SLC39A1 | 1.05743 | YLR119W | SRN2 | CCDC58 |
| YLR131C | ACE2 | COIL | 0.771944 | YLR130C | ZRT2 | SLC39A1 |
| YLR136C | TIS11 | RC3H2 | 0.99998 | YLR131C | ACE2 | KLF11 |
| YLR149C | YLR149C | WDR33 | 0.146457 | YLR136C | TIS11 | ZFP36 |
| YLR205C | HMX1 | HMOX1 | 1.50909 | YLR149C | YLR149C | WDR20 |
| YLR218C | COA4 | CHCHD8 | 1.99984 | YLR205C | HMX1 | HMOX1 |
| YLR258W | GSY2 | GYS1 | 1.00594 | YLR218C | COA4 | CHCHD8 |
| YLR262C | YPT6 | RAB6C | 1.11937 | YLR258W | GSY2 | GYS1 |

TABLE S10-continued

Humanized Complete a-synuclein network yeast-|

| Humanized Complete (OE, pooled, deletion screens) Synuclein Network INPUT Yeast Gene (ORF) | Standard Name | Selected Human Homolog | Homology weight (DCA analysis) | Humanized Complete (OE, pooled, deletion screens) Synuclein Network OUTPUT (does not include predicted nodes) Yeast Gene (ORF) | Standard Name | Selected Human Homolog in Network Output |
|---|---|---|---|---|---|---|
| YLR264W | RPS28b | RPS28 | 1.49986 | YLR262C | YPT6 | RAB6A |
| YLR287C-A | RPS30a | FAU | 1.24455 | YLR264W | RPS28b | RPS28 |
| YLR309C | IMH1 | CCDC63 | 0.999931 | YLR287C-A | RPS30a | FAU |
| YLR371W | ROM2 | ARHGEF18 | 0.712642 | YLR309C | IMH1 | GCC2 |
| YLR375W | STP3 | CST2 | 0.889758 | YLR371W | ROM2 | ARHGEF11 |
| YLR399C | BDF1 | BRD3 | 0.778568 | YLR375W | STP3 | EGR4 |
| YLR425W | TUS1 | PLEKHG5 | 0.348774 | YLR399C | BDF1 | BRDT |
| YLR429W | CRN1 | CORO1C | 1.16963 | YLR425W | TUS1 | ARHGEF11 |
| YLR431C | ATG23 | CCDC110 | 0.370474 | YLR429W | CRN1 | CORO2A |
| YLR433C | CNA1 | PPP3CA | 0.845391 | YLR431C | ATG23 | CCDC110 |
| YLR438C-A | LSM3 | LSM3 | 1.11641 | YLR433C | CNA1 | PPP3CA |
| YML001W | YPT7 | RAB7A | 1.03722 | YLR438C-A | LSM3 | LSM3 |
| YML016C | PPZ1 | PPP2CB | 0.484984 | YML001W | YPT7 | RAB7A |
| YML026C | RPS18b | RPS18 | 1.75025 | YML016C | PPZ1 | PPP6C |
| YML028W | TSA1 | PRDX2 | 0.662934 | YML026C | RPS18b | RPS18 |
| YML057W | CMP2 | PPP3CA | 0.843875 | YML028W | TSA1 | PRDX2 |
| YML081W | TDA9 | ZNF518B | 0.12187 | YML057W | CMP2 | PPP3CA |
| YML100W | TSL1 | NPAT | 0.523867 | YML081W | TDA9 | EGR4 |
| YML113W | DAT1 | RBM11 | 0.999966 | YML100W | TSL1 | NPAT |
| YMR001C | CDC5 | PLK3 | 1.34482 | YML113W | DAT1 | RBM11 |
| YMR002W | MIC17 | CHCHD2 | 1.7524 | YMR001C | CDC5 | PLK3 |
| YMR003W | AIM34 | XRCC6 | 0.497711 | YMR002W | MIC17 | CHCHD2 |
| YMR020W | FMS1 | SMOX | 1.20317 | YMR003W | AIM34 | XRCC6 |
| YMR035W | IMP2 | IMMP2L | 1.50832 | YMR020W | FMS1 | MAOA |
| YMR037C | MSN2 | POGZ | 0.484718 | YMR035W | IMP2 | IMMP2L |
| YMR039C | SUB1 | SUB1 | 1.99981 | YMR037C | MSN2 | EGR3 |
| YMR080C | NAM7 | UPF1 | 1.99994 | YMR039C | SUB1 | SUB1 |
| YMR092C | AIP1 | WDR1 | 1.15586 | YMR080C | NAM7 | UPF1 |
| YMR101C | SRT1 | DHDDS | 1.25541 | YMR092C | AIP1 | WDR1 |
| YMR104C | YPK2 | MARCKSL1 | 0.641391 | YMR101C | SRT1 | DHDDS |
| YMR111C | YMR111C | EHBP1 | 0.597354 | YMR104C | YPK2 | AKT1 |
| YMR114C | YMR114C | C3orf37 | 1.99984 | YMR111C | YMR111C | BICD2 |
| YMR186W | HSC82 | HSP90AA1 | 0.850465 | YMR114C | YMR114C | C3orf37 |
| YMR187C | YMR187C | 5-Mar | 0.999974 | YMR187C | YMR187C | 5-Mar |
| YMR202W | ERG2 | SIGMAR1 | 1.9999 | YMR202W | ERG2 | SIGMAR1 |
| YMR205C | PFK2 | PFKL | 0.976387 | YMR205C | PFK2 | PFKM |
| YMR207C | HFA1 | ACACA | 0.978948 | YMR207C | HFA1 | ACACB |
| YMR232W | FUS2 | DNMBP | 1.5016 | YMR232W | FUS2 | DNMBP |
| YMR261C | TPS3 | CEP350 | 0.495604 | YMR261C | TPS3 | CEP350 |
| YMR263W | SAP30 | SAP30L | 1.42846 | YMR263W | SAP30 | SAP30 |
| YMR291W | TDA1 | ADAMTS18 | 0.498183 | YMR291W | TDA1 | STK36 |
| YMR304W | UBP15 | USP7 | 1.50468 | YMR304W | UBP15 | USP47 |
| YNL003C | PET8 | SLC25A26 | 1.00121 | YNL003C | PET8 | SLC25A26 |
| YNL006W | LST8 | MLST8 | 1.06964 | YNL006W | LST8 | MLST8 |
| YNL014W | HEF3 | ABCF1 | 0.351947 | YNL014W | HEF3 | ABCF1 |
| YNL021W | HDA1 | HDAC6 | 1.17738 | YNL021W | HDA1 | HDAC4 |
| YNL025C | SSN8 | CCNC | 1.25968 | YNL025C | SSN8 | CCNC |
| YNL027W | CRZ1 | ZNF541 | 0.453312 | YNL027W | CRZ1 | ZNF174 |
| YNL041C | COG6 | COG6 | 1.99984 | YNL041C | COG6 | COG6 |
| YNL044W | YIP3 | RABAC1 | 1.99991 | YNL044W | YIP3 | RABAC1 |
| YNL051W | COG5 | COG5 | 1.99984 | YNL051W | COG5 | COG5 |
| YNL052W | COX5a | COX4I1 | 1.49332 | YNL052W | COX5a | COX4I1 |
| YNL055C | POR1 | VDAC3 | 1.18397 | YNL055C | POR1 | VDAC1 |
| YNL071W | LAT1 | DLAT | 1.38332 | YNL071W | LAT1 | DLAT |
| YNL076W | MKS1 | STOX2 | 1.32616 | YNL076W | MKS1 | STOX2 |
| YNL077W | APJ1 | DNAJB8 | 0.339149 | YNL077W | APJ1 | DNAJB6 |
| YNL097C | PHO23 | ING3 | 0.656848 | YNL097C | PHO23 | ING1 |
| YNL101W | AVT4 | SLC36A1 | 0.78967 | YNL101W | AVT4 | SLC36A4 |
| YNL224C | SQS1 | NKRF | 0.756669 | YNL224C | SQS1 | RBM10 |
| YNL229C | URE2 | GSTT1 | 0.622901 | YNL229C | URE2 | GSTT2 |
| YNL287W | SEC21 | COPG | 1.99965 | YNL287W | SEC21 | COPG |
| YNL320W | YNL320W | ABHD13 | 1.68678 | YNL320W | YNL320W | ABHD13 |
| YNR051C | BRE5 | G3BP1 | 0.929739 | YNR051C | BRE5 | G3BP1 |

TABLE S10-continued

Humanized Complete a-synuclein network yeast-|

| Humanized Complete (OE, pooled, deletion screens) Synuclein Network INPUT Yeast Gene (ORF) | Standard Name | Selected Human Homolog | Homology weight (DCA analysis) | Humanized Complete (OE, pooled, deletion screens) Synuclein Network OUTPUT (does not include predicted nodes) Yeast Gene (ORF) | Standard Name | Selected Human Homolog in Network Output |
|---|---|---|---|---|---|---|
| YOL001W | PHO80 | CCNYL2 | 0.702355 | YOL001W | PHO80 | CCNYL2 |
| YOL013C | HRD1 | SYVN1 | 1.75303 | YOL013C | HRD1 | SYVN1 |
| YOL062C | APM4 | AP2M1 | 0.943063 | YOL028C | YAP7 | CENPK |
| YOL071W | EMI5 | SDHAF2 | 1.99984 | YOL028C | YAP7 | WDR20 |
| YOL108C | INO4 | MLX | 0.522519 | YOL062C | APM4 | AP2M1 |
| YOR002W | ALG6 | ALG6 | 1.52386 | YOL071W | EMI5 | SDHAF2 |
| YOR014W | RTS1 | PPP2R5D | 1.21713 | YOL108C | INO4 | MLX |
| YOR109W | INP53 | INPP5B | 0.818723 | YOR002W | ALG6 | ALG6 |
| YOR129C | AFI1 | AVL9 | 0.999977 | YOR014W | RTS1 | PPP2R5A |
| YOR137C | SIA1 | CPPED1 | 0.642723 | YOR109W | INP53 | SYNJ1 |
| YOR155C | ISN1 | PMM2 | 0.507537 | YOR129C | AFI1 | AVL9 |
| YOR179C | SYC1 | CPSF3 | 0.999995 | YOR137C | SIA1 | CPPED1 |
| YOR195W | SLK19 | CTAGE4 | 0.365666 | YOR155C | ISN1 | PMM1 |
| YOR208W | PTP2 | PTPRJ | 0.468537 | YOR179C | SYC1 | CPSF3 |
| YOR216C | RUD3 | TRIP11 | 1.00041 | YOR195W | SLK19 | CCDC110 |
| YOR221C | MCT1 | MCAT | 1.54557 | YOR208W | PTP2 | PTPRK |
| YOR273C | TPO4 | SPNS3 | 0.20444 | YOR216C | RUD3 | CCDC110 |
| YOR291W | YPK9 | ATP13A3 | 1.27086 | YOR221C | MCT1 | MCAT |
| YOR296W | YOR296W | CADPS2 | 0.999946 | YOR273C | TPO4 | SPNS3 |
| YOR307C | SLY41 | SLC35E1 | 0.872191 | YOR291W | YPK9 | ATP13A2 |
| YOR324C | FRT1 | ZNF292 | 0.211526 | YOR296W | YOR296W | CDH19 |
| YOR338W | YOR338W | TADA2A | 0.54221 | YOR307C | SLY41 | SLC35E1 |
| YOR340C | RPA43 | TWISTNB | 1.99985 | YOR324C | FRT1 | CKAP4 |
| YOR360C | PDE2 | PDE9A | 1.15414 | YOR338W | YOR338W | TADA2A |
| YPL047W | SGF11 | ATXN7L3 | 1.99988 | YOR340C | RPA43 | TWISTNB |
| YPL057C | SUR1 | A4GNT | 1.15822 | YOR360C | PDE2 | PDE8B |
| YPL072W | UBP16 | USP16 | 0.473987 | YPL047W | SGF11 | ATXN7L3 |
| YPL072W | UBP16 | USP16 | 0.473987 | YPL057C | SUR1 | A46NT |
| YPL089C | RLM1 | MEF2D | 1.01592 | YPL072W | UBP16 | USP16 |
| YPL095C | EEB1 | ABHD1 | 0.7125 | YPL072W | UBP16 | USP30 |
| YPL172C | COX10 | COX10 | 1.99987 | YPL089C | RLM1 | MEF2D |
| YPL177C | CUP9 | PKNOX1 | 0.932147 | YPL095C | EEB1 | ABHD3 |
| YPL181W | CTI6 | EXPH5 | 0.999894 | YPL172C | COX10 | COX10 |
| YPL184C | MRN1 | SPEN | 0.785353 | YPL177C | CUP9 | MEIS1 |
| YPL195W | APL5 | AP3D1 | 1.72423 | YPL181W | CTI6 | PHF13 |
| YPL203W | TPK2 | PRKX | 0.341985 | YPL184C | MRN1 | SPEN |
| YPL208W | RKM1 | SETD4 | 0.647491 | YPL195W | APL5 | AP3D1 |
| YPL265W | DIP5 | SLC7A2 | 0.49445 | YPL203W | TPK2 | PRKACG |
| YPR119W | CLB2 | CCNB2 | 0.541424 | YPL208W | RKM1 | SETD4 |
| YPR145W | ASN1 | ASNS | 1.4977 | YPL265W | DIP5 | SLC7A2 |
| YPR198W | SGE1 | SLC18A2 | 0.204627 | YPR119W | CLB2 | CCNA2 |
| | | | | YPR145W | ASN1 | ASNS |
| | | | | YPR198W | SGE1 | SLC18A2 |

TABLE S11

Predicted Nodes Inferred In PCSF Humanized Networks

| aSyn OE Network | TDP43 OE Network | Abeta OE Network | Complete eSyn (OE, pooled, deletion) Network |
|---|---|---|---|
| AKT1 | ABCA1 | ADAP1 | ABCA1 |
| AP1B1 | ADAT2 | ARHGAP26 | AKAP10 |
| AP2A1 | AKAP13 | BNIP3L | ALDH2 |
| CCDC121 | ARAP1 | C1orf9 | ANKRD28 |
| DCTN2 | ARHGAP30 | CARM1 | AOX1 |
| DPM1 | ARHGEF1 | CCNI | AP1M1 |
| FGR | ARHGEF6 | CD44 | ARNTL |
| IGBP1 | ASH2L | CDC5L | ATG12 |
| LRRK2 | ATXN2L | CDK19 | BAD |
| NHLRC1 | CCAR1 | CEBPD | BAG2 |
| NSF | CEACAM6 | COG6 | C10orf107 |
| PNPT1 | CEACAM8 | CRK | CARM1 |

TABLE S11-continued

Predicted Nodes Inferred In PCSF Humanized Networks

| aSyn OE Network | TDP43 OE Network | Abeta OE Network | Complete eSyn (OE, pooled, deletion) Network |
|---|---|---|---|
| PPFIA1 | CFL1 | CYCS | CDH18 |
| PPP2CA | DBNL | DCP1A | CDH2 |
| PPP2R1A | DCP1B | DUSP15 | CDH6 |
| PPP4C | GALM | ENTPD5 | COG4 |
| RAF1 | GRAMD1C | ERICH1 | CPLX1 |
| RELA | H6PD | EXOSC1 | CSDE1 |
| SENP3 | HCFC2 | EXOSC3 | CSNK1E |
| SGK1 | HNRNPA0 | FAM40A | CTGF |
| SLMAP | HNRNPA1L2 | FAM40B | CTLA4 |
| SNCA | HNRNPA2B1 | FBXL13 | DKK1 |
| SOD1 | KIAA0141 | FOX04 | DOCK5 |
| STUB1 | MAGEE1 | GMPR | FBXL3 |
| TMOD3 | MAPKAPK2 | HECW1 | FDFT1 |
| VDAC2 | MARK1 | HECW2 | FECH |
| | MAST1 | HIST2H2AC | FOSL1 |
| | MEAF6 | HMGCLL1 | FTL |
| | MLST8 | HMGN1 | GBP5 |
| | MUC12 | HNRNPR | GLI1 |
| | NADK | HPRT1 | HAX1 |
| | NCAPD2 | ILF3 | IKZF1 |
| | PAQR3 | K1AA0408 | INPP1 |
| | PASK | KIAA1109 | IRAK2 |
| | PRC1 | KRT18 | IRAK4 |
| | PSG2 | KRT2 | LRP6 |
| | PTPRJ | MAP2K1 | LRRK2 |
| | RAB31P | MAP3K11 | MAML1 |
| | RHOB | MEPCE | MAVS |
| | RHOT1 | METTL14 | MFN2 |
| | RHOT2 | MITF | MYD88 |
| | ROCK1 | MOCS3 | NADSYN1 |
| | ROCK2 | NCOA2 | NPATC2 |
| | RPTOR | NOTCH1 | PBX1 |
| | RRAGB | OR4Q3 | PDE3B |
| | RTN4 | PCBD1 | PDHA1 |
| | SARDH | PICK1 | PHTF1 |
| | SNTB2 | PKN2 | PIK3R6 |
| | SRF | PLD1 | PIP5K1C |
| | UBD | PPARA | PLIN1 |
| | UPF3B | PPM1D | PNKP |
| | USP20 | PPM1E | PPP1R15A |
| | UTRN | PPP1R12A | PRCC |
| | YWHAB | PPP2R1A | PRL |
| | ZC3H4 | PPP2R1B | QKI |
| | | PPP2R5B | RABGGTB |
| | | PPP4R2 | RBM15 |
| | | PRKAR2A | RORC |
| | | PSTPIP1 | RPS6KB1 |
| | | RAB4A | SLC22A2 |
| | | RACGAP1 | SLU7 |
| | | RAP1A | SNCA |
| | | RFC3 | STK11 |
| | | RFC4 | STT3A |
| | | RGS17 | TKTL1 |
| | | RHAG | TLN1 |
| | | ROCK2 | TOE1 |
| | | RPS6KB1 | UBIAD1 |
| | | RTN4 | UTRN |
| | | SH3KBP1 | WDR76 |
| | | SH3YL1 | WDR77 |
| | | STAM | |
| | | STX8 | |
| | | TAF12 | |
| | | TAF1B | |
| | | TCF4 | |
| | | TP53RK | |
| | | WT1 | |
| | | YAP1 | |

| SCROLL DOWN FOR EACH STEM | | | PANTHERDB GENE ONTOLOGY HUMAN GENES (PROCESS) | | | | | | |
|---|---|---|---|---|---|---|---|---|---|
| BICD2 STEM | GO Group (Attribute) | Human Genes | GO biological process complete | # | # | expected | Fold Enrichm | +/- | P value |
| AFF2 | vesicle trafficking stem | AFF2 | GO biological process complete | 2 | 2 | 0 > 100 | | + | 0.0257 |
| ATP2C1 | vesicle trafficking stem | ATP2C1 | cargo loading into COPII-coated vesicle | 1158 | 11 | 1.49 | 7.38 | + | 0.000668 |
| BICD2 | vesicle trafficking stem | BICD2 | intracellular transport | 1436 | 11 | 1.85 | 5.95 | + | 0.0058 |
| CCDC58 | vesicle trafficking stem | CCDC58 | establishment of localization in cell | 1241 | 11 | 1.6 | 6.88 | + | 0.00135 |
| CCNYL2 | vesicle trafficking stem | CCNYL2 | vesicle-mediated transport | 308 | 6 | 0.4 | 15.13 | + | 0.0184 |
| CTDSPL | vesicle trafficking stem | CTDSPL | Golgi vesicle transport | 15 | 3 | 0.02 > 100 | | + | 0.00852 |
| GCC2 | vesicle trafficking stem | GCC2 | protein targeting to lysosome | 256 | 7 | 0.33 | 21.24 | + | 0.000233 |
| GPRIN3 | vesicle trafficking stem | GPRIN3 | vacuolar transport | 20 | 3 | 0.03 > 100 | | + | 0.0201 |
| NANP | vesicle trafficking stem | NANP | protein localization to lysosome | 18 | 3 | 0.02 > 100 | | + | 0.0147 |
| NPAT | vesicle trafficking stem | NPAT | protein targeting to Golgi | 24 | 3 | 0.03 | 97.09 | + | 0.0346 |
| OSBPL1A | vesicle trafficking stem | OSBPL1A | retrograde transport, vesicle recycling within | 20 | 3 | 0.03 > 100 | | + | 0.0201 |
| PMM1 | vesicle trafficking stem | PMM1 | establishment of protein localization to Golgi | | | | | | |
| RAB1A | vesicle trafficking stem | RAB1A | retrograde transport, endosome to Golgi | 73 | 6 | 0.09 | 63.84 | + | 0.00000399 |
| RAB6A | vesicle trafficking stem | RAB6A | cytosolic transport | 114 | 6 | 0.15 | 40.88 | + | 0.0000558 |
| RAB7A | vesicle trafficking stem | RAB7A | endosomal transport | 230 | 6 | 0.3 | 20.26 | + | 0.00341 |
| RABAC1 | vesicle trafficking stem | RABAC1 | | | | | | | |
| RABGGTA | vesicle trafficking stem | RABGGTA | | | | | | | |
| RABGGTB | vesicle trafficking stem | RABGGTB | | | | | | | |
| RNF115 | vesicle trafficking stem | RNF115 | | | | | | | |
| SLC35E1 | vesicle trafficking stem | SLC35E1 | | | | | | | |
| SORL1 | vesicle trafficking stem | SORL1 | | | | | | | |
| TBC1D20 | vesicle trafficking stem | TBC1D20 | | | | | | | |
| TRAPPC9 | vesicle trafficking stem | TRAPPC9 | | | | | | | |
| VPS26B | vesicle trafficking stem | VPS26B | | | | | | | |
| VPS29 | vesicle trafficking stem | VPS29 | | | | | | | |
| VPS35 | vesicle trafficking stem | VPS35 | | | | | | | |
| WDR4 | vesicle trafficking stem | WDR4 | | | | | | | |
| YBR062C | vesicle trafficking stem | | | | | | | | |
| YBR215W | vesicle trafficking stem | | | | | | | | |
| YDL019C | vesicle trafficking stem | | | | | | | | |
| YDR074W | vesicle trafficking stem | | | | | | | | |
| YDR143C | vesicle trafficking stem | | | | | | | | |
| YDR165W | vesicle trafficking stem | | | | | | | | |
| YDR407C | vesicle trafficking stem | | | | | | | | |
| YFL027C | vesicle trafficking stem | | | | | | | | |
| YFL038C | vesicle trafficking stem | | | | | | | | |
| YGL167C | vesicle trafficking stem | | | | | | | | |
| YGL222C | vesicle trafficking stem | | | | | | | | |
| YGL224C | vesicle trafficking stem | | | | | | | | |
| YHR012W | vesicle trafficking stem | | | | | | | | |
| YHR073W | vesicle trafficking stem | | | | | | | | |
| YIL173W | vesicle trafficking stem | | | | | | | | |
| YJL031C | vesicle trafficking stem | | | | | | | | |
| YJL053W | vesicle trafficking stem | | | | | | | | |
| YJL154C | vesicle trafficking stem | | | | | | | | |
| YLL010C | vesicle trafficking stem | | | | | | | | |
| YLR119W | vesicle trafficking stem | | | | | | | | |
| YLR262C | vesicle trafficking stem | | | | | | | | |

| COG6 STEM | GO Group (Attribute) |
|---|---|
| YLR309C | vesicle trafficking stem |
| YML001W | vesicle trafficking stem |
| YML100W | vesicle trafficking stem |
| YMR111C | vesicle trafficking stem |
| YNL044W | vesicle trafficking stem |
| YOL001W | vesicle trafficking stem |
| YOR155C | vesicle trafficking stem |
| YOR307C | vesicle trafficking stem | www.geneontology.org enrichment HUMAN GENES (PROCESS)

| COG6 STEM | GO Group (Attribute) | Human Genes | # | # | expected | Fold Enrichm | +/− | P value |
|---|---|---|---|---|---|---|---|---|
| A4GNT | vesicle trafficking stem | A4GNT | | | | | | |
| ARFGAP2 | vesicle trafficking stem | ARFGAP2 | | | | | | |
| BET1 | vesicle trafficking stem | BET1 | | | | | | |
| C3orf37 | vesicle trafficking stem | C3orf37 | | | | | | |
| CCDC104 | vesicle trafficking stem | CCDC104 | | | | | | |
| CNIH4 | vesicle trafficking stem | CNIH4 | | | | | | |
| COG4 | vesicle trafficking stem | COG4 | | | | | | |
| COG5 | vesicle trafficking stem | COG5 | | | | | | |
| COG6 | vesicle trafficking stem | COG6 | | | | | | |
| GOSR1 | vesicle trafficking stem | GOSR1 | GO biological process complete | 164 | 9 | 0.2 | 44.27 | + | 2.44E−09 |
| GSTT2 | vesicle trafficking stem | GSTT2 | ER to Golgi vesicle-mediated transport | 308 | 10 | 0.38 | 26.19 | + | 1.61E−08 |
| MOCS3 | vesicle trafficking stem | MOCS3 | Golgi vesicle transport | 1338 | 12 | 1.66 | 7.23 | + | 1.52E−04 |
| OBFC1 | vesicle trafficking stem | OBFC1 | establishment of protein localization | 1228 | 11 | 1.52 | 7.23 | + | 7.57E−04 |
| POTEC | vesicle trafficking stem | POTEC | protein transport | 1732 | 12 | 2.15 | 5.59 | + | 2.59E−03 |
| SLC39A1 | vesicle trafficking stem | SLC39A1 | protein localization | 49 | 4 | 0.06 | 65.85 | + | 3.45E−03 |
| SLC7A2 | vesicle trafficking stem | SLC7A2 | intra-Golgi vesicle-mediated transport | 1158 | 10 | 1.44 | 6.97 | + | 4.96E−03 |
| SURF4 | vesicle trafficking stem | SURF4 | intracellular transport | 1241 | 10 | 1.54 | 6.5 | + | 9.34E−03 |
| SYVN1 | vesicle trafficking stem | SYVN1 | vesicle-mediated transport | 2091 | 12 | 2.59 | 4.63 | + | 1.96E−02 |
| TMED9 | vesicle trafficking stem | TMED9 | macromolecule localization | 77 | 4 | 0.1 | 41.9 | + | 2.05E−02 |
| TMEM208 | vesicle trafficking stem | TMEM208 | retrograde vesicle-mediated transport, Golgi t | 1436 | 10 | 1.78 | 5.62 | + | 3.49E−02 |
| TREML2 | vesicle trafficking stem | TREML2 | establishment of localization in cell | | | | | | |
| TTC35 | vesicle trafficking stem | TTC35 | | | | | | | |
| UNC50 | vesicle trafficking stem | UNC50 | | | | | | | |
| WDR76 | vesicle trafficking stem | WDR76 | | | | | | | |
| WRB | vesicle trafficking stem | WRB | | | | | | | |
| YAR002C-A | vesicle trafficking stem | YKT6 | | | | | | | |
| YBR067C | vesicle trafficking stem | | | | | | | | |
| YDL213C | vesicle trafficking stem | | | | | | | | |
| YDR082W | vesicle trafficking stem | | | | | | | | |
| YER122C | vesicle trafficking stem | | | | | | | | |
| YGL002W | vesicle trafficking stem | | | | | | | | |
| YGL020C | vesicle trafficking stem | | | | | | | | |
| YGL053W | vesicle trafficking stem | | | | | | | | |
| YGL054C | vesicle trafficking stem | | | | | | | | |
| YGR284C | vesicle trafficking stem | | | | | | | | |
| YHL031C | vesicle trafficking stem | | | | | | | | |
| YHR111W | vesicle trafficking stem | | | | | | | | |
| YJR088C | vesicle trafficking stem | | | | | | | | |
| YKL006C-A | vesicle trafficking stem | | | | | | | | |
| YKL063C | vesicle trafficking stem | | | | | | | | |
| YKL196C | vesicle trafficking stem | | | | | | | | |
| YKR030W | vesicle trafficking stem | | | | | | | | |

| | |
|---|---|
| YKT6 | vesicle trafficking stem |
| YLR065C | vesicle trafficking stem |
| YLR130C | vesicle trafficking stem |
| YMR114C | vesicle trafficking stem |
| YNL041C | vesicle trafficking stem |
| YNL051W | vesicle trafficking stem |
| YNL229C | vesicle trafficking stem |
| YOL013C | vesicle trafficking stem |
| YPL057C | vesicle trafficking stem |
| YPL265W | vesicle trafficking stem |

| LRRK2 STEM | GO Group (Attribute) | www.geneontology.org enrichment HUMAN GENES (PROCESS) | | | | | | |
|---|---|---|---|---|---|---|---|---|
| | | Human Genes | GO biological process complete | # | # expected | Fold Enrichm | +/− | P value |
| PSMD4 | vesicle trafficking stem | PSMD4 | GO biological process complete | | | | | |
| NEDD4 | vesicle trafficking stem | NEDD4 | regulation of synaptic vesicle transport | 30 | 3  0.02 > 100 | | + | 8.49E-03 |
| YER125W | vesicle trafficking stem | YER125W | positive regulation of catabolic process | 326 | 5  0.22 | 22.98 | + | 1.30E-02 |
| LRRK2 | vesicle trafficking stem | LRRK2 | | | | | | |
| SNCA | vesicle trafficking stem | SNCA | | | | | | |
| MEIS1 | vesicle trafficking stem | MEIS1 | | | | | | |
| RNF11 | vesicle trafficking stem | RNF11 | | | | | | |
| TWISTNB | vesicle trafficking stem | TWISTNB | | | | | | |
| STOX2 | vesicle trafficking stem | STOX2 | | | | | | |
| YNL076W | vesicle trafficking stem | YNL076W | | | | | | |
| NDFIP1 | vesicle trafficking stem | NDFIP1 | | | | | | |
| PRL | vesicle trafficking stem | PRL | | | | | | |
| TOR1A | vesicle trafficking stem | TOR1A | | | | | | |
| PBX1 | vesicle trafficking stem | PBX1 | | | | | | |
| TGFBI | vesicle trafficking stem | TGFBI | | | | | | |
| YJR091C | vesicle trafficking stem | VDAC1 | | | | | | |
| YLR001C | vesicle trafficking stem | | | | | | | |
| YOR340C | vesicle trafficking stem | | | | | | | |
| YBR290W | vesicle trafficking stem | | | | | | | |
| YNL055C | vesicle trafficking stem | | | | | | | |
| YKL034W | vesicle trafficking stem | | | | | | | |
| YHR200W | vesicle trafficking stem | | | | | | | |
| YPL177C | vesicle trafficking stem | | | | | | | |
| VDAC1 | vesicle trafficking stem | | | | | | | |

| CTLA4 STEM | GO Group (Attribute) | www.geneontology.org enrichment HUMAN GENES (PROCESS) | | | | | | |
|---|---|---|---|---|---|---|---|---|
| | | Human Genes | GO biological process complete | # | # expected | Fold Enrichm | +/− | P value |
| ANKRD28 | vesicle trafficking stem | ANKRD28 | GO biological process complete | | | | | |
| AP2M1 | vesicle trafficking stem | AP2M1 | ER to Golgi vesicle-mediated transport | 164 | 6  0.1 | 59.02 | + | 3.02E-06 |
| AP2S1 | vesicle trafficking stem | AP2S1 | vesicle-mediated transport | 1241 | 9  0.77 | 11.7 | + | 4.12E-05 |
| CANX | vesicle trafficking stem | CANX | Golgi vesicle transport | 308 | 6  0.19 | 31.43 | + | 1.27E-04 |
| COPE | vesicle trafficking stem | COPE | establishment of localization in cell | 1436 | 9  0.89 | 10.11 | + | 1.48E-04 |
| COPG | vesicle trafficking stem | COPG | intracellular transport | 1158 | 8  0.72 | 11.14 | + | 6.97E-04 |
| CTLA4 | vesicle trafficking stem | CTLA4 | cellular localization | 1880 | 9  1.17 | 7.72 | + | 1.54E-03 |
| MRPS36 | vesicle trafficking stem | MRPS36 | antigen processing and presentation of exogen | 92 | 4  0.06 | 70.14 | + | 2.07E-03 |
| PPCDC | vesicle trafficking stem | PPCDC | antigen processing and presentation of peptide | 94 | 4  0.06 | 68.65 | + | 2.25E-03 |
| PPP6C | vesicle trafficking stem | PPP6C | antigen processing and presentation of peptide | 98 | 4  0.06 | 65.85 | + | 2.66E-03 |
| SEC31A | vesicle trafficking stem | SEC31A | clathrin-mediated endocytosis | 36 | 3  0.02 > 100 | | + | 1.15E-02 |
| SLC36A4 | vesicle trafficking stem | SLC36A4 | establishment of organelle localization | 353 | 5  0.22 | 22.85 | + | 1.25E-02 |
| TEX261 | vesicle trafficking stem | TEX261 | antigen processing and presentation of exogen | 163 | 4  0.1 | 39.59 | + | 1.99E-02 |

-continued

| | | | | | | | |
|---|---|---|---|---|---|---|---|
| YAL058W | vesicle trafficking stem | antigen processing and presentation of exogen | 170 | 4 | 0.11 | 37.96 | + | 2.35E-02 |
| YDL047W | vesicle trafficking stem | organelle localization | 411 | 5 | 0.25 | 19.63 | + | 2.63E-02 |
| YDL195W | vesicle trafficking stem | antigen processing and presentation of peptide | 179 | 4 | 0.11 | 36.05 | + | 2.88E-02 |
| YDR436W | vesicle trafficking stem | | | | | | | |
| YFR049W | vesicle trafficking stem | | | | | | | |
| YHR181W | vesicle trafficking stem | | | | | | | |
| YIL076W | vesicle trafficking stem | | | | | | | |
| YJR058C | vesicle trafficking stem | | | | | | | |
| YML016C | vesicle trafficking stem | | | | | | | |
| YNL101W | vesicle trafficking stem | | | | | | | |
| YNL287W | vesicle trafficking stem | | | | | | | |
| YOL062C | vesicle trafficking stem | | | | | | | |

| PPP3CA imm | GO Group (Attribute) | www.geneontology.org enrichment HUMAN GENES (PROCESS) | | | | | | |
|---|---|---|---|---|---|---|---|---|
| Human Genes | | | # | # | expected | Fold Enrichm | +/- | P value |
| BAD | Calcium/NFAT signaling | GO biological process complete | 8 | 3 | 0 > 100 | | + | 1.28E-04 |
| CALM1 | Calcium/NFAT signaling | calcineurin-NFAT signaling cascade | 18 | 3 | 0.01 > 100 | | + | 1.45E-03 |
| NFATC2 | Calcium/NFAT signaling | inositol phosphate-mediated signaling | 160 | 5 | 0.1 | 50.41 | + | 2.55E-04 |
| PPM1G | Calcium/NFAT signaling | second-messenger-mediated signaling | 89 | 5 | 0.06 | 90.63 | + | 1.39E-05 |
| PPP2R2C | Calcium/NFAT signaling | calcium-mediated signaling | 37 | 3 | 0.02 > 100 | | + | 1.25E-02 |
| PPP2R5A | Calcium/NFAT signaling | Wnt signaling pathway, calcium modulating pi | 134 | 4 | 0.08 | 48.16 | + | 9.17E-03 |
| PPP3CA | Calcium/NFAT signaling | Fc-epsilon receptor signaling pathway | 198 | 4 | 0.12 | 32.59 | + | 4.28E-02 |
| PPP3R1 | Calcium/NFAT signaling | Fc receptor signaling pathway | | | | | | |
| RCAN2 | Calcium/NFAT signaling | | | | | | | |
| SYNJ1 | Calcium/NFAT signaling | | | | | | | |
| UTRN | Calcium/NFAT signaling | | | | | | | |
| YBR125C | Calcium/NFAT signaling | | | | | | | |
| YGL190C | Calcium/NFAT signaling | | | | | | | |
| YKL159C | Calcium/NFAT signaling | | | | | | | |
| YKL190W | Calcium/NFAT signaling | | | | | | | |
| YLR433C | Calcium/NFAT signaling | | | | | | | |
| YML057W | Calcium/NFAT signaling | | | | | | | |
| YOR014W | Calcium/NFAT signaling | | | | | | | |
| YOR109W | Calcium/NFAT signaling | | | | | | | |

| IKZF1 stem | GO Group (Attribute) | www.geneontology.org enrichment HUMAN GENES (PROCESS) | | | | | | |
|---|---|---|---|---|---|---|---|---|
| Human Genes | | | # | # | expected | Fold Enrichm | +/- | P value |
| DCLRE1C | DNA damage repair | GO biological process complete | 49 | 3 | 0.02 > 100 | | + | 5.71E-03 |
| IKZF1 | DNA damage repair | double-strand break repair via nonhomologoo | 54 | 3 | 0.02 > 100 | | + | 7.63E-03 |
| IKZF4 | DNA damage repair | non-recombinational repair | 3942 | 8 | 1.5 | 5.32 | + | 1.26E-02 |
| PNKP | DNA damage repair | nucleic acid metabolic process | 4484 | 8 | 1.71 | 4.68 | + | 3.52E-02 |
| RNF8 | DNA damage repair | nucleobase-containing compound metabolic proces | 4620 | 8 | 1.76 | 4.54 | + | 4.47E-02 |
| WTAP | DNA damage repair | heterocycle metabolic process | 4669 | 8 | 1.78 | 4.49 | + | 4.87E-02 |
| XRCC6 | DNA damage repair | cellular aromatic compound metabolic proces | 1599 | 6 | 0.61 | 9.84 | + | 3.87E-02 |
| ZNF639 | DNA damage repair | positive regulation of nucleobase-containing of | | | | | | |
| YBR057C | DNA damage repair | | | | | | | |
| YDR463W | DNA damage repair | | | | | | | |
| YGR229C | DNA damage repair | | | | | | | |
| YHR036W | DNA damage repair | | | | | | | |
| YHR115C | DNA damage repair | | | | | | | |
| YMR003W | DNA damage repair | | | | | | | |
| ZNF639 | DNA damage repair | | | | | | | |

-continued

| UTRN stem | GO Group (Attribute) | Human Genes | Geneontology.org process enrichment; DAVID functional enrichment (process) see to the right | # | # | expected | Fold Enrichm | +/- | P value |
|---|---|---|---|---|---|---|---|---|---|
| 5-Mar | Ubiquitin conjugation/Macroautophagy | ATG12 | GO biological process complete | 117 | 4 | 0.07 | 59.75 | + | 3.73E-03 |
| ATG12 | Ubiquitin conjugation/Macroautophagy | ATG7 | protein deubiquitination | 134 | 4 | 0.08 | 52.17 | + | 6.38E-03 |
| ATG7 | Ubiquitin conjugation/Macroautophagy | DAK | protein modification by small protein removal | | | | | | |
| DAK | Ubiquitin conjugation/Macroautophagy | MAV5 | | | | | | | |
| MAV5 | Ubiquitin conjugation/Macroautophagy | MFN2 | | | | | | | |
| MFN2 | Ubiquitin conjugation/Macroautophagy | MRPS23 | | | | | | | |
| MRPS23 | Ubiquitin conjugation/Macroautophagy | SDHAF2 | | | | | | | |
| SDHAF2 | Ubiquitin conjugation/Macroautophagy | USP16 | | | | | | | |
| USP16 | Ubiquitin conjugation/Macroautophagy | USP21 | | | | | | | |
| USP21 | Ubiquitin conjugation/Macroautophagy | USP30 | | | | | | | |
| USP30 | Ubiquitin conjugation/Macroautophagy | UTRN | | | | | | | |
| UTRN | Ubiquitin conjugation/Macroautophagy | | | | | | | | |
| YDL122W | Ubiquitin conjugation/Macroautophagy | | | | | | | | |
| YDR069C | Ubiquitin conjugation/Macroautophagy | | | | | | | | |
| YFL053W | Ubiquitin conjugation/Macroautophagy | | | | | | | | |
| YHR171W | Ubiquitin conjugation/Macroautophagy | | | | | | | | |
| YIL093C | Ubiquitin conjugation/Macroautophagy | | | | | | | | |
| YIL156W | Ubiquitin conjugation/Macroautophagy | | | | | | | | |
| YKR098C | Ubiquitin conjugation/Macroautophagy | | | | | | | | |
| YMR187C | Ubiquitin conjugation/Macroautophagy | | | | | | | | |
| YOL071W | Ubiquitin conjugation/Macroautophagy | | | | | | | | |
| YPL072W | Ubiquitin conjugation/Macroautophagy | | | | | | | | |
| AP1M1 | inositol phosphorylation/ | AP1M1 | inositol phosphate dephosphorylation | 10 | 3 | 0.01 > 100 | | + | 7.09E-04 |
| CDH18 | inositol phosphorylation/ | CDH18 | phosphorylated carbohydrate dephosphorylat | 11 | 3 | 0.01 > 100 | | + | 9.44E-04 |
| CDH19 | inositol phosphorylation/ | CDH19 | inositol phosphate catabolic process | 12 | 3 | 0.01 > 100 | | + | 1.22E-03 |
| CDH2 | inositol phosphorylation/ | CDH2 | polyol catabolic process | 20 | 3 | 0.02 > 100 | | + | 5.64E-03 |
| CDH6 | inositol phosphorylation/ | CDH6 | alcohol catabolic process | 40 | 3 | 0.03 | 87.38 | + | 4.47E-02 |
| COX10 | inositol phosphorylation/ | COX10 | adherens junction organization | 71 | 4 | 0.06 | 65.64 | + | 3.12E-03 |
| FECH | inositol phosphorylation/ | FECH | cell-cell junction organization | 161 | 5 | 0.14 | 36.18 | + | 1.69E-03 |
| FTL | inositol phosphorylation/ | FTL | cell junction organization | 187 | 5 | 0.16 | 31.15 | + | 3.53E-03 |
| IMPA2 | inositol phosphorylation/ | IMPA2 | homophilic cell adhesion via plasma membrane | 156 | 5 | 0.13 | 37.34 | + | 1.45E-03 |
| INPP1 | inositol phosphorylation/ | INPP1 | cell-cell adhesion via plasma-membrane adhesion | 209 | 5 | 0.18 | 27.87 | + | 6.09E-03 |
| KIF13A | inositol phosphorylation/ | KIF13A | cell-cell adhesion | 617 | 7 | 0.53 | 13.22 | + | 3.68E-03 |
| PIP5K1C | inositol phosphorylation/ | PIP5K1C | vesicle-mediated transport | 1241 | 8 | 1.07 | 7.51 | + | 3.10E-02 |
| SNX5 | inositol phosphorylation/ | SNX5 | | | | | | | |
| SYNJ1 | inositol phosphorylation/ | SYNJ1 | | | | | | | |
| TLN1 | inositol phosphorylation/ | TLN1 | | | | | | | |
| TXNDC5 | inositol phosphorylation/ | TXNDC5 | | | | | | | |
| WDR1 | inositol phosphorylation/ | WDR1 | | | | | | | |
| YDL115C | inositol phosphorylation/membrane trafficking | | | | | | | | |
| YHR046C | inositol phosphorylation/membrane trafficking | | | | | | | | |
| YIL005W | inositol phosphorylation/membrane trafficking | | | | | | | | |
| YKL079W | inositol phosphorylation/membrane trafficking | | | | | | | | |
| YMR092C | inositol phosphorylation/membrane trafficking | | | | | | | | |
| YOR109W | inositol phosphorylation/membrane trafficking | | | | | | | | |
| YOR296W | inositol phosphorylation/membrane trafficking | | | | | | | | |
| YPL172C | inositol phosphorylation/membrane trafficking | | | | | | | | |

-continued

| PIK3R6 stem | GO Group (Attribute) | Human Genes | www.geneontology.org enrichment HUMAN GENES (PROCESS) | | | | | |
|---|---|---|---|---|---|---|---|---|
| | | | | # | # expected | Fold Enrichm | +/− | P value |
| ATIC | Purine metabolism | ATIC | GO biological process complete | 357 | 6 0.14 | 44.06 | + | 5.33E−06 |
| CTPS2 | Purine metabolism | CTPS2 | ribonucleotide metabolic process | 372 | 6 0.14 | 42.28 | + | 6.82E−06 |
| GMPS | Purine metabolism | GMPS | ribose phosphate metabolic process | 887 | 7 0.34 | 20.69 | + | 1.50E−05 |
| ITPA | Purine metabolism | ITPA | organophosphate metabolic process | 485 | 6 0.19 | 32.43 | + | 3.32E−05 |
| PDE3B | Purine metabolism | PDE3B | nucleotide metabolic process | 493 | 6 0.19 | 31.9 | + | 3.66E−05 |
| PDE8B | Purine metabolism | PDE8B | nucleoside phosphate metabolic process | 552 | 6 0.21 | 28.49 | + | 7.17E−05 |
| PIK3R6 | Purine metabolism | PIK3R6 | nucleobase-containing small molecule metabolic | 342 | 5 0.13 | 38.33 | + | 5.00E−04 |
| RAPGEF3 | Purine metabolism | RAPGEF3 | purine ribonucleotide metabolic process | 361 | 5 0.14 | 36.31 | + | 6.53E−04 |
| YFR022W | Purine metabolism | | purine nucleotide metabolic process | 25 | 3 0.01 > 100 | | + | 7.61E−04 |
| YJR069C | Purine metabolism | | purine ribonucleotide catabolic process | 26 | 3 0.01 > 100 | | + | 8.56E−04 |
| YJR103W | Purine metabolism | | ribonucleotide catabolic process | 393 | 5 0.15 | 33.35 | + | 9.95E−04 |
| YKL211C | Purine metabolism | | purine-containing compound metabolic process | 38 | 3 0.01 > 100 | | + | 2.67E−03 |
| YLR028C | Purine metabolism | | purine nucleotide catabolic process | 1038 | 6 0.4 | 15.15 | + | 3.04E−03 |
| YOR360C | Purine metabolism | | carbohydrate derivative metabolic process | 44 | 3 0.02 > 100 | | + | 4.14E−03 |
| | | | purine-containing compound catabolic process | 2046 | 7 0.78 | 8.97 | + | 4.96E−03 |
| | | | phosphate-containing compound metabolic process | 2052 | 7 0.78 | 8.94 | + | 5.06E−03 |
| | | | phosphorus metabolic process | 57 | 3 0.02 > 100 | | + | 8.97E−03 |
| | | | nucleotide catabolic process | 65 | 3 0.02 > 100 | | + | 1.33E−02 |
| | | | nucleoside phosphate catabolic process | 1636 | 6 0.62 | 9.61 | + | 4.43E−02 |
| | | | small molecule metabolic process | | | | | |

| PPP2R2C upp | GO Group (Attribute) | Human Genes | www.geneontology.org enrichment HUMAN GENES (PROCESS) | | | | | |
|---|---|---|---|---|---|---|---|---|
| | | | | # | # expected | Fold Enrichm | +/− | P value |
| BAG2 | mRNA metabolism | BAG2 | GO biological process complete | 373 | 7 0.25 | 28.11 | + | 1.40E−05 |
| C16orf61 | mRNA metabolism | C16orf61 | RNA splicing | 849 | 7 0.57 | 12.35 | + | 3.83E−03 |
| CPSF3 | mRNA metabolism | CPSF3 | RNA processing | 436 | 7 0.29 | 24.05 | + | 4.08E−05 |
| HUNK | mRNA metabolism | HUNK | mRNA processing | 613 | 7 0.41 | 17.11 | + | 4.21E−04 |
| LSM3 | mRNA metabolism | LSM3 | mRNA metabolic process | 4136 | 2 2.76 | 0.72 | − | 0.00E+00 |
| MYBL2 | mRNA metabolism | MYBL2 | Unclassified | | | | | |
| PRCC | mRNA metabolism | PRCC | | | | | | |
| QKI | mRNA metabolism | QKI | | | | | | |
| RBM10 | mRNA metabolism | RBM10 | | | | | | |
| RBM11 | mRNA metabolism | RBM11 | | | | | | |
| SLU7 | mRNA metabolism | SLU7 | | | | | | |
| TOE1 | mRNA metabolism | TOE1 | | | | | | |
| WDR77 | mRNA metabolism | WDR77 | | | | | | |
| YBL054W | mRNA metabolism | ZC3H4 | | | | | | |
| YBL059C-A | mRNA metabolism | | | | | | | |
| YCR008W | mRNA metabolism | | | | | | | |
| YDL053C | mRNA metabolism | | | | | | | |
| YDL167C | mRNA metabolism | | | | | | | |
| YLR438C-A | mRNA metabolism | | | | | | | |
| YML113W | mRNA metabolism | | | | | | | |
| YNL224C | mRNA metabolism | | | | | | | |
| YOR179C | mRNA metabolism | | | | | | | |
| ZC3H4 | mRNA metabolism | | | | | | | |

-continued

| PPP2R2C low | GO Group (Attribute) | Human Genes | www.geneontology.org enrichment HUMAN GENES (PROCESS) | | | | | |
|---|---|---|---|---|---|---|---|---|
| | | | | # | # expected | Fold Enrichm | +/− | P value |
| ABHD13 | Toll receptor signaling | ABHD13 | GO biological process complete | 15 | 3 | 0.01 > 100 | + | 2.47E-04 |
| CKAP4 | Toll receptor signaling | CKAP4 | toll-like receptor 9 signaling pathway | 85 | 4 | 0.04 > 100 | + | 2.70E-04 |
| DOLPP1 | Toll receptor signaling | DOLPP1 | toll-like receptor signaling pathway | 109 | 4 | 0.05 | 85.51 | + | 7.26E-04 |
| IRAK2 | Toll receptor signaling | IRAK2 | pattern recognition receptor signaling pathway | 195 | 4 | 0.08 | 47.8 | + | 7.31E-03 |
| IRAK4 | Toll receptor signaling | IRAK4 | innate immune response-activating signal trar | 204 | 4 | 0.09 | 45.69 | + | 8.75E-03 |
| MYD88 | Toll receptor signaling | MYD88 | activation of innate immune response | 246 | 4 | 0.11 | 37.89 | + | 1.83E-02 |
| STT3A | Toll receptor signaling | STT3A | positive regulation of innate immune response | 34 | 4 | 0.01 > 100 | + | 6.97E-06 |
| TLR5 | Toll receptor signaling | TLR5 | MyD88-dependent toll-like receptor signaling | 85 | 3 | 0.04 | 82.24 | + | 4.43E-02 |
| YTHDF1 | Toll receptor signaling | YTHDF1 | JNK cascade | | | | | |
| YDR374C | Toll receptor signaling | | | | | | | |
| YDR380W | Toll receptor signaling | | | | | | | |
| YGR036C | Toll receptor signaling | | | | | | | |
| YNL320W | Toll receptor signaling | | | | | | | |
| YOR324C | Toll receptor signaling | | | | | | | |
| YTHDF1 | Toll receptor signaling | | | | | | | |

| LRP6 lower s | GO Group (Attribute) | Human Genes | www.geneontology.org enrichment HUMAN GENES (PROCESS) |
|---|---|---|---|
| ABCF1 | | ABCF1 | None |
| AKAP10 | | AKAP10 | |
| ALG6 | | ALG6 | |
| ANKZF1 | | ANKZF1 | |
| ATP13A2 | | ATP13A2 | |
| C10orf107 | | C10orf107 | |
| DKK1 | | DKK1 | |
| FUNDC2 | | FUNDC2 | |
| GAB4 | | GAB4 | |
| HAX1 | | HAX1 | |
| LMAN2 | | LMAN2 | |
| LRP6 | | LRP6 | |
| POMT1 | | POMT1 | |
| PRRT2 | | PRRT2 | |
| SIGMAR1 | | SIGMAR1 | |
| YAL008W | | | |
| YDR049W | | | |
| YGR041W | | | |
| YGR199W | | | |
| YIL056W | | | |
| YKR044W | | | |
| YMR202W | | | |
| YNL014W | | | |
| YOR002W | | | |
| YOR291W | | | |

-continued

| PPP1CB lowe | GO Group (Attribute) | Human Genes | www.geneontology.org enrichment HUMAN GENES (PROCESS) | | | | | |
|---|---|---|---|---|---|---|---|---|
| ABHD4 | Glycogen metabolism | ABHD4 | glycogen biosynthetic process | 26 | 3 | 0.03 > 100 | + | 2.32E-02 |
| ABHD5 | Glycogen metabolism | ABHD5 | glycogen metabolic process | 57 | 5 | 0.06 | 83.62 | + | 3.03E-05 |
| CCNC | Glycogen metabolism | CCNC | cellular glucan metabolic process | 58 | 5 | 0.06 | 82.18 | + | 3.30E-05 |
| CPPED1 | Glycogen metabolism | CPPED1 | cellular polysaccharide metabolic process | 74 | 5 | 0.08 | 64.41 | + | 1.10E-04 |
| GYG1 | Glycogen metabolism | GYG1 | polysaccharide metabolic process | 81 | 5 | 0.08 | 58.84 | + | 1.73E-04 |
| GYS1 | Glycogen metabolism | GYS1 | cellular carbohydrate metabolic process | 146 | 5 | 0.15 | 32.65 | + | 3.15E-03 |
| HIPK4 | Glycogen metabolism | HIPK4 | glucan metabolic process | 58 | 5 | 0.06 | 82.18 | + | 3.30E-05 |
| IMMP2L | Glycogen metabolism | IMMP2L | energy reserve metabolic process | 73 | 5 | 0.08 | 65.29 | + | 1.03E-04 |
| KIAA1383 | Glycogen metabolism | KIAA1383 | energy derivation by oxidation of organic com | 235 | 6 | 0.25 | 24.34 | + | 1.02E-03 |
| MAML1 | Glycogen metabolism | MAML1 | generation of precursor metabolites and energy | 314 | 6 | 0.33 | 18.22 | + | 5.51E-03 |
| NUCB1 | Glycogen metabolism | NUCB1 | glucan biosynthetic process | 26 | 3 | 0.03 > 100 | | + | 2.32E-02 |
| PLIN1 | Glycogen metabolism | PLIN1 | | | | | | | |
| PPP1CB | Glycogen metabolism | PPP1CB | | | | | | | |
| PPP1R15A | Glycogen metabolism | PPP1R15A | | | | | | | |
| PPP1R3B | Glycogen metabolism | PPP1R3B | | | | | | | |
| SLC13A3 | Glycogen metabolism | SLC13A3 | | | | | | | |
| SMARCB1 | Glycogen metabolism | SMARCB1 | | | | | | | |
| SPEN | Glycogen metabolism | SPEN | | | | | | | |
| SSX5 | Glycogen metabolism | SSX5 | | | | | | | |
| TSKS | Glycogen metabolism | TSKS | | | | | | | |
| UGP2 | Glycogen metabolism | UGP2 | | | | | | | |
| ZNF174 | Glycogen metabolism | ZNF174 | | | | | | | |
| YBR289W | Glycogen metabolism | | | | | | | | |
| YDL134C | Glycogen metabolism | | | | | | | | |
| YER054C | Glycogen metabolism | | | | | | | | |
| YER167W | Glycogen metabolism | | | | | | | | |
| YGR110W | Glycogen metabolism | | | | | | | | |
| YHL025W | Glycogen metabolism | | | | | | | | |
| YJL106W | Glycogen metabolism | | | | | | | | |
| YJL146W | Glycogen metabolism | | | | | | | | |
| YJL198W | Glycogen metabolism | | | | | | | | |
| YKL035W | Glycogen metabolism | | | | | | | | |
| YKL109W | Glycogen metabolism | | | | | | | | |
| YLR094C | Glycogen metabolism | | | | | | | | |
| YLR099C | Glycogen metabolism | | | | | | | | |
| YLR258W | Glycogen metabolism | | | | | | | | |
| YMR035W | Glycogen metabolism | | | | | | | | |
| YNL025C | Glycogen metabolism | | | | | | | | |
| YNL027W | Glycogen metabolism | | | | | | | | |
| YOR137C | Glycogen metabolism | | | | | | | | |
| YPL184C | Glycogen metabolism | | | | | | | | |
| ZNF174 | Glycogen metabolism | | | | | | | | |

| STK11 stem | GO Group (Attribute) | Human Genes | www.geneontology.org enrichment HUMAN GENES (PROCESS) | | | | | |
|---|---|---|---|---|---|---|---|---|
| | | | | # | # | expected | Fold Enrichm | +/- | P value |
| ACACB | acetyl coA and oxidative metabolism | | GO biological process complete | 9 | 3 | 0.01 > 100 | | + | 1.28E-03 |
| AP3D1 | acetyl coA and oxidative metabolism | | acetyl-CoA biosynthetic process from pyruvate | 13 | 3 | 0.01 > 100 | | + | 3.85E-03 |
| CCDC66 | acetyl coA and oxidative metabolism | | acetyl-CoA biosynthetic process | 27 | 4 | 0.03 > 100 | | + | 2.31E-04 |
| CENPK | acetyl coA and oxidative metabolism | | acetyl-CoA metabolic process | 84 | 4 | 0.1 | 41.61 | + | 2.07E-02 |
| CHCHD2 | acetyl coA and oxidative metabolism | | acyl-CoA metabolic process | | | | | | |
| COX4I1 | acetyl coA and oxidative metabolism | | coenzyme metabolic process | 269 | 6 | 0.31 | 19.49 | + | 3.96E-03 |
| COX5B | acetyl coA and oxidative metabolism | | cofactor metabolic process | 340 | 6 | 0.39 | 15.42 | + | 1.53E-02 |

-continued

| CARM1 stem | GO Group (Attribute) | | | | | |
|---|---|---|---|---|---|---|
| CTGF | acetyl coA and oxidative metabolism | thioester metabolic process | 84 | 4 | 0.1 | 41.61 | + | 2.07E-02 |
| DLAT | acetyl coA and oxidative metabolism | acyl-CoA biosynthetic process | 55 | 4 | 0.06 | 63.55 | + | 3.89E-03 |
| EXOC5 | acetyl coA and oxidative metabolism | thioester biosynthetic process | 55 | 4 | 0.06 | 63.55 | + | 3.89E-03 |
| LDHD | acetyl coA and oxidative metabolism | pyruvate metabolic process | 71 | 4 | 0.08 | 49.23 | + | 1.07E-02 |
| MCAT | acetyl coA and oxidative metabolism | small molecule metabolic process | 1636 | 10 | 1.87 | 5.34 | + | 4.73E-02 |
| MLX | acetyl coA and oxidative metabolism | intracellular lipid transport | 20 | 3 | 0.02 | >100 | + | 1.39E-02 |
| MXD4 | acetyl coA and oxidative metabolism | cellular respiration | 160 | 5 | 0.18 | 27.31 | + | 7.85E-03 |
| PDHA1 | acetyl coA and oxidative metabolism | energy derivation by oxidation of organic com | 235 | 6 | 0.27 | 22.31 | + | 1.81E-03 |
| PFKM | acetyl coA and oxidative metabolism | generation of precursor metabolites and energy | 314 | 6 | 0.36 | 16.7 | + | 9.69E-03 |
| RPE | acetyl coA and oxidative metabolism | monosaccharide metabolic process | 174 | 5 | 0.2 | 25.11 | + | 1.18E-02 |
| SLC25A26 | acetyl coA and oxidative metabolism | | | | | |
| SLC35F5 | acetyl coA and oxidative metabolism | | | | | |
| STK11 | acetyl coA and oxidative metabolism | | | | | |
| TKTL1 | acetyl coA and oxidative metabolism | | | | | |
| WDR20 | acetyl coA and oxidative metabolism | | | | | |
| YBR036C | acetyl coA and oxidative metabolism | | | | | |
| YDL174C | acetyl coA and oxidative metabolism | | | | | |
| YDR051C | acetyl coA and oxidative metabolism | | | | | |
| YGL005C | acetyl coA and oxidative metabolism | | | | | |
| YGL187C | acetyl coA and oxidative metabolism | | | | | |
| YHR195W | acetyl coA and oxidative metabolism | | | | | |
| YIL111W | acetyl coA and oxidative metabolism | | | | | |
| YJL121C | acetyl coA and oxidative metabolism | | | | | |
| YJL204C | acetyl coA and oxidative metabolism | | | | | |
| YLR149C | acetyl coA and oxidative metabolism | | | | | |
| YMR002W | acetyl coA and oxidative metabolism | | | | | |
| YMR205C | acetyl coA and oxidative metabolism | | | | | |
| YMR207C | acetyl coA and oxidative metabolism | | | | | |
| YNL003C | acetyl coA and oxidative metabolism | | | | | |
| YNL052W | acetyl coA and oxidative metabolism | | | | | |
| YNL071W | acetyl coA and oxidative metabolism | | | | | |
| YOL028C | acetyl coA and oxidative metabolism | | | | | |
| YOL108C | acetyl coA and oxidative metabolism | | | | | |
| YOR221C | acetyl coA and oxidative metabolism | | | | | |

| CARM1 stem | GO Group (Attribute) | Human Genes | www.geneontology.org enrichment HUMAN GENES (PROCESS) | | | | | |
|---|---|---|---|---|---|---|---|---|
| | | | GO biological process complete | # | # | expected | Fold Enrichm | +/− | P value |
| ABCA1 | lipid metabolic process | ABCA1 | lipid metabolic process | 1158 | 8 | 0.72 | 11.14 | + | 6.97E-04 |
| ABHD3 | lipid metabolic process | ABHD3 | | | | | | | |
| ACOX3 | lipid metabolic process | ACOX3 | | | | | | | |
| ACSL1 | lipid metabolic process | ACSL1 | | | | | | | |
| ANKRD1 | lipid metabolic process | ANKRD1 | | | | | | | |
| AP3D1 | lipid metabolic process | AP3D1 | | | | | | | |
| ARHGEF11 | lipid metabolic process | ARHGEF11 | | | | | | | |
| CARM1 | lipid metabolic process | CARM1 | | | | | | | |
| CTGF | lipid metabolic process | CTGF | | | | | | | |
| DHDDS | lipid metabolic process | DHDDS | | | | | | | |
| FDFT1 | lipid metabolic process | FDFT1 | | | | | | | |
| PRMT1 | lipid metabolic process | PRMT1 | | | | | | | |
| SLC27A1 | lipid metabolic process | | | | | | | | |
| YBR034C | lipid metabolic process | | | | | | | | |
| YBR041W | lipid metabolic process | | | | | | | | |
| YER015W | lipid metabolic process | | | | | | | | |

| | | Human Genes | GO Group (Attribute) | | | | | | | |
|---|---|---|---|---|---|---|---|---|---|---|
| YGL205W | | | lipid metabolic process | | | | | | | |
| YIR033W | | | lipid metabolic process | | | | | | | |
| YLR371W | | | lipid metabolic process | | | | | | | |
| YLR425W | | | lipid metabolic process | | | | | | | |
| YMR101C | | | lipid metabolic process | | | | | | | |
| YPL095C | | | lipid metabolic process | | | | | | | |
| YPL195W | | | lipid metabolic process | | | | | | | |

| CSNK1A1 stem | GO Group (Attribute) | Human Genes | www.geneontology.org enrichment HUMAN GENES (PROCESS) | | | | | | |
|---|---|---|---|---|---|---|---|---|---|
| | | | | # | # | expected | Fold Enrichm | +/− | P value |
| | Neurotransmitter release | | GO biological process complete | | | | | | |
| ALDH2 | Neurotransmitter release | ALDH2 | regulation of neurotransmitter levels | 182 | 5 | 0.1 | 48.01 | + | 2.99E-04 |
| AOX1 | Neurotransmitter release | AOX1 | neurotransmitter secretion | 102 | 4 | 0.06 | 68.54 | + | 2.16E-03 |
| ASNS | Neurotransmitter release | ASNS | signal release from synapse | 102 | 4 | 0.06 | 68.54 | + | 2.16E-03 |
| AVL9 | Neurotransmitter release | AVL9 | presynaptic process involved in chemical syna | 106 | 4 | 0.06 | 65.95 | + | 2.52E-03 |
| CPLX1 | Neurotransmitter release | CPLX1 | neurotransmitter transport | 146 | 4 | 0.08 | 47.88 | + | 8.96E-03 |
| CSNK1A1 | Neurotransmitter release | CSNK1A1 | signal release | 166 | 4 | 0.09 | 42.11 | + | 1.49E-02 |
| FHIT | Neurotransmitter release | FHIT | vitamin B6 metabolic process | 4 | 2 | 0 | > 100 | + | 1.93E-02 |
| MAOA | Neurotransmitter release | MAOA | | | | | | | |
| PNPO | Neurotransmitter release | PNPO | | | | | | | |
| SLC18A2 | Neurotransmitter release | SLC18A2 | | | | | | | |
| SLC22A2 | Neurotransmitter release | SLC22A2 | | | | | | | |
| SLC32A1 | Neurotransmitter release | SLC32A1 | | | | | | | |
| YDR305C | Neurotransmitter release | | | | | | | | |
| YER123W | Neurotransmitter release | | | | | | | | |
| YGR017W | Neurotransmitter release | | | | | | | | |
| YIL088C | Neurotransmitter release | | | | | | | | |
| YMR020W | Neurotransmitter release | | | | | | | | |
| YOR129C | Neurotransmitter release | | | | | | | | |
| YPR145W | Neurotransmitter release | | | | | | | | |
| YPR198W | Neurotransmitter release | | | | | | | | |

| UPF1 core stem | GO Group (Attribute) | Human Genes | www.geneontology.org enrichment HUMAN GENES (PROCESS) | | | | | | |
|---|---|---|---|---|---|---|---|---|---|
| | | | | # | # | expected | Fold Enrichm | +/− | P value |
| | | | GO biological process complete | | | | | | |
| ADIPOR2 | mRNA metabolism and translation | ADIPOR2 | nuclear-transcribed mRNA catabolic process | 187 | 15 | 0.41 | 36.57 | + | 5.70E-16 |
| ATE1 | mRNA metabolism and translation | ATE1 | mRNA catabolic process | 199 | 15 | 0.44 | 34.37 | + | 1.42E-15 |
| ATXN2 | mRNA metabolism and translation | ATXN2 | RNA catabolic process | 226 | 15 | 0.5 | 30.26 | + | 9.24E-15 |
| BSDC1 | mRNA metabolism and translation | BSDC1 | nuclear-transcribed mRNA catabolic process, | 119 | 12 | 0.26 | 45.97 | + | 2.92E-13 |
| CAMKK1 | mRNA metabolism and translation | CAMKK1 | nucleobase-containing compound catabolic process | 338 | 15 | 0.74 | 20.23 | + | 3.31E-12 |
| CCDC110 | mRNA metabolism and translation | CCDC110 | translational initiation | 152 | 12 | 0.33 | 35.99 | + | 5.25E-12 |
| CEP350 | mRNA metabolism and translation | CEP350 | heterocycle catabolic process | 366 | 15 | 0.8 | 18.68 | + | 1.05E-11 |
| CHCHD8 | mRNA metabolism and translation | CHCHD8 | cellular nitrogen compound catabolic process | 372 | 15 | 0.82 | 18.38 | + | 1.33E-11 |
| CORO2A | mRNA metabolism and translation | CORO2A | aromatic compound catabolic process | 379 | 15 | 0.83 | 18.04 | + | 1.74E-11 |
| CSDE1 | mRNA metabolism and translation | CSDE1 | organic cyclic compound catabolic process | 400 | 15 | 0.88 | 17.1 | + | 3.79E-11 |
| EIF4G1 | mRNA metabolism and translation | EIF4G1 | SRP-dependent cotranslational protein targeting | 95 | 10 | 0.21 | 47.99 | + | 1.03E-10 |
| FAU | mRNA metabolism and translation | FAU | protein targeting to ER | 101 | 10 | 0.22 | 45.14 | + | 1.88E-10 |
| G3BP1 | mRNA metabolism and translation | G3BP1 | cotranslational protein targeting to membrane | 103 | 10 | 0.23 | 44.26 | + | 2.28E-10 |
| GBP5 | mRNA metabolism and translation | GBP5 | establishment of protein localization to endopoint | 105 | 10 | 0.23 | 43.42 | + | 2.76E-10 |
| GPX7 | mRNA metabolism and translation | GPX7 | viral transcription | 115 | 10 | 0.25 | 39.64 | + | 6.75E-10 |
| MRPL10 | mRNA metabolism and translation | MRPL10 | mRNA metabolic process | 613 | 16 | 1.34 | 11.9 | + | 9.84E-10 |
| OSBPL8 | mRNA metabolism and translation | OSBPL8 | protein localization to endoplasmic reticulum | 124 | 10 | 0.27 | 36.77 | + | 1.41E-09 |
| PABPC1 | mRNA metabolism and translation | PABPC1 | viral gene expression | 126 | 10 | 0.28 | 36.18 | + | 1.65E-09 |
| PAN2 | mRNA metabolism and translation | PAN2 | multi-organism metabolic process | 138 | 10 | 0.3 | 33.04 | + | 4.03E-09 |
| PAQR3 | mRNA metabolism and translation | PAQR3 | | | | | | | |

-continued

| | | | | | | | |
|---|---|---|---|---|---|---|---|
| PHF13 | mRNA metabolism and translation | PHF13 | protein targeting to membrane | 161 | 10 | 0.35 | 28.32 | + | 1.82E-08 |
| PHTF1 | mRNA metabolism and translation | PHTF1 | ribosome biogenesis | 312 | 12 | 0.68 | 17.54 | + | 2.31E-08 |
| RBM15 | mRNA metabolism and translation | RBM15 | cellular macromolecule catabolic process | 794 | 16 | 1.74 | 9.19 | + | 4.81E-08 |
| RORC | mRNA metabolism and translation | RORC | translation | 442 | 13 | 0.97 | 13.41 | + | 6.93E-08 |
| RPL17 | mRNA metabolism and translation | RPL17 | ribonucleoprotein complex biogenesis | 448 | 13 | 0.98 | 13.23 | + | 8.18E-08 |
| RPS14 | mRNA metabolism and translation | RPS14 | peptide biosynthetic process | 465 | 13 | 1.02 | 12.75 | + | 1.29E-07 |
| RPS16 | mRNA metabolism and translation | RPS16 | macromolecule biosynthetic process | 931 | 16 | 2.04 | 7.84 | + | 5.07E-07 |
| RPS18 | mRNA metabolism and translation | RPS18 | amide biosynthetic process | 524 | 13 | 1.15 | 11.31 | + | 5.60E-07 |
| RPS25 | mRNA metabolism and translation | RPS25 | rRNA processing | 253 | 10 | 0.55 | 18.02 | + | 1.44E-06 |
| RPS26 | mRNA metabolism and translation | RPS26 | rRNA metabolic process | 259 | 10 | 0.57 | 17.6 | + | 1.81E-06 |
| RPS28 | mRNA metabolism and translation | RPS28 | establishment of protein localization to memt | 267 | 10 | 0.59 | 17.08 | + | 2.42E-06 |
| RPS29 | mRNA metabolism and translation | RPS29 | peptide metabolic process | 594 | 13 | 1.3 | 9.98 | + | 2.58E-06 |
| RPS6 | mRNA metabolism and translation | RPS6 | viral life cycle | 290 | 10 | 0.64 | 15.72 | + | 5.33E-06 |
| RPS6KB1 | mRNA metabolism and translation | RPS6KB1 | protein localization to organelle | 563 | 12 | 1.23 | 9.72 | + | 1.88E-05 |
| RUNX3 | mRNA metabolism and translation | RUNX3 | cellular amide metabolic process | 721 | 13 | 1.58 | 8.22 | + | 2.64E-05 |
| SETD3 | mRNA metabolism and translation | SETD3 | establishment of protein localization to organism | 364 | 10 | 0.8 | 12.53 | + | 4.61E-05 |
| SETD4 | mRNA metabolism and translation | SETD4 | viral process | 621 | 12 | 1.36 | 8.81 | + | 5.57E-05 |
| SETD6 | mRNA metabolism and translation | SETD6 | multi-organism cellular process | 624 | 12 | 1.37 | 8.77 | + | 5.88E-05 |
| SPNS3 | mRNA metabolism and translation | SPNS3 | protein localization to membrane | 378 | 10 | 0.83 | 12.06 | + | 6.57E-05 |
| STK36 | mRNA metabolism and translation | STK36 | cellular catabolic process | 1324 | 16 | 2.9 | 5.51 | + | 8.15E-05 |
| TIAL1 | mRNA metabolism and translation | TIAL1 | ncRNA processing | 395 | 10 | 0.87 | 11.54 | + | 9.93E-05 |
| UBIAD1 | mRNA metabolism and translation | UBIAD1 | interspecies interaction between organisms | 666 | 12 | 1.46 | 8.21 | + | 1.20E-04 |
| UPF1 | mRNA metabolism and translation | UPF1 | symbiosis, encompassing mutualism through | 666 | 12 | 1.46 | 8.21 | + | 1.20E-04 |
| UPF2 | mRNA metabolism and translation | UPF2 | protein targeting | 412 | 10 | 0.9 | 11.07 | + | 1.47E-04 |
| USP10 | mRNA metabolism and translation | USP10 | RNA processing | 849 | 13 | 1.86 | 6.98 | + | 1.83E-04 |
| YBR030W | mRNA metabolism and translation | | single-organism intracellular transport | 466 | 10 | 1.02 | 9.78 | + | 4.64E-04 |
| YBR043C | mRNA metabolism and translation | | organic substance catabolic process | 1540 | 16 | 3.38 | 4.74 | + | 6.72E-04 |
| YBR181C | mRNA metabolism and translation | | catabolic process | 1638 | 16 | 3.59 | 4.45 | + | 1.57E-03 |
| YBR212W | mRNA metabolism and translation | | organonitrogen compound biosynthetic process | 1033 | 13 | 2.27 | 5.74 | + | 1.77E-03 |
| YCR031C | mRNA metabolism and translation | | ncRNA metabolic process | 544 | 10 | 1.19 | 8.38 | + | 1.93E-03 |
| YDL061C | mRNA metabolism and translation | | nuclear-transcribed mRNA poly(A) tail shorter | 25 | 4 | 0.05 | 72.95 | + | 2.55E-03 |
| YDL083C | mRNA metabolism and translation | | single-organism membrane organization | 735 | 11 | 1.61 | 6.82 | + | 3.38E-03 |
| YDL202W | mRNA metabolism and translation | | RNA metabolic process | 3429 | 22 | 7.52 | 2.93 | + | 5.46E-03 |
| YDR068W | mRNA metabolism and translation | | peptidyl-lysine monomethylation | 8 | 3 | 0.02 > 100 | | + | 6.71E-03 |
| YDR151C | mRNA metabolism and translation | | cellular protein metabolic process | 3482 | 22 | 7.64 | 2.88 | + | 7.15E-03 |
| YDR257C | mRNA metabolism and translation | | intracellular protein transport | 669 | 10 | 1.47 | 6.81 | + | 1.25E-02 |
| YDR492W | mRNA metabolism and translation | | nucleic acid metabolic process | 3942 | 23 | 8.65 | 2.66 | + | 1.42E-02 |
| YER131W | mRNA metabolism and translation | | membrane organization | 890 | 11 | 1.95 | 5.63 | + | 2.17E-02 |
| YER151C | mRNA metabolism and translation | | single-organism cellular localization | 713 | 10 | 1.56 | 6.39 | + | 2.20E-02 |
| YER165W | mRNA metabolism and translation | | cellular macromolecule metabolic process | 6693 | 30 | 14.68 | 2.04 | + | 2.94E-02 |
| YGL017W | mRNA metabolism and translation | | cellular metabolic process | 8525 | 34 | 18.7 | 1.82 | + | 3.96E-02 |
| YGL049C | mRNA metabolism and translation | | cellular protein localization | 1156 | 12 | 2.54 | 4.73 | + | 4.22E-02 |
| YGL094C | mRNA metabolism and translation | | cellular macromolecule localization | 1166 | 12 | 2.56 | 4.69 | + | 4.61E-02 |
| YGL179C | mRNA metabolism and translation | | | | | | | | |
| YGR027C | mRNA metabolism and translation | | | | | | | | |
| YGR052W | mRNA metabolism and translation | | | | | | | | |
| YGR162W | mRNA metabolism and translation | | | | | | | | |
| YGR178C | mRNA metabolism and translation | | | | | | | | |
| YHL039W | mRNA metabolism and translation | | | | | | | | |
| YHR077C | mRNA metabolism and translation | | | | | | | | |
| YIR037W | mRNA metabolism and translation | | | | | | | | |
| YJL177W | mRNA metabolism and translation | | | | | | | | |
| YKL043W | mRNA metabolism and translation | | | | | | | | |

-continued

| Gene | Ontology |
|---|---|
| YKL048C | mRNA metabolism and translation |
| YKR003W | mRNA metabolism and translation |
| YLR023C | mRNA metabolism and translation |
| YLR136C | mRNA metabolism and translation |
| YLR218C | mRNA metabolism and translation |
| YLR264W | mRNA metabolism and translation |
| YLR287C-A | mRNA metabolism and translation |
| YLR429W | mRNA metabolism and translation |
| YLR431C | mRNA metabolism and translation |
| YML026C | mRNA metabolism and translation |
| YMR080C | mRNA metabolism and translation |
| YMR261C | mRNA metabolism and translation |
| YMR291W | mRNA metabolism and translation |
| YNR051C | mRNA metabolism and translation |
| YOR195W | mRNA metabolism and translation |
| YOR216C | mRNA metabolism and translation |
| YOR273C | mRNA metabolism and translation |
| YPL181W | mRNA metabolism and translation |
| YPL208W | mRNA metabolism and translation |
| ZFP36 | mRNA metabolism and translation |

| Gene | Ontology |
|---|---|
| A4GNT | vesicle trafficking stem |
| ABCA1 | lipid metabolic process |
| ABHD13 | Toll receptor signaling |
| ABHD3 | lipid metabolic process |
| ABHD4 | Glycogen metabolism |
| ABHD5 | Glycogen metabolism |
| ACACB | acetyl coA and oxidative metabolism |
| ACOX3 | lipid metabolic process |
| ACSL1 | lipid metabolic process |
| ADIPOR2 | mRNA metabolism and translation |
| AFF2 | vesicle trafficking stem |
| ALDH2 | Neurotransmitter release |
| ANKRD1 | lipid metabolic process |
| ANKRD28 | vesicle trafficking stem |
| AOX1 | Neurotransmitter release |
| AP1M1 | inositol phosphorylation/membrane trafficking |
| AP2M1 | vesicle trafficking stem |
| AP2S1 | vesicle trafficking stem |
| AP3D1 | acetyl coA and oxidative metabolism |
| ARFGAP2 | lipid metabolic process |
| ARHGEF11 | vesicle trafficking stem |
| ASNS | Neurotransmitter release |
| ATE1 | mRNA metabolism and translation |
| ATG12 | Ubiquitin conjugation/Macroautophagy |
| ATG7 | Ubiquitin conjugation/Macroautophagy |
| ATIC | Purine metabolism |
| ATP2C1 | vesicle trafficking stem |
| ATXN2 | mRNA metabolism and translation |
| AVL9 | Neurotransmitter release |

-continued

| | |
|---|---|
| BAD | Calcium/NFAT signaling |
| BAG2 | mRNA metabolism |
| BET1 | vesicle trafficking stem |
| BICD2 | vesicle trafficking stem |
| BSDC1 | mRNA metabolism and translation |
| C16orf61 | mRNA metabolism |
| C3orf37 | vesicle trafficking stem |
| CALM1 | Calcium/NFAT signaling |
| CAMKK1 | mRNA metabolism and translation |
| CANX | vesicle trafficking stem |
| CARM1 | lipid metabolic process |
| CCDC104 | vesicle trafficking stem |
| CCDC110 | mRNA metabolism and translation |
| CCDC58 | vesicle trafficking stem |
| CCDC66 | acetyl coA and oxidative metabolism |
| CCNC | Glycogen metabolism |
| CCNYL2 | vesicle trafficking stem |
| CDH18 | inositol phosphorylation/membrane trafficking |
| CDH19 | inositol phosphorylation/membrane trafficking |
| CDH2 | inositol phosphorylation/membrane trafficking |
| CDH6 | inositol phosphorylation/membrane trafficking |
| CENPK | acetyl coA and oxidative metabolism |
| CEP350 | mRNA metabolism and translation |
| CHCHD2 | acetyl coA and oxidative metabolism |
| CHCHD8 | mRNA metabolism and translation |
| CKAP4 | Toll receptor signaling |
| CNIH4 | vesicle trafficking stem |
| COG4 | vesicle trafficking stem |
| COG5 | vesicle trafficking stem |
| COG6 | vesicle trafficking stem |
| COPE | vesicle trafficking stem |
| COPG | vesicle trafficking stem |
| CORO2A | mRNA metabolism and translation |
| COX10 | inositol phosphorylation/membrane trafficking |
| COX4I1 | acetyl coA and oxidative metabolism |
| COX5B | acetyl coA and oxidative metabolism |
| CPLX1 | Neurotransmitter release |
| CPPED1 | Glycogen metabolism |
| CPSF3 | mRNA metabolism |
| CSDE1 | mRNA metabolism and translation |
| CSNK1A1 | Neurotransmitter release |
| CTDSPL | vesicle trafficking stem |
| CTGF | acetyl coA and oxidative metabolism |
| CTGF | lipid metabolic process |
| CTLA4 | vesicle trafficking stem |
| CTPS2 | Purine metabolism |
| DAK | Ubiquitin conjugation/Macroautophagy |
| DCLRE1C | DNA damage repair |
| DHDDS | lipid metabolic process |
| DLAT | acetyl coA and oxidative metabolism |
| DOLPP1 | Toll receptor signaling |
| EIF4G1 | mRNA metabolism and translation |
| EXOC5 | acetyl coA and oxidative metabolism |

-continued

| | |
|---|---|
| FAU | mRNA metabolism and translation |
| FDFT1 | lipid metabolic process |
| FECH | inositol phosphorylation/membrane trafficking |
| FHIT | Neurotransmitter release |
| FTL | inositol phosphorylation/membrane trafficking |
| G3BP1 | mRNA metabolism and translation |
| GBP5 | mRNA metabolism and translation |
| GCC2 | vesicle trafficking stem |
| GMPS | Purine metabolism |
| GOSR1 | vesicle trafficking stem |
| GPRIN3 | vesicle trafficking stem |
| GPX7 | mRNA metabolism and translation |
| GSTT2 | vesicle trafficking stem |
| GYG1 | Glycogen metabolism |
| GYS1 | Glycogen metabolism |
| HIPK4 | Glycogen metabolism |
| HUNK | mRNA metabolism |
| IKZF1 | DNA damage repair |
| IKZF4 | DNA damage repair |
| IMMP2L | Glycogen metabolism |
| IMPA2 | inositol phosphorylation/membrane trafficking |
| INPP1 | inositol phosphorylation/membrane trafficking |
| IRAK2 | Toll receptor signaling |
| IRAK4 | Toll receptor signaling |
| ITPA | Purine metabolism |
| KIAA1383 | Glycogen metabolism |
| KIF13A | inositol phosphorylation/membrane trafficking |
| LDHD | acetyl coA and oxidative metabolism |
| LRRK2 | vesicle trafficking stem |
| LSM3 | mRNA metabolism |
| MAML1 | Neurotransmitter release |
| MAOA | Ubiquitin conjugation/Macroautophagy |
| MAVS | acetyl coA and oxidative metabolism |
| MCAT | Ubiquitin conjugation/Macroautophagy |
| MEIS1 | vesicle trafficking stem |
| MFN2 | Ubiquitin conjugation/Macroautophagy |
| MLX | acetyl coA and oxidative metabolism |
| MOCS3 | vesicle trafficking stem |
| MRPL10 | mRNA metabolism and translation |
| MRPS23 | Ubiquitin conjugation/Macroautophagy |
| MRPS36 | vesicle trafficking stem |
| MXD4 | acetyl coA and oxidative metabolism |
| MYBL2 | mRNA metabolism |
| MYD88 | Toll receptor signaling |
| NANP | vesicle trafficking stem |
| NDFIP1 | vesicle trafficking stem |
| NEDD4 | vesicle trafficking stem |
| NFATC2 | Calcium/NFAT signaling |
| NPAT | vesicle trafficking stem |
| NUCB1 | Glycogen metabolism |
| OBFC1 | vesicle trafficking stem |
| OSBPL1A | vesicle trafficking stem |
| OSBPL8 | mRNA metabolism and translation |

-continued

| | |
|---|---|
| PABPC1 | mRNA metabolism and translation |
| PAN2 | mRNA metabolism and translation |
| PAQR3 | mRNA metabolism and translation |
| PBX1 | vesicle trafficking stem |
| PDE3B | Purine metabolism |
| PDE8B | Purine metabolism |
| PDHA1 | acetyl coA and oxidative metabolism |
| PFKM | acetyl coA and oxidative metabolism |
| PHF13 | mRNA metabolism and translation |
| PHTF1 | mRNA metabolism and translation |
| PIK3R6 | Purine metabolism |
| PIP5K1C | inositol phosphorylation/membrane trafficking |
| PLIN1 | Glycogen metabolism |
| PMM1 | vesicle trafficking stem |
| PNKP | DNA damage repair |
| PNPO | Neurotransmitter release |
| POTEC | vesicle trafficking stem |
| PPCDC | vesicle trafficking stem |
| PPM1G | Calcium/NFAT signaling |
| PP1CB | Glycogen metabolism |
| PPP1R15A | Glycogen metabolism |
| PPP1R3B | Glycogen metabolism |
| PPP2R2C | Calcium/NFAT signaling |
| PPP2R5A | Calcium/NFAT signaling |
| PPP3CA | Calcium/NFAT signaling |
| PPP3R1 | Calcium/NFAT signaling |
| PPP6C | vesicle trafficking stem |
| PRCC | mRNA metabolism |
| PRL | vesicle trafficking stem |
| PRMT1 | lipid metabolic process |
| PSMD4 | vesicle trafficking stem |
| QKI | mRNA metabolism |
| RAB1A | vesicle trafficking stem |
| RAB6A | vesicle trafficking stem |
| RAB7A | vesicle trafficking stem |
| RABAC1 | vesicle trafficking stem |
| RABGGTA | vesicle trafficking stem |
| RABGGTB | vesicle trafficking stem |
| RAPGEF3 | Purine metabolism |
| RBM10 | mRNA metabolism |
| RBM11 | mRNA metabolism |
| RBM15 | mRNA metabolism and translation |
| RCAN2 | Calcium/NFAT signaling |
| RNF11 | vesicle trafficking stem |
| RNF115 | vesicle trafficking stem |
| RNF8 | DNA damage repair |
| RORC | mRNA metabolism and translation |
| RPE | acetyl coA and oxidative metabolism |
| RPL17 | mRNA metabolism and translation |
| RPS14 | mRNA metabolism and translation |
| RPS16 | mRNA metabolism and translation |
| RPS18 | mRNA metabolism and translation |
| RPS25 | mRNA metabolism and translation |

-continued

| | |
|---|---|
| RPS26 | mRNA metabolism and translation |
| RPS28 | mRNA metabolism and translation |
| RPS29 | mRNA metabolism and translation |
| RPS6 | mRNA metabolism and translation |
| RPS6KB1 | mRNA metabolism and translation |
| RUNX3 | mRNA metabolism and translation |
| SDHAF2 | Ubiquitin conjugation/Macroautophagy |
| SEC31A | vesicle trafficking stem |
| SETD3 | mRNA metabolism and translation |
| SETD4 | mRNA metabolism and translation |
| SETD6 | mRNA metabolism and translation |
| SLC13A3 | Glycogen metabolism |
| SLC18A2 | Neurotransmitter release |
| SLC22A2 | Neurotransmitter release |
| SLC25A26 | acetyl coA and oxidative metabolism |
| SLC27A1 | lipid metabolic process |
| SLC32A1 | Neurotransmitter release |
| SLC35E1 | vesicle trafficking stem |
| SLC35F5 | acetyl coA and oxidative metabolism |
| SLC36A4 | vesicle trafficking stem |
| SLC39A1 | vesicle trafficking stem |
| SLC7A2 | vesicle trafficking stem |
| SLU7 | mRNA metabolism |
| SMARCB1 | Glycogen metabolism |
| SNCA | vesicle trafficking stem |
| SNX5 | inositol phosphorylation/membrane trafficking |
| SORL1 | vesicle trafficking stem |
| SPEN | Glycogen metabolism |
| SPNS3 | mRNA metabolism and translation |
| SSX5 | Glycogen metabolism |
| STK11 | acetyl coA and oxidative metabolism |
| STK36 | mRNA metabolism and translation |
| STOX2 | vesicle trafficking stem |
| STT3A | Toll receptor signaling |
| SURF4 | vesicle trafficking stem |
| SYNJ1 | Calcium/NFAT signaling |
| SYNJ1 | inositol phosphorylation/membrane trafficking |
| SYVN1 | vesicle trafficking stem |
| TBC1D20 | vesicle trafficking stem |
| TEX261 | vesicle trafficking stem |
| TGFBI | vesicle trafficking stem |
| TIAL1 | mRNA metabolism and translation |
| TKTL1 | acetyl coA and oxidative metabolism |
| TLN1 | inositol phosphorylation/membrane trafficking |
| TLR5 | Toll receptor signaling |
| TMED9 | vesicle trafficking stem |
| TMEM208 | vesicle trafficking stem |
| TOE1 | mRNA metabolism |
| TOR1A | vesicle trafficking stem |
| TRAPPC9 | vesicle trafficking stem |
| TREML2 | vesicle trafficking stem |
| TSKS | Glycogen metabolism |
| TTC35 | vesicle trafficking stem |

-continued

| | |
|---|---|
| TWISTNB | vesicle trafficking stem |
| TXNDC5 | inositol phosphorylation/membrane trafficking |
| UBIAD1 | mRNA metabolism and translation |
| UGP2 | Glycogen metabolism |
| UNC50 | vesicle trafficking stem |
| UPF1 | mRNA metabolism and translation |
| UPF1 core stem | GO Group (Attribute) |
| UPF2 | mRNA metabolism and translation |
| USP10 | mRNA metabolism and translation |
| USP16 | Ubiquitin conjugation/Macroautophagy |
| USP21 | Ubiquitin conjugation/Macroautophagy |
| USP30 | Ubiquitin conjugation/Macroautophagy |
| UTRN | Calcium/NFAT signaling |
| UTRN | Ubiquitin conjugation/Macroautophagy |
| VDAC1 | vesicle trafficking stem |
| VPS26B | vesicle trafficking stem |
| VPS29 | vesicle trafficking stem |
| VPS35 | vesicle trafficking stem |
| WDR1 | inositol phosphorylation/membrane trafficking |
| WDR20 | acetyl coA and oxidative metabolism |
| WDR4 | vesicle trafficking stem |
| WDR76 | vesicle trafficking stem |
| WDR77 | mRNA metabolism |
| WRB | vesicle trafficking stem |
| WTAP | DNA damage repair |
| XRCC6 | DNA damage repair |
| YAL058W | vesicle trafficking stem |
| YAR002C-A | vesicle trafficking stem |
| YBL054W | mRNA metabolism |
| YBL059C-A | mRNA metabolism |
| YBR030W | mRNA metabolism and translation |
| YBR034C | lipid metabolic process |
| YBR036C | acetyl coA and oxidative metabolism |
| YBR041W | lipid metabolic process |
| YBR043C | mRNA metabolism and translation |
| YBR057C | DNA damage repair |
| YBR062C | vesicle trafficking stem |
| YBR067C | vesicle trafficking stem |
| YBR125C | Calcium/NFAT signaling |
| YBR181C | mRNA metabolism and translation |
| YBR212W | mRNA metabolism and translation |
| YBR215W | vesicle trafficking stem |
| YBR289W | Glycogen metabolism |
| YBR290W | vesicle trafficking stem |
| YCR008W | mRNA metabolism |
| YCR031C | mRNA metabolism and translation |
| YDL019C | vesicle trafficking stem |
| YDL047W | vesicle trafficking stem |
| YDL053C | mRNA metabolism |
| YDL061C | mRNA metabolism and translation |
| YDL083C | mRNA metabolism and translation |

-continued

| | |
|---|---|
| YDL115C | inositol phosphorylation/membrane trafficking |
| YDL122W | Ubiquitin conjugation/Macroautophagy |
| YDL134C | Glycogen metabolism |
| YDL167C | mRNA metabolism |
| YDL174C | acetyl coA and oxidative metabolism |
| YDL195W | vesicle trafficking stem |
| YDL202W | mRNA metabolism and translation |
| YDL213C | vesicle trafficking stem |
| YDR051C | acetyl coA and oxidative metabolism |
| YDR068W | mRNA metabolism and translation |
| YDR069C | Ubiquitin conjugation/Macroautophagy |
| YDR074W | vesicle trafficking stem |
| YDR082W | vesicle trafficking stem |
| YDR143C | vesicle trafficking stem |
| YDR151C | mRNA metabolism and translation |
| YDR165W | vesicle trafficking stem |
| YDR257C | mRNA metabolism and translation |
| YDR305C | Neurotransmitter release |
| YDR374C | Toll receptor signaling |
| YDR380W | Toll receptor signaling |
| YDR407C | vesicle trafficking stem |
| YDR436W | vesicle trafficking stem |
| YDR463W | DNA damage repair |
| YDR492W | mRNA metabolism and translation |
| YER015W | lipid metabolic process |
| YER054C | Glycogen metabolism |
| YER122C | vesicle trafficking stem |
| YER123W | Neurotransmitter release |
| YER125W | vesicle trafficking stem |
| YER131W | mRNA metabolism and translation |
| YER151C | mRNA metabolism and translation |
| YER165W | mRNA metabolism and translation |
| YER167W | Glycogen metabolism |
| YFL027C | vesicle trafficking stem |
| YFL038C | vesicle trafficking stem |
| YFL053W | Ubiquitin conjugation/Macroautophagy |
| YFR022W | Purine metabolism |
| YFR049W | vesicle trafficking stem |
| YGL002W | vesicle trafficking stem |
| YGL005C | acetyl coA and oxidative metabolism |
| YGL017W | mRNA metabolism and translation |
| YGL020C | vesicle trafficking stem |
| YGL049C | mRNA metabolism and translation |
| YGL053W | vesicle trafficking stem |
| YGL054C | vesicle trafficking stem |
| YGL094C | mRNA metabolism and translation |
| YGL167C | vesicle trafficking stem |
| YGL179C | mRNA metabolism and translation |
| YGL187C | acetyl coA and oxidative metabolism |
| YGL190C | Calcium/NFAT signaling |
| YGL205W | lipid metabolic process |
| YGL222C | vesicle trafficking stem |
| YGL224C | vesicle trafficking stem |

-continued

| | |
|---|---|
| YGR017W | Neurotransmitter release |
| YGR027C | mRNA metabolism and translation |
| YGR036C | Toll receptor signaling |
| YGR052W | mRNA metabolism and translation |
| YGR110W | Glycogen metabolism |
| YGR162W | mRNA metabolism and translation |
| YGR178C | mRNA metabolism and translation |
| YGR229C | DNA damage repair |
| YGR284C | vesicle trafficking stem |
| YHL025W | Glycogen metabolism |
| YHL031C | vesicle trafficking stem |
| YHL039W | mRNA metabolism and translation |
| YHR012W | vesicle trafficking stem |
| YHR036W | DNA damage repair |
| YHR046C | inositol phosphorylation/membrane trafficking |
| YHR073W | vesicle trafficking stem |
| YHR077C | mRNA metabolism and translation |
| YHR111W | vesicle trafficking stem |
| YHR115C | DNA damage repair |
| YHR171W | Ubiquitin conjugation/Macroautophagy |
| YHR181W | vesicle trafficking stem |
| YHR195W | acetyl coA and oxidative metabolism |
| YHR200W | vesicle trafficking stem |
| YIL005W | inositol phosphorylation/membrane trafficking |
| YIL076W | vesicle trafficking stem |
| YIL088C | Neurotransmitter release |
| YIL093C | Ubiquitin conjugation/Macroautophagy |
| YIL111W | acetyl coA and oxidative metabolism |
| YIL156W | Ubiquitin conjugation/Macroautophagy |
| YIL173W | vesicle trafficking stem |
| YIR033W | lipid metabolic process |
| YIR037W | mRNA metabolism and translation |
| YJL031C | vesicle trafficking stem |
| YJL053W | vesicle trafficking stem |
| YJL106W | Glycogen metabolism |
| YJL121C | acetyl coA and oxidative metabolism |
| YJL146W | Glycogen metabolism |
| YJL154C | vesicle trafficking stem |
| YJL177W | mRNA metabolism and translation |
| YJL198W | Glycogen metabolism |
| YJL204C | acetyl coA and oxidative metabolism |
| YJR058C | vesicle trafficking stem |
| YJR069C | Purine metabolism |
| YJR088C | vesicle trafficking stem |
| YJR091C | vesicle trafficking stem |
| YJR103W | Purine metabolism |
| YKL006C-A | vesicle trafficking stem |
| YKL034W | vesicle trafficking stem |
| YKL035W | Glycogen metabolism |
| YKL043W | mRNA metabolism and translation |
| YKL048C | mRNA metabolism and translation |
| YKL063C | vesicle trafficking stem |
| YKL079W | inositol phosphorylation/membrane trafficking |

-continued

| | |
|---|---|
| YKL109W | Glycogen metabolism |
| YKL159C | Calcium/NFAT signaling |
| YKL190W | Calcium/NFAT signaling |
| YKL196C | vesicle trafficking stem |
| YKL211C | Purine metabolism |
| YKR003W | mRNA metabolism and translation |
| YKR030W | vesicle trafficking stem |
| YKR098C | Ubiquitin conjugation/Macroautophagy |
| YKT6 | vesicle trafficking stem |
| YLL010C | vesicle trafficking stem |
| YLR001C | vesicle trafficking stem |
| YLR023C | mRNA metabolism and translation |
| YLR028C | Purine metabolism |
| YLR065C | vesicle trafficking stem |
| YLR094C | Glycogen metabolism |
| YLR099C | Glycogen metabolism |
| YLR119W | vesicle trafficking stem |
| YLR130C | vesicle trafficking stem |
| YLR136C | mRNA metabolism and translation |
| YLR149C | acetyl coA and oxidative metabolism |
| YLR218C | mRNA metabolism and translation |
| YLR258W | Glycogen metabolism |
| YLR262C | vesicle trafficking stem |
| YLR264W | mRNA metabolism and translation |
| YLR287C-A | mRNA metabolism and translation |
| YLR309C | vesicle trafficking stem |
| YLR371W | lipid metabolic process |
| YLR425W | lipid metabolic process |
| YLR429W | mRNA metabolism and translation |
| YLR431C | mRNA metabolism and translation |
| YLR433C | Calcium/NFAT signaling |
| YLR438C-A | mRNA metabolism |
| YML001W | vesicle trafficking stem |
| YML016C | vesicle trafficking stem |
| YML026C | mRNA metabolism and translation |
| YML057W | Calcium/NFAT signaling |
| YML100W | vesicle trafficking stem |
| YML113W | mRNA metabolism |
| YMR002W | acetyl coA and oxidative metabolism |
| YMR003W | DNA damage repair |
| YMR020W | Neurotransmitter release |
| YMR035W | Glycogen metabolism |
| YMR080C | mRNA metabolism and translation |
| YMR092C | inositol phosphorylation/membrane trafficking |
| YMR101C | lipid metabolic process |
| YMR111C | vesicle trafficking stem |
| YMR114C | vesicle trafficking stem |
| YMR187C | Ubiquitin conjugation/Macroautophagy |
| YMR205C | acetyl coA and oxidative metabolism |
| YMR207C | acetyl coA and oxidative metabolism |
| YMR261C | mRNA metabolism and translation |
| YMR291W | mRNA metabolism and translation |
| YNL003C | acetyl coA and oxidative metabolism |

-continued

| | |
|---|---|
| YNL025C | Glycogen metabolism |
| YNL027W | Glycogen metabolism |
| YNL041C | vesicle trafficking stem |
| YNL044W | vesicle trafficking stem |
| YNL051W | vesicle trafficking stem |
| YNL052W | acetyl coA and oxidative metabolism |
| YNL055C | vesicle trafficking stem |
| YNL071W | acetyl coA and oxidative metabolism |
| YNL076W | vesicle trafficking stem |
| YNL101W | vesicle trafficking stem |
| YNL224C | mRNA metabolism |
| YNL229C | vesicle trafficking stem |
| YNL287W | vesicle trafficking stem |
| YNL320W | Toll receptor signaling |
| YNR051C | mRNA metabolism and translation |
| YOL001W | vesicle trafficking stem |
| YOL013C | vesicle trafficking stem |
| YOL028C | acetyl coA and oxidative metabolism |
| YOL062C | vesicle trafficking stem |
| YOL071W | Ubiquitin conjugation/Macroautophagy |
| YOL108C | acetyl coA and oxidative metabolism |
| YOR014W | Calcium/NFAT signaling |
| YOR109W | Calcium/NFAT signaling |
| YOR109W | inositol phosphorylation/membrane trafficking |
| YOR129C | Neurotransmitter release |
| YOR137C | Glycogen metabolism |
| YOR155C | vesicle trafficking stem |
| YOR179C | mRNA metabolism |
| YOR195W | mRNA metabolism and translation |
| YOR216C | mRNA metabolism and translation |
| YOR221C | acetyl coA and oxidative metabolism |
| YOR273C | mRNA metabolism and translation |

-continued

| | |
|---|---|
| YOR296W | inositol phosphorylation/membrane trafficking |
| YOR307C | vesicle trafficking stem |
| YOR324C | Toll receptor signaling |
| YOR340C | vesicle trafficking stem |
| YOR360C | Purine metabolism |
| YPL057C | vesicle trafficking stem |
| YPL072W | Ubiquitin conjugation/Macroautophagy |
| YPL095C | lipid metabolic process |
| YPL172C | inositol phosphorylation/membrane trafficking |
| YPL177C | vesicle trafficking stem |
| YPL181W | mRNA metabolism and translation |
| YPL184C | Glycogen metabolism |
| YPL195W | lipid metabolic process |
| YPL208W | mRNA metabolism and translation |
| YPL265W | vesicle trafficking stem |
| YPR145W | Neurotransmitter release |
| YPR198W | Neurotransmitter release |
| YTHDF1 | Toll receptor signaling |
| ZC3H4 | mRNA metabolism |
| ZFP36 | mRNA metabolism and translation |
| ZNF174 | Glycogen metabolism |
| ZNF639 | DNA damage repair |

TABLE S13

Overlap between α-syn (HiTox) and
α-syn/DVPS35 strain modifier, and gene enrichment

| Modifiers that don't rescue VPS35/α-syn | Modifiers that do modify α-syn/VPS35 | Enriched GO biological process complete (Amigo/Panther, Bonferroni correction, p < 0.05) | Gene Name |
|---|---|---|---|
| CDC5 | AFI1 | ER to Golgi vesicle-mediated transport | |
| ERV29 | AVT4 | Golgi vesicle transport | |
| ISN1 | BET4 | veicle-mediated transport | |
| JSN1 | BRE5 | | |
| OSH2 | CAB3 | Key vesicle-mediated transport genes | |
| PTP2 | CAX4 | ID | |
| SFT1 | CCC1 | GLO3 | AGP-ribosylation factor GTPase-activating protein GLO3 |
| TRS120 | CDC4 | PMR1 | Calcium-transporting ATPase 1 |
| UGP1 | CUP9 | YCK3 | Casein kinase1 homolog 3 |
| | DIP5 | SEC28 | Coatomer subunit epsilon |
| | EPS1 | SEC21 | Coatomer subunit gamma |
| | FZF1 | YPT1 | GTP-binding protein YPT1 |
| | GIP2 | GYP8 | GTPase-activating protein GYP8 |
| | GLO3 | OSH3 | Oxysterol-binding protein homolog 3 |
| | GOS1 | YIP3 | Prenylated Rab acceptor 1 |
| | GYP8 | GOS1 | Protein transport protein GOS1 |
| | HAP4 | SEC31 | Protein transport protein SEC31 |
| | HRD1 | YKT6 | Synaptobrevin homolog YKT6 |
| | ICY1 | SLY41 | Uncharacterized transporter SLY41 |
| | ICY2 | BET4 | Alpha subunit of Type II geranylgeranyltransferase; |
| | IDS2 | | |
| | IME2 | | |
| | IZH3 | | |
| | LST8 | | |
| | MATALPHA1 | | |
| | MGA2 | | |
| | MKS1 | | |
| | MUM2 | | |
| | NTH1 | | |
| | NVJ1 | | |
| | OSH3 | | |
| | PDE2 | | |
| | PFS1 | | |
| | PHO80 | | |
| | PMR1 | | |
| | PPZ1 | | |
| | PPZ2 | | |
| | PTC4 | | |
| | QDR3 | | |
| | RCK1 | | |
| | RKM3 | | |
| | SEC21 | | |
| | SEC28 | | |
| | SEC31 | | |
| | SIT4 | | |
| | SLY41 | | |
| | STB3 | | |
| | SUT2 | | |
| | TIF4632 | | |
| | TPO4 | | |
| | TPS3 | | |
| | UBP11 | | |
| | UBP3 | | |
| | UBP7 | | |
| | UIP5 | | |
| | VHR1 | | |
| | YCK3 | | |
| | YDL121C | | |
| | YIP3 | | |
| | YKL036C | | |
| | YKT6 | | |
| | YML081W | | |
| | YML083C | | |

TABLE S13-continued

Overlap between α-syn (HiTox) and
α-syn/DVPS35 strain modifier, and gene enrichment

| Modifiers that don't rescue VPS35/α-syn | Modifiers that do modify α-syn/VPS35 | Enriched GO biological process complete (Amigo/Panther, Bonferroni correction, p < 0.05) | Gene Name |
|---|---|---|---|
| | YMR111C | | |
| | YNR014W | | |
| | YPK9 | | |
| | YPT1 | | |

TABLE S14

| Human Gene | Cellular Process | Disease/Syndrome (strong/weak association) | Human Genetics | Yeast Gene(s) | Yeast Screen (or the Humanized Network in which gene was predicted node) |
|---|---|---|---|---|---|
| PARK GENES | | | | | |
| PARK1/SNCA | Vesicle trafficking | PD, PDD DLB (strong association). Lewy α-syn pathology | GWAS Mendelian AD | N/A | [Predicted Node: OE. Full] |
| PARK2/PARKIN | Mitophagy, mitochondrial degradation | Juvenile Parkinsonism (strong), sometimes with Lewy α-syn pathology | Mendelian AR | N/A Cdc4 is the homolog of Fbxw7, an Fbox protein that may be a component of a Parkin SCF complex[69] (also see VCP entry below) | OE: Supp Pooled OE: Supp |
| PARK5/UCHL1 | Ubiquit in-protein hydrolase | ?PD (highly controversial association) | Mendelian AD | N/A | [Predicted Node: OE] |
| PARK8/LRRK2 | Kinase and GTPase activity; poorly defined function. | PD (strong association), most with Lewy α-syn pathology | GWAS Mendelian AD | N/A | [Predicted Node: OE, Full] |
| PARK9/ATP13A2 | Metal ion (Zn, Mn) homeostasis | Juvenile parkinsonism, spasticity, vertical gaze palsy; NBIA and ceroid lipofuscinosis (Kufor-Rakeb Syndrome)[70] | Mendelian AR | Ypk9 | OE: Supp Deletion: Enh |
| PARK16/RAB7L1 | Endocytosis | PD (strengthening association[41], although other candidate genes have been proposed for PARK16[40]) | GWAS | Ypt7 | [Candidate OE: Supp; Deletion: Enh] |
| PARK17/VPS35 | Retromer; endosome-to-Golgi trafficking | Classic PD/PDD (strong association) with presumed Lewy α-syn pathology[45] | Mendelian AD | Vps35 | Deletion: Enh |
| PARK18/EIF4G1 | Translation initiation | Classic PD/PDD with Lewy α-syn pathology (highly controversial association)[55,59,71] {Nichols: 2015cz} | Mendelian AD | Tif4631 Tif4632 | OE: Supp |
| PARK20/SYNJ1 | Inositol 5-phosphatase; role in clathrin-mediated endocytosis | Atypical Parkinsonism; unknown neuropathology (strengthening association)[72,73] | Mendelian | Inp53 | Deletion: Enh |
| OTHER | | | | | |
| ATG7 | Autophagy | PD (weak association): Promoter poly-morphisms decrease ATG7 activity in PD patients; DA neurodegeneration in ATG7 null mouse) | N/A | Atg7 | Deletion: Enh |

TABLE S14-continued

| Human Gene | Cellular Process | Disease/Syndrome (strong/weak association) | Human Genetics | Yeast Gene(s) | Yeast Screen (or the Humanized Network in which gene was predicted node) |
|---|---|---|---|---|---|
| ATXN2 | mRNA translation | SCA type 2; Ataxia; Parkinsonism (common); Dementia; Motor Neuronopathy | Mendelian AD (polyQ expansion) | Pbp1 | Pooled OE: Supp |
| ATXN7 | Transcription (SAGA complex) | SCA type-7 Ataxia; Retinal degeneration; Parkinsonism and DA degeneration (occasional) | Mendelian AD (polyQ expansion) | SGF73 | Pooled OE: Supp Deletion: Enh |
| ATXN12 (PPP2R2B) | Protein phosphatase 2A regulatory subunit | SCA-type-12 Ataxia: tremor; mild parkinsonism; mild dementia | Mendelian AD | Cdc55 | Deletion: Enh |
| BICD2 | Protein and mRNA trafficking (dynein-mediated, vesicular transport, cla) | Spinal muscular atrophy | Mendelian AD | Ymr111c | OE: Supp |
| CHCHD2 CHCHD10 (paralogs) | Mitochondrial function | CHCHD2: Parkinsonism CHCHD10 ALS, myopathy, ataxia, frontemporal dementia, parkinsonism | Mendelian AD | Mic17 (Mix17) | Pooled OE: Enh |
| COX10 | Mitochondrial Cytochrome C Oxidase | Neonatal multisystem disease, Leigh Syndrome, Neuropathy, Myopathy | Mendelian AR | Cox10 | Deletion: Enh |
| DHDDS | Dolichol synthesis | Retinitis pigmentosa[83] | Mendealian AR | Srt1 | Deletion: Enh |
| DNAJB6 | Hsp40 Chaperone | (upregulated in PD brain; in Lewy bodies and astrocytes) | N/A | Apj1 | Deletion: Enh |
| FTL | Ferritin subunit | NBIA | Mendelian AD | N/A | [Predicted node: Full] |
| MEIS1 | Transcription Factor[84] | Restless leg syndrome | GWAS | Cup9 | Pooled OE: Supp |
| NSF | Fusion protein required for vesicle mediated transport | ? Atypical parkinsonism (Telomeric end of MAPT haplotype block, associated with PSP and CBD) | Candidate association studies | N/A | [Hidden Node: OE] |
| PANK2 | NBIA | Parkinsonism | Mendelian/AR | Cab3 (Acetyl coA synthetic pathway downstream of PANK2/Cab1) | OE: Supp |
| PDE8B | Phosphodiesterase | Autosomal dominant striatal degeneration; Parkinsonism. | Mendelian AD | Pde2 | OE: Supp Pooled OE: Supp |
| RAB39B | Endocytic trafficking | PD plus syndrome; pathology: α-syn, tau, iron accumulation.[42] | X-linked (hemizygous) | Ypt7 | [Candidate OE: Supp; Deletion: Enh] |
| RAB7A | Superoxide dismutase; antioxidant | ALS, (weak association in one study with parkinsonism) | Mendelian/AD | N/A | [Candidate OE: Supp; Deletion: Enh] |
| SOD1 | Superoxide dismutase; antioxidant | ALS, (weak association in one study with parkinsonism) | Mendelian/AD | N/A | [Hidden Node: OE] |
| SORL1 | Intracellular Trafficking (multiple steps) | Alzheimer disease risk factor | GWAS | Vth1 | Deletion: Enh |
| STUB1 (CHIP/SCAR6) | Ubiquitin ligase/ chaperone involved in ER stress; may complex with Parkin | Spinocerebellar ataxia | Mendelian/AR | N/A | [Hidden Node: OE] |
| VCP | Protein quality control and degrdation (ER, mtochondria); required for Pink1/Parkin-dependent mitophagy[68]. | ALS + syndromes. Broad spectrum of degeneration: classic is inclusion body myostis, paget's disease, disease, frontemporal dementia. More recently, parkinsonism described. | Mendelian/AR | Cdc48 complexes with/functions with: 1) Hrd1 (ER-associated degradation) 2) Vms1 (mitochonria- | Extrapolated [Hrd1: OE Supp Vms1: Deletion Enh] |

TABLE S14-continued

| Human Gene | Cellular Process | Disease/Syndrome (strong/weak association) | Human Genetics | Yeast Gene(s) | Yeast Screen (or the Humanized Network in which gene was predicted node) |
|---|---|---|---|---|---|
| | Other important roles (eg endocytosis). | | | associated degradation) | |

TABLE S15

KEGG_CITRATE_CYCLE_TCA_CYCLE
KEGG_OXIDATIVE_PHOSPHORYLATION
KEGG_PURINE_METABOLISM
KEGG_PYRIMIDINE_METABOLISM
KEGG_ALANINE_ASPARTATE_AND_GLUTAMATE_METABOLISM
KEGG_GLYCINE_SERINE_AND_THREONINE_METABOLISM
KEGG_CYSTEINE_AND_METHIONINE_METABOLISM
KEGG_ARGININE_AND_PROLINE_METABOLISM
KEGG_TRYPTOPHAN_METABOLISM
KEGG_BETA_ALANINE_METABOLISM
KEGG_SELENOAMINO_ACID_METABOLISM
KEGG_GLUTATHIONE_METABOLISM
KEGG_N_GLYCAN_BIOSYNTHESIS
KEGG_AMINO_SUGAR_AND_NUCLEOTIDE_SUGAR_METABOLISM
KEGG_INOSITOL_PHOSPHATE_METABOLISM
KEGG_GLYCOSYLPHOSPHATIDYLINOSITOL_GPI_ANCHOR_BIOSYNTHESIS
KEGG_GLYCEROPHOSPHOLIPID_METABOLISM
KEGG_PYRUVATE_METABOLISM
KEGG_ONE_CARBON_POOL_BY_FOLATE
KEGG_PORPHYRIN_AND_CHLOROPHYLL_METABOLISM
KEGG_TERPENOID_BACKBONE_BIOSYNTHESIS
KEGG_AMINOACYL_TRNA_BIOSYNTHESIS
KEGG_DRUG_METABOLISM_OTHER_ENZYMES
KEGG_RIBOSOME
KEGG_RNA_DEGRADATION
KEGG_RNA_POLYMERASE
KEGG_BASAL_TRANSCRIPTION_FACTORS
KEGG_DNA_REPLICATION
KEGG_SPLICEOSOME
KEGG_PROTEASOME
KEGG_PROTEIN_EXPORT
KEGG_BASE_EXCISION_REPAIR
KEGG_NUCLEOTIDE_EXCISION_REPAIR
KEGG_MISMATCH_REPAIR
KEGG_HOMOLOGOUS_RECOMBINATION
KEGG_CELL_CYCLE
KEGG_OOCYTE_MEIOSIS
KEGG_UBIQUITIN_MEDIATED_PROTEOLYSIS
KEGG_REGULATION_OF_AUTOPHAGY
KEGG_LYSOSOME
KEGG_ENDOCYTOSIS
KEGG_PEROXISOME
KEGG_CYTOSOLIC_DNA_SENSING_PATHWAY
KEGG_PROGESTERONE_MEDIATED_OOCYTE_MATURATION
KEGG_ALZHEIMERS_DISEASE
KEGG_PARKINSONS_DISEASE
KEGG_HUNTINGTONS_DISEASE
KEGG_VIBRIO_CHOLERAE_INFECTION
KEGG_EPITHELIAL_CELL_SIGNALING_IN_HELICOBACTER_PYLORI_INFECTION
KEGG_PATHWAYS_IN_CANCER

Star Methods
Experimental Models and Subject Details
Yeast Strains:

For the deletion screen, strains were in the BY4741 background and have been described in detail elsewhere (Baryshnikova et al., 2010; Tong and Boone, 2006)

For all experiments except the deletion screen and validation, the yeast strains used were in the w303 background (MATa can1-100, his3-11,15, leu2-3,112, trp1-1, ura3-1, ade2-1). The vector control strain contained empty vector at the trp and ura loci (pAG304Gal, pAG306GAL). The NoTox α-syn strain contained α-syn fused to green fluorescent protein (α-syn-GFP) inserted at the his locus (pAG303Gal-α-syn-GFP). IntTox and HiTox α-syn strains contained multiple tandem copies of α-syn-GFP inserted at this and trp loci (pRS303GAL-α-syn-GFP, pRS304GAL-α-syn-GFP). IntTox strains have 4-5 copies of α-syn while HiTox cells have >6 copies of α-syn. The ΔPARK17/α-syn and ΔPARK9/α-syn were generated by replacing the PARK17/

VPS35 or PARK9/SPFI gene loci in IntTox α-syn strains with a kanamycin resistance cassette (VPS35::kanMX or SPFI::kanMX).

Human iPSc Lines:

iPSCs from control individuals and PD patients carrying G2019S LRRK2 along with isogenic gene-corrected controls were generated as previously described (Reinhardt et al., 2013). Skin biopsy, human dermal fibroblast culture, iPS cell generation and mutation correction for the patient harboring the A53T mutation (α-syn$^{A53T}$) have been described previously (Cooper et al., 2006; Soldner et al., 2011). In that previous publication the A53T iPS line was referred to as WIBR-IPS-SNCA$^{A53T}$. For all iPSc lines, informed consent was obtained from patients prior to cell donation using a written form, and the protocol was approved by the relevant institutional review board: for LRRK2 iPSCs this was the Ethics Committee of the Medical Faculty and the University Hospital Tübingen (Ethik-Kommission der Medizinischen Fakultät am Universitätsklinikum Tubingen); for the A53T line, the IRB of the Boston University Medical Campus and the MIT Committee on the Use of Humans as Experimental Subjects.

Human iPSC Generation and Differentiation into Midbrain Dopaminergic (DA) Neurons for LRRK2 Mutant Lines iPSCs were differentiated into mDA neurons using a floor plate-based protocol with minor modifications (Kriks et al., 2011; Schöndorf et al., 2014). Differentiation was based on exposure to LDN193189 (100 nM, Stemgent) from days 0-11, SB431542 (10 mM, Tocris) from days 0-5, SHH C25II (100 ng/mL, R&D), purmorphamine (2 mM, EMD) and FGF8 (100 ng/mL, Peprotech) from days 1-7 and CHIR99021 (CHIR; 3 mM, Stemgent) from days 3-13. Cells were grown for 11 days on Matrigel (BD) in knockout serum replacement medium (KSR) containing DMEM, 15% knockout serum replacement, 2 mM L-glutamine and 10 μM β-mercaptoethanol. KSR medium was gradually shifted to N2 medium starting on day 5 of differentiation. On day 11, media was changed to Neurobasal/B27/L-Glut containing medium (NB/B27; Invitrogen) supplemented with CHIR (until day 13) and with BDNF (brain-derived neurotrophic factor, 20 ng/ml; R&D), ascorbic acid (0.2 mM, Sigma), GDNF (glial cell line-derived neurotrophic factor, 20 ng/ml; R&D), TGFβ3 (transforming growth factor type β3, 1 ng/ml; R&D), dibutyryl cAMP (0.5 mM; Sigma), and DAPT (10 μM; Tocris) for 9 days. On day 18, cells were dissociated using Accutase (Innovative Cell Technology) and replated under high cell density conditions on dishes pre-coated with 15 μg/ml polyornithine and 1 μg/ml laminin in differentiation medium (NB/B27+BDNF, ascorbic acid, GDNF, dbcAMP, TGFβ3 and DAPT). At DIV30, cells were collected and, after centrifugation, cell pellets were stored at −80° C. until further analysis.

Human Pluripotent Stem Cell Culture for α-Syn Mutant Lines

Skin biopsy, human dermal fibroblast culture, iPS cell generation and mutation correction for the patient harboring the A53T mutation (WIBR-IPS-$^{A53T}$) have been described previously (Cooper et al., 2006; Soldner et al., 2011). In that previous publication the A53T iPS line was referred to as WIBR-IPS-SNCA$^{A53T}$.

Our pluripotent stem cell lines were initially maintained (5% $O_2$, 3% $CO_2$) on mitomycin C inactivated mouse embryonic fibroblast (MEF) feeder layers in hES medium [DMEM/F12 (Invitrogen) supplemented with 15% fetal bovine serum (FBS) (Hyclone), 5% KnockOut Serum Replacement (Invitrogen), 1 mM glutamine (Invitrogen), 1% nonessential amino acids (Invitrogen), 0.1 mM β-mercaptoethanol (Sigma) and 4 ng/ml FGF2 (R&D systems)]. Cultures were passaged every 5 to 7 days either manually or enzymatically with collagenase type IV (Invitrogen; 1.5 mg/ml). At around 50 passages prior to differentiation, lines were passaged to plates pre-coated with growth factor-reduced matrigel (BD Biosciences; 1:30 in DMEM:F12) and cultured (21% $O_2$, 5% $CO_2$) in mTESR-1 medium (Stem Cell Technologies), thereafter being passaged every 5 to 7 days enzymatically with dispase (Invitrogen; 1 mg/mL) until differentiation (at passage 40-90). For karyotyping, standard G-banding chromosomal analysis of cell lines was performed every 10-20 passages (Cell Line Genetics, Inc). We confirmed mycoplasma-negative status of our cultures every 2-4 weeks (MycoAlert, Lonza).

Primary Rat Cortical Cultures

All animal work was approved by the MIT Committee on Animal Care. Embryos were harvested by cesarean section from anesthetized pregnant Sprague-Dawley rats at embryonic day 18. Cerebral cortices were isolated and dissociated with Accumax (Innovative Cell Technologies, Inc) digestion for 20 min at 37° C. and triutration with Pasteur pipette. Poly-ornithine and laminin-coated 96 well plates were seeded with $4 \times 10^4$ cells respectively in neurobasal medium (Life Technologies) supplemented with B27 (Life Technologies), 0.5 mM glutamine, 25 μM β-mercaptoethanol, penicillin (100 IU/ml) and streptomycin (100 μg/ml). One third of the medium was changed every 3 to 4 days.

Method Details

Yeast-to-Human Homology

Since yeast and human are evolutionarily distant species, to identify human homologs for yeast proteins, we developed a four-tiered meta-analysis pipeline. Our meta-analysis started at the sequence level, in which we first identify genes/proteins that are similar across yeast and humans. We then extend this analysis to the structural level, where we investigate the proteins that are structurally, and thus more distantly, similar across the species. Next, we identify proteins that are similar within each species by using a network-topology based approach. Finally, we introduce an approach to integrate similarity across sequence, structure and network topology. Details are as follows:

1) Sequence Similarity. To compute the sequence similarity between a yeast protein and a human protein, we used NCBI protein BLAST with the BLOSUM62 substitution matrix (Altschul et al., 1990; 1997). Sequence similarity was computed for all pairs of yeast proteins and human proteins. We used an E-value threshold=1E-5 to determine significance. We also used DIOPT (GTEx Consortium, 2013; Hu et al., 2011; Reinhardt et al., 2013; Soding et al., 2005), an integrative ortholog prediction webserver, to predict human orthologs for each yeast protein. We stored all filtered yeast-human protein pairs together with their BLAST E-values, bit scores and DIOPT scores.

2) Evolutionary and Structural Similarity. For each yeast and human protein, we applied PSI-BLAST to construct a multiple sequence alignment and build a profile hidden Markov model to encode a remote evolutionary signature. We then applied HHpred (Kriks et al., 2011; Robinson and Oshlack, 2010; Schondorf et al., 2014; Soding et al., 2005; Voevodski et al., 2009), with the profile hidden Markov models and secondary structure annotations as input, to compare all pairs of yeast proteins and human proteins. As with the sequence similarity calculation, we also used an E-value=1E-5 threshold. We stored all filtered yeast-human protein pairs with their HHpred E-values and bit scores.

3) Network Topology (Diffusion Component Analysis; DCA). The central idea behind our network topology approach is to try to capture functionally-related modules at the protein level, so that each node can be represented with a low-dimensional vector, instead of a single score, that captures homologous proteins in the network, along with conserved patterns of interactions. The eventual goal (see Integrative Approach, below) is to be able to compare low-dimensional representations of node vectors across species to yield information in other organisms. However, if we follow a straightforward PageRank-like approach (Cho et al., 2015; Tuncbag et al., 2016; Voevodski et al., 2009) to compute each node's vector, we get inaccuracies in functional similarity prediction due to network noise. Thus, using the intuition that compression decreases noise, we reduce the dimensionality of the vectors using sophisticated machine learning techniques. Our approach has been shown to reduce noise and be better able to extract topological network information such as functional similarity (Bailly-Bechet et al., 2011; Cho et al., 2015). The approach has recently been generalized into a method called Mashup (Cho, H. et al 2016).

More formally, let A denote the adjacency matrix of a (weighted) molecular interaction network G=(V; E) with n nodes, each denoting a gene or a protein. Each entry $B_{i,j}$ in the transition probability matrix, which stores the probability of a transition from node i to node j, is computed as $B_{i,j}=A_{i,j}/\Sigma_k A_{i,k}$. The diffusion algorithm is then defined as $$s_i^{t+1}=(1-p)s_i^t B + pe_i$$

until convergence, where p is the probability of restart, controlling the relative influence of local and global information in the network; $e_i$ is a binary vector with $e_i(i)=1$ for node i itself and $e_i(j)=0$ for other nodes j. When the diffusion patterns of two nodes are similar to each other, it implies that they are in proximal locations in the network with respect to other nodes, which potentially suggest functional similarity. In practice, diffusion vectors obtained in this manner are still noisy, in part due to their high dimensionality as well as the noise and incompleteness of the original high-throughput network data. With the goal of noise and dimensionality reduction, we approximate each diffusion vector with a multinomial logistic model based on a latent vector representation of nodes that uses far fewer dimensions than the original vector. Specifically, we compute the probability assigned to node j in the diffusion vector of node i as:

$$\widetilde{s_{ij}} = \exp(w_i^T x_j)/\Sigma_k \exp(w_i^T x_k)$$

where superscript T denotes vector transposition; $w_i$ and $x_i$ are low-dimension vectors. Each node is given two vector representations, $w_i$ and $x_i$. We refer to $w_i$ as the context feature and $x_i$ as the node feature of node i, both capturing the intrinsic topological properties in the network. This multinomial logistic regression model is applied to model the relevance between a node and other nodes in a network, which can be modeled as a discrete distribution over all nodes in a network. To obtain w and x vectors for all nodes, we optimize the KL-divergence (or relative entropy) between the diffusion vectors $s_i$ and the model vectors $\tilde{s}_i$:

$$\min_{w,x} C(s, \tilde{s}) = \sum_i D_{KL}(s_i \| \widetilde{s_i})$$

Akin to PCA, which reveals the internal low-dimensional linear structure of matrix data that best explains the variance, this approach computes a low-dimensional vector-space representation for all genes such that the connectivity patterns in the network can be best explained. Comprehensive experiments showed that these low-dimensional vectors w and x are more accurate at identifying functional association within the network (Cho et al., 2016.; Tuncbag et al., 2013).

4) Integrative Approach. To compare proteins from yeast and human, we extended the above DCA method to consider the topology of both interactomes as well as the sequence/structural similarity between them. We converted the sequence and structure similarity scores to a probability distribution, and feature vectors of all pairs of nodes, including the sparse vector representations ones, were jointly computed by minimizing the Kullbeck-Leibler (KL) divergence between the relevance vectors and the parameterized multinomial distributions.

Formally, here we have two interactomes, $G_Y$ for yeast and $G_H$ for human. To capture the topological similarity within interactomes, we perform the described diffusion algorithm on $G_Y$ and $G_H$ separately and then obtain diffusion vectors $s_i^Y$ for yeast protein i and $s_j^H$ for human protein j. Similar to DCA on a single network, we also assign vectors $w_i^Y$, $x_i^Y$ for each yeast protein, and vectors $w_i^H$, $x_i^H$ for each human protein. To the sequence/structural similarity between obvious homologs, we normalize the BLAST bit scores between each yeast protein i and its human homologs j into a probability distribution as $b_{ij}^Y=bit_{ij}/\Sigma_k bit_{ik}$. Similarly we also normalize the BLAST bit scores between each human protein j and its yeast homologs i into a probability distribution as $b_{ji}^H=bit_{ij}/\Sigma_k bit_{ik}$. We likewise do the same normalization for HHpred bit scores as $h_{ij}^Y$ and $h_{ji}^H$, and $h_{ij}^Y$ and $d_{ji}^H$ for DIOPT scores. Between each yeast protein i and human protein j, we approximate each normalized bit score distribution vector with a multinomial logistic model as:

$$\widetilde{t_{ij}} = \exp(w_i^T x_j)/\Sigma_k \exp(w_i^T x_k)$$

Similar to the definition of $\widetilde{s_{ij}}$ for genes in the same molecular network, $\widetilde{t_{ij}}$ captures the homologous similarity between a yeast gene and a human gene. In this way, although in different networks, yeast and human genes are represented in the same vector space.

Finally, we optimize an extended DCA objective function as:

$$\min_{w^Y, w^H, x^Y, x^H} \sum_{i \in V_Y} D_{KL}(s_i \| \widetilde{s_i}) + \sum_{j \in V_H} D_{KL}(s_j \| \widetilde{s_j}) +$$

$$\alpha_{Blast} \sum_{i \in V_Y} D_{KL}(b_i \| \widetilde{t_i}) + \alpha_{HHpred} \sum_{i \in V_Y} D_{KL}(h_i \| \widetilde{t_i}) + \alpha_{Diopt} \sum_{i \in V_Y} D_{KL}(d_i \| \widetilde{t_i}) +$$

$$\alpha_{Blast} \sum_{j \in V_H} D_{KL}(b_j \| \widetilde{t_j}) + \alpha_{HHpred} \sum_{j \in V_H} D_{KL}(h_j \| \widetilde{t_j}) + \alpha_{Diopt} \sum_{j \in V_H} D_{KL}(d_j \| \widetilde{t_j})$$

where $\alpha_{Blast}$, $\alpha_{HHpred}$ and $\alpha_{Diopt}$ are parameters to tune the importance of each similarity component. Importantly, by optimizing these vectors, we integrate both molecular network connectivity and sequence similarity information into the same vector space for the purpose of comparison.

Here we used a greedy method to select these parameters. Specifically, we incrementally added each term and find the optimal or reasonable weight for the term, according to the functional concordance between the predicted yeast-human homology pairs. The details of the parameter selection procedure can be found in the "Parameter Tuning" section below. On the basis of the analyses included therein, we chose $\alpha_{Blast}$=10, $\alpha_{HHpred}$=5 and $\alpha_{Diopt}$=5. Finally, we computed the integrated homologous association $p_{ij}=(\widetilde{t_{ij}}+\widetilde{t_{ij}})/2$ between yeast protein i and a human protein.

Figure 8A:
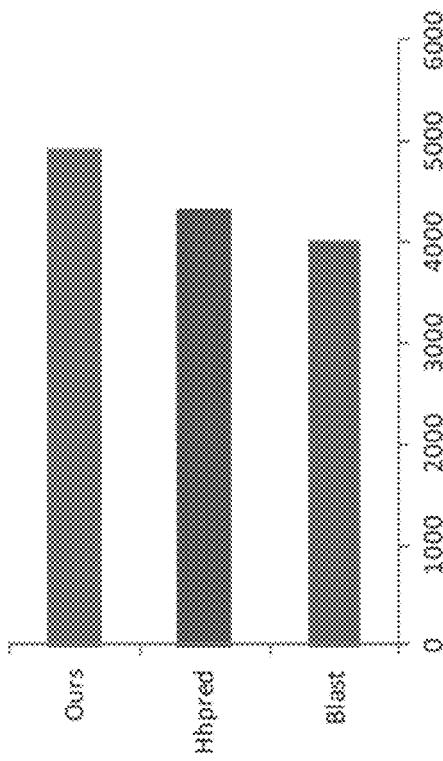
FIG. 8 shows that the diffusion Component Analysis (DCA) algorithm outperforms BLAST and HHpred. We evaluated performance of homology tools using three metrics: coverage, Gene Ontology (GO) accuracy, Jaccard similarity. The coverage is defined as the number of yeast (or human) genes for which a method can predict statistically significant human (or yeast) homologs. The GO accuracy is computed as the percentage of overlapped GO labels between a yeast (or human) gene and a predicted human (or yeast) homolog. The Jaccard similarity score is the number of overlapped GO labels divided by the total number of unique GO labels of the yeast (or human) gene and its human (or yeast) homolog. To compare with other BLAST and HHpred tools, we computed the average GO accuracy and Jaccard similarity score of the top 5 homologs predicted by BLAST, HHpred and our DCA method. We chose the top 5 homologs since yeast (or human) proteins often have more than one good human (or yeast) homolog. (A and B) We first evaluated our method for human homologs of yeast proteins. Our method predicted homologs for significantly more yeast genes (4923) than either BLAST (4023) or HHpred (4312) (A). We evaluated the predicted GO accuracy and the Jaccard similarity for predictions (B). Since our method predicted homologs for more proteins than BLAST and HHpred, we computed the accuracy metrics only on proteins for which BLAST or HHpred could identify homologs. Our method outperformed BLAST and HHpred on both accuracy metrics. All these comparisons were statistically significant (p-values less than 0.001 by paired t-test). We also computed the average accuracy and Jaccard similarity on all 4923 proteins for which our tool could predict homologs. The performance (31.6% GO accuracy and 0.248 Jaccard similarity score) was similar to that of HHpred or BLAST, but for many more proteins covered. (C and D) We next tested our method for yeast homologs of human proteins. The improvement of the coverage over BLAST and HHpred is even more substantial than that in the yeast experiment. Our method predicted homologs for 15200 proteins, whereas BLAST and HHpred predicted yeast homologs for many fewer humn proteins (7248 and 9577 respectively). Comparisons with the accuracy metrics were similar to those observed in (B). Our method improved the predictive power compared BLAST and HHpred on proteins for which BLAST or HHpred could find yeast homologs, with respect to both GO accuracy and Jaccard simialrity score. These comparisons were all statistically significant (p-values <0.0001 by paired t-test).

To find significant homology pairs, we computed $p_{ij}$ for all yeast-human protein pairs and constructed the empirical background distribution. We used 0.0005 as the empirical p-value cut-off to predict putative human homologs for yeast proteins and remove the homolog j if $p_{ij}$<0.5 $\max_{k}\{p_{ik}\}$. The background distribution is generated by randomly pairing human and yeast genes. Utilizing this cutoff, there were 4923 yeast proteins with predicted human homologs, greatly improving the coverage of BLAST (4023 yeast proteins) and HHpred (4312 yeast proteins) (FIG. 8A).

Preprocessing of Interactomes

We downloaded both yeast and human interactomes from the STRING v9.1 (string-db.org). In STRING, $q_{ij}$ are the confidence values assigned for each edge in the interactome. We removed predicted interactions and re-calibrated the confidence for each interaction pair, such that $q_{ij}=1-(1-q_{ij}^{experiment})*(1-q_{ij}^{database})$ with only "experimental" and "database" channels included. We also removed interaction pairs with low confidence $q_{ij}$<0.2. After the preprocessing, we obtained a yeast interactome with 372026 interactions and 6164 proteins and a human interactome with 643822 interactions and 15317 proteins.

For the human networks, we also included two recently published high-quality binary human interactome datasets (11045 from high-quality re-curated binary interactions extracted from 7 public repositories; and 13944 from a recent yeast-2-hybrid experimental dataset) (Geetha et al., 1999; Hu et al., 2011; Rolland et al., 2014). Since these interactions were unweighted, we needed to assign confidence scores for them. To estimate a good confidence value, we extracted all physical binary interactions from the BIOGRID database (v3.2.116) and computed the statistics of STRING confidence scores of these interactions. Since interactions from BIOGRID are mostly from high-throughput experiments and they are binary, we used the mean or median statistics to assign confidence scores for new binary interactions. The quantile statistics of STRING confidence scores of BIOGRID interactions were 25%: 0.391, 50%: 0.620 and 75% 0.717. The average value of STRING confidence scores of BIOGRID interactions was 0.588. We thus considered it reasonable to assign a 0.6 confidence score for each unweighted binary interaction in these datasets.

As we were modeling neurodegenerative proteinopathies in the current work, we further pruned the human interactome to be brain-specific. To do so, we took GTEX gene expression dataset to only include genes appreciably expressed in brain (GTEx Consortium, 2013; Hu et al., 2011; SWding et al., 2005). Specifically, we normalized 357 GTEX brain RNA-seq datasets by the RPKM method (Robinson and Oshlack, 2010; SWding et al., 2005; Voevodski et al., 2009). We then filtered our human interactome such that only proteins with normalized brain expression level greater than (in at least one of 357 RNA-seq datasets) were included. In the end, our brain-specific interactome contained 369634 interactions and 10365 proteins.

Augmentation of Human Interactome with Yeast-to-Yeast Edges (for Humanized Networks Only)

Since genetic interactions are sparse in the human interactome, we used inferred homology to augment the human interactome by transferring edges from the yeast interactome. To do so, we added an edge between human proteins j and k if there exist a pair of yeast proteins i and l such that the integrated homologous association $p_{ij}$ and $p_{kl}$ satisfy $p_{ij}*p_{kl}$>0.2 (see definitions above). This threshold was chosen to make the augmented brain interactome attain a similar density (~0.018) to that of yeast interactome (~0.019) with 751282 interaction pairs transferred.

Prize-Collecting Steiner Forest Algorithm

We used the prize-collecting Steiner forest (PCSF) construction to analyze yeast networks and the augmented human-yeast network described above (Cho et al., 2015; Tuncbag et al., 2013; 2016.; Voevodski et al., 2009). For a network G (V, E, c, p) of node (gene) set V and edge (interaction) set E (where p(v)≥0 assigns a prize to each node v ∈ V, and c(e)≥0 assigns a cost to each edge e ∈ E), the goal of PCSF is to find a set of trees $F(V_F,E_F)$ to minimize the following cost function:

$$f(F) = \sum_{v \notin V_F} (\beta \cdot p(v) - \mu \cdot d(v)) + \sum_{e \in E_F} c(e) + \omega \cdot \kappa$$

where κ is the number of connected components or trees in the forest F; β is a parameter quantifying the trade-off between node prize and edge cost; d(v) is the degree of node v; μ is a parameter to penalize hub nodes with a large number of neighbors in the network. In this way, the algorithm searches for a network of relatively high-confidence edges linking the experimental data.

To optimize the objective function $f(F)$, we introduced an extra root node $v_0$ into the network connected to each node V ∈ V by an edge (v, $v_0$) with cost ω. This step transforms the PCSF problem into a Prize-collecting Steiner Tree problem (PCST), which can be solved by a previously published message-passing-algorithm (Bailly-Bechet et al., 2011; Cho et al., 2015) After the tree solution was obtained, we removed node $v_0$ and all edges that point to it from the tree solution and obtained the forest solution. It is not hard to show that the tree solution is optimal for the above PCST if and only if the forest solution is optimal for the original PCSF. Although the message-passing algorithm is not guaranteed to find the optimal solution, it works very well in practice(Cho et al., 2015; Tuncbag et al., 2013), and more importantly, it is substantially faster than linear programming approaches, which cannot handle large networks such as the yeast and human interactomes.

A computational difficulty of PCSF is how to tune the parameters β, ω and μ. Since β controls the scale of the prize values for nodes, we assigned a constant prize value (100) to each gene from our screens in our experiments. A perturbation of any parameter can potentially change the topology of the network structure, making the choice of parameters critical. (Altschul et al., 1997; 1990; Ashburner et al., 2000; Tuncbag et al., 2013) Thus, instead of choosing a single set of parameters, we developed an ensemble approach to obtain the consensus network from multiple reasonable parameter settings.

To decide the range of parameters, we set the upper and lower bounds such that: the network solution of PCSF contained sufficient number of predicted proteins (which is half of the number of input prize genes); the network solution did not introduce hub nodes with more than 1000 neighbors in the input network. We discretized the range of the parameters into a grid and enumerated all possible parameter combinations for PCSF runs. For the yeast network, the range of β was {1,2,4,6,8,10,12}; the range of a was {1,2,3,4,5,6,7,8}; the range of μ was {0.001,0.003}. For the humanized network, the range of β was {4,6,8,10,12, 14,16}; the range of ω was {3,4,5,6,7,8,9,10}; the range of μ was {0.003,0.005}. We also injected edge noise for PCSF runs to test for robustness, using the default Gaussian noise setting in the PCSF program. After obtaining the solutions for each PCSF parameter setting, we computed the frequency of each possible edge appearing in the ensemble of all solutions. The frequency of an edge is a surrogate for the robustness of the edge across different parameter settings. Finally, we took as input the edges and their frequencies in the ensemble of all solutions and applied a maximum spanning tree algorithm to find the most robust, representative network.

To evaluate the significance of the selected nodes in the solution, we constructed a background distribution for each node by simulating the same PCSF and ensemble process using a random selection of the same number of yeast genes as input. We computed background distributions using random gene sets with identical degree distribution to that of the prize node lists. Specifically, we binned all yeast genes into four categories, each containing genes with degrees [1-5], [5-10], [10-100] and [>100] respectively. Random gene sets are then sampled without replacement from these categories such that the statistics of the degree distribution were identical to those of a prize node list. We then performed PCSF and generated 10000 random ensembles of forests from 1000 random sets to compute the empirical distributions of each node in the background.

To evaluate the significance of the overlaps of the forests relating to different proteinopathies (FIG. 1D), we also calculated pairwise and triple-wise intersections of these random sets as background distributions. For example, we randomly paired the random ensembles generated for α-syn and random ensembles for tdp-43 and computed the distribution of the sizes of their overlaps. In this way, we constructed background distributions to evaluate the significance of the overlaps compared that simply caused by the increased size of the networks. Empirical p-values are also computed. Similar to our previous results, all the pairwise overlaps were statistically significant ($p<=0.002$). For the triple-wise intersections, the p-value was even more significant ($p<=0.001$).

Node and Edge Setup for Yeast and Humanized Steiner Networks

Aside from differences in parameterization (noted above), there were some important differences between the yeast networks and the "humanized" networks.

For the yeast networks (FIG. 2), "prize nodes" were modifier hits from yeast genetic screens. Each prized node was assigned "100" as the arbitrary prize value. Edges for yeast networks were derived from STRING experimental and database edges. As described above, each edge was assigned a weight $q_{ij}$.

For the humanized networks (FIGS. 3 and 4), "prize nodes" were similarly defined as modifier hits from yeast genetic screens. Yeast-to-human edges were weighted by the strength of homology ($p_{ij}$ above) between yeast proteins and their human homologs. On the humanized networks, these are the first-order links seen between the red triangles (which are hits from the screen) and blue circles (human homologs). If one of the clear human homologs of a yeast modifier was a known parkinsonism or neurodegenerative gene—for example, a PARK locus gene—an arbitrary reward of 0.5 was added to $p_{ij}$ to favor inclusion of that node over other potential homologs. Finally, edges between human proteins in the humanized networks were derived from STRING, but also from other sources, as described in "Pre-processing of interactomes" and "Augmentation of human interactome with yeast-to-yeast edges" above.

Parameter Tuning for Computational Pipelines

Here, we provide analyses and guidelines for the parameters used in our paper.

Weights for BLAST, HHpred and Diopt in the DCA Homology Tool.

Since it is impossible to select the optimal parameters without enumerating all possible combinations, we performed a greedy analysis for the parameter selection for the extended DCA objective function. Specifically, we incrementally added each term and found the optimal or reasonable weight for the term.

Since BLAST is the most sensitive method for sequence homology detection, we first explored a reasonable parameter interval for BLAST. We only retained the two network topology terms and the BLAST terms in the extended DCA objective function and enumerated alpha_BLAST from the set of {1,2,5,10, 20,100}. To evaluate the performance, we computed the average accuracy of Gene Ontology (GO) of the top 5 homologs predicted by our method, as outlined in the Methods section. In Supp FIG. 2A it is readily seen that when the BLAST weight was too small (<10), our method was not able to fully exploit the homology information from BLAST. When this weight was greater than or equal to 10, the predictive performance became saturated and only provided slight performance improvement over the original BLAST method. When the weight became too large (=100), the predictive performance dropped and was identical to that of BLAST. This is because that the effect of network topology is diminished and our method simply reconstructed BLAST's results. Thus, on the basis of the analysis we simply fixed the BLAST parameter to 10, although there might be better choices at extra computational cost by enumerating a larger and more refined set of possible values.

After we fixed the BLAST weight, we added the HHpred terms and performed the same analysis for HHpred weight. From the performance curve (Supp FIG. 2B), we observed that the optimal HHpred weight was around 5. This weight is smaller than BLAST weight, presumably at least in part because BLAST already captures most relevant homology information, while HHpred's results extend BLAST by including extra remote sequence and structural homologs.

Figures 7A, 7B, 7C:
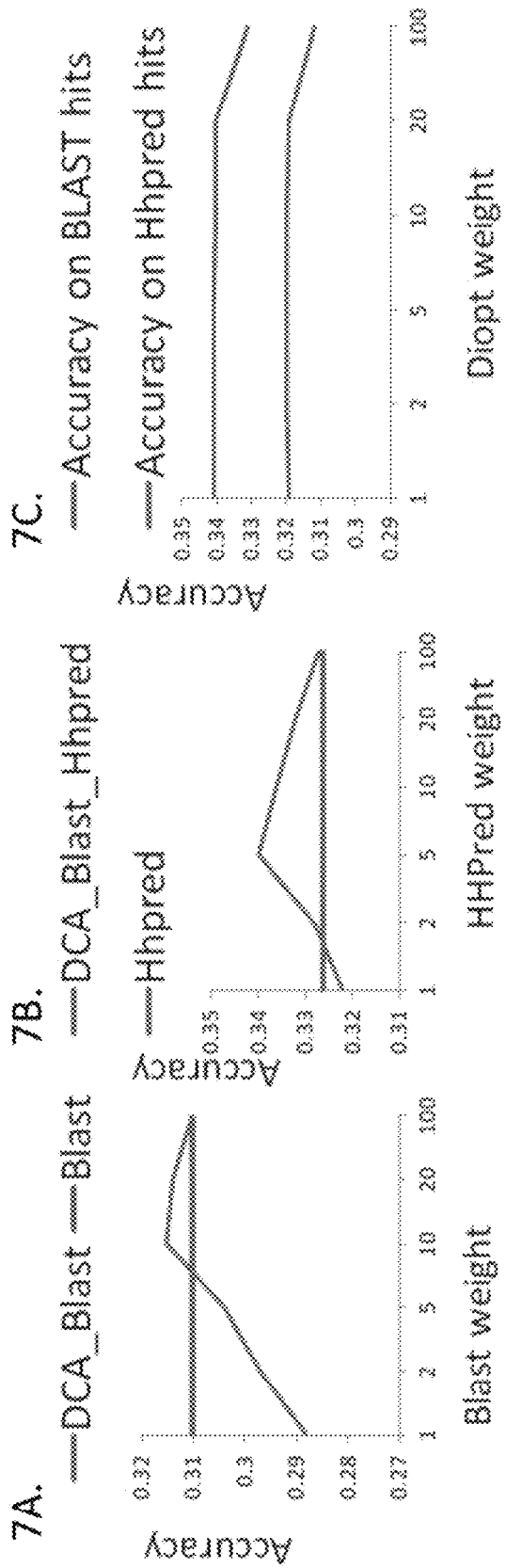
FIG. 7A-FIG. 7C show parameter tuning for a Diffusion Component Analysis (DCA) algorithm. We computed the average accuracy of Gene Ontology (GO) of the top 5 homologs predicted by our method as relative weights were changed for the different homology methods we incorporate into DCA. See Methods for more details.

Finally, we fixed both BLAST and HHpred weights and performed the analysis for Diopt weights (FIG. 7C). For Diopt, the performance difference was very small as long as the weight was not too large (<20). This was consistent with the Diopt database only providing a few additional sequence homologs missed by both BLAST and HHpred. For simplicity, we chose its weighting equal to 5 as well.

Significance Threshold for BLAST and HHpred in the DCA Homology Tool

We chose 1E-5 because it is a reasonably stringent threshold that is typically used for sequence homology or structure prediction (Geetha et al., 1999). Other choices of the threshold are possible but we believe that the results are not appreciably different from our setting. The following website and paper indicates 1E-5 is a reasonably stringent cutoff for protein BLAST.

Reward to Homologs of Known Parkinson Genes

The major reason why we added reward values to homologs of known Parkinson genes is that the prize-collecting Steiner forest (PCSF) algorithm is not guaranteed to include all prize nodes in the final network. In addition, our homology tool can sometimes assign similar scores to two homologs, one with known literature support, the other without. Although the PCSF algorithm itself is able to distinguish most correct homologs by considering the connectivity, we found that by rewarding well-known homologs the noise can be further reduced. The reward parameter 0.5 is chosen such that existing homologs of well-known Parkinson's genes from our screens are included in the final networks. It is obvious that larger reward values can have also the similar effect, but we didn't explore those choices because we hoped to not to overtune the effect of this reward heuristic in our pipeline.

Confidence Threshold for Existing Interactomes and Predicted Links

The choice of confidence threshold for STRING is indeed a trade-off between false-positives and true-positives. A stringent threshold, e.g. 0.8, can reduce the number of false-positives but the truncated yeast and human interactomes appeared to be too sparse and disconnected. Such thresholds may work well for signaling pathways or other well-studied and localized biological pathways but we did not feel this was an appropriate approach for complex proteinopathies, where mechanisms are poorly understood (and casting a "broader net" seems more appropriate) and where the connections between seemingly disparate disease-relevant genes are not well understood. Thus, we selected 0.2 to only exclude very low-confidence interactions and still maintain the major connectivity of the interactomes.

Confidence Score for New High-Throughput Binary Interactomes

Since the new high-throughput binary interactomes are unweighted, we need to assign an appropriate score to merge them with STRING interactions. To estimate an appropriate confidence value, we extracted all physical binary interactions from the most recent BIOGRID database and computed the statistics of STRING confidence scores of these interactions. Since interactions from BIOGRID are mostly from high-throughput experiments and they are binary, we can use the mean or median statistics to assign confidence scores for new binary interactions. The quantile statistics of STRING confidence scores of BIOGRID interactions are 25%: 0.391, 50%: 0.620 and 75% 0.717. The mean value of STRING confidence scores of BIOGRID interactions is 0.588. We thus assigned 0.6 since it closely related to both the median and mean statistics, judging it a reasonable assignment for incorporating new high-throughput binary interactions into existing STRING database.

Parameters for Prize-Collecting Steiner Forest Algorithm (PCSF)

As noted above, we used an ensemble approach to avoid the problem of parameter selection. There is no obvious way to determine the effectiveness of a set of parameters for PCSF. Furthermore, since there are several parameters, enumeration of all combinations becomes computationally infeasible. To address this issue, as noted above, we selected a wide-range of possible parameters, ran PCSF with all parameter combinations and made an ensemble network from single networks generated from each parameter combinations. These parameters are chosen such that the final network can connect 80% prize nodes in the network. Our parameter range also excludes networks that are overly distorted by "greedy" hyperconnected hubs like ubiquitin. As noted in our methods section, we further tested robustness by injecting noise into the edge distribution. There is no question that there is an element of subjectivity here, as with any parameterized model but we have taken great pains to be as broad as we feel we possibly can. Ultimately, the purpose is to generate tenable hypotheses or to predict biologically meaningful interactions.

Spotting Assays

Yeast were cultured in synthetic media consisting of 0.67% yeast nitrogen base without amino acids (Fischer Scientific) supplemented with amino acids (MP Biomedicals) and 2% sugar. For most experiments, cells were first grown to mid-log phase in synthetic media containing glucose and then re-cultured overnight in synthetic media containing 2% raffinose. Mid-log phase cells were then diluted in synthetic media containing galactose. Typically, cells were induced for six hours at 30° C.

Each strain was diluted to a starting $OD_{600}$=1.0 and serially diluted five-fold and then spotted on agar plates containing galactose (inducing) or glucose (control) plates.

Screening Against Known α-Syn Modifiers in ΔPARK17/α-Syn and ΔPARK9/α-Syn Strains.

The standard lithium acetate transformation protocol was adapted for use with 96-well plates(Cooper et al., 2006; D. Gietz et al., 1992; R. D. Gietz et al., 1995). Following transformation, cells were grown to saturation in synthetic media with raffinose lacking uracil for selection of yeast transformed with the desired plasmid. Once at saturation, they were spotted onto synthetic media plates with either glucose or galactose. Following two days of growth, galactose and glucose plates were photographed and analyzed by eye. In parallel experiments, transformed yeast were rediluted to $OD_{600}$=0.01 in 35 μL of galactose media in 384-well plates. Growth in 384-plates was monitored by measuring the $OD_{600}$ after 18, 24, and 48 hours of growth (Tecan safire[2]) giving a quantifiable measure of growth.

Small Molecule (NAB2) Treatment

Control, TDP-43 or α-syn yeast strains were grown to log-phase ($OD_{600}$ ~0.5) in complete synthetic media containing raffinose (non-inducing). Cultures were then diluted to an $OD_{600}$ of 0.01 (TDP-43 experiment) and 0.025 (α-syn experiment) in complete synthetic media containing 2% galactose to induce expression of the toxic protein. For NAB treatment, 10 μM (for α-syn) or 20 μM (for TDP-43) were added to the cultures and incubated in a Bioscreen instrument with intermittent shaking at 30° C. for two days.

Pooled α-Syn Overexpression Screen

Pooled genetic screens were carried out in a YFP control strain and an α-syn strain. The yeast FLEXgene library representing most yeast open reading frames (Hu et al., 2007) was pooled from an arrayed bacterial library stock and grown to saturation in deep 96 well plates at 37° C. Cultures were pooled and plasmids isolated using Qiagen maxi prep kits. The pooled FLEXgene library was then transformed en masse into either control YFP or α-syn-expressing yeast strains and selected on five square 15 cm solid agar plates lacking uracil for plasmid selection. Approximately 10⁷ CFUs were obtained, representing an approximate 200-fold coverage of the ~6,000 yeast genes. Colonies were rinsed off of each plate, pooled, brought to 20% glycerol, aliquoted to individual use tubes (~100 μL), snap frozen in liquid nitrogen, and stored at −80° C.

Pooled screens were executed as follows. An aliquot of pooled yeast library was thawed on ice and diluted at three different concentrations into 3×30 mL flasks with SRafUra (~0.025, 0.05, and 0.1). After shaking at 30° C. overnight, the culture with an $OD_{600}$ between 0.4 and 0.8 was selected to begin the pooled screen. Cultures were then diluted to and $OD_{600}$ of 0.1 in SGal Ura to induce expression of either YFP or α-syn. 50 OD units were kept as time zero and centrifuged, washed with water, and frozen. Cultures were then maintained in log phase growth for 24 hours, making appropriate dilutions when needed to maintain and $OD_{600}$ under 0.8. After this time, 50 OD units worth of culture were centrifuged, washed with water, and pellets frozen.

Plasmids were then isolated from yeast using Qiagen minipreps with the following adaptations. Five minipreps were done per 50 OD units. Cell pellets were resuspended in buffer and lysed by bead beating with small acid-washed beads. Beads were removed and the lysate then taken through the conventional miniprep protocol. The purified plasmids from the five preps were then pooled. The yeast ORFs contained on the FLEXgene plasmids were then amplified using PCR primers that annealed to the attR Gateway sequences flanking the ORFs. HiFidelty Platinum Taq was used for amplification. 5 uL DNA was used per 50 uL reaction and four reactions were performed per sample. 30+ cycles with a ~6' extension time was used to ensure amplification of longer ORFs. PCR product was purified using Qiagen PCR columns. Two micrograms of PCR product was then sonicated, purified on Qiagen Minelute PCR columns, and the $OD_{260}$ re-analyzed. This product was then used as input for library generation and sequencing by the Whitehead Institute Genome Technology Core. Illumina HiSeq platform was used to sequence approximately 120 million 40 bp single end reads.

Reads were mapped to the yeast ORFs sequences with bowtie (Langmead et al., 2009). We made a bowtie index with the DNA sequences of the yeast ORFs reported in Hu et al. (Hu et al., 2007), plus 903 ORFs that were present in SGD but were not included in the list of sequences from in Hu et al. Reads were mapped allowing 2 mismatches (–n 2) in the seed, seed length of 40 (–140), suppressing all alignments that map to more than one place (–m 1) and using "--best" and "--strata". Unmapped reads were trimmed with fastx_trimmer (On the world wide web at hannonlab.cshl.edu/fastx_toolkit/commandline.html) to remove the first 20 nt, and remapped with bowtie using the following parameters: "–n 0 –1 20--best-strata –m 1". The number of reads mapping to each ORF was obtained parsing the output sam files. Differential expression analysis was done with the R package Noiseq (Tarazona et al., 2011). NOISeq is a nonparametric method to identify differentially expressed genes from count data. NOISeq calculates fold change values and probability of differential expression. The probability (P-val) of differential expression for each gene is derived from the joint distribution of fold-change differences (M)-absolute expression differences (D) values for all the genes within the Table Set.

A gene was selected for validation if it was: (A) up or down consistently in the two pooled α-syn screens (|log2 fold change|>0.8 in both screens) except when neither experiment was associated with a P-val of >0.5); (B) had an average fold change with absolute value of >2.5 (regardless of P-val); (C) known modifiers from previous experimentation that had a fold-change in the pooled screen consistent with that source. Any gene with an |log2 fold change|>1.0 in the YFP control (in the same direction as the putative suppressor or enhancer) was excluded, as well as genes associated with galactose metabolism that would be expected to alter expression of gal-inducible transgenes. Thresholds were guided by knowledge gained from our previous extensive characterization of the arrayed α-syn over-expression screen hits (see FIG. 1). Put another way, our previous over-expression screen was used as a "gold standard" to analyze the pooled over-expression data.

Pooled Screen-QPCR Verification

Transformed cells generated from the pooled screen ("Pooled α-syn overexpression Screen" method) were thawed on ice and diluted in SRaf-Ura to resulting ODs of approximately 0.03, 0.05 and 0.1. Cultures were grown at 30° C. overnight and cultures with an OD of 0.4-0.8 were chosen for induction. These cultures were diluted to an OD of 0.1 in SGal-Ura. 50 OD units were stocked representing the time zero time point. Induced cultures were grown for 24 hours and 50 OD units were stocked representing the 24 hr time point. Plasmids were isolated using the Qiagen miniprep kit (27106) splitting the 50OD units for each time point in to 5 samples. Following cell resuspension in P1 buffer cells were lysed by bead beating using acid-washed beads. Following bead beating, beads were removed from samples and lysates subjected to the standard miniprep kit protocol. Resulting plasmids were pooled and used for QPCR analysis. The standard attF primer was used in combination with an orf specific reverse primer (sequence generated by Primer3 such that the product <150 bp in size) for QPCR analysis. Multiple negative controls used to normalize samples and positive controls were run on all QPCR plates. QPCR analysis was performed using technical triplicates of biological triplicates on the Applied Biosystems (7900HT) using the SYBR green fluorescence detection system (Applied Biosystems). The program for amplification comprised 40 cycles of 95° C. for 15 seconds and 60° C. for 1 minute.

Pooled Screen-Growth Curve Analysis

Each individual putative modifier was overexpressed in the α-syn strain using the Flexgene overexpression library. Three independent Ura$^+$ transformants were grown in SRaf-Ura at 30° C. overnight. Cultures were subcultured in SRaf-Ura and at an OD of 0.4-0.8 were diluted in Sgal-Ura for induction. Each isolate was set up in triplicate and growth was monitored every 15 mins for approximately 60 hours.

Genome-Wide Deletion Screen (Synthetic Gene Array Methodology)

The method used was essentially as described previously (Baryshnikova et al., 2010; Tong and Boone, 2006). Briefly, deletion strains were pinned on to YPD+G418 plates. Query strains (α-syn and wild-type control) were grown in 5 ml overnight cultures in YPD at 30° C. and spread on YPD plates and grown overnight. Deletion strains were mated to each query strain by pinning together on YPD and grown for 48 hrs at 30° C. Resulting diploids were pinned to SD/MSG-Ura+G418 and grown for 2 days at 30° C. Cells were pinned to sporulation media plates and incubated at 23° C. for 7 days. Spores were pinned to SD-His/Arg/Lys+canavanine+thialysine and grown for 2 days at 30° C. Cells were pinned to fresh SD-His/Arg/Lys+canavanine+thialysine and grown for 1 day at 30° C. Cells were pinned to SD/MSG-His/Arg/Lys+canavanine+thialysine+G418 and grown for 2 days at 30° C. and then pinned to SD/MSG-His/Arg/Lys/Ura+canavanine+thialysine+G418 and grown for 2 days at 30° C. For the initial screen, cells were pinned both to SD/MSG-His/Arg/Lys/Ura +canavanine+thialysine+G418 and to Sgal/MSG-His/Arg/Lys/Ura +canavanine+thialysine+G418 and spot growth was monitored. For validation studies, cells were pinned to liquid SD/MSG-His/Arg/Lys/Ura+canavanine+thialysine+G418 and grown overnight at 30° C. and then pinned both to SD/MSG-His/Arg/Lys/Ura +canavanine+thialysine+G418 and to Sgal/MSG-His/Arg/Lys/Ura +canavanine+thialysine+G418 and spot growth was monitored. Stock solutions (1000X) were prepared as follows: G418 200 mg/ml, canavanine 50 mg/ml, thialysine 50 mg/ml. The method above was used for the initial screen and repeated, in duplicate, using 96-well plate format for validation of the initial screen hits.

Human iPSC Generation and Differentiation into Midbrain Dopaminergic (DA) Neurons for LRRK2 Mutant Lines.

iPSCs from control individuals and PD patients carrying G2019S LRRK2 along with isogenic gene corrected controls were generated as previously described (Reinhardt et al., 2013). iPSCs were differentiated into mDA neurons using a floor plate-based protocol with minor modifications (Kriks et al., 2011; Schöndorf et al., 2014). Differentiation was based on exposure to LDN193189 (100 nM, Stemgent) from days 0-11, SB431542 (10 mM, Tocris) from days 0-5, SHH C25II (100 ng/mL, R&D), purmorphamine (2 mM, EMD) and FGF8 (100 ng/mL, Peprotech) from days 1-7 and CHIR99021 (CHIR; 3 mM, Stemgent) from days 3-13. Cells were grown for 11 days on Matrigel (BD) in knockout serum replacement medium (KSR) containing DMEM, 15% knockout serum replacement, 2 mM L-glutamine and 10 µM β-mercaptoethanol. KSR medium was gradually shifted to N2 medium starting on day 5 of differentiation. On day 11, media was changed to Neurobasal/B27/L-Glut containing medium (NB/B27; Invitrogen) supplemented with CHIR (until day 13) and with BDNF (brain-derived neurotrophic factor, 20 ng/ml; R&D), ascorbic acid (0.2 mM, Sigma), GDNF (glial cell line-derived neurotrophic factor, 20 ng/ml; R&D), TGFβ (transforming growth factor type β3, 1 ng/ml; R&D), dibutyryl cAMP (0.5 mM; Sigma), and DAPT (10 µM; Tocris,) for 9 days. On day 18, cells were dissociated using Accutase (Innovative Cell Technology) and replated under high cell density conditions on dishes pre-coated with 15 µg/ml polyornithine and 1 µg/ml laminin in differentiation medium (NB/B27+BDNF, ascorbic acid, GDNF, dbcAMP, TGFβ3 and DAPT). At DIV30, cells were collected and, after centrifugation, cell pellets were stored at −80° C. until further analysis.

Human Pluripotent Stem Cell Culture for α-Syn Mutant Lines

Skin biopsy, human dermal fibroblast culture, iPS cell generation and mutation correction for the patient harboring the A53T mutation (WIBR-IPS-$^{A53T}$) have been described previously (Cooper et al., 2006; Soldner et al., 2011). In that previous publication the A53T iPS line was referred to as WIBR-IPS-SNCA$^{A53T}$.

Our pluripotent stem cell lines were initially maintained (5% $O_2$, 3% $CO_2$) on mitomycin C inactivated mouse embryonic fibroblast (MEF) feeder layers in hES medium [DMEM/F12 (Invitrogen) supplemented with 15% fetal bovine serum (FBS) (Hyclone), 5% KnockOut Serum Replacement (Invitrogen), 1 mM glutamine (Invitrogen), 1% nonessential amino acids (Invitrogen), 0.1 mM β-mercaptoethanol (Sigma) and 4 ng/ml FGF2 (R&D systems)]. Cultures were passaged every 5 to 7 days either manually or enzymatically with collagenase type IV (Invitrogen; 1.5 mg/ml). At around 50 passages prior to differentiation, lines were passaged to plates pre-coated with growth factor-reduced matrigel (BD Biosciences; 1:30 in DMEM:F12) and cultured (21% $O_2$, 5% $CO_2$) in mTESR-1 medium (Stem Cell Technologies), thereafter being passaged every 5 to 7 days enzymatically with dispase (Invitrogen; 1 mg/mL) until differentiation (at passage 40-90). For karyotyping, standard G-banding chromosomal analysis of cell lines was performed every 10-20 passages (Cell Line Genetics, Inc.). We confirmed *mycoplasma*-negative status of our cultures every 2-4 weeks (MycoAlert, Lonza).

Human Neural Induction by Embryoid Body (EB) Formation

A previously published protocol was used without modification (Chung et al., 2013; Hu et al., 2007; J.-E. Kim et al., 2011). This protocol has been repeated here for completeness.

To initiate differentiation, on day 0 human ES or iPS cell colonies were pretreated for 30-60 min with 5 µM Y-27632/ROCK inhibitor (Calbiochem), single cell-dissociated after 5-10 min exposure to accutase (StemPro Accutase; Life Technologies) and then re-suspended in neural base (NB) medium, which is DMEM/F12 (Gibco/Life Technologies) supplemented with N2 and B27. N2 and B27 supplements from Life Technologies and used at ½-1% and 1-2%, respectively. Cells were plated in AggreWell 800 microwells (StemCell Technologies; priming and plating per manufacturer's protocol; 2.4×10$^6$ cells were well) in NB medium supplemented with dual SMAD inhibitors (Chambers et al., 2009; Langmead et al., 2009) recombinant human Noggin (R&D Systems) at 200 ng/mL and 10 µM SB431542 (Tocris Bioscience), as well as 5 µM Y-27632. Noggin and SB431542 remained in the medium at these concentrations throughout the neural differentiation protocol.

On day 1 medium was ½-changed. By day 2, well-formed neuralized EBs (NEBs) were typically observed in the AggreWells and transferred to Petri dishes (4 AggreWell wells/Petri dish) overnight, in NB medium. On day 4, NEBs were transferred to a dish coated with growth factor-reduced Matrigel (1:30 in DMEM:F12; BD Biosciences) for attachment. Y-27632 was omitted from this day onward. From day 5 to day 10, attached NEBs were additionally exposed to 20 ng/mL FGF2 (R&D Systems) and recombinant human Dkk1 at 200 ng/mL (R&D Systems). On day 10, neural rosettes were dissected (P20 pipette tip), incubated in accutase supplemented with DnaseI (Sigma Aldrich) for 10 min at 37° C. and gently dissociated to small cellular clumps and single cells. After washing, the rosettes were re-plated on plastic dishes pre-coated with poly-L-omithine and laminin (BD Biocoat) at high density (200,000/cm$^2$) in neural progenitor cell (NPC) medium, which is NB medium supplemented with 20 ng/mL FGF2. (Life Technologies), supplemented overnight with 10 µm Y-27632. Typically, one Aggrewell 800 well provided enough NPCs for at least 1-2 6-wells at passage 0.

Thereafter, the surviving NPCs proliferated. Medium change was daily. They could be passaged up to 10 times before neural differentiation, and could successfully be freeze/thawed at early passage (p1 to p5) without compromising differentiation potential. Freezing medium was NPC medium with 10% FBS (Hyclone).

Human Cortical Neural Differentiation

A previously published protocol was used without modification (Chung et al., 2013; Hu et al., 2007; J.-E. Kim et al., 2011). This protocol has been repeated here for completeness.

To begin neural differentiation, NPCs were dissociated with accutase and re-plated on matrigel-coated T75 flasks (CytoOne). The next, day medium was fully changed to Neural Differentiation (ND) medium, which is NB medium supplemented with recombinant human BDNF and GNDF (both at 10 ng/mL; R&D Systems) and dibutyryl cyclic AMP (Sigma; 500 µM), and without FGF-2. Thereafter, media was ½-changed every other day. On day 7-9, differentiating neurons were gently dissociated to single cell, resuspended in pre-chilled Hank's balanced salt solution (HBSS; Gibco/Life Technologies) supplemented with 0.1% bovine serum albumin (Gibco/Life Technologies). After a wash step, cells were plated on 6- or 24-well plastic plates pre-coated with poly-ornithine and laminin (BD Biocoat) for biochemical assays. Medium was ½-changed every 3 days for up to 12 weeks.

Primary Rat Cortical Cultures

Embryos were harvested by cesarean section from anesthetized pregnant Sprague-Dawley rats at embryonic day 18. Cerebral cortices were isolated and dissociated with Accumax (Innovative Cell Technologies, Inc) digestion for 20 min at 37° C. and trituration with Pasteur pipette. Poly-ornithine and laminin-coated 96 well plates were seeded with 4×10$^4$ cells respectively in neurobasal medium (Life Technologies) supplemented with B27 (Life Technologies), 0.5 mM glutamine, 25 μM β-mercaptoethanol, penicillin (100 IU/ml) and streptomycin (100 μg/ml). One third of the medium was changed every 3 to 4 days.

AAV-1 Transduction of iPS Neurons

Plasmids containing verified TALE-TFs were purified endotoxin-free (Qiagen) and packaging into adeno-associated viruses serotype 1 (AAV-1) was conducted by the Gene Transfer Vector Core, Massachusetts Eye and Ear Infirmary/MEEI, Harvard Medical School (mini-scale production). A53T and mutation-corrected cortical neurons were aged for 4-7 weeks at a plating density of 0.25-0.75×10$^6$ cells/cm$^2$. Cells were transduced with 30 μl of the mini scale produced MEEI AAV-1 titer, containing a single TALE-TF or the TALE cloning backbone alone, in 500 μl ND medium. ND medium was changed 12-16 hours post-transduction.

Antibodies

| Mouse anti-Carboxypeptidase Y | Life Technologies A66428 | Western blot | 1:10 000 |
| Rabbit anti-Nicastrin | Cell Signaling 3632 | Western blot | 1:1000 |
| phospho eIF2A | Cell Signaling 9721 | Western blot | 1:1000 |
| total eIF2A | Cell Signaling 2103 | Western blot | 1:1000 |
| LRRK2 | Abcam Ab133474 | Western blot | 1:500 |

Protein Labeling with $^{35}$S-Methionine/-Cysteine

A53T and mutation-corrected cortical neurons were aged for 4-8 weeks at a plating density of 0.25-0.75×10$^6$ cells/cm$^2$. Prior to the protein labeling the cortical neuronal cultures were kept in Neural Differentiation (ND) medium without methionine and cysteine for 90 min. ND medium was DMEM complemented with 1% (v/v) B-27, 0.5% (v/v)N-2 and 1% (v/v) GlutaMAX supplement, 1% (v/v) MEM non-essential amino acids, 1% (v/v) Penicillin-Streptomycin (all Life Technologies) as well as 10 ng/ml BDNF and GDNF (both R&D Systems) and 500 μM cAMP (Sigma-Aldrich). For protein labeling the neuronal cell cultures were incubated in ND medium supplemented with $^{35}$S-methionine and -cysteine (Perkin Elmer) at a final concentration of 100 μCi/ml for various duration. After a quick wash with cold PBS, cells were lysed in a buffer containing 50 mM Tris-HCl and 2% (w/v) SDS, supplemented with protease inhibitor cocktail (Sigma-Aldrich). The samples were boiled at 100° C. for 5 min and spun down at 10,000 g for 15 min. The supernatant was collected and the protein concentration was determined using BCA assay (Pierce, Thermo Fisher Scientific). $^{35}$S labeled samples were run in 4-12% Nupage Bis-Tris gel (Life Technologies). As a loading control, gels were stained with SimplyBlue SafeStain (Life Technologies), and destained by incubation in water. Thereafter, the gels were incubated in 11.2% (v/v) salicylic acid and 10% glycerol (v/v) for 15 min. The gels were dried and exposed to a phosphor screen (Fujifilm) for a minimum of 48 hours. The screen was scanned using the phosphorimager BAS-2500 (Fujifilm) and $^{35}$S incorporation was determined by measuring the intensity of each lane (MultiGauge Analysis Software v2.2, Fujifilm).

Free $^{35}$S-Methionine/-Cysteine in the Cytosol

Rat primary neurons overexpressing either GFP or αSyn-GFP were incubated with $^{35}$S-methionine and -cysteine at 100 μCi/ml for various durations. After a quick wash with cold PBS, cells were lysed in RIPA buffer for 20 min on ice and the debris was removed by centrifugation. Proteins in the lysates were precipitated by adding 1 volume 100% TCA to 4 volume of lysate and incubate 10 min at 4° C. After centrifugation at 14K rpm for 10 min, supernatant was collected to measure a cytosolic pool of free $^{35}$S-methionine/-cysteine. $^{35}$S incorporation was determined by quantifying using an LS 6500 liquid scintillation counter (Beckman Coulter) with 5 μl of the sample being immersed in 7 ml scintillation cocktail (National Diagnostics).

Cell Lysis and Endoglycosidase H Digestion

Cells were lysed in a buffer containing 20 mM HEPES, 150 mM NaCl, 10% (v/v) glycerol, 1 mM EGTA, 1.5 mM MgCl$_2$, 1% (v/v) Triton X-100, pH to 7.4, protease inhibitor cocktail (Sigma-Aldrich), and protein phosphatase inhibitor cocktail 1 and 2 (Sigma-Aldrich), and incubated in an ice/water slurry for 20 min, followed by 2 freeze-thaw cycles (−80° C./37° C., ~1 min each). Supernatant was collected after ultracentrifugation at 100,000 g, 4° C., for 30 min. Protein concentration was determined using BCA assay (Pierce, Thermo Fisher Scientific). Endoglycosidase (Endo) H (New England Biolabs) digestion was performed based on the manufacturer's instructions. Briefly, 20-40 μg bulk protein was assembled in 15.3 μl reaction volume; 1.7 μl denaturing buffer was added and samples were boiled for 10 min at 100° C. Then 2 μl of G5 buffer and 1 μl of Endo H or 1 μl H$_2$O were added to the denatured reaction and incubated for 2 hours at 37° C.

Western Blotting

For protein trafficking after Endo H digestion, protein samples were denatured in sample buffer (20 mM Tris-Cl pH 6.8, 4% (v/v) glycerol, 180 mM 2-mercaptoethanol, 0.0003% (v/v) bromophenol blue and 2% (v/v) SDS), run in 10% Tris-glycine gel, and wet transferred with 20% methanol onto PVDF membranes (BioRad). Blots were blocked in a 1:1 dilution of Odyssey blocking buffer (Li-Cor Biosciences) and PBS for 1 hour at room temperature, followed by incubation with primary antibodies in a 1:1 dilution of Odyssey blocking buffer (Li-Cor Biosciences) and PBS containing 0.1% Tween 20 (PBST) at 4° C. overnight with gentle rocking. After three 5 min washes with PBST, blots were incubated with secondary antibodies such as anti-mouse or -rabbit IgG conjugated to IRDye 680 or 800 (1:10,000, Rockland) in a 1:1 dilution of Odyssey blocking buffer and PBST for 2 hours at room temperature. After three 5 min washes with PBST and two with water, blots were scanned using the Odyssey quantitative fluorescent imaging system (Li-Cor Biosciences) and bands were quantitated using Odyssey Software v2.1 (Li-Cor Biosciences).

For other Western blots, samples were lysed in RIPA buffer and run in either 8 or 10% Nupage Bis-Tris gel (Life Technologies) and transferred using iBlot (Life Technologies). Blocking was in 5% nonfat dry milk in PBST. As for the secondary antibodies and chemiluminescent detection, anti-mouse, -rabbit IgG or avidin conjugated to HRP was used with SuperSignal West Pico chemiluminescent substrate (Thermo Fisher Scientific).

TALE-TF Design

TALE-TFs were designed to target between 200 bp upstream (5') and 50 bp downstream (3') of the transcription start site (TSS) of ATXN2 or EIF2G transcripts. Within these regions near the TSS, we identified DNAseI hypersensitive regions from human ventromedial prefrontal cortex samples (Thurman et al., 2012, PMID: 22955617). Within these DNAseI HS regions, we designed 5 TALE-TFs for each transcript.

Each TALE-TF was designed to target a 14 bp genomic sequence consisting of an initial thymidine (T) plus 12 full repeats and 1 half repeat. For each TALE-TF, the TALE repeats were cloned into an rAAV transfer plasmid using a PCR-based, Golden Gate cloning strategy as previously described (Konermann et al., 2014; Sanjana et al., 2012; Tarazona et al., 2011). The rAAV transfer plasmid contained the TALE backbone fused to the synthetic VP64 activator domain along with a 2A-linked EGFP that is cleaved during translation.

TALE-TF Assembly 14-mer transcription activator-like effector transcription factors (TALE-TFs) were constructed using Golden Gate cloning as described previously (Sanjana et al. 2012). For each gene, ATXN2 and eIF4G1 (transcript variant 7), five different TALE-TFs were designed with the 14 bp long target loci being located in the proximal promoter region (ATXN2 TALE-TF #1: 5'-TGTCCAGATAAAGG-3'(SEQ ID NO: 1), #2: 5'-TGAACCTATGTTCC-3'(SEQ ID NO: 2), #3: 5'-TGCCAGATTCAGGG-3'(SEQ ID NO: 3), #4: 5'-TGGAGCGAGCGCCA-3'(SEQ ID NO: 4), #5: 5'-TAGCTGGTCATGGT-3'(SEQ ID NO: 5); edF4G1 TALE-TF #1: 5'-TGTCACGTGACGGG-3'(SEQ ID NO: 6), #2: 5'-TGTGGCTGTCACGT-3'(SEQ ID NO: 7), #3: 5'-TCAAAGTTCGGGAG-3'(SEQ ID NO: 8), #4: 5'-TCGCGGAACAGAGA-3'(SEQ ID NO: 9), #5: 5'-TCTCCTGCCTCAGC-3'(SEQ ID NO: 10)). For each TALE-TF the correct sequence of the DNA-binding domain was verified by Sanger sequencing and all TALE-TF clones with non-silent mutations were excluded.

Ribosomal Footprint Profiling

For ribosome footprint profiling, 12-week old cells were treated with cycloheximide (100 ug/mL) for 5 min at 37° C. to stop translation elongation. Cells were washed twice with ice-cold 9.5 mM PBS, pH 7.3, containing 100 µg ml$^{-1}$ cycloheximide, and lysed by adding lysis buffer (10 mM Tris-HCl, pH 7.4, 5 mM MgCl2, 100 mM KCl, 2 mM dithiothreitol, 100 µg ml$^{-1}$ cycloheximide, 1% Triton X-100, 500 U ml$^{-1}$ RNasin Plus, and protease inhibitor (1× complete, EDTA-free, Roche)), scrapping cells from the plate, and then triturating four times with a 26-gauge needle. After centrifuging the crude lysate at 1,300 g for 10 min at 4° C., the supernatant was removed and flash-frozen in liquid nitrogen. The lysate was thawed on ice, after which ribosome profiling and mRNA-seq were performed as described previously (Subtelny et al., 2014) using a detailed protocol available at http://bartellab.wi.mit.edu/protocols.html. The 4-week old cells were washed twice with 37° C. growth media, then after removing the media by aspiration the plates were sealed and then plunged into liquid nitrogen. Cells were then lysed with lysis buffer as described above, but cycloheximide was excluded from all solutions including the sucrose gradients. After thawing on ice, a small amount of cycloheximide-free zebrafish RPF lysate was spiked into the 4-week old cell lysates (10-fold less based on $A_{260}$) prior to digestion with RNase I.

RPF and RNA-seq tags were mapped to the ORFs, as described previously (Subtelny et al., 2014). To account for the zebrafish reads present in the 4-week old samples, indexes comprising both the zebrafish and human genomes or transcriptomes were created and these data were mapped to the combined indexes. Only reads mapping uniquely were considered, and those mapping to zebrafish were excluded from the analysis.

Enriched pathways in the translational profiling for the 4-week and 12-week datasets were computed with the Gene Set Enrichment Analysis tool, available at the Broad Institute website (available on the world wide web at software.broadinstitute.org/gsea/index.jsp).

Quantification and Statistical Analysis

Comparison with Existing Homology Prediction Approaches

Figure 8B:
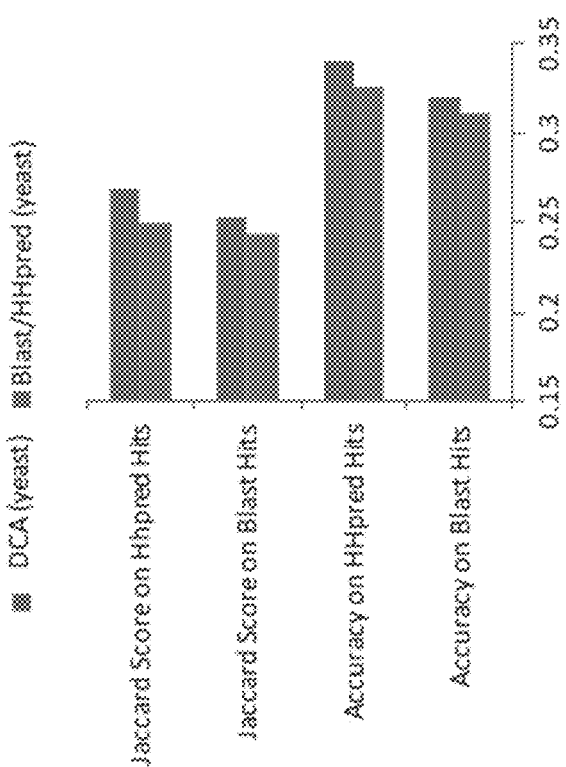
Figure 8C:
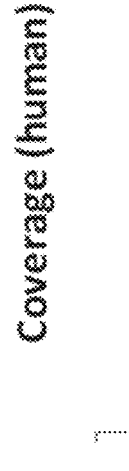
Figure 8D:
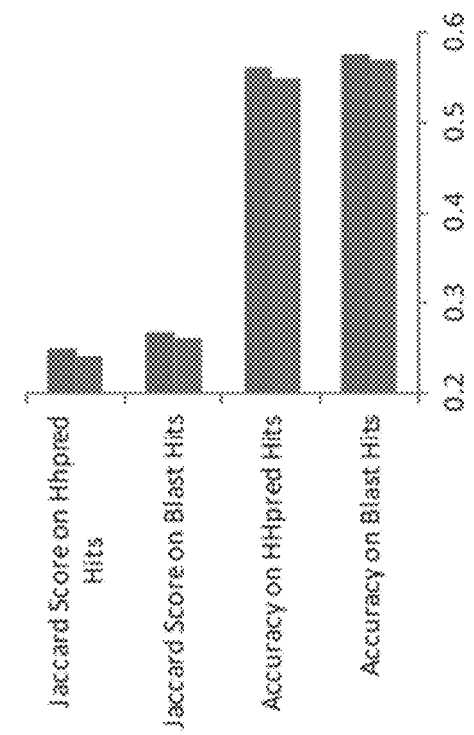

To evaluate the functional association between yeast proteins and the predicted human homologs, we computed the average accuracy of Gene Ontology (GO) of the top 5 homologs predicted by our method, HHpred and BLAST (Altschul et al., 1997; 1990; Ashburner et al., 2000; Tuncbag et al., 2013) (FIG. 8B). We chose the top 5 homologs since yeast proteins often have more than one good human homolog. The accuracy of a homolog was calculated as the percentage of overlapped GO labels between the yeast protein and the putative homolog. We noted that the number of assigned GO labels per gene varied considerably between yeast and human proteomes, so that the GO accuracy metric favored predicted homologs with a large number of labels and query proteins with a small number of GO labels, potentially biasing the analysis. Furthermore, false positives were not considered by this metric. To address these issues, we computed the widely used Jaccard similarity score, which is the number of overlapping GO labels divided by the total number of unique GO labels of the yeast (or human) gene and its human (or yeast) homolog. BLAST's accuracy for 4023 yeast proteins was 31.1%. HHpred in conjunction with BLAST achieved of 32.6% for accuracy for 4312 yeast proteins. Our method obtained 31.6% accuracy for a significantly greater number, 4923, of yeast proteins. It also outperformed BLAST on 4023 yeast proteins with BLAST output (32.0% vs 31.1% accuracy and 25.2% vs 24.3% Jaccard similarity) and HHpred on 4312 proteins with HHpred output (34.1% vs 32.6% accuracy and 26.9% vs 24.9% Jaccard Similarity). The improvements over BLAST and HHpred were significant (paired t-test p-values <0.01).

We then tested our method on finding yeast homologs for human proteins (FIGS. 3C and 3D). The improvement of the coverage over BLAST and HHpred was even more substantial than for generating human homologs from yeast proteins. Our method predicted homologs for 15200 proteins but BLAST and HHpred only covered a relatively small portion of human proteome (7248 and 9577 respectively). Accuracy metrics also favored the DCA method. Our method improved the predictive power over BLAST (57.6% vs 57% accuracy and 26% vs 26.6% Jaccard similarity) and HHpred (56% vs 54.9% accuracy and 25% vs 24.2% Jaccard similarity) on proteins which BLAST or HHpred can find yeast homologs on both GO accuracy and Jaccard similarity score. These comparisons were all statistically significant (all p-values <0.01 by paired t-test).

We also compared our homology tool to the state-of-the-art Ensembl Compara method. Ensembl Compara identifies high confidence homolog pairs through phylogenetic tree-based clustering and analysis across multiple species. This sequence-based method sacrifices coverage for accuracy, and these pairs are considered a gold standard for traditional analyses (Vilella et al., 2009). We downloaded the Ensembl Compara v85, and mapped gene ids to the gene names used in our homology tool, identifying 5093 high-confidence yeast/human pairs for 2409 yeast genes. Among these pairs, there are three major categories: "one-to-one", "one-to-many" and "many-to-many". To evaluate our DCA homology tool, we checked whether it performed at least as well for high-confidence yeast/human pairs, whether predicted as one-to-one, one-to-many or many-to-many by Ensembl Compara. Since orthology relationships between human and yeast genes can be ambiguous due to their remote evolutionary distance, DCA and Ensemble Compara may predict different putative homologs, especially for the many-to-many case. For such cases, we also computed the GO accuracy as the percentage of overlapping GO labels between a yeast protein and the predicted homolog. For clear one-to-one pairs by Ensembl Compara, DCA differed in only 25 of 1040 genes. Of those 25 genes that differed, our method achieved comparable accuracy in ontology prediction (0.394) as compared to Ensembl Compara (0.388) based on ontology matching. There were 1518 entries in the "many2many" prediction category. For these, our method achieved a correct pairing (0.414) equivalent to Ensembl Compara (0.412). Finally, for the yeast genes in which a one-to-many correspondence was predicted, there were 2535 entries. Again, our method identified homologs by gene ontology (0.391) similar to Ensembl Compara (0.390). Among the differences, we observed most of them to be similar genes within the same family; moreover, these differences are not statistically significant. Thus, our approach does not disrupt homology prediction for high-confidence orthology pairs, a surrogate for false-positivity in the absence of any other gold standard yeast-to-human homolog pairing. From these results, we demonstrated that DCA provides comparable yeast-to-human accuracy as Ensembl Compara for the same input yeast genes.

Recently, Kachroo et al. (Kachroo et al., 2015) carefully tested 414 essential yeast genes for complementation by homologs that were clear by sequence. Thus, for each of these 414 yeast/human gene pairs, the complementation assay provided a binary and experimentally strong readout of homology. Kachroo et al. developed a method to predict which of these high confidence pairs were likely to be actual positive complementation pairs. They utilized more than 100 features, including careful manual curation of sequence properties, network features, transcriptional and translational features, and expression abundances, to establish a predictive tool. They showed that this predictive tool could be trained on a subset of the experimentally tested yeast/human pairs to correctly identify functional replaceability in a separate test set. To demonstrate the effectiveness of integration of DCA, we trained a DCA-based classifier, using only sequence and network information, to predicted true yeast-human complementation pairs. In particular, to check the predictive power of our DCA pipeline, we built a classifier based on the low-dimensional gene vectors obtained from our joint DCA learning pipeline. For each pair of yeast/human genes, we built features based on the gene vectors to consider their sequence similarity and topological roles in their molecular networks. These features, including element-wise product and difference and sum of two gene vectors, were used as input to a gradient boosted forest classifier. We tested whether this classifier, for our more elemental, automated DCA tool based on only sequence/network features, could be tuned to also predict the functional complementation between yeast and human. When we trained our DCA classifier via 5-fold cross-validation on the yeast/human pairs from Kachroo et al. we achieved a high rate of prediction accuracy (AUC=0.82, SD=0.08). This was comparable to the intricate, manual integrated method of Kachroo et al., demonstrating that our automated homology tool, based on only sequence and network topology, is sufficient for training a classifier for this specific homology task. It is worth noting that methods utilizing sequence-similarity alone, including BLAST and HHpred, performed considerably worse than DCA (0.70 and 0.69, respectively). It is clear that our DCA-based classifier, which effectively integrates network topology and sequence similarity, is just as effective as the method in Kachroo et al. that utilizes more than 100 features, thus overcoming the barrier of major time-consuming manual feature curation.

Evaluation of PCSF and Humanized Steiner Networks

We tested PCSF on two separate datasets and demonstrate vastly superior performance when compared to existing methods. For comparison, we identified two popular algorithms, DAPPLE (Rossin et al., 2011) and PEXA (Tu et al., 2009), and implemented them. Both methods take seed genes and identify subnetworks that span the seed genes to reveal possible functional interconnectedness of these genes. The first algorithm, DAPPLE, identifies significant direct and one-hop indirect edges in the human interactome to connect as many seed genes as possible. The second algorithm, PEXA, utilizes existing pathway annotations, such as KEGG or Reactome, to cover seed genes. Merging and pruning are then applied to link connected components and remove hanging genes. For these comparisons, we provided each algorithm with yeast-to-human homology links and injected yeast interaction edges into the human network, just as we provide for our PCSF method. For DAPPLE, we used the predicted dense network with significant one-hop indirect edges, since the sparse direct network is not able to identify hidden genes. We curated hits from 15 complete screens in yeast (Tong, 2004). In these screens, a gene is deleted as well as its genetic interactors or modifiers. We used these genetic modifiers as input for the network algorithms. The inactivated gene was hidden from the algorithm, and was used to evaluate the predicted network. Taking cues from previously-published methods (Yeger-Lotem et al., 2009), here we considered an algorithm successful in discovering the cellular response if the predicted hidden human genes were significantly enriched for specific gene ontology biological process terms attributed to the hidden inactivated yeast gene (hypergeometric test; p-value <0.01). We generated humanized networks with PCSF, and two alternative methods: DAPPLE (Rossin et al., 2011) and PEXA (Tu et al., 2009). For these screens, the success rate of PCSF was 47%, as compared to DAPPLE and PEXA which were 6.6% and 13%, respectively. These results suggest superior performance of PCSF over DAPPLE and PEXA.

To better understand the relevance of genes and predicted pathways recovered by PCSF, DAPPLE and PEXA, we designed a well-controlled simulation. To mimic genetic screens of perturbed pathways, we selected individual pathways from the well-known human pathway database KEGG and identified all genes in each pathway (Supplemental Table S15). We then identified yeast homologs via stringent Ensembl one-to-one mapping. We treated those human genes with clear yeast homologs as "perturbed" and picked their homologs' genetic interaction neighboring genes as hits from a "virtual yeast genetic screen". Virtual screens like these minimize experimental noise as a confounding factor and enable cleaner evaluation of algorithm performance. Since we know the "true" pathway information, this method can be used to test the sensitivity and specificity of algorithms by quantifying how often "relevant" genes in the original KEGG pathway are recovered as predicted (non-seed) genes. We chose 50 KEGG pathways that had at least 5 human genes with clear yeast homologs and created 50 associated "virtual" screens for testing (Table S15). We used two performance metrics: precision, i.e. the percentage of predicted hidden genes shown in the original KEGG pathway, and recall, i.e. the percentage of the original KEGG genes shown as hidden nodes in the predicted pathway. Ideally, these values would be 100% for perfect predictions. For PCSF, the average precision and recall values are 63% and 74% resp. In contrast, for DAPPLE, the average precision and recall values are 6% and 47% resp., whereas for PEXA, they are 8% and 83% resp. The differences between three precision values are substantial: PCSF has much higher precision within very compact subnetworks, while both DAPPLE and PEXA predict huge "hair ball" networks with low precision. It is worth noting that PEXA has a very high recall value likely because it uses the KEGG pathways to build networks, and thus predictably has high recall (because the simulated screens here are generated from KEGG pathways); however, its precision metric is very low.

TABLE S15. KEGG PATHWAYS FOR SIMULATIONS, Related to FIG. 2 and FIG. 9.

Further, we tested the effectiveness of injected yeast genetic interactions into networks through the simulated yeast genetic screens we generated, and cross-compare our PCSF method with the other algorithms, DAPPLE and PEXA. First, we tested performance by removing all injected yeast interactions. For PCSF, the average precision and recall values are 37% and 54% resp. For DAPPLE, the average precision and recall values are 8% and 27% resp. Compared to the precision and recall results (i.e., 63% and 74% for PCSF versus 6% and 47% for DAPPLE), it is clear that both PCSF and DAPPLE have much lower recall if yeast interactions are excluded. This analysis thus confirms with data that injection of yeast interactions into "humanized" networks provide key connections between genetic modifiers to the perturbed genes. For PEXA, the average precision value is 9%., similar to that with yeast injection, whereas the recall rate is again predictably very high. Secondly, we tested the effects of randomly removing a portion of injected genetic interactions over 10 trials. The average precision and recall values are shown in FIG. 9, demonstrating the relationship between the accuracy of these methods and the percentage of injected yeast interactions. A notable observation is that the performance becomes reasonable when >40% of interactions are injected. The performance of PEXA remains relatively unchanged because it utilizes the human KEGG pathway information in its algorithm, as noted above. In terms of false-positives and -negatives, there is clearly a trade-off between the different methods. PCSF works best for our current work, as PCSF identifies a small set of relevant genes for cost-effective experimental explorations.

Statistical Methods and Data Analysis for Cell-Based Assays

Sample sizes for all experimentation were chosen based on our previous extensive experience with the methods and assays in these studies. For most experiments in mammalian cells, robustness and consistency of the results are typically established after three biological replicates are analyzed. Unless otherwise stated in the figure legends, this was the standard number of replicates required for all experiments. For all human and rat cellular experiments, significance was then determined by appropriate statistical tests that are standard in the field. The two-tail t-test was applied when there were only two conditions to compare within the experiments. One-Way ANOVA with a multiple comparisons post-hoc test was performed when experiments include multiple conditions. Data points were excluded based on the following pre-established criteria: 1) errors were introduced to the particular sample while performing the experiments, 2) the values are greater or less than two standard deviation from the mean. For yeast spot assays, results were considered significant when three biological replicates (unless otherwise stated) demonstrated the same trend by eye. Methods used for FIG. 5E are outlined in the figure legend. For the pooled screen yeast assay (FIG. 4A, FIG. 11) detailed statistical methods for reads and cutoff thresholds are supplied above in the methods. The statistical methods for the computational analysis are described in detail in the methods sections above.

Data and Software Availability

The TransposeNet pipeline is described at http://transposenet.csail.mit.edu.

The DCA/Mashup web portal is http://mashup.csail.mit.edu. The PCSF web portal is http://fraenkel-nsf.csbi.mit.edu/omicsintearator/.

REFERENCES

Altschul, S. F., Gish, W., Miller, W., Myers, E. W., Lipman, D. J., 1990. Basic local alignment search tool. J Mol Biol 215, 403-410. doi:10.1016/S0022-2836(05)80360-2

Altschul, S. F., Madden, T. L., Schäffer, A. A., Zhang, J., Zhang, Z., Miller, W., Lipman, D. J., 1997. Gapped BLAST and PSI-BLAST: a new generation of protein database search programs. Nucleic Acids Res 25, 3389-3402.

Ashburner, M., Ball, C. A., Blake, J. A., Botstein, D., Butler, H., Cherry, J. M., Davis, A. P., Dolinski, K., Dwight, S. S., Eppig, J. T., Harris, M. A., Hill, D. P., Issel-Tarver, L., Kasarskis, A., Lewis, S., Matese, J. C., Richardson, J. E., Ringwald, M., Rubin, G. M., Sherlock, G., 2000. Gene ontology: tool for the unification of biology. The Gene Ontology Consortium. Nat Genet 25, 25-29. doi:10.1038/75556

Bailly-Bechet, M., Borgs, C., Braunstein, A., Chayes, J., Dagkessamanskaia, A., Franeois, J.-M., Zecchina, R., 2011. Finding undetected protein associations in cell signaling by belief propagation. Proc Nal Acad Sci USA 108, 882-887. doi:10.1073/pnas.1004751108

Baryshnikova, A., Costanzo, M., Kim, Y., Ding, H., Koh, J., Toufighi, K., Youn, J.-Y., Ou, J., San Luis, B.-J., Bandyopadhyay, S., Hibbs, M., Hess, D., Gingras, A.-C., Bader, G. D., Troyanskaya, O. G., Brown, G. W., Andrews, B., Boone, C., Myers, C. L., 2010. Quantitative analysis of fitness and genetic interactions in yeast on a genome scale. Nat Methods 7, 1017-1024. doi:10.1038/nmeth.1534

Beilina, A., Rudenko, I. N., Kaganovich, A., Civiero, L., Chau, H., Kalia, S. K., Kalia, L. V., Lobbestael, E., Chia, R., Ndukwe, K., Ding, J., Nalls, M. A., International Parkinson's Disease Genomics Consortium, North American Brain Expression Consortium, Olszewski, M., Hauser, D. N., Kumaran, R., Lozano, A. M., Baekelandt, V., Greene, L. E., Taymans, J.-M., Greggio, E., Cookson, M. R., 2014. Unbiased screen for interactors of leucine-rich repeat kinase 2 supports a common pathway for sporadic and familial Parkinson disease. Proc Natl Acad Sci USA 111, 2626-2631. doi:10.1073/pnas.1318306111

Berger, B., Peng, J., Singh, M., 2013. Computational solutions for omics data. Nat Rev Genet 14, 333-346. doi:10.1038/nrg3433

Bras, J., Guerreiro, R., Hardy, J., 2015. SnapShot: Genetics of Parkinson's Disease. Cell 160, 570-570.el. doi:10.1016/j.cell.2015.01.019

Caraveo, G., Auluck, P. K., Whitesell, L., Chung, C. Y., Baru, V., Mosharov, E. V., Yan, X., Ben-Johny, M., Soste, M., Picotti, P., Kim, H., Caldwell, K. A., Caldwell, G. A., Sulzer, D., Yue, D. T., Lindquist, S., 2014. Calcineurin determines toxic versus beneficial responses to -synuclein. Proc Natl Acad Sci USA. doi:10.1073/pnas.1413201111

Casals, F., Bertranpetit, J., 2012. Human Genetic Variation, Shared and Private. Science 337, 39-40. doi:10.1126/science.1224528

Chambers, S. M., Fasano, C. A., Papapetrou, E. P., Tomishima, M., Sadelain, M., Studer, L., 2009. Highly efficient neural conversion of human ES and iPS cells by dual inhibition of SMAD signaling. Nat Biotechnol 27, 275-280. doi:10.1038/nbt.1529

Chartier-Harlin, M.-C., Dachsel, J. C., Vilariflo-Giell, C., Lincoln, S. J., Leprêtre, F., Hulihan, M. M., Kachergus, J., Milnerwood, A. J., Tapia, L., Song, M.-S., Le Rhun, E., Mutez, E., Larvor, L., Duflot, A., Vanbesien-Mailliot, C., Kreisler, A., Ross, O. A., Nishioka, K., Soto-Ortolaza, A. I., Cobb, S. A., Melrose, H. L., Behrouz, B., Keeling, B. H., Bacon, J. A., Hentati, E., Williams, L., Yanagiya, A., Sonenberg, N., Lockhart, P. J., Zubair, A. C., Uitti, R. J., Aasly, J. O., Krygowska-Wajs, A., Opala, G., Wszolek, Z. K., Frigerio, R., Maraganore, D. M., Gosal, D., Lynch, T., Hutchinson, M., Bentivoglio, A. R., Valente, E. M., Nichols, W. C., Pankratz, N., Foroud, T., Gibson, R. A., Hentati, F., Dickson, D. W., Destée, A., Farrer, M. J., 2011. Translation Initiator EIF4G1 Mutations in Familial Parkinson Disease. Am J Hum Genet 89, 398-406. doi:10.1016/j.ajhg.2011.08.009

Cho, H., Peng, J., Berger, B., 2015 Diffusion Component Analysis: Unraveling Functional Topology in Biological Networks. RECOMB.

Cho, H., Berger, B., Peng, J., 2016. Mashup: Compact Integration of Multi-Network Topology for Functional Analysis of Genes. Cell Systems In Press.

Cho, H. J., Yu, J., Xie, C., Rudrabhatla, P., Chen, X., Wu, J., Parisiadou, L., Liu, G., Sun, L., Ma, B., Ding, J., Liu, Z., Cai, H., 2014. Leucine-rich repeat kinase 2 regulates Sec16A at ER exit sites to allow ER-Golgi export. Embo J 33, 2314-2331. doi:10.15252/embj.201487807

Chung, C. Y., Khurana, V., Auluck, P. K., Tardiff, D. F., Mazzulli, J. R., Soldner, F., Baru, V., Lou, Y., Freyzon, Y., Cho, S., Mungenast, A. E., Muffat, J., Mitalipova, M., Pluth, M. D., Jui, N. T., Schile, B., Lippard, S. J., Tsai, L.-H., Krainc, D., Buchwald, S. L., Jaenisch, R., Lindquist, S., 2013. Identification and rescue of α-synuclein toxicity in Parkinson patient-derived neurons. Science 342, 983-987. doi:10.1126/science.1245296

Cooper, A. A., Gitler, A. D., Cashikar, A., Haynes, C. M., Hill, K. J., Bhullar, B., Liu, K., Xu, K., Strathearn, K. E., Liu, F., Cao, S., Caldwell, K. A., Caldwell, G. A., Marsischky, G., Kolodner, R. D., LaBaer, J., Rochet, J.-C., Bonini, N. M., Lindquist, S., 2006. Alpha-synuclein blocks ER-Golgi traffic and Rab1 rescues neuron loss in Parkinson's models. Science 313, 324-328. doi:10.1126/science.1129462

Dhungel, N., Eleuteri, S., Li, L.-B., Kramer, N. J., Chartron, J. W., Spencer, B., Kosberg, K., Fields, J. A., Stafa, K., Adame, A., Lashuel, H., Frydman, J., Shen, K., Masliah, E., Gitler, A. D., 2014. Parkinson's Disease Genes VPS35 and EIF4G1 Interact Genetically and Converge on α-Synuclein. Neuron. doi:10.1016/j.neuron.2014.11.027

Elden, A. C., Kim, H.-J., Hart, M. P., Chen-Plotkin, A. S., Johnson, B. S., Fang, X., Armakola, M., Geser, F., Greene, R., Lu, M. M., Padmanabhan, A., Clay-Falcone, D., McCluskey, L., Elman, L., Juhr, D., Gruber, P. J., Rüb, U., Auburger, G., Trojanowski, J. Q., Lee, V. M.-Y., Van Deerlin, V. M., Bonini, N. M., Gitler, A. D., 2010. Ataxin-2 intermediate-length polyglutamine expansions are associated with increased risk for ALS. Nature 466, 1069-1075. doi:10.1038/nature09320

Fuchs, J., Tichopad, A., Golub, Y., Munz, M., Schweitzer, K. J., Wolf, B., Berg, D., Mueller, J. C., Gasser, T., 2008. Genetic variability in the SNCA gene influences alpha-synuclein levels in the blood and brain. Faseb J 22, 1327-1334. doi:10.1096/fj.07-9348com Funayama, M., Ohe, K., Amo, T., Furuya, N., Yamaguchi, J., Saiki, S., Li, Y., Ogaki, K., Ando, M., Yoshino, H., Tomiyama, H., Nishioka, K., Hasegawa, K., Saiki, H., Satake, W., Mogushi, K., Sasaki, R., Kokubo, Y., Kuzuhara, S., Toda, T., Mizuno, Y., Uchiyama, Y., Ohno, K., Hattori, N., 2015. CHCHD2 mutations in autosomal dominant late-onset Parkinson's disease: a genome-wide linkage and sequencing study. Lancet Neurol 14, 274-282. doi:10.1016/S1474-4422(14)70266-2

Geetha, V., Di Francesco, V., Garnier, J., Munson, P. J., 1999. Comparing protein sequence-based and predicted secondary structure-based methods for identification of remote homologs. Protein Eng. 12, 527-534.

Gehrke, S., Wu, Z., Klinkenberg, M., Sun, Y., Auburger, G., Guo, S., Lu, B., 2015. PINK1 and Parkin control localized translation of respiratory chain component mRNAs on mitochondria outer membrane. Cell Metab. 21, 95-108. doi:10.1016/j.cmet.2014.12.007

Gietz, D., St Jean, A., Woods, R. A., Schiestl, R. H., 1992. Improved method for high efficiency transformation of intact yeast cells. Nucleic Acids Res 20, 1425.

Gietz, R. D., Schiestl, R. H., Willems, A. R., Woods, R. A., 1995. Studies on the transformation of intact yeast cells by the LiAc/SS-DNA/PEG procedure. Yeast 11, 355-360. doi:10.1002/yea.320110408

GTEx Consortium, 2013. The Genotype-Tissue Expression (GTEx) project. Nat Genet 45, 580-585. doi:10.1038/ng.2653

Guerreiro, R., Bras, J., Hardy, J., 2015. SnapShot: Genetics of ALS and FTD. Cell 160, 798-798.e1. doi:10.1016/j.cell.2015.01.052

Hasson, S. A., Kane, L. A., Yamano, K., Huang, C.-H., Sliter, D. A., Buehler, E., Wang, C., Heman-Ackah, S. M., Hessa, T., Guha, R., Martin, S. E., Youle, R. J., 2013. High-content genome-wide RNAi screens identify regulators of parkin upstream of mitophagy. Nature 504, 291-295. doi:10.1038/nature12748

Hu, Y., Flockhart, I., Vinayagam, A., Bergwitz, C., Berger, B., Perrimon, N., Mohr, S. E., 2011. An integrative approach to ortholog prediction for disease-focused and other functional studies. BMC Bioinformatics 12, 357. doi:10.1186/1471-2105-12-357

Hu, Y., Rolfs, A., Bhullar, B., Murthy, T. V. S., Zhu, C., Berger, M. F., Camargo, A. A., Kelley, F., McCarron, S., Jepson, D., Richardson, A., Raphael, J., Moreira, D., Taycher, E., Zuo, D., Mohr, S., Kane, M. F., Williamson, J., Simpson, A., Bulyk, M. L., Harlow, E., Marsischky, G., Kolodner, R. D., LaBaer, J., 2007. Approaching a complete repository of sequence-verified protein-encoding clones for Saccharomyces cerevisiae. Genome Res 17, 536-543. doi:10.1101/gr.6037607

Huang, S.-S. C., Fraenkel, E., 2009. Integrating proteomic, transcriptional, and interactome data reveals hidden components of signaling and regulatory networks. Science signaling 2, ra40. doi:10.1126/scisignal.2000350

Huang, Z., Chen, K., Zhang, J., Li, Y., Wang, H., Cui, D., Tang, J., Liu, Y., Shi, X., Li, W., Liu, D., Chen, R., Sucgang, R. S., Pan, X., 2013. A functional variomics tool for discovering drug-resistance genes and drug targets. CellReports 3, 577-585. doi:10.1016/j.celrep.2013.01.019

Kachroo, A. H., Laurent, J. M., Yellman, C. M., Meyer, A. G., Wilke, C. O., Marcotte, E. M., 2015. Evolution. Systematic humanization of yeast genes reveals conserved functions and genetic modularity. Science 348, 921-925. doi:10.1126/science.aaa0769

Khurana, V., Lindquist, S., 2010. Modelling neurodegeneration in *Saccharomyces cerevisiae*: why cook with baker's yeast? Nat Rev Neurosci 11, 436-449. doi:10.1038/nrn2809

Khurana, V., Tardiff, D. F., Chung, C. Y., Lindquist, S., 2015. Toward stem cell-based phenotypic screens for neurodegenerative diseases. Nat Rev Neurol 11, 339-350. doi:10.1038/nrneurol.2015.79

Kim, H.-J., Raphael, A. R., LaDow, E. S., McGurk, L., Weber, R. A., Trojanowski, J. Q., Lee, V. M.-Y., Finkbeiner, S., Gitler, A. D., Bonini, N. M., 2013. Therapeutic modulation of eIF2. Nat Genet 46, 152-160. doi:10.1038/ng.2853

Kim, J.-E., O'Sullivan, M. L., Sanchez, C. A., Hwang, M., Israel, M. A., Brennand, K., Deerinck, T. J., Goldstein, L. S. B., Gage, F. H., Ellisman, M. H., Ghosh, A., 2011. Investigating synapse formation and function using human pluripotent stem cell-derived neurons. Proc Natd Acad Sci USA 108, 3005-3010. doi:10.1073/pnas.1007753108

Konermann, S., Brigham, M. D., Trevino, A. E., Joung, J., Abudayyeh, O. O., Barcena, C., Hsu, P. D., Habib, N., Gootenberg, J. S., Nishimasu, H., Nureki, O., Zhang, F., 2014. Genome-scale transcriptional activation by an engineered CRISPR-Cas9 complex. Nature. doi:10.1038/nature14136

Kong, S. M. Y., Chan, B. K. K., Park, J.-S., Hill, K. J., Aitken, J. B., Cottle, L., Farghaian, H., Cole, A. R., Lay, P. A., Sue, C. M., Cooper, A. A., 2014. Parkinson's disease-linked human PARK9/ATP13A2 maintains zinc homeostasis and promotes α-Synuclein externalization via exosomes. Hum Mol Genet 23, 2816-2833. doi:10.1093/hmg/ddu099

Kriks, S., Shim, J.-W., Piao, J., Ganat, Y. M., Wakeman, D. R., Xie, Z., Carrillo-Reid, L., Auyeung, G., Antonacci, C., Buch, A., Yang, L., Beal, M. F., Surmeier, D. J., Kordower, J. H., Tabar, V., Studer, L., 2011. Dopamine neurons derived from human ES cells efficiently engraft in animal models of Parkinson's disease. Nature 480, 547-551. doi:10.1038/nature10648

Langmead, B., Trapnell, C., Pop, M., Salzberg, S. L., 2009. Ultrafast and memory-efficient alignment of short DNA sequences to the human genome. Genome Biol 10, R25. doi:10.1186/gb-2009-10-3-r25

Liu, G., Aliaga, L., Cai, H., 2012. α-synuclein, LRRK2 and their interplay in Parkinson's disease. Future Neurol 7, 145-153.

Liu, Z., Guo, J., Li, K., Qin, L., Kang, J., Shu, L., Zhang, Y., Wei, Y., Yang, N., Luo, Y., Sun, Q., Xu, Q., Yan, X., Tang, B., 2015. Mutation analysis of CHCHD2 gene in Chinese familial Parkinson's disease. Neurobiol Aging 36, 3117.e7-8. doi:10.1016/j.neurobiolaging.2015.08.010

Macleod, D. A., Rhinn, H., Kuwahara, T., Zolin, A., Di Paolo, G., Maccabe, B. D., Marder, K. S., Honig, L. S., Clark, L. N., Small, S. A., Abeliovich, A., 2013. RAB7L1 Interacts with LRRK2 to Modify Intraneuronal Protein Sorting and Parkinson's Disease Risk. Neuron 77, 425-439. doi:10.1016/j.neuron.2012.11.033

Martin, I., Dawson, V. L., Dawson, T. M., 2011. Recent Advances in the Genetics of Parkinson's Disease. Annual review of genomics and human genetics 12, 301-325. doi:10.1146/annurev-genom-082410-101440

Martin, I., Kim, J. W., Lee, B. D., Kang, H. C., Xu, J.-C., Jia, H., Stankowski, J., Kim, M.-S., Zhong, J., Kumar, M., Andrabi, S. A., Xiong, Y., Dickson, D. W., Wszolek, Z. K., Pandey, A., Dawson, T. M., Dawson, V. L., 2014. Ribosomal protein s15 phosphorylation mediates LRRK2 neurodegeneration in Parkinson's disease. Cell 157, 472-485. doi:10.1016/j.cell.2014.01.064

Nalls, M. A., Pankratz, N., Lill, C. M., Do, C. B., Hernandez, D. G., Saad, M., DeStefano, A. L., Kara, E., Bras, J., Sharma, M., Schulte, C., Keller, M. F., Arepalli, S., Letson, C., Edsall, C., Stefinsson, H., Liu, X., Pliner, H., Lee, J. H., Cheng, R., Ikram, M. A., Ioannidis, J. P. A., Hadjigeorgiou, G. M., Bis, J. C., Martinez, M., Perlmutter, J. S., Goate, A., Marder, K., Fiske, B., Sutherland, M., Xiromerisiou, G., Myers, R. H., Clark, L. N., Stefansson, K., Hardy, J. A., Heutink, P., Chen, H., Wood, N. W., Houlden, H., Payami, H., Brice, A., Scott, W. K., Gasser, T., Bertram, L., Eriksson, N., Foroud, T., Singleton, A. B., 2014. Large-scale meta-analysis of genome-wide association data identifies six new risk loci for Parkinson's disease. Nat Genet 1-7. doi:10.1038/ng.3043

Nelson, M. R., Wegmann, D., Ehm, M. G., Kessner, D., St Jean, P., Verzilli, C., Shen, J., Tang, Z., Bacanu, S.-A., Fraser, D., Warren, L., Aponte, J., Zawistowski, M., Liu, X., Zhang, H., Zhang, Y., Li, J., Li, Y., Li, L., Woollard, P., Topp, S., Hall, M. D., Nangle, K., Wang, J., Abecasis, G., Cardon, L. R., Zöllner, S., Whittaker, J. C., Chissoe, S. L., Novembre, J., Mooser, V., 2012. An abundance of rare functional variants in 202 drug target genes sequenced in 14,002 people. Science 337, 100-104. doi:10.1126/science.1217876

Nuytemans, K., Bademci, G., Inchausti, V., Dressen, A., Kinnamon, D. D., Mehta, A., Wang, L., Zuchner, S., Beecham, G. W., Martin, E. R., Scott, W. K., Vance, J. M., 2013. Whole exome sequencing of rare variants in EIF4G1 and VPS35 in Parkinson disease. Neurology 80, 982-989. doi:10.1212/WNL.0b013e31828727d4

Nykjaer, A., Willnow, T. E., 2012. Sortilin: a receptor to regulate neuronal viability and function. Trends Neurosci 35, 261-270. doi:10.1016/j.tins.2012.01.003

Ogaki, K., Koga, S., Heckman, M. G., Fiesel, F. C., Ando, M., Labbé, C., Lorenzo-Betancor, O., Moussaud-Lamodière, E. L., Soto-Ortolaza, A. I., Walton, R. L., Strongosky, A. J., Uitti, R. J., McCarthy, A., Lynch, T., Siuda, J., Opala, G., Rudzinska, M., Krygowska-Wajs, A., Barcikowska, M., Czyzewski, K., Puschmann, A., Nishioka, K., Funayama, M., Hattori, N., Parisi, J. E., Petersen, R. C., Graff-Radford, N. R., Boeve, B. F., Springer, W., Wszolek, Z. K., Dickson, D. W., Ross, O. A., 2015. Mitochondrial targeting sequence variants of the CHCHD2 gene are a risk for Lewy body disorders. Neurology 10.1212/WNL.0000000000002170. doi:10.1212/WNL.0000000000002170

Olgiati, S., De Rosa, A., Quadri, M., Criscuolo, C., Breedveld, G. J., Picillo, M., Pappati, S., Quarantelli, M., Barone, P., De Michele, G., Bonifati, V., 2014. PARK20 caused by SYNJ1 homozygous Arg258Gln mutation in a new Italian family. Neurogenetics 15, 183-188. doi:10.1007/s10048-014-0406-0

Osborn, M. J., Miller, J. R., 2007. Rescuing yeast mutants with human genes. Brief Funct Genomic Proteomic 6, 104-111. doi:10.1093/bfgp/elm017

Outeiro, T. F., Lindquist, S., 2003. Yeast cells provide insight into alpha-synuclein biology and pathobiology. Science 302, 1772-1775. doi:10.1126/science.1090439

Park, J.-S., Koentjoro, B., Veivers, D., Mackay-Sim, A., Sue, C. M., 2014. Parkinson's disease-associated human ATP13A2 (PARK9) deficiency causes zinc dyshomeostasis and mitochondrial dysfunction. Hum Mol Genet 23, 2802-2815. doi:10.1093/hmg/ddt623

Rajput, A., Dickson, D. W., Robinson, C. A., Ross, O. A., Dichsel, J. C., Lincoln, S. J., Cobb, S. A., Rajput, M. L., Farrer, M. J., 2006. Parkinsonism, Lrrk2 G2019S, and tau neuropathology. Neurology 67, 1506-1508. doi:10.1212/01.wnl.0000240220.33950.0c Ramonet, D., Podhajska, A., Stafa, K., Sonnay, S., Trancikova, A., Tsika, E., Pletnikova, O., Troncoso, J. C., Glauser, L., Moore, D. J., 2012. PARK9-associated ATP13A2 localizes to intracellular acidic vesicles and regulates cation homeostasis and neuronal integrity. Hum Mol Genet 21, 1725-1743. doi:10.1093/hmg/ddr606

Reinhardt, P., Schmid, B., Burbulla, L. F., Schandorf, D. C., Wagner, L., Glatza, M., Höing, S., Hargus, G., Heck, S. A., Dhingra, A., Wu, G., Miiller, S., Brockmann, K., Kluba, T., Maisel, M., Kruger, R., Berg, D., Tsytsyura, Y., Thiel, C. S., Psathaki, O.-E., Klingauf, J., Kuhlmann, T., Klewin, M., Miller, H., Gasser, T., Schuler, H. R., Sterneckert, J., 2013. Genetic correction of a LRRK2 mutation in human iPSCs links parkinsonian neurodegeneration to ERK-dependent changes in gene expression. Cell Stem cell 12, 354-367. doi:10.1016/j.stem.2013.01.008

Robinson, M. D., Oshlack, A., 2010. A scaling normalization method for differential expression analysis of RNA-seq data. Genome Biol 11, R25. doi:10.1186/gb-2010-11-3-r25

Rogaeva, E., Meng, Y., Lee, J. H., Gu, Y., Kawarai, T., Zou, F., Katayama, T., Baldwin, C. T., Cheng, R., Hasegawa, H., Chen, F., Shibata, N., Lunetta, K. L., Pardossi-Piquard, R., Bohm, C., Wakutani, Y., Cupples, L. A., Cuenco, K. T., Green, R. C., Pinessi, L., Rainero, I., Sorbi, S., Bruni, A., Duara, R., Friedland, R. P., Inzelberg, R., Hampe, W., Bujo, H., Song, Y.-Q., Andersen, O. M., Willnow, T. E., Graff-Radford, N., Petersen, R. C., Dickson, D., Der, S. D., Fraser, P. E., Schmitt-Ulms, G., Younkin, S., Mayeux, R., Farrer, L. A., St George-Hyslop, P., 2007. The neuronal sortilin-related receptor SORL1 is genetically associated with Alzheimer disease. Nat Genet 39, 168-177. doi:10.1038/ng1943

Rolland, T., Tagan, M., Charloteaux, B., Pevzner, S. J., Zhong, Q., Sahni, N., Yi, S., Lemmens, I., Fontanillo, C., Mosca, R., Kamburov, A., Ghiassian, S. D., Yang, X., Ghamsari, L., Balcha, D., Begg, B. E., Braun, P., Brehme, M., Broly, M. P., Carvunis, A.-R., Convery-Zupan, D., Corominas, R., Coulombe-Huntington, J., Dann, E., Dreze, M., Dricot, A., Fan, C., Franzosa, E., Gebreab, F., Gutierrez, B. J., Hardy, M. F., Jin, M., Kang, S., Kiros, R., Lin, G. N., Luck, K., MacWilliams, A., Menche, J., Murray, R. R., Palagi, A., Poulin, M. M., Rambout, X., Rasla, J., Reichert, P., Romero, V., Ruyssinck, E., Sahalie, J. M., Scholz, A., Shah, A. A., Sharma, A., Shen, Y., Spirohn, K., Tam, S., Tejeda, A. O., Trigg, S. A., Twizere, J.-C., Vega, K., Walsh, J., Cusick, M. E., Xia, Y., Barabisi, A.-L., Iakoucheva, L. M., Aloy, P., Las Rivas, De, J., Tavernier, J., Calderwood, M. A., Hill, D. E., Hao, T., Roth, F. P., Vidal, M., 2014. A proteome-scale map of the human interactome network. Cell 159, 1212-1226. doi:10.1016/j.cell.2014.10.050

Rossin, E. J., Lage, K., Raychaudhuri, S., Xavier, R. J., Tatar, D., Benita, Y., International Inflammatory Bowel Disease Genetics Consortium, Cotsapas, C., Daly, M. J., 2011. Proteins encoded in genomic regions associated with immune-mediated disease physically interact and suggest underlying biology. PLoS Genet 7, e1001273. doi:10.1371/journal.pgen.1001273

Sanjana, N. E., Cong, L., Zhou, Y., Cunniff, M. M., Feng, G., Zhang, F., 2012. A transcription activator-like effector toolbox for genome engineering. Nat Protoc 7, 171-192. doi:10.1038/nprot.2011.431

Schneider, S. A., Paisan-Ruiz, C., Quinn, N. P., Lees, A. J., Houlden, H., Hardy, J., Bhatia, K. P., 2010. ATP13A2 mutations (PARK9) cause neurodegeneration with brain iron accumulation. Mov Disord 25, 979-984. doi:10.1002/mds.22947

Schöndorf, D. C., Aureli, M., McAllister, F. E., Hindley, C. J., Mayer, F., Schmid, B., Sardi, S. P., Valsecchi, M., Hoffmann, S., Schwarz, L. K., Hedrich, U., Berg, D., Shihabuddin, L. S., Hu, J., Pruszak, J., Gygi, S. P., Sonnino, S., Gasser, T., Deleidi, M., 2014. iPSC-derived neurons from GBA1-associated Parkinson's disease patients show autophagic defects and impaired calcium homeostasis. Nature Communications 5, 1-17. doi:10.1038/ncomms5028

Seaman, M. N., Marcusson, E. G., Cereghino, J. L., Emr, S. D., 1997. Endosome to Golgi retrieval of the vacuolar protein sorting receptor, Vps10p, requires the function of the VPS29, VPS30, and VPS35 gene products. J Cell Biol 137, 79-92.

Shalem, O., Sanjana, N. E., Hartenian, E., Shi, X., Scott, D. A., Mikkelsen, T. S., Heckl, D., Ebert, B. L., Root, D. E., Doench, J. G., Zhang, F., 2014. Genome-scale CRISPR-Cas9 knockout screening in human cells. Science 343, 84-87. doi:10.1126/science.1247005

Shulman, J. M., De Jager, P. L., Feany, M. B., 2010. Parkinson's Disease: Genetics and Pathogenesis. Annual review of pathology. doi:10.1146/annurev-pathol-011110-130242

Singh, R., Xu, J., Berger, B., 2008. Global alignment of multiple protein interactionnetworks with application to functionalorthology detection. Proc Natd Acad Sci USA 105, 12763-12768.

Small, S. A., Kent, K., Pierce, A., Leung, C., Kang, M. S., Okada, H., Honig, L., Vonsattel, J.-P., Kim, T.-W., 2005. Model-guided microarray implicates the retromer complex in Alzheimer's disease. Ann Neurol 58, 909-919. doi:10.1002/ana.20667

Soldner, F., Laganiere, J., Cheng, A. W., Hockemeyer, D., Gao, Q., Alagappan, R., Khurana, V., Golbe, L. I., Myers, R. H., Lindquist, S., Zhang, L., Guschin, D., Fong, L. K., Vu, B. J., Meng, X., Urnov, F. D., Rebar, E. J., Gregory, P. D., Zhang, H. S., Jaenisch, R., 2011. Generation of isogenic pluripotent stem cells differing exclusively at two early onset Parkinson point mutations. Cell 146, 318-331. doi:10.1016/j.cell.2011.06.019

Soper, J. H., Kehm, V., Burd, C. G., Bankaitis, V. A., Lee, V. M.-Y., 2011. Aggregation of α-Synuclein in S. cerevisiae is Associated with Defects in Endosomal Trafficking and Phospholipid Biosynthesis. J Mol Neurosci 43, 391-405. doi:10.1007/s12031-010-9455-5

Söding, J., Biegert, A., Lupas, A. N., 2005. The HHpred interactive server for protein homology detection and structure prediction. Nucleic Acids Res 33, W244-8. doi:10.1093/nar/gki408

Subtelny, A. O., Eichhorn, S. W., Chen, G. R., Sive, H., Bartel, D. P., 2014. Poly(A)-tail profiling reveals an embryonic switch in translational control. Nature 508, 66-71. doi:10.1038/nature13007

Szklarczyk, D., Franceschini, A., Wyder, S., Forslund, K., Heller, D., Huerta-Cepas, J., Simonovic, M., Roth, A., Santos, A., Tsafou, K. P., Kuhn, M., Bork, P., Jensen, L. J., Mering, von, C., 2014. STRING v10: protein-protein interaction networks, integrated over the tree of life. Nucleic Acids Res. doi:10.1093/nar/gku1003

Tarazona, S., Garcia-Alcalde, F., Dopazo, J., Ferrer, A., Conesa, A., 2011. Differential expression in RNA-seq: a matter of depth. Genome Res 21, 2213-2223. doi: 10.1101/gr.124321.111

Tardiff, D. F., Jui, N. T., Khurana, V., Tambe, M. A., Thompson, M. L., Chung, C. Y., Kamadurai, H. B., Kim, H. T., Lancaster, A. K., Caldwell, K. A., Caldwell, G. A., Rochet, J.-C., Buchwald, S. L., Lindquist, S., 2013. Yeast reveal a "druggable" Rsp5/Nedd4 network that ameliorates α-synuclein toxicity in neurons. Science 342, 979-983. doi:10.1126/science.1245321

Tardiff, D. F., Khurana, V., Chung, C. Y., Lindquist, S., 2014. From yeast to patient neurons and back again: A powerful new discovery platform. Mov Disord 10, 1231-1240. doi:10.1002/mds.25989

Tennessen, J. A., Bigham, A. W., O'Connor, T. D., Fu, W., Kenny, E. E., Gravel, S., McGee, S., Do, R., Liu, X., Jun, G., Kang, H. M., Jordan, D., Leal, S. M., Gabriel, S., Rieder, M. J., Abecasis, G., Altshuler, D., Nickerson, D. A., Boerwinkle, E., Sunyaev, S., Bustamante, C. D., Bamshad, M. J., Akey, J. M., Broad G O, Seattle G O, NHLBI Exome Sequencing Project, 2012. Evolution and functional impact of rare coding variation from deep sequencing of human exomes. Science 337, 64-69. doi:10.1126/science.1219240

Tong, A. H. Y., 2004. Global Mapping of the Yeast Genetic Interaction Network. Science 303, 808-813. doi:10.1126/science.1091317

Tong, A. H. Y., Boone, C., 2006. Synthetic genetic array analysis in *Saccharomyces cerevisiae*. Methods Mol Biol 313, 171-192.

Treusch, S., Hamamichi, S., Goodman, J. L., Matlack, K. E. S., Chung, C. Y., Baru, V., Shulman, J. M., Parrado, A., Bevis, B. J., Valastyan, J. S., Han, H., Lindhagen-Persson, M., Reiman, E. M., Evans, D. A., Bennett, D. A., Olofsson, A., DeJager, P. L., Tanzi, R. E., Caldwell, K. A., Caldwell, G. A., Lindquist, S., 2011. Functional links between Aβ toxicity, endocytic trafficking, and Alzheimer's disease risk factors in yeast. Science 334, 1241-1245. doi:10.1126/science.1213210

Tsunemi, T., Krainc, D., 2014. $Zn^{2+}$ dyshomeostasis caused by loss of ATP13A2/PARK9 leads to lysosomal dysfunction and alpha-synuclein accumulation. Hum Mol Genet 23, 2791-2801. doi:10.1093/hmg/ddtS72

Tu, Z., Argmann, C., Wong, K. K., Mitnaul, L. J., Edwards, S., Sach, I. C., Zhu, J., Schadt, E. E., 2009. Integrating siRNA and protein-protein interaction data to identify an expanded insulin signaling network. Genome Res 19, 1057-1067. doi:10.1101/gr.087890.108

Tuncbag, N., Braunstein, A., Pagnani, A., Huang, S.-S. C., Chayes, J., Borgs, C., Zecchina, R., Fraenkel, E., 2013. Simultaneous reconstruction of multiple signaling pathways via the prize-collecting steiner forest problem. J. Comput. Biol. 20, 124-136. doi:10.1089/cmb.2012.0092

Tuncbag, N., Gosline, S. J. C., Kedaigle, A., Soltis, A. R., Gitter, A., Fraenkel, E., 2016. Network-Based Interpretation of Diverse High-Throughput Datasets through the Omics Integrator Software Package. PLoS Comput. Biol. 12, e1004879. doi:10.1371/journal.pcbi.1004879

Verstraeten, A., Theuns, J., Van Broeckhoven, C., 2015. Progress in unraveling the genetic etiology of Parkinson disease in a genomic era. Trends Genet 31, 140-149. doi:10.1016/j.tig.2015.01.004

Vilella, A. J., Severin, J., Ureta-Vidal, A., Heng, L., Durbin, R., Birney, E., 2009. EnsemblCompara GeneTrees: Complete, duplication-aware phylogenetic trees in vertebrates. Genome Res 19, 327-335. doi:10.1101/gr.073585.107

Voevodski, K., Teng, S.-H., Xia, Y., 2009. Finding local communities in protein networks. BMC Bioinformatics 10, 297. doi:10.1186/1471-2105-10-297

Wang, T., Wei, J. J., Sabatini, D. M., Lander, E. S., 2014. Genetic screens in human cells using the CRISPR-Cas9 system. Science 343, 80-84. doi:10.1126/science.1246981

Wilson, G. R., Sim, J. C. H., McLean, C., Giannandrea, M., Galea, C. A., Riseley, J. R., Stephenson, S. E. M., Fitzpatrick, E., Haas, S. A., Pope, K., Hogan, K. J., Gregg, R. G., Bromhead, C. J., Wargowski, D. S., Lawrence, C. H., James, P. A., Churchyard, A., Gao, Y., Phelan, D. G., Gillies, G., Salce, N., Stanford, L., Marsh, A. P. L., Mignogna, M. L., Hayflick, S. J., Leventer, R. J., Delatycki, M. B., Mellick, G. D., Kalscheuer, V. M., D'Adamo, P., Bahlo, M., Amor, D. J., Lockhart, P. J., 2014. Mutations in RAB39B Cause X-Linked Intellectual Disability and Early-Onset Parkinson Disease with α-Synuclein Pathology. Am J Hum Genet 95, 729-735. doi:10.1016/j.ajhg.2014.10.015

Yeger-Lotem, E., Riva, L., Su, L. J., Gitler, A. D., Cashikar, A. G., King, O. D., Auluck, P. K., Geddie, M. L., Valastyan, J. S., Karger, D. R., Lindquist, S., Fraenkel, E., 2009. Bridging high-throughput genetic and transcriptional data reveals cellular responses to alpha-synuclein toxicity. Nat Genet 41, 316-323. doi:10.1038/ng.337

Zimprich, A., Benet-Pagès, A., Struhal, W., Graf, E., Eck, S. H., Offman, M. N., Haubenberger, D., Spielberger, S., Schulte, E. C., Lichtner, P., Rossle, S. C., Klopp, N., Wolf, E., Seppi, K., Pirker, W., Presslauer, S., Mollenhauer, B., Katzenschlager, R., Foki, T., Hotzy, C., Reinthaler, E., Harutyunyan, A., Kralovics, R., Peters, A., Zimprich, F., Brucke, T., Poewe, W., Auff, E., Trenkwalder, C., Rost, B., Ransmayr, G., Winkelmann, J., Meitinger, T., Strom, T. M., 2011. A Mutation in VPS35, Encoding a Subunit of the Retromer Complex, Causes Late-Onset Parkinson Disease. Am J Hum Genet 89, 168-175. doi:10.1016/j.ajhg.2011.06.008.

We claim:

1. A computer-implemented method of modeling a physiologic or pathologic process of an animal to identify a druggable target, comprising:
    (a) providing a set of candidate yeast genes identified in a genome-wide screen of yeast genes in a yeast analogue of the physiologic or pathologic process of the animal;
    (b) providing interactions between yeast genes comprising the candidate yeast genes of step (a);
    (c) providing interactions between genes of the animal;
    (d) determining a set of genes of the animal homologous to the set of candidate yeast genes;
    (e) creating a model of the physiologic or pathologic process in the animal by augmenting interactions between the set of genes of the animal obtained in step (d) with gene interactions based on the interactions between yeast genes of step (b) homologous to the set of genes of the animal;
    (f) identifying one or more gene or protein nodes of the model created in step (e) as a druggable target, and
    (g) generating a cell having altered expression of the gene node identified as a druggable target or altered activity of a gene product of the gene node identified as a druggable tart,
    wherein step (e), and optionally one or both of steps (b) and (c), comprises utilizing a computer system comprising one or more processors programmed to execute one or more computer-executable instructions which causes the computer system to perform the Prize-Collecting Steiner Forest (PCSF) algorithm to connect gene or protein nodes through genetic interactions, physical interactions and annotated pathways from one or more curated databases while minimizing costs to obtain a network, wherein the network is a representative network obtained by varying algorithm parameters to generate multiple networks and creating a representative network from the multiple networks with a maximum spanning tree algorithm.

2. A method of modeling a physiologic or pathologic process of an animal to identify a druggable target, comprising:
   (a) providing a set of candidate yeast genes identified in a genome-wide screen of yeast genes in a yeast analogue of the physiologic or pathologic process of the animal;
   (b) providing interactions between yeast genes comprising the candidate yeast genes of step (a);
   (c) providing interactions between genes of the animal;
   (d) determining a set of genes of the animal homologous to the set of candidate yeast genes;
   (e) creating a model of the physiologic or pathologic process in the animal by augmenting interactions between the set of genes of the animal obtained in step (d) with gene interactions based on the interactions between yeast genes of step (b) homologous to the set of genes of the animal; and
   (f) identifying one or more gene or protein nodes of the model created in step (e) as a druggable target, and
   (g) generating a cell having altered expression of the gene node identified as a druggable target or altered activity of a gene product of the gene node identified as a druggable target,
   wherein step (e), and optionally one or both of steps (b) and (c), comprises using the Prize-Collecting Steiner Forest (PCSF) algorithm to connect gene or protein nodes through genetic interactions, physical interactions and annotated pathways from one or more curated databases while minimizing costs to obtain a network, wherein the network is a representative network obtained by varying algorithm parameters to generate multiple networks and creating a representative network from the multiple networks with a maximum spanning tree algorithm, and
   wherein the set of candidate yeast genes of step (a) were obtained by a method comprising:
   (i) providing a yeast cell modified to have increased or decreased expression or activity of a protein encoded by a yeast gene under conditions being a yeast analogue of the physiologic or pathologic process,
   (ii) determining whether the modification modulates the yeast cell response to the conditions, and
   (iii) identifying the yeast gene as a candidate yeast gene when the yeast cell response is modulated.

3. The method of claim 2, wherein the conditions comprise aberrant expression of one or more genes and/or the one or more genes comprise a non-endogenous gene.

4. The method of claim 2, wherein the modulation of yeast cell response of step (ii) comprises a change in at least one phenotype, a change in expression of at least one gene, a change in activity of at least one protein, or a change in cell viability.

5. The method of claim 2, wherein the identification of a candidate yeast gene of step (iii) comprises identification of a change in at least one phenotype, a change in expression of at least one gene, a change in activity of at least one protein, or a change in cell viability.

6. The method of claim 2, wherein the interactions of step (b) comprise predicted gene or protein nodes not included in the set of candidate yeast genes of step (a).

7. The method of claim 2, wherein the physiologic or pathologic process is a neurodegenerative disease.

8. A method of modeling a physiologic or pathologic process of an animal to identify a druggable target, comprising:
   (a) providing a set of candidate yeast genes identified in a genome-wide screen of yeast genes in a yeast analogue of the physiologic or pathologic process of the animal;
   (b) providing interactions between yeast genes comprising the candidate yeast genes of step (a);
   (c) providing interactions between genes of the animal;
   (d) determining a set of genes of the animal homologous to the set of candidate yeast genes;
   (e) creating a model of the physiologic or pathologic process in the animal by augmenting interactions between the set of genes of the animal obtained in step (d) with gene interactions based on the interactions between yeast genes of step (b) homologous to the set of genes of the animal; and
   (f) identifying one or more gene or protein nodes of the model created in step (e) as a druggable target, and
   (g) generating a cell having altered expression of the gene node identified as a druggable target or altered activity of a gene product of the gene node identified as a druggable target,
   wherein step (e), and optionally one or both of steps (b) and (c), comprises using the Prize-Collecting Steiner Forest (PCSF) algorithm to connect gene or protein nodes through genetic interactions, physical interactions and annotated pathways from one or more curated databases while minimizing costs to obtain a network, wherein the network is a representative network obtained by varying algorithm parameters to generate multiple networks and creating a representative network from the multiple networks with a maximum spanning tree algorithm.

9. The method of claim 8, wherein step (g) comprises introducing an addition, deletion, disruption or mutation into the genome of a cell.

10. The method of claim 8, further comprising:
    (h) identifying one or more targets for therapy in a second animal comprising determining that the second animal harbors a mutation, altered expression, or altered activity in any of the gene or protein nodes identified as druggable targets in step (f).

11. The method of claim 7, further comprising screening compounds to identify a modulator of the identified gene or protein node druggable target.

12. The method of claim 8, wherein the set of candidate yeast genes of step (a) were obtained by a method comprising:
    (i) providing a yeast cell modified to have increased or decreased expression or activity of a protein encoded by a yeast gene under conditions being a yeast analogue of the physiologic or pathologic process,
    (ii) determining whether the modification modulates the yeast cell response to the conditions, and
    (iii) identifying the yeast gene as a candidate yeast gene when the yeast cell response is modulated.

13. The method of claim 12, wherein the conditions comprise aberrant expression of one or more genes.

14. The method of claim 13, wherein the one or more genes comprise a non-endogenous gene.

15. The method of claim 12, wherein the modulation of yeast cell response of step (ii) comprises a change in at least one phenotype, a change in expression of at least one gene, a change in activity of at least one protein, or a change in cell viability.

16. The method of claim 12, wherein the identification of a candidate yeast gene of step (iii) comprises identification of a change in at least one phenotype, a change in expression of at least one gene, a change in activity of at least one protein, or a change in cell viability.

17. The method of claim 8, wherein the interactions of step (b) comprise predicted gene or protein nodes not included in the set of candidate yeast genes of step (a).

18. The method of claim 8, wherein step (d) comprises:
  (i) determining sequence similarity between the animal genes and the candidate yeast genes;
  (ii) determining evolutionary and structural similarity between the animal genes and the candidate yeast genes; and
  (iii) determining molecular interaction similarity between the animal genes and the candidate yeast genes; and
  (iv) determining a set of genes in the animal homologous to the set of candidate yeast genes by integrating the similarities in steps (i) through (iii) using diffusion component analysis.

19. The method of claim 8, wherein one or both of steps (b) and (c) comprises using the Prize-Collecting Steiner Forest (PCSF) algorithm to connect gene or protein nodes through genetic interactions, physical interactions and annotated pathways from one or more curated databases while minimizing costs to obtain a network, wherein the network is a representative network obtained by varying algorithm parameters to generate multiple networks and creating a representative network from the multiple networks with a maximum spanning tree algorithm.

20. The method of claim 8, wherein the physiologic or pathologic process is a neurodegenerative disease.

* * * * *

UNITED STATES PATENT AND TRADEMARK OFFICE
CERTIFICATE OF CORRECTION

| | | |
|---|---|---|
| PATENT NO. | : 12,068,059 B2 | Page 1 of 1 |
| APPLICATION NO. | : 16/481061 | |
| DATED | : August 20, 2024 | |
| INVENTOR(S) | : Vikram Khurana et al. | |

It is certified that error appears in the above-identified patent and that said Letters Patent is hereby corrected as shown below:

In the Claims

Claim 1, Line 65: "druggable tart" should read --druggable target--;

Claim 11, Line 54: "claim 7" should read --claim 8--.

Signed and Sealed this
Twenty-ninth Day of October, 2024

Katherine Kelly Vidal
*Director of the United States Patent and Trademark Office*